(12) United States Patent
Busfield et al.

(10) Patent No.: US 6,989,144 B1
(45) Date of Patent: Jan. 24, 2006

(54) GLYCOPROTEIN VI ANTIBODIES AND USES THEREOF

(75) Inventors: Samatha J. Busfield, Maddington (AU); Jean-Luc Villeval, Needham, MA (US); Martine Jandrot-Perrus, Vanves (FR); William Vainchencker, Paris (FR); Davinder Singh Gill, Burlington, MA (US); Ming Diana Qian, Cambridge, MA (US); Gillian Kingsbury, W. Roxbury, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/610,118

(22) Filed: Jun. 30, 2000

Related U.S. Application Data

(63) Continuation-in-part of application No. 09/503,387, filed on Feb. 14, 2000, now abandoned, which is a continuation-in-part of application No. 09/454,824, filed on Dec. 6, 1999, now abandoned, which is a continuation-in-part of application No. 09/345,468, filed on Jun. 30, 1999, now Pat. No. 6,245,527.

(51) Int. Cl.
*A61K 39/395* (2006.01)
*C07K 16/28* (2006.01)
*C12P 21/08* (2006.01)

(52) U.S. Cl. .............. 424/130.1; 424/135.1; 435/810; 530/387.1; 530/387.3; 530/388.2; 530/388.7; 530/391.3; 530/391.7

(58) Field of Classification Search .............. 530/387.1, 530/387.3, 388.2, 388.7, 391.7, 391.3, 388.15, 530/391.1; 424/130.1, 135.1, 133.1, 142.1, 424/178.1; 435/810
See application file for complete search history.

(56) References Cited

U.S. PATENT DOCUMENTS

| | | |
|---|---|---|
| 5,272,057 A | 12/1993 | Smulson et al. |
| 5,459,039 A | 10/1995 | Modrich et al. |
| 5,854,005 A | 12/1998 | Coller |
| 5,976,532 A | 11/1999 | Coller et al. |

FOREIGN PATENT DOCUMENTS

| | | |
|---|---|---|
| WO | WO 95/11259 | 4/1995 |
| WO | WO 98/32845 | 7/1998 |
| WO | WO 99/11662 | 3/1999 |
| WO | WO 00/68377 | 11/2000 |

OTHER PUBLICATIONS

Janeway et al Immunobiology 4th Edition, Garland Press London, 1999.*

Adams MD et al., "Initial assessment of human gene diversity and expression patterns based upon 83 million nucleotides of cDNA sequence", Nature. Sep. 28, 1995;377(6547 Suppl):3–174.

Altschul SF et al., "Basic local alignment search tool", J Mol Biol. Oct. 5, 1990;215(3):403–10.

Altschul SF et al., "Gapped BLAST and PSI–BLAST: a new generation of protein database search programs", Nucleic Acids Res. Sep. 1, 1997;25(17):3389–402.

Arai M et al., "Platelets with 10% of the normal amount of glycoprotein VI have an impaired response to collagen that results in a mild bleeding tendency", Br J Haematol. Jan. 1995;89(1):124–30.

Asselin J et al., "Monomeric (glycine–proline–hydroxyproline)10 repeat sequence is a partial agonist of the platelet collagen receptor glycoprotein VI", Biochem J. Apr. 15, 1999;339 (Pt 2):413–8.

Barany F., "Genetic disease detection and DNA amplification using cloned thermostable ligase", Proc Natl Acad Sci U S A. Jan. 1, 1991;88(1):189–93.

Barnes MJ et al., "The collagen–platelet interaction", Curr Opin Hematol. Sep. 1998;5(5):314–20.

Briddon SJ and Watson SP, "Evidence for the involvement of p59fyn and p53/56lyn in collagen receptor signalling in human platelets", Biochem J. Feb. 15, 1999;338 (Pt 1):203–9.

Carlsson LE et al., "Heparin–induced thrombocytopenia: new insights into the impact of the FcgRlla–R–H131 polymorphism", Blood, Sep. 1, 1998;92(5):1526–31.

Chiang TM and Kang AH, "Isolation and purification of collagen alpha 1(I) receptor from human platelet membrane", J Biol Chem. Jul. 10, 1982;257(13):7581–6.

Chiang TM et al., "Cloning, characterization, and functional studies of a nonintegrin platelet receptor for type I collagen", J Clin Invest. Aug. 1997; 100(3):514–521.

Clemetson KJ, "Platelet activation: signal transduction via membrane receptors", Thromb Haemost. Jul. 1995;74(1):111–6.

Clemetson JM et al., "The Platelet Collagen Receptor Glycoprotein VI Is a Member of the Immunoglobulin Superfamily Closely Related to FcalphaR and the Natural Killer Receptors", J Biol Chem. Oct. 8, 1999;274(41):29019–29024.

(Continued)

*Primary Examiner*—Christina Chan
*Assistant Examiner*—Phuong Huynh
(74) *Attorney, Agent, or Firm*—Millennium Pharmaceuticals Inc.

(57) ABSTRACT

The invention provides isolated nucleic acid molecules and polypeptide molecules that encode glycoprotein V1, a platelet membrane glycoprotein that is involved platelet-collagen interactions. The invention also provides antisense nucleic acid molecules, expression vectors containing the nucleic acid molecules of the invention, host cells into which the exposure vectors have been introduced, and non-human transgenic animals in which a nucleic acid molecule of the invention has been introduced or disrupted. The invention still further provides isolated polypeptides, fusion polypeptides, antigenic peptides and antibodies. Diagnostic, screening and therapeutic methods utilizing compositions of the invention are also provided.

16 Claims, 40 Drawing Sheets

OTHER PUBLICATIONS

Clemetson KJ et al., "Characterization of the platelet membrane glycoprotein abnormalities in Bernard–Soulier syndrome and comparison with normal by surface–labeling techniques and high–resolution two–dimensional gel electrophoresis", J Clin Invest. Aug. 1982;70(2):304–11.

Coller et al., 1985, "A new murine monoclonal antibody reports an activation–dependent change in the conformation and/or microenvironment of the platelet glycoprotein IIb/IIIa complex", J Clin Invest. 76(1):101–8.

Cotton RG, "Current methods of mutation detection", Mutat Res. Jan. 1993;285(1):125–44.

Cotton RG et al., "Reactivity of cytosine and thymine in single–base–pair mismatches with hydroxylamine and osmium tetroxide and its application to the study of mutations", Proc Natl Acad Sci U S A. Jun. 1988;85(12)4397–401.

Cronin MT et al., "Cystic fibrosis mutation detection by hybridization to light–generated DNA probe arrays", Hum Mutat. 1996;7(3):244–55.

Ezumi et al., 2000, "Molecular cloning, genomic structure, chromosomal localization, and alternative splice forms of the platelet collagen receptor glycoprotein VI", Biochem Biophys Res Commun 277(1): 27–36.

Ezumi Y et al., "Physical and functional association of the Src family kinases Fyn and Lyn with the collagen receptor glycoprotein VI-Fc receptor gamma chain complex on human platelets", J Exp Med. Jul. 20, 1998;188(2):267–76.

Fan et al., 1987, "Structure of the inhibitory receptor for human natural killer cells resembles haematopoietic receptors" Nature. 389(6646):96–100.

Gibbins JM et al., "Glycoprotein VI is the collagen receptor in platelets which underlies tyrosine phosphorylation of the Fc receptor gamma–chain", FEBS Lett. Aug. 18, 1997;413(2):255–9.

Gibbins JM et al., "The p85 subunit of phosphatidylinositol 3–kinase associates with the Fc receptor gamma–chain and linker for activitor of T cells (LAT) in platelets stimulated by collagen and convulxin", J Biol Chem. Dec. 18, 1998;273(51):34437–43.

Gibbs RA et al., "Detection of single DNA base differences by competitive oligonucleotide priming", Nucleic Acids Res. Apr. 11, 1989;17(7):2437–48.

Handa M et al., "Platelet unresponsiveness to collagen: involvement of glycoprotein Ia–IIa (alpha 2 beta 1 integrin) deficiency associated with a myeloproliferative disorder", Thromb Haemost. Mar. 1995;73(3):521–8.

Hayashi K., "PCR–SSCP: a method for detection of mutations", Genet Anal Tech Appl. Jun. 1992;9(3):73–9.

Heemskerk JW et al., "Function of glycoprotein VI and integrin alpha2beta1 in the procoagulant response of single, collagen–adherent platelets", Thromb Haemost. May 1999;81(5):782–92.

Hsu IC et al., "Detection of DNA point mutations with DNA mismatch repair enzymes", Carcinogenesis. Aug. 1994;15(8):1657–62.

Ichinohe T et al., "Collagen–stimulated activation of Syk but not c–Src is severely compromised in human platelets lacking membrane glycoprotein VI", J Biol Chem. Jan. 3, 1997;272(1):63–8.

Ichinohe T et al., "Cyclic AMP–insensitive activation of c–Src and Syk protein–tyrosine kinases through platelet membrane glycoprotein VI", J Biol Chem. Nov. 24, 1995;270(47):28029–36.

Inoue K et al., "Signal transduction pathways mediated by glycoprotein Ia/IIa in human platelets: comparison with those of glycoprotein VI", Biochem Biophys Res Commun. Mar. 5, 1999;256(1):114–20.

Ishibashi T, Sugiyama T, Ichinohe T, Takayama H, Okuma M. Purification of p62, a putative platelet collagen receptor, and its functional significance in collagen–induced platelet aggregation. XIVth Congress of the International Society on Thrombosis and Haemostasis, New York. Thrombosis and Haemostasis. Jul. 1993; Abstract No. 1638.

Ishibashi T, Ichinohe T, Sugiyama T, Takayama H, Titani K, Okuma M. Functional significance of platelet membrane glycoprotein p62 (GP VI), a putative collagen receptor. Int J Haematol. Aug. 1995;62(2):107–15.

Jandrot–Perrus et al., 2000, "Cloning, characterization, and functional studies of human and mouse glycoprotein VI: a platelet–specific collagen receptor from the immunoglobulin superfamily", Blood 96(5): 1798–1807.

Jandrot–Perrus M et al., "Adhesion and activation of human platelets induced by convulxin involve glycoprotein VI and integrin alpha2beta1", J Biol Chem. Oct. 24, 1997;272(43):27035–41.

Karlin S, and Altschul SF, "Methods for assessing the statistical significance of molecular sequence features by using general scoring schemes", Proc Natl Acad Sci U S A. Mar. 1990;87(6):2264–8.

Karlin S and Altschul SF, "Applications and statistics for multiple high–scoring segments in molecular sequences", Proc Natl Acad Sci U S A. Jun. 15, 1993;90(12):5873–7.

Keen J et al., "Rapid detection of single base mismatches as heteroduplexes on Hydrolink gels", Trends Genet. Jan. 1991;7(1):5.

Kehrel B et al., "Glycoprotein VI is a major collagen receptor for platelet activation: it recognizes the platelet–activating quaternary structure of collagen, whereas CD36, glycoprotein IIb/IIIa, and von Willebrand factor do not", Blood. Jan. 15, 1998;91(2):491–9.

Knight CG et al., "Collagen–platelet interaction: Gly–Pro–Hyp is uniquely specific for platelet Gp VI and mediates platelet activation by collagen", Cardiovasc Res. Feb. 1999;41(2):450–7.

Kotite NJ and Cunningham LW, "Specific adsorption of platelet membrane glycoprotein by human insoluble collogen", J Biol Chem. Jun. 25, 1986;261(18):8342–7.

Kozal MJ et al., "Extensive polymorphisms observed in HIV–1 clade B protease gene using high–density oligonucleotide arrays", Nat Med. Jul. 1996;2(7):753–9.

Lagrue AH et al., "Phosphatidylinositol 3'–kinase and tyrosine–phosphatase activation positively modulate Convulxin–induced platelet activation. Comparison with collagen", FEBS Lett. Apr. 1, 1999;448(1):95–100.

Lefkovits et al. 1995, Platelet glycoprotein IIb/IIIa receptors in cardiovascular medicine. N Engl J Med. 332(23):1553–9.

Maliszewski CR et al., "Expression cloning of a human Fc receptor for IgA", J Exp Med. Dec. 1, 1990;172(6):1665–72.

Martin M et al., "Colon–cancer cell variants producing regressive tumors in syngeneic rats, unlike variants yielding progressive tumors, attach to interstitial collagens through integrin alpha2beta1", Int J Cancer. Mar. 15, 1996;65(6):796–804.

Miura et al., 2000, "Cloning and expression of the platelet–specific collagen receptor glycoprotein VI", Thromb Res.98(4):301–9.

Moroi M et al., "A patient with platelets deficient in glycoprotein VI that lack both collagen–induced aggregation and adhesion", J Clin Invest. Nov. 1989;84(5):1440–5.

Moroi M et al, "Analysis of platelet adhesion to a collagen-coated surface under flow conditions: the involvement of glycoprotein VI in the platelet adhesion" Blood. Sep. 15, 1996;88(6):2081–92.

Moroi M and Jung SM, "Platelet receptors for collagen", Thromb Haemost. Jul. 1997;78(1):439–44.

Moshfegh K et al., "Association of two silent polymorphisms of platelet glycoprotein Ia/IIa receptor with risk of myocardial infarction: a case–control study", Lancet. Jan. 30, 1999;353(9150):351–4.

Myers RM et al., "Detection of single base substitutions by ribonuclease cleavage at mismatches in RNA:DNA duplexes", Science. Dec. 13, 1985;230(4731):1242–6.

Nakamura T et al., "Platelet adhesion to native type I collagen fibrils. Role of GPVI in divalent cation–dependent and –independent adhesion and thromboxane A2 generation", J Biol Chem. Feb. 20, 1998;273(8):4338–44.

Nielsen H et al., "Identification of prokaryotic and eukaryotic signal peptides and prediction of their cleavage sites", Protein Eng. Jan. 1997;10(1):1–6.

Orita M et al., "Detection of polymorphisms of human DNA by gel electrophoresis as single–strand conformation polymorphisms", Proc Natl Acad Sci U S A. Apr. 1989;86(8):2766–70.

Pearson WR and Lipman DJ, "Improved tools for biological sequence comparison", Proc Natl Acad Sci U S A. Apr. 1988;85(8):2444–8.

Pfam: http://pfam.wustl.edu Accession No. PF00047 "Immunoglobulin domain" (Bateman A and Sonnhammer ELL).

Phillips DR and Agin PP, "Platelet plasma membrane glycoproteins. Evidence for the presence of nonequivalent disulfide bonds using nonreduced–reduced two–dimensional gel electrophoresis", J Biol Chem. Mar. 25, 1977;252(6):2121–6.

Polgar J et al., "Platelet activation and signal transduction by convulxin, a C–type lectin from *Crotalus durissus terrificus* (tropical rattlesnake) venom via the p62/GPVI collagen receptor", J Biol Chem. May 23, 1997;272(21):13576–83.

Poole A et al., "The Fc receptor gamma–chain and the tyrosine kinase Syk are essential for activation of mouse platelets by collagen", EMBO J. May 1, 1997;16(9):2333–41.

Quek LS et al., "A role for Bruton's tyrosine kinase (Btk) in platelet activation by collagen", Curr Biol. Oct. 8, 1998:8(20):1137–40.

Rosenbaum V and Riesner D, "Temperature–gradient gel electrophoresis. Thermodynamic analysis of nucleic acids and proteins in purified form and in cellular extracts", Biophys Chem. May 9, 1987;26(2–3):235–46.

Ryo R et al., "Deficiency of P62, a putative collagen receptor, in platelets from a patient with defective collagen–induced platelet aggregation", Am J Hematol. Jan. 1992;39(1):25–31.

Saiki RK et al., "Analysis of enzymatically amplified beta-globin and HLA–DQ alpha DNA with allele–specific oligonucleotide probes", Nature, Nov. 13–19, 1986;324(6093):163–6.

Saiki RK et al., "Genetic analysis of amplified DNA with immobilized sequence–specific oligonucleotide probes", Proc Natl Acad Sci U S A. Aug. 1989;86(16):6230–4.

Saleeba JA and Cotton RG, "Chemical cleavage of mismatch to detect mutations", Methods Enzymol. 1993;217:286–95.

Sugiyama T et al., "A novel platelet aggregating factor found in a patient with defective collagen–induced platelet aggregation and autoimmune thrombocytopenia", Blood. Jun. 1987;69(6):1712–20.

Sugiyama T, Ishibashi T, Okuma M. Functional role of the antigen recognized by an antiplatelet antibody specific for a putative collagen receptor in platelet–collagen interaction. Int J Hematol. Aug. 1993;58(1–2):99–104.

Sixma J.J., van Zanten H, Saelman E.U.M., Verkleiji M., Lankhof H., Nieuwenhuis H.K., de Groot P.G. Platelet Adhesion to Collagen Thrombosis and Haemostasis 1995 74(1):454–459.

Takahashi H et al., "Platelet membrane glycoprotein VI (GPVI) is necessary for collagen–induced aggregation and adhesion and anti–GP VI antibody induces platelet aggregation: An evidence obtained from a patient with systemic lupus erythematosus", Thromb Haemostas. 1995; 73:1197 (Abstract).

Torelli A and Robotti CA, ADVANCE and ADAM: two algorithms for the analysis of global similarity between homologous informational sequences. Comput Appl Biosci. Feb. 1994;10(1):3–5.

Tsuji M et al., "A novel association of Fc receptor gamma–chain with glycoprotein VI and their co–expression as a collagen receptor in human platelets", J Biol Chem. Sep. 19, 1997;272(38):23528–31.

Verkleij MW et al., "Simple collagen–like peptides support platelet adhesion under static but not under flow conditions: interaction via alpha2 beta1 and von Willebrand factor with specific sequences in native collagen is a requirement to resist shear forces", Blood. May 15, 1998;91(10):3808–16.

www.ncbi.nlm.nih.gov Genbank Accession No. AA308708 "EST179519 HCC cell line (matastasis to liver in mouse) II *Homo sapiens* cDNA 5' end similar to EST containing Alu repeat, mRNA sequence" (Adams, M.D. et al.).

www.ncbi.nlm.nih.gov Genbank Accession No. AA494446 "ne38a02.s1 NCI_CGAP_Co3 *Homo sapiens* cDNA clone IMAGE:899594 3', mRNA sequence" (NCI–CGAP http://www.ncbi.nlm.nih.gov/ncicgap).

www.ncbi.nlm.hih.gov. Genbank Accession No. AB035073 "*Homo sapiens* mRNA for platelet glycoprotein VI, complete cds" (Miura, Y.).

www.ncbi.nlm.nih.gov. Genbank Accession No. AB043819 "*Homo sapiens* GPVI mRNA for platelet glycoprotein VI–3, complete cds" (Ezumi and Takayama).

www.ncbi.nlm.nih.gov. Genbank Accession No. AB043820 "*Homo sapiens* GPVI mRNA for platelet glycoprotein VI–1, complete cds", (Ezumi and Takayama).

www.ncbi.nlm.nih.gov. Genbank Accession No. AB043821 "*Homo sapiens* GPVI mRNA for platelet glycoprotein VI–2, complete cds", (Ezumi and Takayama).

www.ncbi.nlm.nih.gov. Genbank Accession No. AB043943 "*Homo sapiens* GPVI gene for platelet glycoprotein VI, partial cds", (Ezumi and Takayama).

www.ncbi.nlm.nih.gov. Genbank Accession No. AX046772 "Sequence 1 from Patent WO 00/68377" (Clemetson, K.J.).

www.ncbi.nlm.nih.gov. Genbank Accession No. NM_016363 "*Homo sapiens* platelet glycoprotein VI (GPVI), mRNA" (Ezumi et al.).

www.ncbi.nlm.nih.gov Genbank Accession No. U91928 "Human clone HL9 monocyte inhibitory receptor precursor mRNA, complete cds" (Arm, J.P.).

Barbas et al., 1992, "Semisynthetic Combinatorial Antibody libraries: A Chemical Solution to the Diversity Problem", Proc. Natl. Acad. Sci. USA 89:4457–4461.

Harlow and Lane, 1988, "Antibodies: A Laboratory Manual", Ch. 14, pp. 555–612, Cold Spring Harbor Laboratory.

Jirholt et al., 1998, "Exploiting Sequence Space: Shuffling in Vivo Formed Complementarity Determining Regions Into A Master Framework", Gene 215:471–476.

Soderlind et al., 1999, "Complementarity Determining Region (CDR) Implantation: A Theme of Recombination", Immunotechnology 4:279–285.

Soderlind et al., 2000. "Recombining Germline–derived CDR Sequences for Creating Diverse Single–framework Antibody Libraries", Nature Biotechnology 18:852–856.

* cited by examiner

```
                                                    M   S   P   S   P   T   A   L   F   C   L    11
GGAGTCGACCCACGCGTCCGCAGGGCTGAGGAACC ATG TCT CCA TCC CCG ACC GCC CTC TTC TGT CTT   68

G   L   C   L   G   R   V   P   A   Q   S   G   P   L   P   K   P   S   L   Q    31
GGG CTG TGT CTG GGG CGT GTG CCA GCG CAG AGT GGA CCG CTC CCC AAG CCC TCC CTC CAG  128

A   L   P   S   S   L   V   P   L   E   K   P   V   T   L   R   C   Q   G   P    51
GCT CTG CCC AGC TCC CTG GTG CCC CTG GAG AAG CCA GTG ACC CTC CGG TGC CAG GGA CCT  188

P   G   V   D   L   Y   R   L   E   K   L   S   S   S   R   Y   Q   D   Q   A    71
CCG GGC GTG GAC CTG TAC CGC CTG GAG AAG CTG AGT TCC AGC AGG TAC CAG GAT CAG GCA  248

V   L   F   I   P   A   M   K   R   S   L   A   G   R   Y   R   C   S   Y   Q    91
GTC CTC TTC ATC CCG GCC ATG AAG AGA AGT CTG GCT GGA CGC TAC CGC TGC TCC TAC CAG  308

N   G   S   L   W   S   L   P   S   D   Q   L   E   L   V   A   T   G   V   F   111
AAC GGA AGC CTC TGG TCC CTG CCC AGC GAC CAG CTG GAG CTC GTT GCC ACG GGA GTT TTT  368

A   K   P   S   L   S   A   Q   P   G   P   A   V   S   S   G   D   V   T   131
GCC AAA CCC TCG CTC TCA GCC CAG CCC GGC CCG GCG GTG TCG TCA GGA GGG GAC GTA ACC  428

L   Q   C   Q   T   R   Y   G   F   D   Q   F   A   L   Y   K   E   G   D   P   151
CTA CAG TGT CAG ACT CGG TAT GGC TTT GAC CAA TTT GCT CTG TAC AAG GAA GGG GAC CCT  488

A   P   Y   K   N   P   E   R   W   Y   R   A   S   F   P   I   I   T   V   T   171
GCG CCC TAC AAG AAT CCC GAG AGA TGG TAC CGG GCT AGT TTC CCC ATC ATC ACG GTG ACC  548

A   A   H   S   G   T   Y   R   C   Y   S   F   S   S   R   D   P   Y   L   W   191
GCC GCC CAC AGC GGA ACC TAC CGA TGC TAC AGC TTC TCC AGC AGG GAC CCA TAC CTG TGG  608

S   A   P   S   D   P   L   E   L   V   V   T   G   T   S   V   T   P   S   R   211
TCG GCC CCC AGC GAC CCC CTG GAG CTT GTG GTC ACA GGA ACC TCT GTG ACC CCC AGC CGG  668

L   P   T   E   P   P   S   S   V   A   E   F   S   E   A   T   A   E   L   T   231
TTA CCA ACA GAA CCA CCT TCC TCG GTA GCA GAA TTC TCA GAA GCC ACC GCT GAA CTG ACC  728

V   S   F   T   N   K   V   F   T   T   E   T   S   R   S   I   T   T   S   P   251
GTC TCA TTC ACA AAC AAA GTC TTC ACA ACT GAG ACT TCT AGG AGT ATC ACC ACC AGT CCA  788

K   E   S   D   S   P   A   G   P   A   R   Q   Y   Y   T   K   G   N   L   V   271
AAG GAG TCA GAC TCT CCA GCT GGT CCT GCC CGC CAG TAC TAC ACC AAG GGC AAC CTG GTC  848

R   I   C   L   G   A   V   I   L   I   I   L   A   G   F   L   A   E   D   W   291
CGG ATA TGC CTC GGG GCT GTG ATC CTA ATA ATC CTG GCG GGG TTT CTG GCA GAG GAC TGG  908

H   S   R   R   K   R   L   R   H   R   G   R   A   V   Q   R   P   L   P   P   311
CAC AGC CGG AGG AAG CGC CTG CGG CAC AGG GGC AGG GCT GTG CAG AGG CCG CTT CCG CCC  968
```

FIG.1A

```
L   P   P   L   P   Q   T   R   K   S   H   G   G   Q   D   G   G   R   Q   D  331
CTG CCG CCC CTC CCG CAG ACC CGG AAA TCA CAC GGG GGT CAG GAT GGA GGC CGA CAG GAT 1028

V   H   S   R   G   L   C   *                                                   340
GTT CAC AGC CGC GGG TTA TGT TCA TGA                                              1055
```

CCGCTGAACCCCAGGCACGGTCGTATCCAAGGGAGGGATCATGGCATGGGAGGCGACTCAAAGACTGGCGTGTGTGGAG 1134

CGTGGAAGCAGGAGGGCAGAGGCTACAGCTGTGGAAACGAGGCCATGCTGCCTCCTCCTGGTGTTCCATCAGGGAGCCG 1213

TTCGGCCAGTGTCTGTCTGTCTGTCTGCCTCTCTGTCTGAGGGCACCCTCCATTTGGGATGGAAGGAATCTGTGGAGAC 1292

CCCATCCTCCTCCCTGCACACTGTGGATGACATGGTACCCTGGCTGGACCACATACTGGCCTCTTTCTTCAACCTCTCT 1371

AATATGGGCTCCAGACGGATCTCTAAGGTTCCCAGCTCTCAGGGTTGACTCTGTTCCATCCTCTGTGCAAAATCCTCCT 1450

GTGCTTCCCTTTGGCCCTCTGTGCTCTTGTCTGGTTTTCCCCAGAAACTCTCACCCTCACTCCATCTCCCACTGCGGTC 1529

TAACAAATCTCCTTTCGTCTCTCAGAACGGGTCTTGCAGGCAGTTTGGGTATGTCATTCATTTTCCTTAGTGTAAAACT 1608

AGCACGTTGCCCGCTTCCCTTCACATTAGAAAACAAGATCAGCCTGTGCAACATGGTGAAACCTCATCTCTACCAACAA 1687

AACAAAAAAAACACAAAAATTAGCCAGGTGTGGTGGTGCATCCCTATACTCCCAGCAACTCGGGGGGCTGAGGTGGGAGA 1766

ATGGCTTGAGCCTGGGAGGCAGAGGTTGCAGTGAGCTGAGATCACACCACTGCACTCTAGCTCGGGTGACGAAGCCTGA 1845

CCTTGTCTCAAAAAATACAGGGATGAATATGTCAATTACCCTGATTTGATCATAGCACGTTGTATACATGTACTGCAAT 1924

ATTGCTGTCCACCCCATAAATATGTACAATTATGTATACATTTTTAAAATCATAAAAATAAGATAATGAAAAAAAAAAA 2003

AAAAAAAAAAAAAAGGGCGGGCCGCTAGACTAGTCTAGAGAACA 2047

FIG.1B

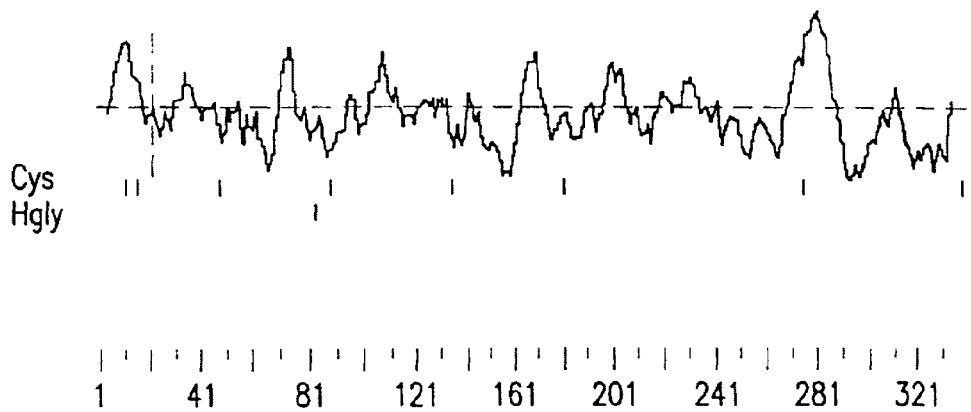

MSPSPTALFCLGLCLGRVPAQSGPLPKPSLQALPSSLVPLEKPVTLRCQGPPGVDLYRLE
KLSSSRYQDQAVLFIPAMKRSLAGRYRCSYQNGSLWSLPSDQLELVATGVFAKPSLSAQP
GPAVSSGGDVTLQCQTRYGFDQFALYKEGDPAPYKNPERWYRASFPIITVTAAHSGTYRC
YSFSSRDPYLWSAPSDPLELVVTGTSVTPSRLPTEPPSSVAEFSEATAELTVSFTNKVFT
TETSRSITTSPKESDSPAGPARQYYTKGNLVRICLGAVILIILAGFLAEDWHSRRKRLRH
RGRAVQRPLPPLPPLPQTRKSHGGQDGGRQDVHSRGLCS

FIG.2

```
            10         20         30         40         50         60         70
inputs ATGACGCCCGCCCTCACAGCCCTGCTCTGCCTTGGGCTGAGTCTGGGCCCCAGGACCCGCGTGCAGGCAG
       :::.: ::  :::   ::  :::::   ::::  :::::::::,:::::::.  :: ..::  ::  :::::. ..:
       ATGTCTCCATCCCCGACCGCCCTCTTCTGTCTTGGGCTGTGTCTGGGGCG-TGTGCCAGC--GCAGAGTG
            10         20         30         40         50         60

80         90        100        110        120        130
inputs GGCCCTTCCCCAAACCCACCCTCTGGGCTGAGCCAGGCTCTGTGAT-CAGCTGGGGGAGCCCCGTGACCA
       :.::  :::::::::.:::.:::  ::::  .:::  ::::   :::.:  :  :::::.,.:::  ::::::
       GACCGCTCCCCAAGCCCTCCCTCCAGGCTCTGCCCAGCTCCCTGGTGCCCCTGGAGAAGCCA-GTGACCC
          70         80         90        100        110        120        130

140        150        160        170        180        190        200
inputs TCTGGTGTCAGGGGAGCCTGGAGGCCCAGGAGTACCGACTGGATAAAGAGGGAAGCCCAGAGCCCTTGGA
       ::  ::::  :::::   .:::        :::::: ::.  ::: ::.           :::  .:::         ...
       TCCGGTGCCAGGG--ACCT------CCGGGCGTG--GACCTGTA--------CCGCCTGGAG-----AAG
            140        150              160        170              180

210        220        230        240        250        260        270
inputs CAGAAATAACCCACTGGAACCCAAGAACAAGGCCAGATTCTCCATCCCATCCATGACAGAGCACCATGCG
       :.::..:  ::  .::::.:::  :.:::.::  :::  .    :::  :::::.::  .:::::  .... . :.. ::
       CTGAGTT--CCAGCAGGTACC-AGGATCA-GGCAGTCCTCTTCATCCCGGCCATGAAGAGAAGTCTGGCT
          190        200        210        220        230        240

280        290        300        310        320        330        340
inputs GGGAGATACCGCTGCCACTATTACAGCTCTGCAG--GCTGGTCAGAGCCCAGCGACCCCCTGGAGCTGGT
       ::. : :::::::::: :::   ::: :::  .:::  ::::::  .::::::::::: ::::::::: ::
       GGACGCTACCGCTGCTCCTAC--CAGAACGGAAGCCTCTGGTCCCTGCCCAGCGACCAGCTGGAGCTCGT
          250        260        270        280        290        300        310

350        360        370        380        390        400        410
inputs GATGACAGGATTCTACAACAAACCCACCCTCTCAGCCCTGCCCAGCCCTGTGGTGGCCTCAGGGGGGAAT
       .    ::,:::  :  :.  .  :::::::::.: ::::::::::::.:::::,::::::  :  ::::  :  :::::,::::.:
       TGCCACGGGAGTTTTTGCCAAACCCTCGCTCTCAGCCCAGCCCGGCCCGGCGGTGTCGTCAGGAGGGGAC
          320        330        340        350        360        370        380

420        430        440        450        460        470        480
inputs ATGACCCTCCGATGTGGCTCACAGAAGGGATATCACCATTTTGTTCTGATGAAGGAAGGAGAACACCAGC
       .:.::::: :...::  , .:.:..:  ::  :.:  ::::.:::: ::::,,  :::::::::
       GTAACCCTACAGTGTCAGACTCGGTATGGCTTTGACCAATTTGCTCTGTACAAGGAAGG----------
          390        400        410        420        430        440

490        500        510        520        530        540        550
inputs TCCCCCGGACCCTGGACTCACAGCAGCTCCACAGTGGGGGGGTTCCAGGCCCTGTTCCCTGTGGGCCCCGT
       :::::::::                                  :  ::::::.              :...
       ------GGACCCTG-------------------------C---GCCCTA-------------CAA
             450                                   460
```

FIG.3A

```
       560       570       580       590       600       610       620
inputs GAACCCCAGCCACAGGTGGAGGTTCACATGCTATTACTATTATATGAACACCCCCCAGGTGTGGTCCCAC
       :::  :::..     :.:..:::.: :. ::::  :    ::         :::::             ::
       GAATCCCGA------GAGATGGTAC-CGGGCTAGT----TT-----------CCCCAT---------CAT
       470       480       490                 500

630       640       650       660       670       680       690
inputs CCCAGTGACCCCCTGGAGATTCTGCCCTCAGGCGTGTCTAGGAAGCCCTCCCTCCTGACCCTGCAGGGCC
       :  :..::.::: ::          :::::..
       CACGGTGACCGCC----------GCCCACAG--------------------------------------
       510                   520

700       710       720       730       740       750       760
inputs CTGTCCTGGCCCCTGGGCAGAGCCTGACCCTCCAGTGTGGCTCTGATGTCGGCTACGACAGATTTGTTCT
                        :.:::.:::..    ::..:::          :::::...:    ::::
       ----------------CGGAACCTA-----CCGATG-------------CTACAGC------TTCT
                       530           540                            550

770       780       790       800       810       820       830
inputs GTATAAGGAGGGGGAACGTGACTTCCTCCAGCGCCCTGGCCAGCAGCCCCAGGCTGGGCTCTCCCAGGCC
                                           :::::::
       ------------------------------------CCAGCAG--------------------------

840       850       860       870       880       890       900
inputs AACTTCACCCTGGGCCCTGTGAGCCCCTCCCACGGGGGCCAGTACAGGTGCTATGGTGCACACAACCTCT
                ::.::::.                                                .::::
       ---------GGACCCA--------------------------------------------TACCT--
                560

910       920       930       940       950       960       970
inputs CCTCCGAGTGGTCGGCCCCCAGCGACCCCCTGAACATCCTGATGGCAGGACAGATCTATGACACCGTCTC
             :::::::::::::::::::::::::::.:           ::.          :..::
       ------GTGGTCGGCCCCCAGCGACCCCCTGGA----------GCT----------TGTG---------
             570       580       590                600

980       990      1000      1010      1020      1030      1040
inputs CCTGTCAGCACAGCCGGGCCCCACAGTGGCCTCAGGAGAGAACGTGACCCTGCTGTGTCAGTCATGGTGG
          ::::       :.:::  :::::::.::                  ::.::.:     :..::
       ---GTCA-------CAGGAACCTCTGTGACC----------------CCCAGC-----CGGT--------
          610       620                               630

1050      1060      1070      1080      1090      1100      1110
inputs CAGTTTGACACTTTCCTTCTGACCAAAGAAGGGGCAGCCCATCCCCCACTGCGTCTGAGATCAATGTACG
                  :.:::..:: :              ::  :::::::                        .::
       -----------TACCAACAGAAC-----------CA--CCTTCC-----------------------TCG
                  640                    650

1120      1130      1140      1150      1160      1170      1180
inputs GAGCTCATAAGTACCAGGCTGAATTCCCCATGAGTCCTGTGACCTCAGCCCACGCGGGGACCTACAGGTG
       :..           ::..:::::::        .:.....::.    ::::.:    :::.:.   ::.. .
       GTA-----------GCAGAATTCTC--------AGAAGCCAC------CGCTGA----ACTG--A
       660           670              680                690
```

FIG.3B

```
        1190      1200      1210      1220      1230      1240      1250
inputs CTACGGCTCATACAGCTCCAACCCCCACCTGCTGTCTTTCCCCAGTGAGCCCCTGGAACTCATGGTCTCA
       C··CGTCTCATTCA···CAAAC········AAAGTCTT··CACAA·······CTGAGACT·····TCT··
           700              710       720              730
        1260      1270      1280      1290      1300      1310      1320
inputs GGACACTCTGGAGGCTCCAGCCTCCCACCCACAGGGCCGCCCTCCACACCTGGTCTGGGAAGATACCTGG
       ········AGGAGTATC··ACCACCAGTCCAAAGGA··GTCAGACTCTCCAG··CTGG············
               740       750              760       770
        1330      1340      1350      1360      1370      1380      1390
inputs AGGTTTTGATTGGGGTCTCGGTGGCCTTCGTCCTGCTGCTCTTCCTCCTCCTCTTCCTCCTCCTCCGACG
       ·····················TCCTGC··········CCGCCAGTA····CTACACCAAGG
                           780              790          800
        1400      1410      1420      1430      1440      1450      1460
inputs TCAGCGTCACAGCAAACACAGGACATCTGACCAGAGAAAGACTGATTTCCAGCGTCCTGCAGGGGCTGCG
       GCAAC···········CTGGTC··············CGGATAT···GCCTC·····GGGGCTG··
       810              820                          830
        1470      1480      1490      1500      1510      1520      1530
inputs GAGACAGAGCCCAAGGACAGGGGCCTGCTGAGGAGGTCCAGCCCAGCTGCTGACGTCCAGGAAGAAAACC
       ·····TGATCCTAATAA·····TCCTG··GCGGGGTTTCTG········GCAGA·GGACTGG········C
            840              850       860              870
        1540      1550      1560      1570      1580      1590      1600
inputs TCTATGCTGCCGTGAAGGACACACAGTCTGAGG·ACAGGGTGGAGCTGGACAGT·CAGAGCCCACACGAT
       AC·····AGCCG··GAGGAAGCGC···CTGCGGCACAGGG····GCAGGGCTGTGCAGAGGCCGCT····
              880       890       900               910       920
        1610      1620      1630      1640      1650      1660      1670
inputs GAAGACCCCCAGGCAGTGACGTATGCCCCGGTGAAACACTCCAGTCCTAGGAGAGAAATGGCCTCTCCTC
       ····TCC················GCCCCTG························CCGC·····C
           930                     940
        1680      1690      1700      1710      1720      1730      1740
inputs CCTCCTCACTGTCTGGGGAATTCCTGGACACAAAGGACAGACAGGTGGAAGAGGACAGGCAGATGGACAC
       CCTCC·CGCAGAC·········CCGGAAATCA·····CA··CGGG········GGTCAGG···ATGGA···
       950                 960                                970       980
        1750      1760      1770      1780      1790      1800      1810
inputs TGAGGCTGCTGCATCTGAAGCCTCCCAGGATGTGACCTACGCCCAGCTGCACAGCTTGACCCTTAGACGG
       ···GGC·····CGAC·········AGGATGTT············CACAGC···········CG·
                               990                      1000
        1820      1830      1840      1850      1860      1870      1880
inputs AAGGCAACTGAGCCTCCTCCATCCCAGGAAGGGGAACCTCCAGCTGAGCCCAGCATCTACGCCACTCTGG
       ·······················CGGGTTATG···············TTCA········
                              1010
        1890
inputs CCATCCAC
       ········
```

FIG.3C

```
            10        20        30        40        50        60
inputs MSPSPTALFCLGLCLG-RVPAQSGPLPKPSLQALPSSLVPLEKPVTLRCQGPPGVDLYRLEKLSSS----
       :::  :::::::: ::  :  : :::: ::: :     :   ::::::.  :   :::: ::  :.
       MTPALTALLCLGLSLGPRTRVQAGPFPKPTLWAEPGSVISWGSPVTIWCQGSLEAQEYRLDKEGSPEPLD
            10        20        30        40        50        60        70

70        80        90        100       110       120       130
inputs RYQ-----DQAVLFIPAMKRSLAGRYRCSYQNGSLWSLPSDQLELVATGVFAKPSLSAQPGPAVSSGGDV
       : .     .:::: :::::: :::::::: : :: ::::::::::: ::  :::::: ::.  :::: .
       RNNPLEPKNKARFSIPSMTEHHAGRYRCHYYSSAGWSEPSDPLELVMTGFYNKPTLSALPSPVVASGGNM
            80        90        100       110       120       130       140 inputs TLQCQT----------------------------------------RY-----------------
       :::::                                          :.
       TLRCGSQKGYHHFVLMKEGEHQLPRTLDSQQLHSGGFQALFPVGPVNPSHRWRFTCYYYYMNTPQVWSHP
            150       160       170       180       190       200       210

140       150
inputs -----------------------------GFDQFALYKEGDP---------------------
                                    ::::::::::::::
       SDPLEILPSGVSRKPSLLTLQGPVLAPGQSLTLQCGSDVGYDRFVLYKEGERDFLQRPGQQPQAGLSQAN
            220       230       240       250       260       270       280

160
inputs -----------APYK-------------NP----------------------------ERW--
                  ::::              ::                            : :
       FTLGPVSPSHGGQYRCYGAHNLSSEWSAPSDPLNILMAGQIYDTVSLSAQPGPTVASGENVTLLCQSWWQ
            290       300       310       320       330       340       350

170       180       190       200
inputs ---------------------YRASFPIITVTAAHSGTYRCYSFSSRDPYLWSAPSDPLELVVTG
                            : :  ::  ::.::: :::::::::.:::::::::::::::::
       FDTFLLTKEGAAHPPLRLRSMYGAHKYQAEFPMSPVTSAHAGTYRCYGSYSSNPHLLSFPSEPLELMVSG
            360       370       380       390       400       410       420

210       220       230       240       250       260
inputs TSVTPSRLPTEPPSS--VAEFSEATAELTVSFTNKVF--------TTETSRSITTSPKESD--SPAGPA-
       :: :  ::::::::   .        ::  .:   :         .  :::: ::::   :   ::
       HSGGSSLPPTGPPSTPGLGRYLEVLIGVSVAFVLLLFLLLFLLLRRQRHSKHRTSDQRKTDFQRPAGAAE
            430       440       450       460       470       480       490

270       280       290
inputs RQYYTKGNLVRICLGAVIL-----IILAGFLAEDW---------------HSRRKR--------
       :      ::::           :     :  ::::                .: : :
       TEPKDRGLLRRSSPAADVQEENLYAAVKDTQSEDRVELDSQSPHDEDPQAVTYAPVKHSSPRREMASPPS
            500       510       520       530       540       550       560

300              310       320       330
inputs ------LRHRGRAVQ--RPL-------------PPLPPLPQTRK------SHGGQDGGRQDVHSRGLC
             : ::  :. :  ::              : : : ::         ::  :::  :  :
       SLSGEFLDTKDRQVEEDRQMDTEAAASEASQDVTYAQLHSLTLRRKATEPPPSQEGEPPAEPSIYATLAI
            570       580       590       600       610       620       630 inputs S
       H
```

FIG.4

```
         *->GesvtLtCsvsgfgppgvsvtWyfkngk.lgpsllgysysrlesgek
            + vtL+C+        + v  y +  k  ++        r++ +
hT268  41   EKPVTLRCQGP-----PGVDLY-RLEKISSS--------RYQDQ-- 70 anlsegrfsissltLtissvekeDsGtYtCvv<-*
                    ++L i     +++  +G Y+C
hT268  71   -----------AVLFIPAMKRSLAGRYRCSY    90
```

FIG.5A

```
         *->GesvtLtCsvsgfgppgvsvtWyfkngk.lgpsllgysysrlesgek
            G++vtL+C+++      +  ++ y k+g++ +        y+++
hT268  127  GGDVTLQCQTR---YGFDQFALY-KEGDpAP-----YKNPERWYR-- 162 anlsegrfsissltLtissvekeDsGtYtCvv<-*
                    ++++i++v++    sGtY+C
hT268  163  -----------ASFPIITVTAAHSGTYRCYS    182
```

FIG.5B

```
                                                                  M   S   P   A    4
GAGTCGACCCACGCGTCCGCTTCCCTGCTTGGCCACATAGCTCAGGACTGGGTTGCAGAACC ATG TCT CCA GCC   74

S   P   T   F   F   C   I   G   L   C   V   L   Q   V   I   Q   T   Q   S   G   24
TCA CCC ACT TTC TTC TGT ATT GGG CTG TGT GTA CTG CAA GTG ATC CAA ACA CAG AGT GGC  134

P   L   P   K   P   S   L   Q   A   Q   P   S   S   L   V   P   L   G   Q   S   44
CCA CTC CCC AAG CCT TCC CTC CAG GCT CAG CCC AGT TCC CTG GTA CCC CTG GGT CAG TCA  194

V   I   L   R   C   Q   G   P   P   D   V   D   L   Y   R   L   E   K   L   K   64
GTT ATT CTG AGG TGC CAG GGA CCT CCA GAT GTG GAT TTA TAT CGC CTG GAG AAA CTG AAA  254

P   E   K   Y   E   D   Q   D   F   L   F   I   P   T   M   E   R   S   N   A   84
CCG GAG AAG TAT GAA GAT CAA GAC TTT CTC TTC ATT CCA ACC ATG GAA AGA AGT AAT GCT  314

G   R   Y   R   C   S   Y   Q   N   G   S   H   W   S   L   P   S   D   Q   L  104
GGA CGG TAT CGA TGC TCT TAT CAG AAT GGG AGT CAC TGG TCT CTC CCA AGT GAC CAG CTT  374

E   L   I   A   T   G   V   Y   A   K   P   S   L   S   A   H   P   S   S   A  124
GAG CTA ATT GCT ACA GGT GTG TAT GCT AAA CCC TCA CTC TCA GCT CAT CCC AGC TCA GCA  434

V   P   Q   G   R   D   V   T   L   K   C   Q   S   P   Y   S   F   D   E   F  144
GTC CCT CAA GGC AGG GAT GTG ACT CTG AAG TGC CAG AGC CCA TAC AGT TTT GAT GAA TTC  494

V   L   Y   K   E   G   D   T   G   P   Y   K   R   P   E   K   W   Y   R   A  164
GTT CTA TAC AAA GAA GGG GAT ACT GGG CCT TAT AAG AGA CCT GAG AAA TGG TAC CGG GCC  554

N   F   P   I   I   T   V   T   A   A   H   S   G   T   Y   R   C   Y   S   F  184
AAT TTC CCC ATC ATC ACA GTG ACT GCT GCT CAC AGT GGG ACG TAC CGG TGT TAC AGC TTC  614

S   S   S   P   Y   L   W   S   A   P   S   D   P   L   V   L   V   V   T      204
TCC AGC TCA TCT CCA TAC CTG TGG TCA GCC CCG AGT GAC CCT CTA GTG CTT GTG GTT ACT  674

G   L   S   A   T   P   S   Q   V   P   T   E   E   S   F   P   V   T   E   S  224
GGA CTC TCT GCC ACT CCC AGC CAG GTA CCC ACG GAA GAA TCA TTT CCT GTG ACA GAA TCC  734

S   R   R   P   S   I   L   P   T   N   K   I   S   T   T   E   K   P   M   N  244
TCC AGG AGA CCT TCC ATC TTA CCC ACA AAC AAA ATA TCT ACA ACT GAA AAG CCT ATG AAT  794

I   T   A   S   P   E   G   L   S   P   P   I   G   F   A   H   Q   H   Y   A  264
ATC ACT GCC TCT CCA GAG GGG CTG AGC CCT CCA ATT GGT TTT GCT CAT CAG CAC TAT GCC  854

K   G   N   L   V   R   I   C   L   G   A   T   I   I   I   I   L   L   G   L  284
AAG GGG AAT CTG GTC CGG ATA TGC CTT GGT GCC ACG ATT ATA ATA ATT TTG TTG GGG CTT  914

L   A   E   D   W   H   S   R   K   K   C   L   Q   H   R   M   R   A   L   Q  304
CTA GCA GAG GAT TGG CAC AGT CGG AAG AAA TGC CTG CAA CAC AGG ATG AGA GCT TTG CAA  974

R   P   L   P   P   L   P   L   A   *                                           314
AGG CCA CTA CCA CCC CTC CCA CTG GCC TAG                                         1004

AAATAACTTGGCTTTCAGCAGAGGGATTGACCAGACATCCATGCACAACCATGGACATCACCACTAGAGCCACAGACAT 1083
GGACATACTCAAGAGTGGGGAGGTTATATAAAAAAATGAGTGTGGAGAATAAATGCAGAGCCAACAAGGTGAAAAAAA 1162
A                                                                               1163
```

FIG.6

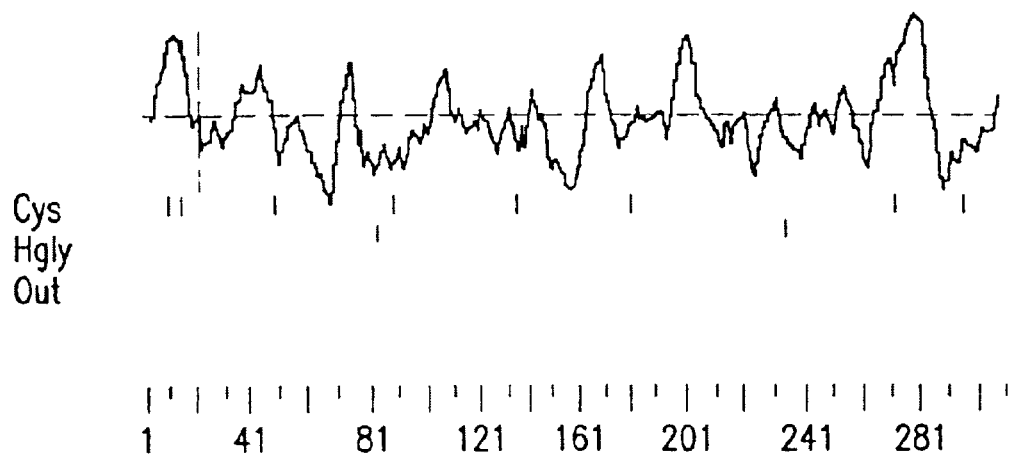

MSPASPTFFCIGLCVLQVIQTQSGPLPKPSLQAQPSSLVPLGQSVILRCQGPPDVDLYRL
EKLKPEKYEDQDFLFIPTMERSNAGRYRCSYQNGSHWSLPSDQLELIATGVYAKPSLSAH
PSSAVPQGRDVTLKCQSPYSFDEFVLYKEGDTGPYKRPEKWYRANFPIITVTAAHSGTYR
CYSFSSSSPYLWSAPSDPLVLVVTGLSATPSQVPTEESFPVTESSRRPSILPTNKISTTE
KPMNITASPEGLSPPIGFAHQHYAKGNLVRICLGATIIIILLGLLAEDWHSRKKCLQHRM
RALQRPLPPLPLA

FIG.7

```
              10         20         30         40         50         60         70
inputs ATGACGCCCGCCCTCACAGCCCTGCTCTGCCTTGGGCTGAGTCTGGGCCCCAGGACCCGCGTGCAGGCAG
       :::.: :: ::: :::: ::    .:: :::  :::..:
       ATGTCTCCAGCC-TCAC··CC····ACTTTCTT···CTGTAT··························
           10         20         30

80         90        100        110        120        130        140
inputs GGCCCTTCCCCAAACCCACCCTCTGGGCTGAGCCAGGCTCTGTGATCAGCTGGGGGAGCCCCGTGACCAT
                               ::::::        :::.. :.::
       ····················TGGGCTG·········TGTGTACTGC·······················
                                              40

150        160        170        180        190        200        210
inputs CTGGTGTCAGGGGAGCCTGGAGGCCCCAGGAGTACCGACTGGATAAAGAGGGAAGCCCAGAGCCCTTGGAC
                              :.:.:..::              :::.: :::::     :::
       ·······················AAGTGATCC··············AAACACAGAG····TGG··
                                  50                      60         70

220        230        240        250        260        270        280
inputs AGAAATAACCCACTGGAACCCAAGAACAAGGCCAGATTCTCCATCCCATCCATGACAGAGCACCATGCGG
       ::::::      :::       ::::          ::.::::  :::: :
       ·······CCCACT····CCC·····CAAG··········CCTTCCC-TCCAGG···············
              80                                90

290        300        310        320        330        340        350
inputs GGAGATACCGCTGCCACTATTACAGCTCTGCAGGCTGGTCAGAGCCCAGCGACCCCCTGGAGCTGGTGAT
       : :.::::                          :::. ::::.: :. :::::::. ::
       ········CTCAGCC·······················CAGTTCCCTG-GTACCCCTGGGTCAG·····
               100                             110        120

360        370        380        390        400        410        420
inputs GACAGGATTCTACAACAAACCCACCCTCTCAGCCCTGCCCAGCCCTGTGGTGGCCTCAGGGGGGAATATG
       .::: :: :.:                             ::..:::: : ::::::.
       -TCAG--TTATTC···························TGAGGTG-C--CAGGGA·········
        130                                      140        150

430        440        450        460        470        480
inputs ACCCTCC-GATGTGGCTCACAGAAGGGATATCACCATTTTGTTCTGATGAAGGAAGGAGAACACCAGCTC
       ::::: :::::::::      :    :::::::..  . ...:::::..
       ··CCTCCAGATGTGG········ATTTATATCGCCTGGAGAAACTGAAA··················
         160                   170        180        190

490        500        510        520        530        540        550
inputs CCCCGGACCCTGGACTCACAGCAGCTCCACAGTGGGGGGTTCCAGGCCCTGTTCCCTGTGGGCCCCGTGA
       :::::    ::          :::. :...:: ::.:  ::: ::       :.:
       ··CCGGA·····GA················AGTATGAAGATCAAGAC···TTTCTCTT·······CATT-
                                        200        210        220
```

FIG. 8A

```
           560       570       580       590       600       610       620
inputs ACCCCAGCCACAGGTGGAGGTTCACATGCTATTACTATTATATGAACACCCCCCAGGTGTGGTCCCACCC
       :::.:::  .:.......:::.   :::::            :.::       ::::.:
       ---CCAACCATGGAAAGAAGTA---ATGCT------------GGAC--------GGTAT----------
          230       240       250                260

630       640       650       660       670       680       690
inputs CAGTGACCCCCTGGAGATTCTGCCCCTCAGGCGTGTCTAGGAAGCCCTCCCTCCTGACCCTGCAGGGCCCT
       :....:   :.::.            :::::.         ..:.:.::  :             .:.::  ::
       CGATG---CTCTTA-----------TCAGA------ATGGGAGTC-------------ACTGGTCTCT
          270                  280                                        290

700       710       720       730       740       750       760
inputs GTCCTGGCCCCTGGGCAGAGCCTGACCCTCCAGTGTGGCTCTGATGTCGGCTACGACAGATTTGTTCTGT
               :::.::       :::::  :  .:.:      :::.:::   :::::
       -------CCCAAG--------TGACCAGCTTGAG-----CTAATT---GCTAC--------------
              300             310                  320

770       780       790       800       810       820       830
inputs ATAAGGAGGGGGAACGTGACTTCCTCCAGCGCCCTGGCCAGCAGCCCCAGGCTGGGCTCTCCCAGGCCAA
          :::.:  :   ...:  .:::   ::::                                  .:::::
       ---AGGTGTGTATGCTAAAC--CCTC--------------------------------ACTCTC--------
          330          340                                          350

840       850       860       870       880       890       900
inputs CTTCACCCTGGGCCCTGTGAGCCCCTCCCACGGGGGCCAGTACAGGTGCTATGGTGCACACAACCTCTCC
                                 ::: :  :::::                      :::
       --------------------AGCTCATCCCA--------------------GCT--------------
                           360

910       920       930       940       950       960       970
inputs TCCGAGTGGTCGGCCCCCAGCGACCCCCTGAACATCCTGATGGCAGGACAGATCTATGACACCGTCTCCC
                          :::::.. :::   ::  :.::::::   :::   .::.:::. :.
       -----------------CAGCAGTCCC-------TC---AAGGCAGG---GAT--GTGACTCTGA----
                          370           380            390          400

980       990       1000      1010      1020      1030      1040
inputs TGTCAGCACAGCCGGGCCCCACAGTGGCCTCAGGAGAGAACGTGACCCTGCTGTGTCAGTCATGGTGGCA
         .::     :::.:. :::: :                                :::: ...:...
       AGT-------GCCAGAGCCCATA----------------------------------CAGTTTTGATGA--
                410                                              420

1050      1060      1070      1080      1090      1100      1110
inputs GTTTGACACTTTCCTTCTGACCAAAGAAGGGGCAGCCCATCCCCCACTGCGTCTGAGATCAATGTACGGA
             .:::  ::::::. .:::::::::::    ::    ::::  :.:: :. :  :....:  ::
       --------ATTCGTTCTATACAAAGAAGGGG------AT-----ACTGGGCCTTATA--AGAGACCTGA
                430       440       450       460          470
```

FIG.8B

```
       1120      1130      1140      1150      1160      1170      1180
inputs GCTCATAAGTACCAGGCTGAATTCCCCATGAGTCCTGTGACCTCAGCCCACGCGGGGACCTACAGGTGCT
       :  ::::::::::::: :::::::::::: : :::::::  ::: :::. :::::.::: :::: :
       G--AAATGGTACCGGGCCAATTTCCCCATCATCACAGTGACTGCTGCTCACAGTGGGACGTACCGGTGTT
          480       490       500       510       520       530       540

1190      1200      1210      1220      1230      1240      1250
inputs ACGGCTCATACAGCTCCAACCCCCACCTGCTGTCTTTCCCCAGTGAGCCCCTGGAACTCATGGTCTCAGG
       ::  :: : :::::: ::: .  ::::: ::: :::.  :::::::. :::: ::.:::  ::: ..::
       ACAGCTTCTCCAGCTCATCTCCATACCTGTGGTCAGCCCCGAGTGACCCTCTAGTGCTTGTGGTTACTGG
          550       560       570       580       590       600       610

1260      1270      1280      1290      1300      1310      1320
inputs ACACTCTGGAGGCTCCAGCCTCCCACCCACAGGGCCGCCCTCCACACCTGGTCTGGGAAGATACCTGGAG
       :: :::::      :::   :::::::::  :::    .::::.:        :::  :::.::::
       ACTCTCTG------CCA--CTCCCAGCC--AGGT--ACCCAC------GGA-AGAATCATTTCCTG---
          620          630       640         650            660

1330      1340      1350      1360      1370      1380      1390
inputs GTTTTGATTGGGGTCTCGGTGGCCTTCGTCCTGCTGCTCTTCCTCCTCCTCTTCCTCCTCCTCCGACGTC
        :::          :.:, :::       :::: . :::::   ::::.   ::. :::    ....
       ----TGA----------CAGAATCCT----CCAGGAGACCTTCCA-----TCTTAC----CCACAAACAAA
                670          680         690           700

1400      1410      1420      1430      1440      1450      1460
inputs AGCGTCACAGCAAACACAGGACATCTGACCAGAGAAAGACTGATTTCCAGCGTCCTGCAGGGGCTGCGGA
       :   : ..:::   :..:    :::::   .  :::.:::::::.   : :::..:  :::.:::::::
       A---TATCTACAA---CTGAA----AAGCCTATGAATATC--ACTGCCT-C-TCCAG-AGGGGCTG----
          710       720           730          740            750

1470      1480      1490      1500      1510      1520      1530
inputs GACAGAGCCCAAGGACAGGGGCCTGCTGAGGAGGTCCAGCCCCAGCTGCTGACGTCCAGGAAGAAAACCTC
       :::::.         ::         :. ::: .:::: :: ::.:::                   :
       -----AGCCCT----------CC-----AATTGGTTTTGCTCATCAGCA-----------------C
            760               770       780

1540      1550      1560      1570      1580      1590      1600
inputs TATGCTGCCGTGAAGGACACACAGTCTGAGGACAGGGTGGAGCTGGACAGTCAGAGCCCACACGATGAAG
       :::::                          ::.:: :::.::::.:                :.:. ::
       TATGC---------------------CAAGGGGAATCTGGTC-------------CGGATATG
          790                        800                           810

1610      1620      1630      1640      1650      1660      1670
inputs ACCCCCAGGCAGTGACGTATGCCCCGGTGAAACACTCCAGTCCTAGGAGAGAAATGGCCTCTCCTCCCTC
          :: ::           :::: :::.             :: .:.:::::
       ---CCTTGG----------TGCCACGAT-------------TATAATAATTTTGT--------------
          820                830                        840

1680      1690      1700      1710      1720      1730      1740
inputs CTCACTGTCTGGGGAATTCCTGGACACAAAGGACAGACAGGTGGAAGAGGACAGGCAGATGGACACTGAG
                 :::::::  ::::  :::.::::.::.              ::::  ::::::::  :     :
       ----------TGGGGCTT--CTAG---CAGAGGATTGGC-----------ACAGTCGGAAGAA-----AT
                 850        860                         870            880
```

FIG.8C

```
        1750      1760      1770      1780      1790      1800      1810
inputs GCTGCTGCATCTGAAGCCTCCCAGGATGTGACCTACGCCCAGCTGCACAGCTTGACCCTTAGACGGAAGG
        ::   ::::::..        ::::::::::.::              ::::  .:             .::::
        GC--CTGCAACA--------CAGGATGAGA----------------GCTTTGC---------AAAGG
               890               900                       910

1820      1830      1840      1850      1860      1870      1880
inputs CAACTGAGCCTCCTCCATCCCAGGAAGGGGAACCTCCAGCTGAGCCCAGCATCTACGCCACTCTGGCCAT
        :  :::.    ::..::             :::::                          :.::::::
        CCACTA-----CCACC---------------CCTCC---------------------CACTGGCC--
          920                           930

1890
inputs CCAC
```

FIG. 8D

```
         10        20        30        40        50        60
inputs MSPASPTFFCIGLCVLQVIQTQSGPLPKPSLQAQPSSLVPLGQSVILRCQGPPDVDLYRLEKL-KPEKYE
       :.::    ...::::  , ...:::::::::  :.:.:.:  : .:.::::::.  ... :::.:   ::  .
       MTPALTALLCLGLSLGPRTRVQAGPFPKPTLWAEPGSVISWGSPVTIWCQGSLEAQEYRLDKEGSPEPLD
         10        20        30        40        50        60        70
       70          80        90       100       110       120       130
inputs DQDFL------F-IPTMERSNAGRYRCSYQNGSHWSLPSDQLELIATGVYAKPSLSAHPSSAVPQGRDV
       .. :        : :::.:    .:::::::  :  ...  :: :::.:::,  ::  :.::.:::  ::..:.  : ..
       RNNPLEPKNKARFSIPSMTEHHAGRYRCHYYSSAGWSEPSDPLELVMTGFYNKPTLSALPSPVVASGGNM
          80        90       100       110       120       130       140 inputs TLKC--QSPY-----------------------------------------------------------
       :::.:   :   :
       TLRCGSQKGYHHFVLMKEGEHQLPRTLDSQQLHSGGFQALFPVGPVNPSHRWRFTCYYYYMNTPQVWSHP
          150       160       170       180       190       200       210

140       150
inputs ----------------------------------------SFDEFVLYKEGD----------------
                                                 ..: ::::::::.
       SDPLEILPSGVSRKPSLLTLQGPVLAPGQSLTLQCGSDVGYDRFVLYKEGERDFLQRPGQQPQAGLSQAN
          220       230       240       250       260       270       280

160
inputs ---------TGPYK----------------------------RP--------------EKW--
                :.:.                                  .:             . :
       FTLGPVSPSHGGQYRCYGAHNLSSEWSAPSDPLNILMAGQIYDTVSLSAQPGPTVASGENVTLLCQSWWQ
         290       300       310       320       330       340       350

170       180       190       200
inputs ----------------------------YRANFPIITVTAAHSGTYRCYSFSSSSPYLWSAPSDPLVLVVTG
                                   :.:.::.  ::.::.:::::::.   :::.: : : :::..::  :.:.:
       FDTFLLTKEGAAHPPLRLRSMYGAHKYQAEFPMSPVTSAHAGTYRCYGSYSSNPHLLSFPSEPLELMVSG
         360       370       380       390       400       410       420

210                     220
inputs LSATPSQVPTEES-------------FPV---------------------------------------
       .. .:  ::           :.
       HSGGSSLPPTGPPSTPGLGRYLEVLIGVSVAFVLLLFLLLFLLLRRQRHSKHRTSDQRKTDFQRPAGAAE
         430       440       450       460       470       480       490

230       240       250       260       270
input  TESS-----RRPS--------ILPTNKISTTEKPMNI-TASPEGLSP-PIGFAH--QHYAKGNLVR--I
       :::        ::::          .     :  ::.  .:    .:   :  .:.   ..:.   ...  .
       TEPKDRGLLRRSSPAADVQEENLYAAVKDTQSEDRVELDSQSPHDEDPQAVTYAPVKHSSPRREMASPPS
         500       510       520       530       540       550       560

280       290              300                  310
inputs CLGATIIIILLGLLAEDWH-----------SRKKCLQHRMRALQRPI-----PP-------LPL
       .:: ..  ..  ..:::..            ::        ::         ::        ::
       SLSGEFLDTKDRQVEEDRQMDTEAAASEASQDVTYAQLHSLTLRRKATEPPPSQFGEPPAEPSIYATLAI
         570       580       590       600       610       620       630 inputs A

```
             *->GesvtLtCsvsgfgppgvsvtWyfkngk.lgpsllgysysrlesgek
                G+sv L+C+         ++v  y +  k ++         +++e  +
mT268    42     GQSVILRCQGP------PDVDLY-RLEKIKP--------EKYEDQ-- 71 anlsegrfsissltLtissvekeDsGtYtCvv<-*
                L i + e++++G Y+C
mT268    72  -----------DFLFIPTMERSNAGRYRCSY     91
```

FIG.10A

```
             *->GesvtLtCsvsgfgppgvsvtWyfkngk.lgpsllgysysrlesgek
                G +vtL C++       ++  y k+g++  +     Y+r+e    +
mT268   128     GRDVTLKCQSP---YSFDEFVLY-KEGDtGP-------YKRPEKW-Y 162 anlsegrfsissltLtissvekeDsGtYtCvv<-*
                +              ++i++v++  sGtY+C
mT268   163  RA-----------NFPIITVTAAHSGTYRCYS    183
```

FIG.10B

```
                  10        20        30        40        50        60
inputs  MSPSPTALFCLGLCLGRV-PAQSGPLPKPSLQALPSSLVPLEKPVTLRCQGPPGVDLYRLEKLSSSRYQD
        ::: :::: ::::: :: :: ::::::::::::: ::::::: :::::::::: ::::::::: : :
        MSPASPTFFCIGLCVLQVIQTQSGPLPKPSLQAQPSSLVPLGQSVILRCQGPPDVDLYRLEKLKPEKYED
                  10        20        30        40        50        60        70

70        80        90       100       110       120       130
inputs  QAVLFIPAMKRSLAGRYRCSYQNGSLWSLPSDQLELVATGVFAKPSLSAQPGPAVSSGGDVTLQCQTRYG
        :  :::::  :: :::::::::::::: ::::::::: :::::: :::::::  :::   ::::  :: ::
        QDFLFIPTMERSNAGRYRCSYQNGSHWSLPSDQLELIATGVYAKPSLSAHPSSAVPQGRDVTLKCQSPYS
           80        90       100       110       120       130       140

140       150       160       170       180       190       200
inputs  FDQFALYKEGDPAPYKNPERWYRASFPIITVTAAMSGTYRCYSFSSRDPYLWSAPSDPLELVVTGTSVTP
        :: :::::::: :::: ::::::: ::::::::: :::::::::::   ::::::::: ::::: :: ::
        FDEFVLYKEGDTGPYKRPEKWYRANFPIITVTAAHSGTYRCYSFSSSSPYLWSAPSDPLVLVVTGLSATP
            150       160       170       180       190       200       210

210       220       230       240       250       260       270
inputs  SRLPTEPPSSVAEFSEATAELTVSFTNKVFTTETSRSITTSPKESDSPAGPARQYYTKGNLVRICLGAVI
        : :: :::: : : :: ::  :    ::  :::  : :::: :::  ::: ::: ::::::::::::::
        SQVPTEESFPVTESSRRPSILP---TNKISTTEKPMNITASPEGLSPPIGFAHQHYAKGNLVRICLGATI
            220       230       240       250       260       270

280       290       300       310       320       330
inputs  LIILAGFLAEDWHSRRKRLRHRGRAVQRPLPPLPPLPQTRKSHGGQDGGRQDVHSRGLCS
        :::: : :::::::::: :: :  :: :::::::: ::
        IIILLGLLAEDWHSRKKCLQHRMRALQRPLPPLP-LA-----------------------
            280       290       300       310
```

FIG.11

LIGHT TRANSMISSION

GLYCOPROTEIN VI ANTIBODIES AND USES THEREOF

This application is a continuation-in-part of U.S. application Ser. No. 09/503,387, filed Feb. 14, 2000, pending, which is a continuation-in-part of U.S. application Ser. No. 09/454,824, filed Dec. 6, 1999, now abandoned, which is continuation-in-part of U.S. application Ser. No. 09/345,468, filed Jun. 30, 1999, now U.S. Pat. No. 6,245,527, the entire contents of each of which is incorporated herein by reference in its entirety.

BACKGROUND OF THE INVENTION

The interaction between collagen and platelets is the first event of the normal hemostatic response to injury. Collagen is the major extracellular matrix protein present in the subendothelium of blood vessels. Upon damage to the endothelium lining, as a consequence of injury to the vessel wall, collagen fibers, fibrous collagen I and III are exposed to platelets. This interaction leads to platelet adhesion, activation with a second phase of adhesion, secretion occurrence, and ultimately aggregation and development of a hemostatic plug (Kehrel et al., 1998, *Blood* 91:491–9).

The mechanism of collagen-platelet interactions is complex. It involves, on one hand, direct binding of collagen to specific platelet receptors (e.g., $\alpha_2\beta_1$ integrin, collagen receptor, glycoprotein IV, and glycoprotein VI) and, on the other hand, indirect binding of collagen via bridging proteins (e.g., von Willebrand Factor (vWF)) that bind to both collagen and membrane receptors on platelets. Recent reports support a two-step mechanism of collagen-platelet interaction, consisting of platelet adhesion followed by platelet activation (Verkleij et al., 1998, *Blood* 91:3808–16). The first step involves the binding of collagen-bound vWF by the platelet receptor complex glycoprotein Ib/IX/V, followed by the direct binding of integrin $\alpha_2\beta_1$ to collagen (Moroi et al., 1997, *Thrombosis and Haemostasis* 78:439–444 and Barnes et al., 1998, *Current Opinion in Hematology* 6:314–320). This step results in platelets adhering to the subendothelium of blood vessels under physiological conditions. The second step of collagen-platelet interaction involves another platelet collagen receptor, glycoprotein VI (Barnes et al., 1998, *Current Opinion in Hematology* 6:314–320). This binding leads to strengthening of attachment and platelet activation. It is believed that glycoprotein VI (GPVI) has a minor importance in the first step of adhesion but plays a major role in the second step of collagen-platelet interaction resulting in full platelet activation and consequently the formation of the platelet aggregates (Arai et al., 1995, *British J. of Haematology* 89:124–130).

Glycoprotein VI

Glycoprotein VI (GPVI) is a platelet membrane glycoprotein that is involved in platelet-collagen interactions. In particular, GPVI is a transmembrane collagen receptor expressed on the surface of platelets. GPVI has an apparent molecular mass of 58 kDa in its non-reduced form and 62 kDa after disulfide bond reduction as determined by its migration via SDS-PAGE. Treatment of platelets with N-glycanase has been shown to result in a faster migration of GPVI in SDS-PAGE by two kDa, which probably corresponds to only one N-glycosylation site.

The existence of a 62 kDa protein, later identified as GPVI, was first detected as an antigen recognized by the sera of a patient with steroid-responsive immune thrombocytopenic purpura associated with defective collagen-induced platelet functions (Sugiyama et al., 1987, *Blood* 69: 1712–1720). The patient's plasma, as well as a preparation of full length IgG antibodies, induced irreversible aggregation and ATP release in normal platelet-rich plasma. However, Fab fragments prepared from the serum of this patient blocked platelet aggregation induced by collagen (Sugiyama et al., 1987, *Blood* 69: 1712–172).

The importance of GPVI in platelet/collagen interactions was further confirmed by comparing the expression of platelet collagen receptors from a different patient, with a mild bleeding disorder, to that of a normal individual (Moroi et al., 1989, *J. Clin. Invest.* 84(5):1440–5). The patient's platelets lacked collagen-induced aggregation and adhesion, but retained normal aggregation and release by other agonists. The expression of a 61 kDa membrane glycoprotein was detected on non-reduced, two-dimensional SDS-PAGE, but was reduced compared to the expression levels found in a normal individual. This glycoprotein was termed glycoprotein VI (GPVI). The patient's platelets did not bind to types I and III collagen fibrils suggesting that GPVI functions as a collagen receptor involved in collagen-induced platelet activation and aggregation.

GPVI has been show to be constitutively associated with the Fc receptor gamma (FcR$\gamma$), and FcR$\gamma$ expression is lacking in GPVI-deficient platelets, suggesting that GPVI and FcR$\gamma$ are co-expressed in platelets (Tsuji et al., 1997, *J. Biol. Chem.* 272:23528–31). Further, cross-linking of GPVI by F(ab')2 fragments of anti-GPVI IgG has been shown to result in the tyrosine phosphorylation of the FcR$\gamma$-chain. FcR$\gamma$ is tyrosine-phosphorylated upon platelet activation by collagen, collagen related peptide (CRP; Gibbins et al., 1997, *FEBS Lett.* 413:255–259) or the snake venom component convulxin that acts as a platelet agonist (Cvx; Lagrue et al., 1999, *FEBS Letts.* 448:95–100). Phosphorylation occurs on the immunoreceptor tyrosine-based activation motifs (ITAM) of FcR$\gamma$ by kinases of the Src family (p59Fyn and p53/56 lyn) (Briddon S J and Watson, 1999, *Biochem J.* 338:203–9). Phosphorylation of FcR$\gamma$ allows Syk, a signaling molecule, to bind and to be in turn phosphorylated and to activate phospholipase C$\gamma$2 (PLC$\gamma$2). Further, platelet stimulation by collagen or Cvx have been shown to involve the association of phosphatidylinositol 3-kinase (P13 kinase) and the adapter protein linker for activator of T cells (LAT) to the FcR$\gamma$ (Carlsson et al., 1998, *Blood* 92:1526–31). Thus, FcR$\gamma$ appears to interact with GPVI to effect signaling.

The results from the GPVI signal transduction pathway activation studies performed suggest that strong similarities exist between the GPVI signaling pathway in platelets and the one used by receptors for immune complexes, such as the high-affinity and low affinity receptors for IgG (FcR$\gamma$I and FcR$\gamma$III), the high-affinity receptor for IgE (FcR$\epsilon$I) and the receptor for IgA (FcR$\alpha$I) (Maliszewski et al., 1990, *J. Exp. Med.* 172:1665–72). These receptors also signal via the FcR$\gamma$ chain and Syk. Expression of the FcR$\gamma$I, FcR$\gamma$III has not been reported in platelets. The FcR$\gamma$IIa seems to be the only IgG Fc-receptor consistently expressed on platelets, and it contains one ITAM. This receptor has been suggested to be involved in thrombocytopenia and thromboembolic complications of heparin-induced thrombocytopenia (HIT), the most common drug-induced immune thrombocytopenia (Carlsson et al., 1998, *Blood 92:1526–31*) and may also be involved in other immune thrombocytopenia such as immune thrombocytopenia purpura (Loscalzo, J., and Schafer, A. I., 1998, *Thrombosis and Hemorrhage,* J. Loscalzo and A. I. Schafer, eds., Baltimore: Williams and Wilkins).

Since its detection, the function of GPVI in platelet-collagen interactions and the signal transduction pathway induced by GPVI has been studied. However, the molecular cloning of GPVI has been elusive due, at least in part, to its extensive O-linked glycosylation. The inability to clone GPVI has limited the experiments that can be performed to better understand the role of GPVI in collagen-induced platelet activation and aggregation. Further, the development of treatments for disorders, such as bleeding disorders, resulting from mutations in GPVI or its promoter, have been hindered by the lack of knowledge about the nucleic acid and amino acid sequences of GPVI.

SUMMARY OF THE INVENTION

The present invention is based, at least in part, on the discovery of cDNA molecules which encode the TANGO 268 proteins, all of which are transmembrane proteins.

In particular, TANGO 268 represents the platelet-expressed collagen receptor GPVI. This conclusion is based, at least in part, on the following evidence: (1) the glycosylated molecular weights of TANGO 268 and GPVI are identical or similar; (2) TANGO 268 and GPVI are both recognized by anti-GPVI antibodies and bind to Cvx; (3) TANGO 268 and GPVI are both preferentially expressed in the megakaryocytic cells; (4) TANGO 268 and GPVI are both predicted to have a single N-glycosylation site; (5) the molecular mass of the 40 kDa unglycosylated TANGO 268 is predicted to be approximately 62 kDa, the apparent molecular mass of GPVI, upon N- and O-linked glycosylation; (6) the presence of two immunoglobulin-like domains in TANGO 268 indicates that, like GPVI TANGO 268 interacts with the FcRγ; (7) the absence of a large intracytoplasmic tail, suggesting that this membrane-bound glycoprotein has no signaling role but associates with another member of the Ig family (e.g., FcRγ) protein to transduce a signal; and (8) the presence of a charged residue (arginine) in the transmembrane domain of TANGO 268 which is predicted to be present in GPVI based on its association with the FcRγ.

The TANGO 268 proteins are members of the Ig superfamily. The TANGO 268 proteins, fragments, derivatives, and variants thereof are collectively referred to herein as "polypeptides of the invention" or "proteins of the invention." Nucleic acid molecules encoding the polypeptides or proteins of the invention are collectively referred to as "nucleic acids of the invention."

The nucleic acids and polypeptides of the present invention are useful as modulating agents in regulating a variety of cellular processes. Accordingly, in one aspect, this invention provides isolated nucleic acid molecules encoding a polypeptide of the invention or a biologically active portion thereof. The present invention also provides nucleic acid molecules which are suitable for use as primers or hybridization probes for the detection of nucleic acids encoding a polypeptide of the invention.

The invention features nucleic acid molecules which are at least 50%, 55%, 65%, 75%, 85%, 95%, or 98% identical to the nucleotide sequence of SEQ ID NO:1 the nucleotide sequence of the cDNA insert of an EpthEa11d1 clone deposited with ATCC® as Accession Number 207180, or a complement thereof.

The invention features nucleic acid molecules which are at least 40%, 45%, 50%, 55%, 65%, 75%, 85%, 95%, or 98% identical to the nucleotide sequence of SEQ ID NO:2 the nucleotide sequence of the cDNA insert of an EpthEa11d1 clone deposited with ATCC® as Accession Number 207180, or a complement thereof.

The invention features nucleic acid molecules which are at least 40%, 45%, 50%, 55%, 65%, 75%, 85%, 95%, or 98% identical to the nucleotide sequence of SEQ ID NO:14 the nucleotide sequence of the cDNA insert of an EpTm268 clone deposited with ATCC® as patent deposit Number PTA-225, or a complement thereof.

The invention features nucleic acid molecules which are at least 35%, 40%, 45%, 50%, 55%, 65%, 75%, 85%, 95%, or 98% identical to the nucleotide sequence of SEQ ID NO:15 the nucleotide sequence of the cDNA insert of an EpTm268 clone deposited with ATCC® as patent deposit Number PTA-225, or a complement thereof.

The invention features nucleic acid molecules which are at least 30%, 35%, 40%, 45%, 50%, 55%, 60%, 65%, 70%, 75%, 80%, 85%, 90%, 95% or 98% identical to the nucleotide sequence of SEQ ID NO: 1, 2, 14, 15, 33, 35, 37, 39, 41, 43, 45 or 47, a complement thereof, or the non-coding strand of EpthEa11d1 or EpTm268 cDNA of ATCC® Accession 207180 or patent deposit Number PTA-225, wherein said nucleic acid molecules encode polypeptides or proteins that exhibit at least one structural and/or functional feature of a polypeptide of the invention.

The invention features nucleic acid molecules which include a fragment of at least 550, 600, 700, 800, 900, 1000, 1100, 1200, 1300, 1400, 1500, 1600, 1700, 1800, 1900 or 2000 contiguous nucleotides of the nucleotide sequence of SEQ ID NO:1, the nucleotide sequence of an EpthEa11d1 cDNA of ATCC® Accession Number 207180, or a complement thereof.

The invention features nucleic acid molecules which include a fragment of at least 50, 100, 200, 300, 400, 500, 600, 700, 800, 900, 950 or 1000 contiguous nucleotides of the nucleotide sequence of SEQ ID NO:2, or a complement thereof.

The invention features nucleic acid molecules which include a fragment of at least 50, 100, 200, 300, 400, 500, 600, 700, 800, 900, 1000 or 1100 contiguous nucleotides of the nucleotide sequence of SEQ ID NO:14 the nucleotide sequence of an EpTm268 cDNA of ATCC® patent deposit Number PTA-225, or a complement thereof.

The invention features nucleic acid molecules which include a fragment of at least 50, 100, 200, 300, 400, 500, 600, 700, 800, 900, 950 or 1000 contiguous nucleotides of the nucleotide sequence of SEQ ID NO:15, or a complement thereof.

The invention features isolated nucleic acid molecules having a nucleotide sequence that is at least about 20, 50, 100, 150, 200, 250, 300, 400, 450, 500, 550, 600, 650, 700 or more contiguous nucleotides identical to the nucleic acid sequence of SEQ ID NOS: 1, 2, 14, 15, 33, 35, 37, 39, 41, 43, 45 or 47, or a complement thereof, or the non-coding strand of EpthEa11d1 or EpTm268 cDNA of ATCC® Accession 207180 or patent deposit Number PTA-225, wherein said nucleic acid molecules encode polypeptides or proteins that exhibit at least one structural and/or functional feature of a polypeptide of the invention.

The invention also features nucleic acid molecules which include a nucleotide sequence encoding a protein having an amino acid sequence that is at least 30%, 35%, 40%, 45%, 50%, 55%, 60%, 65%, 75%, 85%, 95%, or 98% identical to the amino acid sequence of SEQ ID NO:3, the amino acid sequence encoded by an EpthEa11d1 cDNA of ATCC® Accession Number 207180, or a complement thereof.

The invention also features nucleic acid molecules which include a nucleotide sequence encoding a protein having an amino acid sequence that is at least 30%, 35%, 40%, 45%, 50%, 55%, 60%, 65%, 75%, 85%, 95%, or 98% identical to the amino acid sequence of SEQ ID NO:16, the amino acid sequence encoded by an EpTm268cDNA of ATCC® patent deposit Number PTA-225, or a complement thereof.

The invention also features nucleic acid molecules which include a nucleotide sequence encoding a protein having an amino acid sequence that is at least 30%, 35%, 40%, 45%, 50%, 55%, 60%, 65%, 75%, 85%, 95%, or 98% identical to the amino sequence of SEQ ID NO:3, 16, 34, 36, 38, 40, 42, 44, 46 or 48, the amino acid sequence encoded by EpthEa11d1 or EpTm268 of ATCC® Accession Number 207180 or patent deposit Number PTA-225, or a complement thereof, wherein the protein encoded by the nucleotide sequence also exhibits at least one structural and or functional feature of a polypeptide of the invention.

In preferred embodiments, the nucleic acid molecules have the nucleotide sequence of SEQ ID NO: 1, 2, 14, 15 or the nucleotide sequence of the cDNA clones of ATCC® Accession Number 207180 or patent deposit Number PTA-225.

The invention also includes nucleic acid molecules which encode a fragment of a polypeptide having the amino acid sequence of SEQ ID NO:3, or a fragment including at least 15, 25, 30, 50, 75, 100, 125, 150, 175, 200, 225, 250, 275, 300, 315 or 330 contiguous amino acids of SEQ ID NO:3, or the amino acid sequence encoded by an EpthEa11d1 cDNA of ATCC® Accession Number 207180.

The invention also includes nucleic acid molecules which encode a fragment of a polypeptide having the amino acid sequence of SEQ ID NO:16, or a fragment including at least 15, 25, 30, 50, 75, 100, 125, 150, 175, 200, 225, 250, 275 or 300 contiguous amino acids of SEQ ID NO:16, or the amino acid sequence encoded by an EpTm268 cDNA of ATCC® patent deposit Number PTA-225.

The invention also features nucleic acid molecules which encode a polypeptide fragment of at least 15, 25, 30, 50, 75, 100, 125, 150, 175, 200 or more contiguous amino acids of SEQ ID NO:3, 16, 34, 36, 38, 40, 42, 44, 46 or 48, or the amino acid sequence encoded by EpthEa11d1 or EpTm268 of ATCC® Accession Number 207180 or patent deposit Number PTA-225, wherein the fragment also exhibits at least one structural and/or functional feature of a polypeptide of the invention.

The invention also includes nucleic acid molecules which encode a naturally occurring allelic variant of a polypeptide comprising the amino acid sequence of SEQ ID NO:3, 16, 34, 36, 38, 40, 42, 44, 46 or 48, or the amino acid sequence encoded by a cDNA of ATCC® Accession Number 207180 or patent deposit Number PTA-225, wherein the nucleic acid molecule hybridizes to a nucleic acid molecule consisting of a nucleic acid sequence encoding SEQ ID NO:3, 16, 34, 36, 38, 40, 42, 44, 46 or 48, or the amino acid sequence encoded by a cDNA of ATCC® Accession Number 207180 or PTA-225, or a complement thereof under stringent conditions.

The invention also includes isolated polypeptides or proteins having an amino acid sequence that is at least about 30%, preferably 35%, 45%, 55%, 65%, 75%, 85%, 95%, or 98%, identical to the amino acid sequence of SEQ ID NO:3, or the amino acid sequence encoded by an EpthEa11d1 cDNA of ATCC® Accession Number 207180.

The invention also includes isolated polypeptides or proteins having an amino acid sequence that is at least about 30%, preferably 35%, 40%, 45%, 50%, 55%, 65%, 75%, 85%, 95%, or 98% identical to the amino acid sequence of SEQ ID NO:16, or the amino acid sequence encoded by an EpTm268 cDNA of ATCC® patent deposit Number PTA-225.

The invention also features isolated polypeptides or proteins having an amino acid sequence that is at least about 30%, preferably 35%, 40%, 45%, 50%, 55%, 65%, 75%, 85%, 95% or 98% identical to the amino acid sequence of SEQ ID NO:3, 16, 34, 36, 38, 40, 42, 44, 46 or 48, or the amino acid sequence encoded by EpthEa11a1 or EpTm268 of Accession Number 207180 or patent deposit Number PTA-225, respectively, wherein the protein or polypeptides also exhibit at least one structural and or functional feature of a polypeptide of the invention.

The invention also includes isolated polypeptides or proteins which are encoded by a nucleic acid molecule having a nucleotide sequence that is at least about 50%, preferably 55%, 60%, 65%, 75%, 85%, 95% or 98% identical to the nucleic acid sequence encoding SEQ ID NO:3, and isolated polypeptides or proteins which are encoded by a nucleic acid molecule having a nucleotide sequence which hybridizes under stringent hybridization conditions to a nucleic acid molecule having the nucleotide sequence of SEQ ID NO:1 or 2, a complement thereof, or the non-coding strand of an EpthEa11d1 cDNA of ATCC® Accession Number 207180.

The invention also includes isolated polypeptides or proteins which are encoded by a nucleic acid molecule having a nucleotide sequence that is at least about 35%, preferably 40%, 45%, 50%, 55%, 60%, 65%, 75%, 85%, 95% or 98% identical to the nucleic acid sequence encoding SEQ ID NO:16, and isolated polypeptides or proteins which are encoded by a nucleic acid molecule having a nucleotide sequence which hybridizes under stringent hybridization conditions to a nucleic acid molecule having the nucleotide sequence of SEQ ID NO:14 or 15, a complement thereof, or the non-coding strand of an EpTm268 cDNA of ATCC® patent deposit Number PTA-225.

The invention also features isolated polypeptides or proteins which are encoded by a nucleic acid molecule having a nucleotide sequence that is at least about 30%, preferably 35%, 40%, 45%, 50%, 55%, 60%, 65%, 75%, 85%, 95% or 98% identical to a nucleic acid sequence encoding SEQ ID NO:3, 16, 34, 36, 38, 40, 42, 44, 46 or 48, isolated polypeptides or proteins which are encoded by a nucleic acid molecule having a nucleotide sequence which hybridizes under stringent hybridization conditions to a nucleic acid molecule having the nucleotide sequence of SEQ ID NO:1, 2, 14, 15, 33, 35, 37, 39, 41, 43, 45 or 47, a complement thereof, or the non-coding strand of EpthEa11d1 or EpTm268 of ATCC® Accession Number 207180 or patent deposit Number PTA-225, respectively, wherein the polypeptides or proteins also exhibit at least one structural and/or functional feature of a polypeptide of the invention.

The invention also includes polypeptides which are naturally occurring allelic variants of a polypeptide that includes the amino acid sequence of SEQ ID NO:3, 16, 34, 36, 38, 40, 42, 44, 46 or 48, or the amino acid sequence encoded by a cDNA of ATCC® Accession Number 207180 or patent deposit Number PTA-225, wherein the polypeptide is encoded by a nucleic acid molecule which hybridizes to a nucleic acid molecule having the sequence of SEQ ID NO:1, 2, 14, 15, 33, 35, 37, 39, 41, 43, 45 or 47, or a complement thereof under stringent conditions.

The invention also features nucleic acid molecules that hybridize under stringent conditions to a nucleic acid molecule having the nucleotide sequence of SEQ ID NO:1 or 2, an EpthEa11d1 cDNA of ATCC® Accession Number 207180, or a complement thereof. In other embodiments, the nucleic acid molecules are at least 480, 500, 530, 550, 600, 700, 800, 900, 1000, 1100, 1200, 1300, 1400, 1500, 1600, 1700, 1800, 1900 or 2000 contiguous nucleotides in length and hybridize under stringent conditions to a nucleic acid molecule comprising the nucleotide sequence of SEQ ID NO:1, an EpthEa11d1 cDNA of ATCC® Accession Number 207180, or a complement thereof.

The invention also features nucleic acid molecules that hybridize under stringent conditions to a nucleic acid molecule having the nucleotide sequence of SEQ ID NO:14 or 15, an EpTm268 cDNA of ATCC® patent deposit Number PTA-225, or a complement thereof. In other embodiments, the nucleic acid molecules are at least 400, 450, 500, 530, 550, 600, 700, 800, 900, 1000, 1100 or 1150 contiguous nucleotides in length and hybridize under stringent conditions to a nucleic acid molecule comprising the nucleotide sequence of SEQ ID NO:14, an EpTm268 cDNA of ATCC® PTA-225, or a complement thereof.

The invention also features nucleic acid molecules that hybridize under stringent conditions to a nucleic acid molecule having the nucleotide sequence of SEQ ID NO: 1, 2, 14, 15, 33, 35, 37, 39, 41, 43, 45 or 47, or a nucleotide sequence of EpthEa11d1 or EpTm268 cDNA of ATCC® Accession Number 207180 or patent deposit Number PTA-225, or complement thereof, wherein such nucleic acid molecules encode polypeptides or proteins that exhibit at least one standard and/or functional feature of a polypeptide of the invention.

The invention also features nucleic acid molecules at least 15, preferably at least 50, at least 75, at least 100, at least 150, at least 200, at least 250, at least 300, at least 350, at least 400, at least 500, at least 600, at least 700, at least 800, at least 1000, at least 1100 or at least 1200 or more contiguous nucleotides in length which hybridize under stringent conditions to a nucleic acid molecule comprising the nucleotide sequence of SEQ ID NO:1, 2, 14, 15, 33, 35, 37, 39, 41, 43, 45 or 47, or a nucleotide sequence of EpT253, EpTm253, EpT257, EpTm257, EpT258, EpTm258, EpT281 or EpTm281 of ATCC® Accession Number 207222, Accession Number 207215, Accession Number 207217, Accession Number 207221, patent deposit Number PTA-225, or a complement thereof, wherein said nucleic acid molecules encode polypeptides or proteins that exhibit at least one structural and/or functional feature of a polypeptide of the invention.

In one embodiment, the invention provides an isolated nucleic acid molecule which is antisense to the coding strand of a nucleic acid of the invention.

Another aspect of the invention provides vectors, e.g., recombinant expression vectors, comprising a nucleic acid molecule of the invention. In another embodiment, the invention provides host cells containing such a vector or engineered to contain and/or express a nucleic acid molecule of the invention. The invention also provides methods for producing a polypeptide of the invention by culturing, in a suitable medium, a host cell of the invention such that a polypeptide of the invention is produced.

Another aspect of this invention features isolated or recombinant proteins and polypeptides of the invention. Preferred proteins and polypeptides possess at least one biological activity possessed by the corresponding naturally-occurring human polypeptide. An activity, a biological activity, or a functional activity of a polypeptide or nucleic acid of the invention refer to an activity exerted by a protein, polypeptide or nucleic acid molecule of the invention on a responsive cell as determined in vivo or in vitro, according to standard techniques. Such activities can be a direct activity, such as an association with or an enzymatic activity on a second protein, or an indirect activity, such as a cellular signaling activity mediated by interaction of the protein with a second protein.

For TANGO 268, biological activities include, e.g., (1) the ability to modulate, e.g., stabilize, promote, inhibit or disrupt protein-protein interactions (e.g., homophilic and/or heterophilic), and protein-ligand interactions, e.g., in receptor-ligand recognition; (2) the ability to modulate cell-cell interactions and/or cell-extracellular matrix (ECM) interactions, e.g., by modulating platelet interactions with subendothelial components, e.g., collagen, integrins and other ECM proteins; (3) the ability to modulate the host immune response, e.g., by modulating one or more elements in the inflammatory response; (4) the ability to modulate the proliferation, differentiation and/or activity of megakaryocytes and/or platelets; (5) the ability to modulate intracellular signaling cascades (e.g., signal transduction cascades); (6) the ability to modulate immunoregulatory functions; (7) the ability to modulate platelet morphology, migration, aggregation, degranulation and/or function; (8) the ability to interact with (e.g., bind to directly or indirectly, for example, as part of a complex comprising TANGO 268) one or more collagen molecules; (9) the ability to modulate collagen binding to platelets; (10) the ability to mediate and/or modulate intracellular $CA^{2+}$ levels, metabolism and/or turnover of phosphatidylinosides, and phosphorylation of proteins (e.g., c-Src, Syk, PLCγ2 and/or FcRγ) via, for example, their tyrosine residues; (11) the ability to mediate and/or modulate collagen-induced platelet adhesion and aggregation (e.g.,thrombus formation), for example, in mediating and/or modulating secretion of the contents of platelet granules; (12) the ability to mediate and/or modulate platelet adhesion and aggregation; (13) the ability to interact with (e.g., bind to directly or indirectly, for example, as part of a complex comprising TANGO 268) convulxin; (14) the ability to modulate convulxin binding to platelets; (15) the ability to bind to an antibody from a patient with idiopathic thrombocytopenic purpura (ITP); (16) the ability to associate and/or co-express with FcRγ, e.g., FcRγ in platelets; (17) the ability to induce and/or modulate tumor formation, tumor cell migration, and/or tumor cell metastasis; (18) the ability to induce and/or modulate coronary diseases (e.g., atherosclerosis); and (19) the ability to induce and/or modulate cerebral vascular diseases (e.g., strokes and ischemia).

In one embodiment, a polypeptide of the invention has an amino acid sequence sufficiently identical to an identified domain of a polypeptide of the invention. As used herein, the term "sufficiently identical" refers to a first amino acid or nucleotide sequence which contains a sufficient or minimum number of identical or equivalent (e.g., with a similar side chain) amino acid residues or nucleotides to a second amino acid or nucleotide sequence such that the first and second amino acid or nucleotide sequences have or encode a common structural domain and/or common functional activity. For example, amino acid or nucleotide sequences which contain or encode a common structural domain having about 60% identity, preferably 65% identity, more preferably 75%, 85%, 95% or more identity are defined herein as sufficiently identical.

In one embodiment a 268 protein includes at least one or more of the following domains: a signal sequence, an extracellular domain, an immunoglobulin-like domain, a transmembrane domain, and an intracellular domain.

The polypeptides of the present invention, or biologically active portions thereof, can be operably linked to a heterologous amino acid sequences form fusion proteins. The invention further features antibodies, such as monoclonal or polyclonal antibodies, that specifically bind a polypeptide of the invention. In addition, the polypeptides of the invention or biologically active portions thereof can be incorporated into pharmaceutical compositions, which optionally include pharmaceutically acceptable carriers.

In another aspect, the present invention provides methods for detecting the presence, activity or expression of a polypeptide of the invention in a biological sample by contacting the biological sample with an agent capable of detecting an indicator of the presence, activity or expression such that the presence activity or expression of a polypeptide of the invention in the biological sample.

In another aspect, the invention provides methods for modulating activity of a polypeptide of the invention comprising contacting a cell with an agent that modulates (inhibits or stimulates) the activity or expression of a polypeptide of the invention such that activity or expression in the cell is modulated. In one embodiment, the agent is an antibody that specifically binds to a polypeptide of the invention.

In another embodiment, the agent modulates expression of a polypeptide of the invention by modulating transcription, splicing, or translation of an mRNA encoding a polypeptide of the invention. In yet another embodiment, the agent is a nucleic acid molecule having a nucleotide sequence that is antisense to the coding strand of an mRNA encoding a polypeptide of the invention.

In another aspect, the invention provides substantially purified antibodies or fragments thereof, including human, humanized, chimeric and non-human antibodies or fragments thereof, which antibodies or fragments specifically bind to a polypeptide comprising an amino acid sequence of SEQ ID NO:3, 16, 34, 36, 38, 40, 42, 44, 46 or 48, or the amino acid sequence encoded by the EpthEa11d1 or EpTm268 cDNA insert of the plasmid deposited with the ATCC® as Accession Number 207180 or patent deposit Number PTA-225.

In another aspect, the invention provides substantially purified antibodies or fragments thereof, including, e.g., human, non-human, chimeric and humanized antibodies, which antibodies or fragments thereof specifically bind to a polypeptide comprising at least 15 contiguous amino acids of the amino acid sequence of SEQ ID NO:3, 16, 34, 36, 38, 40, 42, 44, 46 or 48, or the amino acid sequence encoded by the EpthEa11d1 or EpTm268 cDNA insert of the plasmid deposited with the ATCC® as Accession Number 207180 or patent deposit number PTA-225, or a complement thereof.

In another aspect, the invention provides substantially purified antibodies or fragments thereof, including, e.g., human, non-human, chimeric and humanized antibodies, which antibodies or fragments thereof specifically bind to a polypeptide comprising at least 95% identical to the amino acid sequence of SEQ ID NO:3, 16, 34, 36, 38, 40, 42, 44, 46 or 48, or the amino acid sequence encoded by the EpthEa11d1 or EpTm268 cDNA insert of the plasmid deposited within the ATCC® Accession Number 207180 or patent deposit number PTA-225, or a complement thereof, wherein the percent identity is determined using the ALIGN program of the GCG software package with a PAM120 weight residue table, a gap length penalty of 12, and a gap penalty of 4.

In another aspect, the invention provides substantially purified antibodies or fragments thereof, including, e.g., human, non-human, chimeric and humanized antibodies, which antibodies or fragments thereof specifically bind to a polypeptide encoded by a nucleic acid molecule which hybridizes to the nucleic acid molecule of SEQ ID NO:1, 2, 14, 15, 33, 35, 37, 39, 41, 43, 45 or 47, or the nucleotide sequence of the cDNA insert of the plasmid deposited with the ATCC® Accession Number 207180 or patent deposit number PTA-225 under conditions of hybridization of 6× SSC at 45° C. and washing in 0.2× SSC, 0.1% SDS at 50° C., 55° C., 60° C., or 65° C., or 6× SSC at 45° C. and washing in 0.1× SSC, 0.2% SDS at 68° C.

Any of the antibodies of the invention or fragments thereof can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material.

The invention also provides a kit containing an antibody of the invention or fragment thereof conjugated to a detectable substance, and instructions for use. Still another aspect of the invention is a pharmaceutical composition comprising an antibody of the invention or a fragment thereof and a pharmaceutically acceptable carrier. In preferred embodiments, the pharmaceutical composition contains an antibody of the invention or fragment thereof, a therapeutic moiety, and a pharmaceutically acceptable carrier.

Still another aspect of the invention is a method of making an antibody that specifically recognizes GPVI, the method comprising immunizing a mammal with a polypeptide. The polypeptide used as an immungen comprises an amino acid sequence selected from the group consisting of: the amino acid sequence of SEQ ID NO:3, 16, 34, 36, 38, 40, 42, 44, 46 or 48, or the amino acid sequence encoded by the cDNA insert of the plasmid deposited with ATCC® as Accession Number 207180, or the amino acid sequence encoded by the cDNA insert of the plasmid deposited with ATCC® at PTA-225; a fragment of at least 15 amino acid residues of the amino acid sequence of SEQ ID NO:3, 16, 34, 36, 38, 40, 42, 44, 46 or 48; an amino acid sequence which is at least 65%, identical to the amino acid sequence of SEQ ID NO:3, 16, 34, 36, 38, 40, 42, 44, 46 or 48, wherein the percent identity is determined using the ALIGN program of the GCG software package with a PAM120 weight residue table, a gap length penalty of 12, and a gap penalty of 4; and an amino acid sequence which is encoded by a nucleic acid molecule which hybridizes to the nucleic acid molecule consisting of SEQ ID NO:1, 2, 14, 15, 33, 35, 37, 39, 41, 43, 45 or 47 under conditions of hybridization of 6× SSC at 45° C. and washing in 0.2× SSC, 0.1% SDS at 50° C., 55° C., 60° C. or 65° C., or 6× SSC at 45° C. and washing in 0.1× SSC, 0.2% SDS at 68° C. After immunization, a sample is collected from the mammal that contains an antibody that specifically recognizes GPVI. Preferably, the polypeptide is recombinantly produced using a non-human host cell. Optionally, the antibodies can be further purified from the sample using techniques well known to those of skill in the art. The method can further comprise producing a monoclonal antibody-producing cell from the cells of the mammal. Optionally, antibodies are collected from the antibody-producing cell.

The present invention also provides methods to treat a subject having a disorder characterized by aberrant activity of a polypeptide of the invention or aberrant expression of a nucleic acid of the invention by administering an agent which is a modulator of the activity of a polypeptide of the invention or a modulator of the expression of a nucleic acid of the invention to the subject. In one embodiment, the modular is a protein of the invention. In another embodiment, the modulator is a nucleic acid of the invention. In other embodiments, the modulator is a peptide, peptidomimetic, or other small molecule.

The present invention also provides diagnostic assays for identifying the presence or absence of a genetic lesion or mutation characterized by at least one of: (i) aberrant modification or mutation of a gene encoding a polypeptide of the invention; (ii) mis-regulation of a gene encoding a polypeptide of the invention; and (iii) aberrant post-translational modification of the invention wherein a wild-type form of the gene encodes a protein having the activity of the polypeptide of the invention.

In another aspect, the invention provides a method for identifying a compound that binds to or modulates the activity of a polypeptide of the invention. In general, such methods can entail measuring a biological activity of the polypeptide in the presence and absence of a test compound and identifying those compounds which alter the activity of the polypeptide. As used herein the term "selectively binds" refers to a compound (e.g., an antibody) that preferentially binds to a TANGO 268 polypeptide or fragment thereof as compared to other unrelated polypeptides. A compound preferentially binds to a TANGO 268 polypeptide or fragment thereof if it has at least a 10%, preferably at least a 25%, at least a 50%, at least a 75%, at least a 90%, at least a 95%, or at least a 98% higher affinity and/or avidity for a TANGO 268 polypeptide or fragment thereof than an unrelated polypeptide.

The invention also features methods for identifying a compound which modulates the expression of a polypeptide or nucleic acid of the invention by measuring the expression of the polypeptide or nucleic acid in the presence and absence of the compound.

Other features and advantages of the invention will be apparent from the following detailed description and claims.

BRIEF DESCRIPTION OF THE DRAWINGS

FIGS. 1A–1B depict the cDNA sequence of human TANGO 268 (SEQ ID NO:1) and the predicted amino acid sequence of human TANGO 268 (SEQ ID NO:3). The open reading frame of SEQ ID NO:1 extends from nucleotide 36 to nucleotide 1052 of SEQ ID NO:1 (SEQ ID NO:2).

FIG. 2 depicts a hydropathy plot of human TANGO 268. Relatively hydrophobic regions of the protein are above the dashed horizontal line, and relatively hydrophilic regions of the protein are below the dashed horizontal line. The cysteine residues (cys) are indicated by short vertical lines just below the hydropathy trace. The dashed vertical line separates the signal sequence (amino acids 1 to 20 of SEQ ID NO:3; SEQ ID NO:4) on the left from the mature protein (amino acids 21 to 339 of SEQ ID NO:3; SEQ ID NO:5) on the right. Below the hydropathy plot, the amino acid sequence of human TANGO 268 is depicted.

FIGS. 3A–3C depict an alignment of the nucleotide sequence of the open reading frame for human monocyte inhibitory receptor precursor (SEQ ID NO:24, GenBank Accession Number U91928) and the nucleotide sequence of the open reading frame for human TANGO 268 (SEQ ID NO:2). The nucleotide sequences of coding regions of human monocyte inhibitory receptor precursor and human TANGO 268 are 37.7% identical. The nucleotide sequences of full-length, including the 5' and 3' untranslated regions (UTRs), human monocyte inhibitory receptor precursor SEQ ID NO:11; GenBank Accession Number U91928) and human TANGO 268 are 49.9% identical. These alignments were performed using the ALIGN alignment program with a PAM120 scoring matrix, a gap length penalty of 12, and a gap penalty of 4.

FIG. 4 depicts an alignment of the amino acid sequent of human monocyte inhibitory receptor precursor (SEQ ID NO:12) and the amino acid sequence of human TANGO 268 (SEQ ID NO:3). The amino acid sequences of human monocyte inhibitory receptor precursor and human TANGO 268 are 23.0% identical. This alignment was performed using the ALIGN alignment program with a PAM120 scoring matrix, a gap length penalty of 12, and a gap penalty of 4.

FIG. 5A depicts an alignment of the amino acid sequence of a typical immunoglobulin domain (SEQ ID NO:13; GenBank Accession Number PF00047) and amino acid residues 41 to 90 of human TANGO 268 (SEQ ID NO:3). This alignment was performed using the ALIGN aligment program with a PAM120 scoring matrix, a gap length penalty of 12, and a gap penalty of 4.

FIG. 5B depicts an alignment of the amino acid sequence of a typical immunoglobulin domain (SEQ ID NO:13; GenBank Accession Number PF00047) and amino acid residues 127 to 182 of human TANGO 268 (SEQ ID NO:3). This alignment was performed using the ALIGN alignment program with a PAM120 scoring matrix, a gap length penalty of 12, and a gap penalty of 4.

FIG. 6 depicts a cDNA sequence of mouse TANGO 268 (SEQ ID NO:14) and the predicted amino acid sequence of mouse TANGO 268 (SEQ ID NO:15). The open reading frame of SEQ ID NO:14 extends from nucleotide 63 to 1001 of SEQ ID NO:14 (SEQ ID NO:15).

FIG. 7 depicts a hydropathy plot of mouse TANGO 268. Relatively hydrophobic regions of the protein are above the dashed horizontal line, and relatively hydrophilic regions of the protein are below and dashed horizontal lines. The cysteine residues (cys) are indicated by short vertical lines just below the hydropathy trace. The dashed vertical line separates the signal sequence (amino acids 1 to 21 of SEQ ID NO:16; SEQ ID NO:17) on the left from the mature protein (amino acids 22 to 313 of SEQ ID NO:16; SEQ ID NO:18) on the right. Below the hydropathy plot, the amino acid sequence of mouse TANGO 268 is depicted.

FIGS. 8A–8D depict an alignment of the nucleotide sequence of the open reading frame for human monocyte inhibitory receptor pressure (SEQ ID NO:24; GenBank Accession Number U91928) and the nucleotide sequence of the open reading frame for mouse TANGO 268 (SEQ ID NO:15). The nucleotide sequences of coding regions of human monocyte inhibitory receptor precursor and mouse TANGO 268 are 34.4% identical. The nucleotide sequences of full-length, including the 5' and 3' untranslated regions (UTRs), human monocyte inhibitory receptor precursor SEQ ID NO:11; GenBank Accession Number U91928) and mouse TANGO 268 and 35.6% identical. These alignments were performed using the ALIGN aligment program with a PAM120 scoring matrix, a gap length penalty of 12, and a gap penalty of 4.

FIG. 9 depicts an alignment of the amino acid sequence of human monocyte inhibitory receptor precursor (SEQ ID NO:12) and the amino acid sequence of mouse TANGO 268 (SEQ ID NO:16). The amino acid sequences of human monocyte inhibitory receptor precursor and mouse TANGO 268 are 20.3% identical. This alignment was performed using the ALIGN alignment program with a PAM120 scoring matrix, a gap length penalty of 12, and a gap penalty of 4.

FIG. 10A depicts an alignment of the amino acid sequence of immunoglobulin domain (SEQ ID NO:12; GenBank Accession Number PF00047) and amino acid residues 42 to 91 of mouse TANGO 268 (SEQ ID NO:16). This alignment was performed using the ALIGN alignment program with a PAM120 scoring matrix, a gap length penalty of 12, and a gap penalty of 4.

FIG. 10B depicts an alignment of the amino acid sequence of a typical immunoglobulin domain (SEQ ID NO:12; GenBank Accession Number PF00047) and amino acid residues 128 to 183 of mouse TANGO 268 (SEQ ID NO:16). This alignment was performed using the ALIGN alignment program with a PAM120 scoring matrix, a gap length penalty of 12, and a gap penalty of 4.

FIG. 11 depicts an alignment of the amino acid sequence of human TANGO 268 (SEQ ID NO:3) and the amino acid sequence of mouse TANGO 268 (SEQ ID NO:16). The alignment demonstrates that the amino acid sequences of human and mouse TANGO 268 are 64.4% identical. The alignment was performed using the ALIGN program with a PAM120 scoring matrix, a gap length penalty of 12 and a gap penalty of 4. The sequences within the boxes are the signal sequences for human and mouse TANGO 268; the line above the two sequences indicates the Ig-like domains for human and mouse TANGO 268; and the arrow above the sequences points to the charged residue (arginine) in human and mouse TANGO 268.

FIG. 14: Tissue expression on hGPVI and mGPVI using RT-PCR, northern blot and ISH analysis;

FIG. 15B: Ba/F3.

FIG. 18: Inhibition of Cvx- or collagen-induced platelet activation by recombinant human soluble GPVI:Fc.

DETAILED DESCRIPTION

Figure 12:
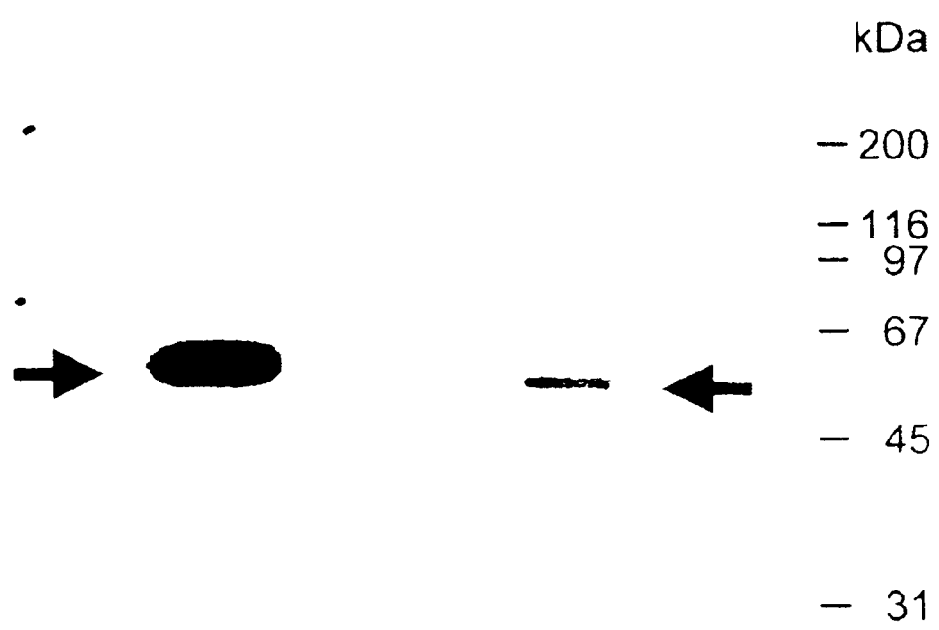
FIG. 12 depicts the results from the ligand blotting assay with $^{125}$I-convulxin (Cvx), demonstrating that TANGO 268 specifically binds Cvx. Lane 1 contains platelet lysate, lane 2 contains lysate from expression vector-only transfected CHO cells, and lane 3 contains TANGO 268-transfected CHO cell lysate. The cell lysates were separated on polyacrylamide gels, transferred to PVDF membranes, and the membranes were incubated with $^{125}$I-Cvx. The interaction between $^{125}$I-Cvx and TANGO 268 was detected by autoradiography.

The TANGO 268 proteins and nucleic acid molecules comprise a family of molecules having certain conserved structural and functional features. As used herein, the term "family" is intended to mean to two or more proteins or nucleic acid molecules having a common structural domain and having sufficient amino acid or nucleotide sequence identity as defined herein. Family members can be from either the same or different species. For example, a family can comprises two or more proteins of human origin, or can comprise one or more proteins of human origin and one or more of non-human origin. Members of the same family may also have common structural domains.

For example, TANGO 268 proteins of the invention have signal sequences. As used herein, a "signal sequence" includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 10 to 40 amino acid residues, preferably about 19–34 amino acid residues, and has at least about 60–80%, more preferably 65–75%, and more preferably at least about 70% hydrophobic residues. A signal sequence serves to direct a protein containing such a sequence to a lipid bilayer. Thus, in one embodiment, a TANGO 268 protein contains a signal sequence at about amino acids 1 to 20 of SEQ ID NO:3 (SEQ ID NO:4) or at about amino acids 1 to 21 of SEQ ID NO:16 (SEQ ID NO:17). The signal sequence is cleaved during processing of the mature protein.

A TANGO 268 family member consists of one or more of the following domains: (1) an extracellular domain; (2) a transmembrane domain; and (3) a cytoplasmic domain. In one embodiment, a TANGO 268 protein contains an extracellular domain at about amino acid residues 21 to 269 of SEQ ID NO:3 (SEQ ID NO:9), a transmembrane domain at about amino acid residues 270 to 288 of SEQ ID NO:3 (SEQ ID NO:8), and a cytoplasmic domain at about amino acid residues 289 to 339 of SEQ ID NO:3 (SEQ ID NO:10). In this embodiment, the mature TANGO 268 protein corresponds to amino acids 21 to 339 of SEQ ID NO:3 (SEQ ID NO:5). In another embodiment, a TANGO 268 family contains an extracellular domain at about amino acid residues 22 to 267 of SEQ ID NO:16 (SEQ ID NO:19), a transmembrane domain at about amino acid residues 268 to 286 of SEQ ID NO:16 (SEQ ID NO:20), and a cytoplasmic domain at about amino acid residues 287 to 313 of SEQ ID NO:16 (SEQ ID NO:21). In this embodiment, the mature TANGO 268 protein corresponds to amino acids 22 to 313 of SEQ ID NO:16 (SEQ ID NO:18).

A TANGO 268 family member contains a charged residue, such as arginine, lysine, histidine, glutamic acid, and aspartic acid, in its transmembrane domain. In one embodiment, a TANGO 268 protein contains a charged amino acid residue, preferably arginine, at amino acid 272 of SEQ ID NO:3. In another embodiment, a TANGO 268 protein contains a charged amino acid residue, preferably arginine, at amino acid 270 of SEQ ID NO:16.

A TANGO 268 family member includes a signal sequence. In certain embodiment, a TANGO 268 family member has the amino acid sequence of SEQ ID NO:3, and the signal sequence is located at amino acids 1 to 18, 1 to 19, 1 to 20, 1 to 21 or 1 to 22. In an another embodiment, a TANGO 268 family member has the amino acid sequence of SEQ ID NO:16, and the signal sequence is located at amino acids 1 to 19, 1 to 20, 1 to 21, 1 to 22 or 1 to 23. In such embodiments of the invention, the extracellular domain and the mature protein resulting from cleavage of such signal peptides are also included herein. For example, the cleavage of a signal sequence consisting of amino acids 1 to 19 results in an extracellular domain consisting of amino acids 20 to 269 of SEQ ID NO:3 and the mature TANGO 268 protein corresponding to amino 20 to 339.

An Ig domain typically has the following consensus sequence, beginning about 1 to 15 amino acid residues, more preferably about 3 to 10 amino acid residues, and most preferably about 5 amino acid residues from the C-terminal end of a protein: (FY)-Xaa-C-Xaa-(VA)-COO—, wherein (FY) is either a phenylalanine or a tyrosine residue (preferably tyrosine), where "Xaa" is any amino acid, C is a cysteine residue, (VA) is either valine or an alanine residue (preferably alanine), and COO— is the protein C-terminus. An Ig-like domain as described herein has the following consensus sequence, beginning about 1 to 15 amino acid residues, more preferably about 3 to 10 amino acid residues, and most preferably about 5 amino acid residues from the domain C-terminus: (FY)-Xaa-C, wherein (FY) is either a phenylalanine or a tyrosine residue (preferably tyrosine), where "Xaa" is any amino acid, and C is a cysteine residue. In one embodiment, a TANGO 268 family member includes one or more Ig-like domains having an amino acid sequence that is at least about 55%, preferably at least about 65%, more preferably at least 75%, yet more preferably at least about 85%, and most preferably at least about 95% identical to amino acids 48 to 88 and/or amino acids 134 to 180 of SEQ ID NO:3, which are the Ig-like domains of human TANGO 268 (these Ig-like domains are also represented as SEQ ID NO:6 and 7, respectively).

In another embodiment, a TANGO 268 family member includes one more Ig-like domains having an amino acid sequence that is at least about 55%, preferably at least about 65%, more preferably at least about 75%, yet more preferably at least about 85%, and most preferably at least about 95% identical to amino acids 48 to 88 and/or amino acids 134 to 180 of SEQ ID NO:3, which are the Ig-like domains of human TANGO 268 (these Ig-like domains are also represented as SEQ ID NO:6 and 7, respectively), includes a conserved cysteine residue about 8 residues downstream from the N-terminus of the Ig-like domain, and has one or more Ig-like domain consensus sequences as described herein.

In another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 48 to 88 and/or amino acids 134 to 180 of SEQ ID NO:3, which are the Ig-like domains of human TANGO 268 (SEQ ID NO:6 and 7, respectively), includes a conserved cysteine residue 8 residues downstream from the N-terminus of the Ig-like domain, has one or more Ig-like domain consensus sequences as described herein, and has a conserved cysteine within the consensus sequence that forms a disulfide with said first conserved cysteine.

In another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 48 to 88 and/or amino acids 134 to 180 of SEQ ID NO:3, which are the Ig-like domains of human TANGO 268 (SEQ ID NO:6 and 7, respectively), includes a conserved cysteine residue 8 residue downstream from the N-terminus of the Ig-like domains, has one or more Ig-like domain consensus sequences as described herein, and has a conserved cysteine within the consensus sequence that forms a disulfide with said first conserved cysteine.

In yet another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 48 to 88 and/or amino acids 134 to 180 of SEQ ID NO:3 (SEQ ID NO:6 and 7, respectively), includes a conserved cysteine residue 8 residues downstream from the N-terminus of the Ig-like domain, has one or more Ig-like domain consensus sequences described herein, has a conserved cysteine within the consensus sequence that forms a disulfide with said first conserved cysteine, and has at least one TANGO 268 biological activity as described herein.

In another embodiment, the Ig-like domain of TANGO 268 is an Ig domain, which has the following consensus sequence at the C-terminus of the domain: (FY)-Xaa-C-Xaa-(VA)-COO—, wherein (FY) is either a phenylalanine or a tyrosine residue (preferably tyrosine), where "Xaa" is any amino acid, C is a cysteine residue, (VA) is a valine or alanine residue, and COO— is the C-terminus of the domain. In this embodiment, a TANGO 268 family member includes one or more Ig-like domains having an amino acid sequence that is at least about 55%, preferably at least about 65%, more preferably at least 75%, yet more preferably at least about 85%, and most preferably at least about 95% identical to amino acids 48 to 90 and/or amino acids 134 to 182 of SEQ ID NO:3.

In another embodiment, a TANGO268 family member includes one or more Ig-like domains having an amino acid sequence that is at least about 55%, preferably at least about 65%, more preferably at least 75%, yet more preferably at least about 85%, and most preferably at least about 95% identical to amino acids 49 to 89 and/or amino acids 135 to 181 of SEQ ID NO:16, which are the Ig-like domains of mouse TANGO 268 (these Ig-like domains are also represented SEQ ID NO:22 and 23, respectively). In another embodiment, a TANGO 268 family member includes one or more Ig-like domains having an amino acid sequence that is at least about 55%, preferably at least about 65%, more preferably at least about 75%, yet more preferably at least about 85%, and most preferably at least about 95% identical to amino acids 49 to 89 and/or amino acids 135 to 181 of SEQ ID NO:16 (SEQ ID NO:22 and 23, respectively), includes a conserved cysteine residue about 8 residues downstream from the N-terminus of the Ig-like domain, and has one or more Ig-like domain consensus sequences as described herein.

In another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 49 to 89 and/or amino acids 135 to 181 of SEQ ID NO:16 (SEQ ID NO:22 and 23, respectively), includes a conserved cysteine residue 8 residues downstream from the N-terminus of the Ig-like domain, has one or more Ig-like domain consensus sequences as described herein, and has a conserved cysteine within the consensus sequence that forms a disulfide with said first conserved cysteine.

In another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 49 to 89 and/or amino acids 135 to 181 of SEQ ID NO:16 (SEQ ID NO:22 and 23, respectively), includes a conserved cysteine residue 8 residues downstream from the N-terminus of the Ig-like domain, has one or more Ig-like domain consensus sequences as described herein, and has a conserved cysteine within the consensus sequence that forms a disulfide with said first conserved cysteine.

In yet another embodiment, a TANGO 268 family member includes one or more Ig-like domains having an amino acid sequence that is at least 55%, preferably at least about 65%, more preferably at least about 75%, yet more preferably at least about 85%, and most preferably at least about 95% identical to amino acids 49 to 89 and/or amino acids 135 to 181 of SEQ ID NO:16 (SEQ ID NO:22 and 23, respectively), includes a conserved cysteine residue 8 residues downstream from the N-terminus of the Ig-like domain, has one or more Ig-like domain consensus sequences as described herein, as a conserved cysteine within the consensus sequence that forms a disulfide with said first conserved cysteine, and has at least one TANGO 268 biological activity as described herein.

In another embodiment, the Ig-like domain of TANGO 268 is an Ig domain, which has the following consensus sequence at the C-terminus end of the domain: (FY)-Xaa-C-Xaa-(VA)-COO—, wherein (FY) is either a phenylalanine or a tyrosine residue (preferably tyrosine), where "Xaa" is any amino acid, C is cysteine residue, (VA) is a valine or alanine residue, and COO— is the C-terminus of the domain. In this embodiment, a TANGO 268 family member includes one or more Ig-like domains having an amino acid sequence that is at least about 55%, preferably at least about 65%, more preferably at least 75%, yet more preferably at least about 85%, and most preferably at least about 95% identical to amino acids 49 to 91 and/or amino acids 135 to 183 of SEQ ID NO:16, which are the Ig-like domains of mouse TANGO 268.

In a preferred embodiment, a TANGO 268 family member has the amino acid sequences of SEQ ID NO:6, wherein the aforementioned Ig-like domain conserved residues are located as follows: the N-terminal conserved cysteine residue is located at amino acid residue position 48 (within the Ig-like domain SEQ ID NO:3) and the C-terminal conserved cysteine residue is located at amino acid position 88 (within the Ig-like domain SEQ ID NO:3). In another preferred embodiment, a TANGO 268 family member has the amino acid sequence of SEQ ID NO:6, wherein the aforementioned Ig-like domain conserved residues are located as follows: the N-terminal conserved cysteine residue is located at amino acid residue position 135 (within the Ig-like domain SEQ ID NO:3) and the C-terminal conserved cysteine residue is located at amino acid position 180 (within the Ig-like domain SEQ ID NO:3). In another preferred embodiment, a TANGO 268 family member has the amino acid sequence of SEQ ID NO:22, wherein the aforementioned Ig-like domain conserved residues are located as follows: the N-terminal conserved cysteine residue is located at amino acid residue position 49 (within the Ig-like domain of SEQ ID NO:16) and the C-terminal conserved cysteine residue is located at amino acid position 89 (within the Ig-like domain of SEQ ID NO:16). In another preferred embodiment, a TANGO 268 family member has the amino acid aqueous of SEQ ID NO:23, wherein the aforementioned Ig-like domain conserved residues are located as follows: the N-terminal conserved cysteine residue is located at amino acid residue position 135 (within the Ig-like domain of SEQ ID NO:16) and the C-terminal conserved cysteine residue is located at amino acid position 181 (within the Ig-like domain of SEQ ID NO:16).

Various features of human and mouse TANGO 268 are summarized below.

Human TANGO 268

A cDNA encoding human TANGO 268 was identified by analyzing the sequences of clones present in a human megakaryocyte cDNA library. This analysis led to the identification of a clone, jthea105c02, encoding full-length human TANGO 268. The human TANGO 268 cDNA of this clone is 2047 nucleotides long (FIG. 1; SEQ ID NO:1). The open reading frame of this cDNA, nucleotides 36 to 1052 of SEQ ID NO:1 (SEQ ID NO:2), encodes a 339 amino acid transmembrane protein (FIGS. 1A–B; SEQ ID NO:3) that, as discussed below, represents a platelet-expressed collagen receptor glycoprotein.

The signal peptide prediction program SIGNALP (Nielsen, et al., 1997, *Protein Engineering* 10:1–6) predicted that human TANGO 268 includes an 20 amino acid signal peptide (amino acid 1 to about amino acid 20 of SEQ ID NO:3; SEQ ID NO:4) preceding the mature human TANGO 268 protein (corresponding to about amino acid 21 to amino acid 339 of SEQ ID NO:3; SEQ ID NO:5). The molecular weight of human TANGO 268 without post-translational modifications is 36.9 kDa prior to the cleavage of the signal peptide, 34.9 kDa after cleavage of the signal peptide.

Human TANGO 268 is a transmembrane protein that is collagen receptor expressed on platelets which consists of one or more of the following domains: (1) an extracellular domain; (2) a transmembrane domain; and (3) a cytoplasmic domain. The human TANGO 268 protein contains an extracellular domain at amino acid residues 21 to 269 of SEQ ID NO:3 (SEQ ID NO:9), a transmembrane domain at amino acid residues 270 to 288 of SEQ ID NO:3 (SEQ ID NO:8), and a cytoplasmic domain at amino acid residues 289 to 339 of SEQ ID NO:3 (SEQ ID NO:10).

FIG. 2 depicts a hydropathy plot of human TANGO 268. Relatively hydrophobic regions of the protein are shown above the horizontal line, and relatively hydrophilic regions of the protein are below the horizontal line. The cysteine residues (cys) and potential N-glycosylation sites (Ngly) are indicated by short vertical lines just below the hydropathy trace. The dashed vertical line separates the signal sequence (amino acids 1 to 20 of SEQ ID NO:3; SEQ ID NO:4) on the left from the mature protein (amino acids 21 to 339 of SEQ ID NO:3; SEQ ID NO:5) on the right.

Human TANGO 268 comprises two immunoglobulin-like domain sequences at amino acids 48 to 88 and at amino acids 134 to 180 of SEQ ID NO:3; SEQ ID NO:6 and SEQ ID NO:7. A single N-glycosylation site having the sequences NGSL is present at about amino acids 92 to 95 of SEQ ID NO:3. Nine protein kinase C phosphorylation sites are present in human TANGO 268. The first has the sequence TLR (at amino acids 45 to 47 of SEQ ID NO:3), the second has the sequence SSR (at amino acids 64 to 66 of SEQ ID NO:3), the third has the sequence TYR (at amino acids 177 to 179 of SEQ ID NO:3), the fourth has the sequence SSR (at amino acids 184 to 186 of SEQ ID NO:3), the fifth has the sequence TNK (at amino acids 235 to 237 of SEQ ID NO:3), the sixth has the sequence TSR (at amino acids 243 to 245 of SEQ ID NO:3), the seventh has the sequence SPK (at amino acids 250 to 252 of SEQ ID NO:3), the eighth has the sequence SSR (at amino acids 293 to 295 of SEQ ID NO:3), and the ninth has the sequence TRK (at amino acids 318 to 320 of SEQ ID NO:3). Four casein kinase II phosphorylation sites are present in human TANGO 268. The first has the sequence SGGD (at amino acids 126 to 129 of SEQ ID NO:3), the second has the sequence SSRD (at amino acids 184 to 187 of SEQ ID NO:3), the third has the sequence SVAE (at amino acids 219 to 222 of SEQ ID NO:3), and the fourth has the sequence SPKE (at amino acids 250 to 253 of SEQ ID NO:3). Human TANGO 268 has two tyrosine kinase phosphorylation sites having the sequences KEGDPAPY (at amino acids 147 to 154 of SEQ ID NO:3) and KNPERWY (at amino acids 155 to 161 of SEQ ID NO:3). Human TANGO 268 has five N-myristylation sites. The first has the sequence GLCLGR (at amino acids 12 to 17 of SEQ ID NO:3), the second has the sequence GSLWSL (at amino acids 93 to 98 of SEQ ID NO:3), the third has the sequence of GGDVTL (at amino acids 127 to 132 of SEQ ID NO:3), the fourth has the sequence GTYRCY (at amino acids 176 to 181 of SEQ ID NO:3), and the fifth has the sequence GGQDGG (at amino acids 323 to 328 of SEQ ID NO:3). Human TANGO 268 is likely to be involved in cell signaling via interaction with a second receptor component. A charged residue is present in the transmembrane domain of human TANGO 268 (arginic at amino acid 272 of SEQ ID NO:3), which is a hallmark of platelet collagen receptors, and which can function as an interaction site for association with other membrane proteins, a second receptor component, e.g., FcRγ.

FIG. 5A depicts the alignment between the first immunoglobulin-like domain of human TANGO 268 (from amino acid residues 41 to 90 of SEQ ID NO:3) and a typical immunoglobulin domain( SEQ ID NO:13; Accession Number PF00047). FIG. 5B depicts the alignment between the second immunoglobulin-like domain of human TANGO 268 (from amino acid residues 127 to 182 of SEQ ID NO:3) and a typical immunoglobulin domain (SEQ ID NO:13; Accession Number PF00047).

Northern blot analysis of human TANGO 268 expression demonstrates expression in bone marrow, fetal liver, and peripheral blood leukocytes. Fetal liver expression reveals one human TANGO 268 mRNA band that is approximately 2 kb. Human TANGO 268 expression was not detected in the following tissues: spleen, lymph node, thymus, brain, heart, skeletal muscle, colon, kidney, liver, small intestine, placenta, or lung. Further analysis predicts that TANGO 268 is specific to the megakaryocyte lineage of hematopoietic cells.

Clone EpthEa11d1, which encodes human TANGO 268, was deposited with the American Type Culture Collection (10801 University Boulevard, Manassas, Va. 20110-2209) on Mar. 30, 1999 and assigned Accession Number 207180. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

FIGS. 3A–3C show an alignment of the human TANGO 268 coding region (SEQ ID NO:2) with the human monocyte inhibitory receptor precursor protein coding region (SEQ ID NO:24). The human monocyte inhibitory receptor has been shown to downregulate activation responses by phosphatases. The nucleotide sequences of coding regions of human monocyte inhibitory receptor precursor and human TANGO 268 are 37.7% identical. The full-length nucleic acid sequence of human TANGO 268 (SEQ ID NO:1) exhibits 49.9% identity to the full-length nucleic acid human monocyte inhibitory receptor precursor (SEQ ID NO:11; Accession Number U91928).

FIG. 4 shows there is an overall 23% identity between the amino acid sequence of the human TANGO 268 protein and the amino acid sequence of the human monocyte inhibitory receptor protein (SEQ ID NO:12; Accession Number U91928).

In general, human TANGO 268 has most homology to various members of the immunoglobulin superfamily that include NK inhibitory and activating receptors and Fc receptors. Specifically, TANGO 268 represents a platelet-specific collagen receptor previously described as Glycoprotein VI (GPVI), and thus can be involved in hemostasis and thrombosis. The fact that TANGO 268 represents GPVI was suggested by the following: (1) TANGO 268 and GPVI are both preferentially expressed in the megakaryocytic cells; (2) the molecular mass of the 40 kDa unglycosylated TANGO 268 is predicted to be approximately 62 kDa, the apparent molecular mass of GPVI, upon N- and O-linked glycosylation; (3) the presence of two immunoglobulin-like domains in TANGO 268 indicates that like GPVI, TANGO 268 interacts with the FcRγ; (4) the absence of a large intracytoplasmic tail, suggesting that this membrane-bound glycoprotein has no signaling role but associates with another member of the IgG family (e.g., FcRγ) protein to transduce a signal; and (5) the presence of a charged residue (arginine) in the transmembrane domain of TANGO 268 which is predicted to be present in GPVI based on its association with the FcRγ. Experimental data confirming that TANGO 268 does, indeed, represent GPVI are presented below.

Mouse TANGO 268

A cDNA encoding mouse TANGO 268 was identified by analyzing the sequences of clones present in a mouse megakaryocyte cDNA library. This analysis led to the identification of a clone, jtmeal05e02, encoding full-length mouse TANGO 268. The murine TANGO 268 cDNA of this clone is 1163 nucleotides long (FIG. 6; SEQ ID NO:14). The open reading frame of this cDNA, nucleotides 63 to 1001 of SEQ ID NO:14 (SEQ ID NO:15), encodes a 313 amino acid transmembrane protein (FIG. 6; SEQ ID NO:16).

The signal peptide prediction program SIGNALP (Nielsen, et al., 1997, *Protein Engineering* 10:1–6) predicted that mouse TANGO 268 nucleotides a 21 amino acid signal peptide (amino acid 1 to amino acid 21 of SEQ ID NO:16) (SEQ ID NO:17) preceding the mature mouse TANGO 268 protein (corresponding to amino acid 22 to amino acid 313 of SEQ ID NO:16)(SEQ ID NO:18). The molecular weight of mouse TANGO 268 without post-translational modifications is 34.5 kDa prior to the cleavage of the signal peptide, 32.3 kDa after cleavage of the signal peptide.

Mouse TANGO 268 is a transmembrane protein which consists of one or more of the following domains: (1) an extracellular domain; (2) a transmembrane domain; and (3) a cytoplasmic domain. The mouse TANGO 268 protein contains an extracellular domain at amino acid residues 1 to 267 of SEQ ID NO:16 (SEQ ID NO:19), a transmembrane domain at amino acid residues 268 to 286 of SEQ ID NO:16 (SEQ ID NO:20), and a cytoplasmic domain at amino acid residues 287 to 313 of SEQ ID NO:16 (SEQ ID NO:21).

FIG. 7 depicts a hydropathy plot of mouse TANGO 268. Relatively hydrophobic regions of the protein are shown above the horizontal line, and relatively hydrophilic regions of the protein are below the horizontal line. The cysteine residues (cys) and potential N-glycosylation sites (Ngly) are indicated by short vertical lines just below the hydropathy trace. The dashed verticalline separates the signal sequence on the left from the mature protein on the right.

Mouse TANGO 268 comprises two immunoglobulin-like domain sequences at amino acids 49 to 89 and at amino acids 135 to 181 of SEQ ID NO:16 and SEQ ID NO:22 and SEQ ID NO:23. Two N-glycosylation sites having the sequences NGSH and NITA are present in mouse TANGO 268 at amino acids 93 to 96 and at amino acids 244 to 247 of SEQ ID NO:16, respectively. Six protein kinase C phosphorylation sites are present in mouse TANGO 268. The first has the sequence TLK (at amino acids 132 to 134 of SEQ ID NO:16), the second has the sequence TYR (at amino acids 178 to 180 of SEQ ID NO:16), the third has the sequence SSR (at amino acids 224 to 226 of SEQ ID NO:16), the fourth has the sequence TNK (at amino acids 233 to 235 of SEQ ID NO:16), the fifth has the sequence TEK (at amino acids 239 to 241 of SEQ ID NO:16), and the sixth has the sequence SRK (at amino acids 291 to 293 of SEQ ID NO:16). Two casein kinase II phosphorylation sites are present in mouse TANGO 268. The first has the sequence SFDE (at amino acids 140 to 143 of SEQ ID NO:16), and the second has the sequence STTE (at amino acids 237 to 240 of SEQ ID NO:16). Mouse TANGO 268 has two tyrosine kinase phosphorylation sites having the sequences KEGDTGPY (at amino acids 148 to 155 of SEQ ID NO:16) and KRPEKWY (at amino acids 156 to 162 of SEQ ID NO:16). Mouse TANGO 268 has two N-myristylation sites. The first has the sequence GSHWSL (at amino acids 94 to 99 of SEQ ID NO:16), and the second has the sequence GTYRCY (at amino acids 177 to 182 of SEQ ID NO:16). A cAMP- and cGMP-dependent protein kinase phosphorylation site is present in the mouse TANGO 268 having the sequence of RRPS (at amino acids 226 to 229 of SEQ ID NO:16). An ABC transport family signature is present in mouse TANGO 268 having the sequence YAKGN-LVRICI.GATI (at amino acid residues 263 to 277 of SEQ ID NO:16). Mouse TANGO 268 does not include any conspicuous inhibitory or activation motifs in the cytoplasmic domain. Mouse TANGO 268 may be involved in cell signaling via interaction with a second receptor component. A charged residue is present in the transmembrane domain of mouse TANGO 268 (arginine at amino acid 270 of SEQ ID NO:16), which may function as an interaction site for association with other membrane proteins, a second receptor component, e.g., FcRγ.

FIG. 10A depicts the alignment between the first immunoglobulin-like domain of mouse TANGO 268 (from amino acid residues 42 to 91 of SEQ ID NO:16) and a typical immunoglobulin domain (SEQ ID NO:13; Accession No. PF00047). FIG. 10B depicts the alignment between the second immunoglobulin-like domain of mouse TANGO 268 (from amino acid residues 128 to 183 of SEQ ID NO:16) and a typical immunoglobulin domain (SEQ ID NO:13; Accession No. PF00047).

In situ expression experiments with a TANGO 268 antisense probe (nucleotides 69 to 670 of SEQ ID NO:14) reveal that during embryogenesis mouse TANGO 268 is expressed exclusively in the liver. The signal pattern is strong and multifocal, suggestive of expression by a scattered cell population. In adult tissues, expression of TANGO 268 in liver is no longer observed but a strong, multifocal signal is seen in spleen. The number of multifocal signals observed in the spleen is significantly reduced compared to the number observed in embryonic liver. All other adult tissues tested negative for TANGO 268 (i.e., no signal was observed in the brain, eye, harderian gland, submandibular gland, bladder, white fat, stomach, brown fat, heart, adrenal gland, colon, small intestine, liver, placenta, thymbus, lymph node, spleen, lung, spinal cord, pancreas, skeletal muscle or testes). A sense probe analogous to the anti-sense TANGO 268 probe tested on the same tissues yielded no signal.

The signal pattern and restricted tissue expression observed during embryogenesis and in adult tissues was identical to that seen with a probe for TANGO 69, a gene known to be expressed by megakaryocytes (PCT Publication Number WO 99/11662, published on Mar. 11, 1999). Like TANGO 69, TANGO 268 was also cloned from a megakaryocyte library. These data, therefore, indicate that TANGO 268 is expressed by megakaryocytes during embryogenesis and in adult mice.

In general, mouse TANGO 268 has most homology to various members of the immunoglobulin superfamily that includes NK inhibitory and activating receptors and Fc receptors. The full-length nucleic acid sequence of mouse TANGO 268 exhibits 35.6% identity to the full-length nucleic acid human monocyte inhibitory receptor precursor (SEQ ID NO:11; Accession Number U91928). FIGS. 8A–8D show an alignment of the mouse TANGO 268 coding region (SEQ ID NO:15) with the human monocyte inhibitory receptor precursor protein coding region (SEQ ID NO:24). The nucleotide sequences of the coding regions of the human monocyte inhibitory receptor precursor and mouse TANGO 268 are 34.4% identical. The nucleotide sequences of the full-length human monocyte inhibitory receptor precursor (SEQ ID NO:11; Accession Number U91928) and full-length mouse TANGO 268 (SEQ ID NO:14) are 35.6% identical. FIG. 9 shows that there is an overall 20.3% identity between the mouse TANGO 268 amino acid sequence and the human monocyte inhibitory receptor protein amino acid sequence (SEQ ID NO:12; Accession Number U91928).

FIG. 11 shows that there is an overall 64.4% identity between the precursor human TANGO 268 amino acid sequence (SEQ ID NO:3) and the precursor mouse TANGO 268 amino acid sequence (SEQ ID NO:16). This homology is spread throughout the molecule, but is slightly higher (78%) over the immunoglobulin-like domains interestingly, both human and mouse GPVI contain conserved variants of the WSXWS box (residues 96–100 and 192–196). This motif is a signature of class I hematopoietic receptors but variants are also found in the sequences of all Killer-cell Inhibitory receptors (KIR) (Fan et al., 1997, Nature 389: 96–100). These motifs have been shown to contribute to tertiary folding. GPVI has a relatively short cytoplasmic tail with no obvious signaling motifs analogous to the ITAM's and immunoreceptor tyrosine-based inhibitory motifs (ITIM's) of other signaling receptors. However, GPVI present a positively charged residue in the transmembrane domain allowing it to form complexes with the FcRγ chain which acts as signaling subunit (Poole et al., 1997, cited below).

Clone EpTm268, which encodes mouse TANGO 268, was deposited with the American Type Culture Collection (10801 University Boulevard, Manassas, Va. 20110-2209) on Jun. 14, 1999 and assigned Accession No. PTA-225. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Functional and Structural Analyses Demonstrating that TANGO 268 is Glycoprotein VI Described below are both functional (ligand binding, cell adhesion and platelet activation) and structural (immunoblot and tissue expression) analysis demonstrating that TANGO 268 is glycoprotein VI.

A. Ligand Binding Assay

Convolxin (Cvx) is a protein purified from the venom of *Crotallus durissus terrifcus*. Cvx is known to act as a potent platelet agonist, and has been shown to bind specifically to GPVI. Described below are Cvx ligand binding studies demonstrating that TANGO 268 specifically binds Cvx.

The ligand binding assay was performed as follows: approximately $5 \times 10^9$ human platelets per milliliter, and $10^6$ expression vector only-transfected CHO cells and full-length TANGO 268 containing expression vector-transfected CHO cells were lysed for 30 min at 4° C. lysis buffer comprising 10 mM Tris, 100 mM NaCl, 5 mM EDTA, pH 8 containing 0.1% Nonidet P40, 2 mM PMSF, 5 IU aprotinin and 20 µM leupeptin (Jandrot-Perrus et al., 1997, J. Biol. Chem. 272:27035–27041; Lagrue et al, 1999, FEBS Lett. 448(1):95–100). Approximately 8 µg of platelet lysate and 40 to 80 µg of CHO cell lysates (expression vector only-transfected and TANGO 268-transfected) were separated on 10% acrylamide slab gels (miniprotean 11 Biorad) in the presence of SDS and then transferred to a PVDF membrane (Amersham). The membrane was saturated with 5% (w/v) non-fat dry milk in PBS. Ligand blotting was performed by the incubating membrane in the presence of $^{125}$I-Cvx ($3\times10^5$ cpm/ml) in PBS pH 7.4 containing 0.5% (w/v) dry milk and 0.2% Tween 20 for 4 hours.

The Cvx utilized in the ligand binding assay was purified from the venom of Crotallus durissus terrificus by two successive chromatography steps (Francischetti et al., 1997, Toxicon 35:121728) and radiolabeled. Briefly, lyophilized venom from Crotallus durissus terrificus was solubilized in ammnoium formate 0.1M, NaCl 0.3 M, pH 3.1 and proteins were separated on a G75 column equilibrated in the same buffer. Cvx contained in the first eluted peak, as assessed by gel electrophoresis and platelet activating activity, was lyophilized. Second, Cvx was solubilized in Tris 0.1M pH8.5 containing 6 M urea (Tris urea buffer) and further purified by chromatography on a G100 column equilibrated in the same buffer. Fractions containing purified Cvx were pooled, dialyzed and lyophilized. After solubilization in the Tris urea buffer, Cvx was dialyzed against PBS (20 mM phosphate, 150 mM NaCl, pH 7.4). Cvx (100 µg) was radiolabeled with 0.5 mCi Na$^{125}$I (Amersham) using Iodogen (Pierce Chemical Corp.) according to the published procedure (Jandrot-Perrus et al., 1997, J. Biol. Chem. 272:27035–27041). Iodinated Cvx was separated from free $^{125}$I by gel filtration on a G25 sephadex column (Pharmacia) in PBS. The activity of $^{125}$I-Cvx was tested on human platelet aggregation.

Following the incubation of the membrane with $^{125}$I-Cvx, the membrane was washed and ligand binding was detected by autoradiography on X-Omat MA films (Kodak). Ligand blotting with $^{125}$I-Cvx (FIG. 12) revealed one specific band in platelet lysates at 56–58 kDa (lane 1), which represents a band previously identified as GPVI (Jandrot-Perrus et al., 1997, J. Biol. Chem. 272:27035–27041). No positive band was observed in lysates (60 µg) from control expression vector only-transfected cells (lane 2). In lysates from CHO cells transfected with TANGO 268 expression vector (60 µg), a positive band migrating at 52–54 kDa was clearly observed (lane 3).

The ligand binding studies demonstrate that convulxin binds to a molecule present on TANGO 268 transfected cells (and not on vector only transfected cells), which has a molecular weight very similar to the molecular weight of GPVI (FIG. 12). The small apparent difference in size between the band in platelet lysates and in CHO lysates can be accounted for by cell-type specific discrepancies in protein glycosylation.

This result demonstrates that convulxin binds to TANGO 268 and that TANGO 268 has a similar or identical molecular weight as GPVI. Since GPVI is the platelet receptor for Cvx (Jandro-Perrus et al., 1997, Journal of Biological Chemistry 272:27035–27041) and TANGO 268 is preferentially expressed in megakaryocytes, this functional evidence indicates that TANGO 268 is GPVI.

B. Immunoblotting Assay

Structural evidence is presented herein that further supports TANGO 268 as corresponding to GPVI. In particular, the immunoblotting results presented herein demonstrate that an IgG preparation containing antibodies directed against GPVI binds specifically to TANGO 268 polypeptide. These studies further demonstrate that binding is successfully competed away when Cvx is introduced.

The immunoblotting assay was performed as follows: platelet, expression vector-only transfected and TANGO 268 containing expression vector-transfected CHO cell lysates were generated as described in A. above. Approximately 8 µg of platelet lysate and 40 to 80 µg of CHO cell lysate (either expression vector-only transfected or TANGO 268-transfected) were separated on 10% arcylamide slab gels (miniprotean II Biorad) in the presence of SDS and then transferred to a PVDF membrane (Amersham). The membrane was saturated with 5% (w/v) non-fat dry milk in PBS, and then incubated for 2 hours at room temperature with 9 µg/ml anti-GPVI IgG in PBS, pH 8.6 containing 0.02% (v/v) Tween 20.

Alternatively, for the competition assay, the membrane was incubated for 2 hours at room temperature with 9 µg/ml anti-GPVI IgG in PBS, pH 8.6 containing 0.02% (v/v) Tween 20 in the presence of a high concentration of cold Cvx (0.5 µM).

The IgG preparation utilized in this assay was generated by purifying IgG from serum of a patient exhibiting idiopathic thrombocytopenic purpura (ITP) (Sugiyama et al., 1987, Blood 69: 1712–1720) as described in Jandrot-Perrus et al., 1997, J. Biol. Chem. 272:27035–27041. Following the incubation with the antibody composition, the membrane was washed and incubated with peroxidase-coupled protein A (Amersham) for 2 hours at room temperature. The immonoblots were developed using enhanced chemiluminescence detection (Amersham).

Figure 13A:
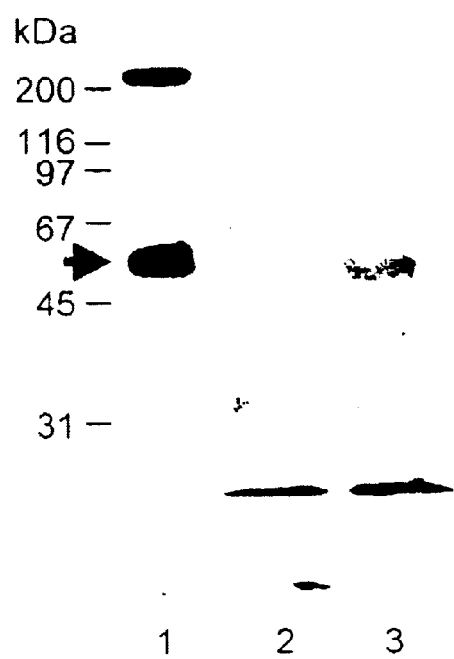
FIG. 13A depicts the results from the immunoblotting assay with anti-GPVI Ig antibody, demonstrating that TANGO 268 specifically binds to anti-GPVI Ig antibody. The cell lysates were separated on polyacrylamide gels, transferred to PVDF membranes, the membranes were incubated with anti-GPVI IgG antibody followed by an incubation with peroxidase-coupled protein A, and TANGO 268 expression was detected by enhanced chemiluminescence.

As shown in FIG. 13A, immunoblotting with the IgG revealed a 56–58 kDa in platelet lysates (lane 1), which corresponds to the molecular mass of GPVI. The high molecular weight band detected in platelet lysates corresponds to platelet IgGs revealed by protein A. The presence of a 52–54 kDa band was detected in TANGO 268-transfected CHO cell lysates (FIG. 13A, lane 3) but not in expression vector only-transfected CHO cell lysates (lane 2) demonstrating that TANGO 268 shares epitope similarities with GPVI. The low molecular weight bands of moderate intensity observed in FIG. 13A, lanes 2 and 3 are non-specific bands since they were detected in both control, expression vector only-transfected and TANGO 268 transfected CHO cell lysates.

Figure 13B:
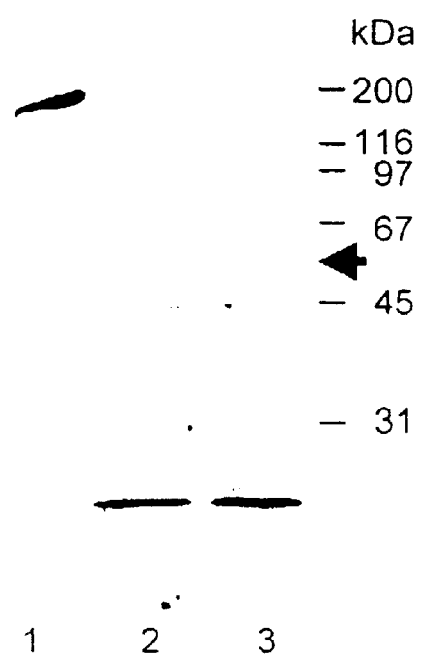
FIG. 13B depicts the results of anti-GPVI IgG binding following competition which Cvx, which demonstrates that Cvx competes with anti-GPVI IgG antibody for binding to TANGO 268. Lane 1 contains platelet lysate, lane 2 contains lysate from expression vector-only transfected CHO cells, and lane 3 contains TANGO 268-transfected CHO cell lysate. The cell lysates were separated on polyacrylamide gels, transferred to PVDF membranes, the membranes were incubated with anti-GPVI IgG antibody in the presence of Cvx followed by an incubation with peroxidase-coupled protein A, and TANGO 268 expression was detected by enhanced chemiluminescence.

The results from the competition assay performed further demonstrate the similarities between TANGO 268 and GPVI. In particular, as shown in FIG. 13B, cold 0.5 µM Cvx successfully competes with and inhibits anti-GPVI binding to GPVI on platelet lysates (lane 1), and likewise, the 52–54 kDa band revealed by the anti-GPVI IgG in TANGO 268-transfected cells lysates (lane 3), was inhibited in the presence of 0.5 µM Cvx.

In summary, the results from both the ligand binding assays and immunoblotting assays described above provide both functional (i.e., binding of Cvx to TANGO 268) and immunological evidence (i.e., recognition by anti-GPVI IgG) that TANGO 268 does, indeed, represent GPVI polypeptide.

C. Tissue Expression of Tango 268/GPVI

To further study tissue distribution of both mouse and human Tango 268/GPVI, Northern blot, RT-PCR and in situ hybridization were preformed. The results presented herein confirmed and extend the experimental results presented above.

Materials & Methods

In situ hybridization: In situ hybridization (ISH) was performed with day 12.5 C57BL/B6 mouse embryos and normal 4- to 6-week-old C57BL/6 mouse femurs. Tissues were fixed in 10% formalin, paraffin embedded and subsequently sectioned at 4 μm onto Superfrost/plus slides. Femurs were decalcified in TBD-2 (Shandon, Pittsburgh, Pa.) prior to paraffin embedding. Sections were deparaffinized in xylene, hydrated through a series of graded ethanol washes and placed in DEPC-treated phosphate-buffered saline (PBS) pH7.4 before being processed for ISH. Sections were incubated at 20 ug/ml proteinase K (Sigma) in DEPC-PBS for 15 minutes at 37° C. and then immersed in 4% formaldehyde/PBS for 5 minutes. Sections were treated with 0.2N HCl for 10 minutes followed by DEPC-PBS. Sections were rinsed in 0.1M triethanolamine-HCl (TEA, pH 8.0), incubated in 0.25% acetic anhydride-TEA for 10 minutes, rinsed in DEPC-PBS, dehydrated through a series of graded ethanol washes and air dried. Labeling and hybridization of $^{35}$S-radiolabeled (2.5×10$^7$ cpm/ml) cRNA anti-sense and sense RNA probes encoding a 599 pb fragment of the 5' end of the GPVI gene (generated with the PCR primers forward 5' CAGCCTCACCCACTTTCTT-3' (SEQ ID NO:25), nt 8–27 and reverse 5'-CCACAAGCACTAGAGGGTCA 3' (SEQ ID NO:26), nt 607–588) were performed as previously described (Busfield et al., 1997, Mol. Cell. Biol. 17: 4007–14). Following hybridization, sections were dehydrated rapidly through serial ethanol-0.3 M sodium acetate before being air dried, dipped in a nuclear track emulsion (NTB-2: Eastman Kodak, Rochester, N.Y.) and exposed for 60 days at room temperature. Slides were developed with D-19 (Kodak, Rochester, N.Y.), stained with hematoxylin and eosin-Y, and coverslipped.

Cell lines: The HEL (erythroid/MK), U937 (monoblast), K562 (erythroid), CEM (T cell), HEPG2 and Hela cell lines were obtained from American Type Culture Collection (ATCC®, Manassas, Va.) and the FDC-P1 and 32D cells from D. Metcalf (The Walter and Eliza hall Institute, Melbourne, Australia). The UT7 (erythroid/MK) transduced by c-mpl (Hong et al., 1998, Blood 91:813–822) TF1 (erythroid), KG1 (myeloblast), HL60 (myeloblast/promyelocyte), MO-7E (MK), Meg-01 (MK) and DAMI (MK) were obtained from the different laboratories which derived them (Avanzi et al., 1988, Br. J. Haematol. 69: 359–366) (Collins et al., 1977, Nature 270: 347–349) (Greenberg et al., 1988, Blood 72: 1968–1977) (Kitamura et al., 1989, J. Cell Physiol. 140:323–334) (Koeffler and Golde, 1977, Science 200:1153–1155.) (Komatsu et al., 1991, Cancer Res. 51: 341–348) (Ogura et al., 1985, Blood 66:1364–1392).

HEL, U937 HL60, Meg-01, KG1 and K562 human cell lines were cultured in IMDM (Gibco/BRL, Grand Island, N.Y.), 10% FCS (Stem cell technology, Vancouver, BC, Canada). The c-mpl UT7, TF1 and MO-7E are factor dependent and were grown either in the presence of 2 ng/ml GM-CSF or 10 ng/ml PEG-rHuMGDF in IMDM 10%FCS. CEM and Hela were grown in RPMI (Gibco/BRL, Grand Island, N.Y.). FDC-P1, 32D and Ba/F3 murine cell lines were cultured in DMEM (Gibco/BRL, Grand Island, N.Y.), 10% FCS (Stem cell technology, Vancouver, BC, Canada). Cultures were performed at 37° C. in a fully humidified atmosphere of 5% CO2.

Samples: Illuman megakaryocytes were obtained as described for the human libraries from mobilized or cord blood CD34 cord blood. A fetal liver was obtained from abortion at 12-week gestation after obtaining informed consent.

Northern Blot/RT PCR analysis: Human multiple tissue northern blots, purchased from Clontech (Palo Alto, Calif.) were hybridized to a 1.0 kb human GPVI probe as described by the manufacturer. Total RNA was isolated using RNA PLUS (Bioprobe systems, France), a modification of the acid-guanidinium thiocyanate-phenol-chloroform extraction method of Chomezynski et Sacchi (Chomezynski and Sacchi 1987). RNA was reverse transcribed with random hexamers using SUPERSCRIPT reverse transciptase (Gibco BRL/Life Technologies, Cergy Pontoise, France).

For human cell lines and tissues, after reverse transcription, each sample was subjected to a specific amplification of GP V1 and β2 microglobulin cDNA. The sequences of the specific primers were: for GP V1 sense primer 5'-TTCTGTCTTGGGCTGTGTCTG-3' (SEQ ID NO:27) and anti-sense primer 5'-CCCGCCAGGATTATTAGGATC-3' (SEQ ID NO:28), for $β_2$-microglobulin sense primer 5'-CCTGAAGCTGACAGCATTCGG-3' (SEQ ID NO:29) and anti-sense primer CTCCTAGAGCTACCTGTGGAG-3' (SEQ ID NO:30). PCR was performed in 25 μl reaction mixture containing 0.3 U Taq polymerase (ATGC Noisy-le-Grand, France), 200 μM dNTP, 30 pmol of oligonucleotide sense and 30 pmol of antisense for GP V1 amplification and 10 pmol of oligonucleotide sense and 10 pmol of antisense for $β_2$-microglobulin amplification, in ATGC buffer. The reaction mixture was subjected to denaturation for 5 min at 95° C. amplified by 35 cycles as follows: denaturation for 30 seconds at 94° C., annealing for 30 seconds at 60° C. and extension at 72° C. for 1 min, with a final 7 mm extension at 72° C. in a thermocycler 2400 (Perkin Elmer Co, Courtaboeuf, France). PCR produces (9 μl) were electrophoresed on a 2% agarose gel. Fragments were visualized by illumination after ethidium bromide staining. MassRuler DNA Ladder, low Range (MBI Fermentas, Amherst, N.Y.) is used as marker.

Results

Figure 14A:
FIG. 14A: In situ hybridization of a day 12.5 mouse embryo. Hybridization is exclusively observed in the liver during embryogenesis. No signal was seen with the sense probe (data not shown). High magnitude resolution shows that the only positive cell population corresponded to fetal megakaryocytes (data not shown). In adult, expression in liver was no longer observed but a strong, multifocal signal was seen in spleen and in the bone marrow.
Figure 14B:
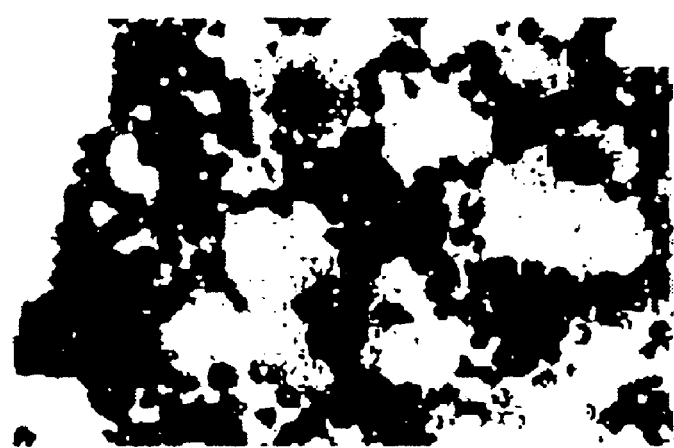
FIG. 14B: high magnitude resolution from a photoemulsion processing carried out on a 6-week-old mouse femur section shows expression restricted to megakaryocytes. No signal was observed in any other adult tissues analyzed (see results).

Human tissues were studied using Northern blot or RT-PCR analysis. Northern blots (FIG. 14D) revealed no specific message in brain, heart, skeletal muscle, colon, thymus, spleen, kidney, liver, small intestine, placenta, lung or lymph nodes. A 2 kb transcript was only observed in bone marrow and fetal liver. A signal was inconsistently observed with peripheral blood cells, probably due to platelet RNA contamination in some samples. Indeed, transcripts for platelet glycoprotein IIb (GPIIb), a platelet specific protein, were also detected in these positive samples.

Figure 14C:
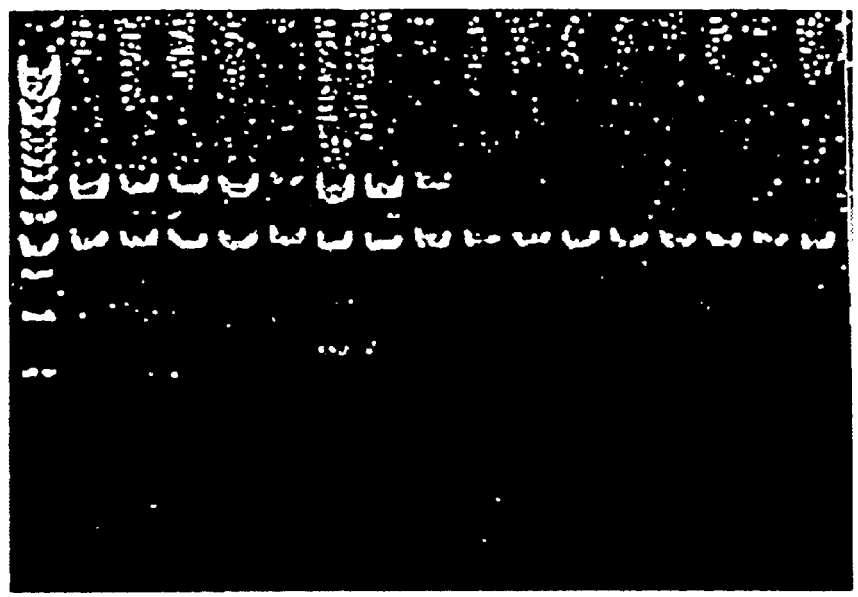
FIG. 14C: RT-PCR analysis from human samples. $\beta_2$microgloubilin and GPVI transcripts were co-amplified. The high molecular weight fragment (830 bp) is generated from the GPVI primers and the low molecular weight fragment (630 bp) is generated from the $\beta_2$ microglobulin primers. The $\beta_2$ microglobulin PCR product, used as a loading control, is present in all the samples in similar quantity. In contrast, GPVI is only amplified in megakaryocyte-enriched samples (adult and newborn), in cell lines displaying strong MKC features (HEL, MEG01, DAMI, MO7E, mpl-UT7) and at a lesser extend in fetal liver cells. A very low signal is also detected in the K562 and KG1 cell lines, two cell lines which also express GPIIb at low level, but no expression was detected in the other samples.
Figure 14D:
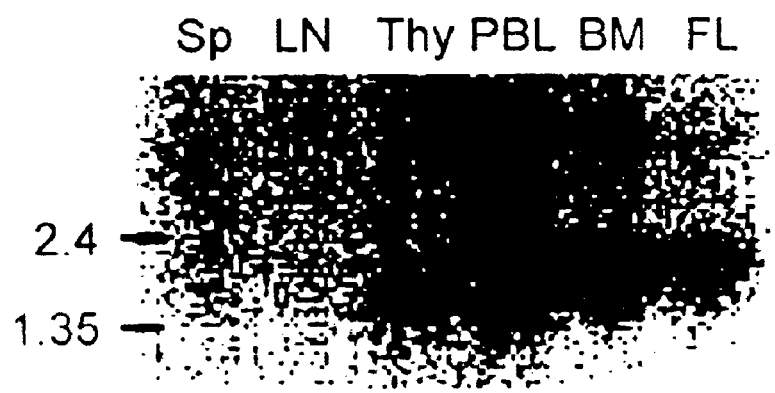
FIG. 14D: Northern blot analysis of human tissues. A 2 kb transcript is only observed in bone marrow and fetal liver. A signal is also observed with peripheral blood leucocytes (PBL). However, when the same blot was hybridized with a GPIIb probe, a platelet protein absent in PBL, transcripts were also detected suggesting that the signal was due to platelet RNA contamination. No signal was observed in a different PBL sample but also in brain, heart, skeletal muscle, colon, thymus, spleen, kidney, liver, small intestine, placenta, lung or lymph nodes (data not shown).

Using RT-PCR analysis, no GPVI transcript was detected in blood cells except in platelets. In cell lines, a strong PCR signal was observed in the HEL, MEG01, DAMI and TPO-stimulated MO7E and mp1 transduced UT7 cell lines (Hong et al., 1998, Blood 91:813–822). A very low signal was also detected in the K562 and KG1 cell lines, two cell lines also expressing GPIIb at low level, but no expression was detected in the HEPG2, CEMT, TF1, U937, HL60 and Hela cells. CD41 positive cells (including more than 95% megakaryocytes) isolated from normal cord blood or chemotherapy-induced mobilized peripheral blood displayed a strong RT-PCR signal. Fetal liver cells expressed a moderate level of expression compared to megakaryocyte-enriched samples (FIG. 14C)

Mouse tissues were studied using northern blot and ISH analysis. ISH reveals that GPVI was exclusively found in the liver during embryogenesis (FIG. 14A). The signal pattern was strong and multifocal, suggestive of expression by a scattered cell population. This signal was observed at embryonic day 13.5, 14.5, 16.5 and decreased in intensity at day 18.5 and in 1.5 day old new born. In adult, expression in liver was no longer observed but a strong, multifocal signal was seen in spleen and in the bone marrow. No signal was observed in any other tissues including brain, eye, harderian gland, submandibular gland, bladder, white fat, stomach, brown fat, heart, adrenal gland, colon, small intestine, liver, placenta, thymus, lymph node, lung, spinal cord, pancreas, skeletal muscle, testes. Photoemulsion processing of the spleen and bone marrow showed that this expression was restricted to megakaryocytes (FIG. 14B).

In conclusion, despite screening a large number of human and mouse tissues, GPVI expression was only detected in megakaryocytes/platelets. This result strongly suggests that GPVI is restricted to this hematopoietic lineage. Presently there are very few molecules that are specific to the megakaryocyte lineage. GPIIb (integrin αIIb), which was long considered to be the prototypic megakaryocyte marker, is also expressed on a subset of hematopoietic progenitors. Other megakaryocyte proteins such as Gp1bα,β and GPIX (CD42) are also expressed by activated endothelial cells. Only PF4 appears to be specific to the megakaryocyte/platelet lineage. For this reason the PF4 promoter has been used to target the megakaryocytes in various transgenic models (Ravid et al., 1991, *Proc. Nat'l. Acad. Sci. USA* 88:1521–5). Thus, the GPVI promoter can also be used to target specifically the megakaryocyte lineage. For example, the polynucleotides of the invention can be used to specifically target, via homologous recombinant, a gene of interest into the GPVI locus under the control of the GPVI promoter. Alternatively, the GPVI promoter region can be cloned using standard techniques known to those in the art (e.g., probing a genomic library by hybridization to the 5' end of the cDNAs of the invention, and more specifically, detecting hybridization of the human TANGO 268 clone to a human genomic library of chromosome 19 in particular).

D. Flow Cytometry To Study Cell Surface Expression of Tango 268/GPVI

In order to determine whether the recombinant GPVI was expressed at the cell surface, different human or murine hematopoietic cell lines were transduced with recombinant retroviruses expressing human or murine GVPI and with the control retrovirus.

Materials & Methods

GPVI expressing cell lines: CHO cells were transfected using lipofectamine (Gibco-BRL, Grand Island, N.Y.), according to manufacturer's instructions. The expression vector (pMET, Millennium Pharmaceuticals, Cambridge, Mass.) containing the full length GPVI cDNA, driven by a SRalpha promoter, was isolated from the cDNA library. Control CHO cells were transfected with the empty vector. Cells were controlled 2 days after transfection and lysed in 12 mM Tris, 300 mM NaCl, 12 mM EDTA, containing 2 μM leupeptin, 2 mM PMSF, 5 KIU aprotinin, and 0.2% (v/v) NP40 (Sigma, St. Louis, Mo.). After 20 min at 4° C. under agitation, samples were configured at 13,000 g for 15 min at 4° C. and the supernatants frozen at 80° C. for analysis.

The human cell lines HEL, U937 and K562 and the murine cell lines FDC-P1, 32D and Ba/F3 murine cell lines were engineered (Burns et al., 1993, *Proc. Nat'l. Acad. Sci. USA* 90: 8033–7) to express GPVI using the pMSCVpac retrovirus (Hawley et al., 1994, *Gene Ther.* 1: 136–8). Briefly, viruses carrying the full length cDNA encoding human GPVI or murine GPVI were constructed using base perfect PCR amplified fragments of the cDNAs (Clontech laboratories Inc., Palo Alto, Calif.). Viral supernatants were generated into the 293-EBNA cells (Invitrogen, Carlsbad, Calif.) by transfecting the retroviral construct and two pN8epsilon vectors containing the gag/pol genes from the murine moloney leukemia virus (MMLV) or the Vesicular Stomatitis Virus envelope glycoprotein G(VSV-G) gene. Concentrated viral supernatants were prepared by centrifugation at 4° C. using a SW28 rotor at 50,000× g (25,000 rpm) for 2 hr. Pellets were resuspended in 1.5 ml of DMEM for 24 hr at 4C, shaken at 4° C. for 24 hours and frozen at −80° C. For transduction, cell lines were incubated with the viral supernatant over-night in 24 well plates, 10×10$^5$ cell/ml, and selected during one week using puromycin (4 μg/ml, Sigma, St. Louis, Mo.). Human and murine GPVI were transduced in human and murine cell lines, respectively. Expression of the genes was verified using PCR analysis. The control cells were transduced with the empty virus.

Convulxin and Bothrojaracin preparation: Convulxin (Cvx) was purified from the venom of *Crotalus durissus terrificus* mainly as described by Francishetti et al, using a two step gel filtration procedure of sephadex G75 (Pharmacia Biotech, Uppsala, Sweden) followed by sephacryl S100 (Pharmacia Biotech, Uppsala, Sweden). Cvx was labeled with $^{125}$I using the iodogen procedure (Pierce Chemical Co, Rockford, Ill.) and Na $^{125}$I (Amersham, Les Ulis, France). Cvx was obtained to FITC by mixing Cvx in 50 mM NaHCO3, 150 mM NaCl, pH 9.5 with a 100 fold molar excess of FITC (Aldrich, St. Quentin Fallavier, France) overnight at 4° C. FITC-coupled Cvx was separated from free FITC by chromatography on a sephadex G25 column (PD10 Pharmacia Biotech, Uppsala, Sweden) in 20 mM phosphate, 150 mM NaCl pH 7.4 (PBS). Bothrojaracin, a specific thrombin inhibitor purified from the venom of Bothrops jararaca as previously described (Arocas et al., 1996, *Biochemistry* 35: 9083–9) was coupled to FITC using the same procedure.

Flow cytometry: Cells transduced with the human or murine GPVI viruses or the control virus were incubated in the presence of 20 nM FITC-Cvx or FITC-bothrojaracin for 60 min. at room temperature. After dilution in PBS cells were analyzed by FACSort flow cytometer (Becton Dickinson, Franklin Lakes, N.J.).

Results

It was observed that the cell lines used for this study express FcRγ-chain, as indicated by immunoblotting studies using a polyclonal anti-FeRγ antibody. Functional characterization of recombinant GPVI was performed using transfected cells which have either no (U937, FDC-P1) or low (HEL) levels of endogenous GPVI. Unlike DAMI cells which do express GPVI mRNA, this allowed us to measure responses independent of endogenous GPVI.

Figure 15A:
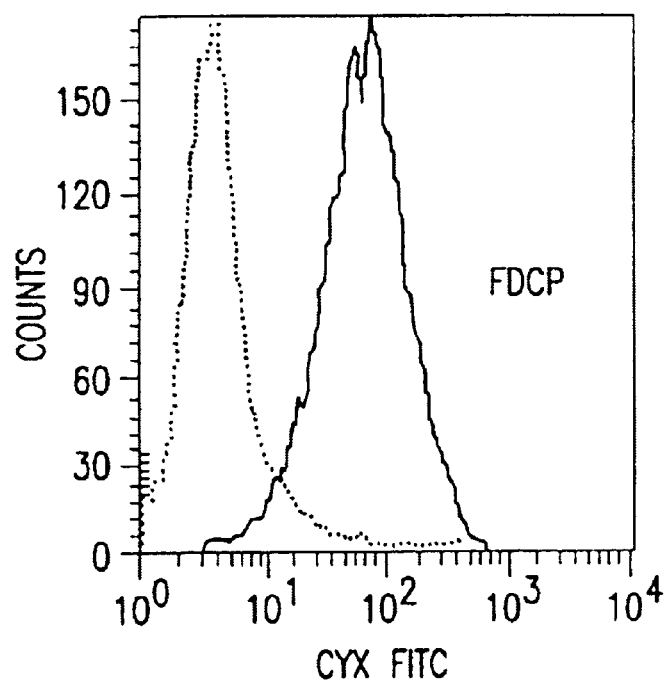
FIG. 15A: FDC-P1.
Figure 15B:
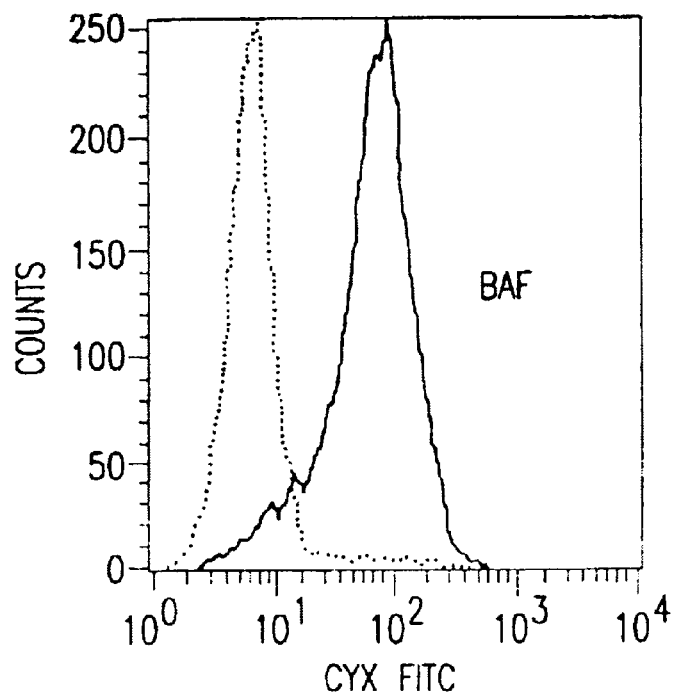
FIG. 15B: Binding of Cvx to murine hematopoietic cell lines. Hematopoietic cell lines were transduced with a retrovirus expressing rmGPVI. Control cells were transduced with the empty vector. Cells were incubated with FITC-coupled Cvx or FITC-coupled bothrojaracin as a control and analyzed by flow cytometry.
Figure 15C:
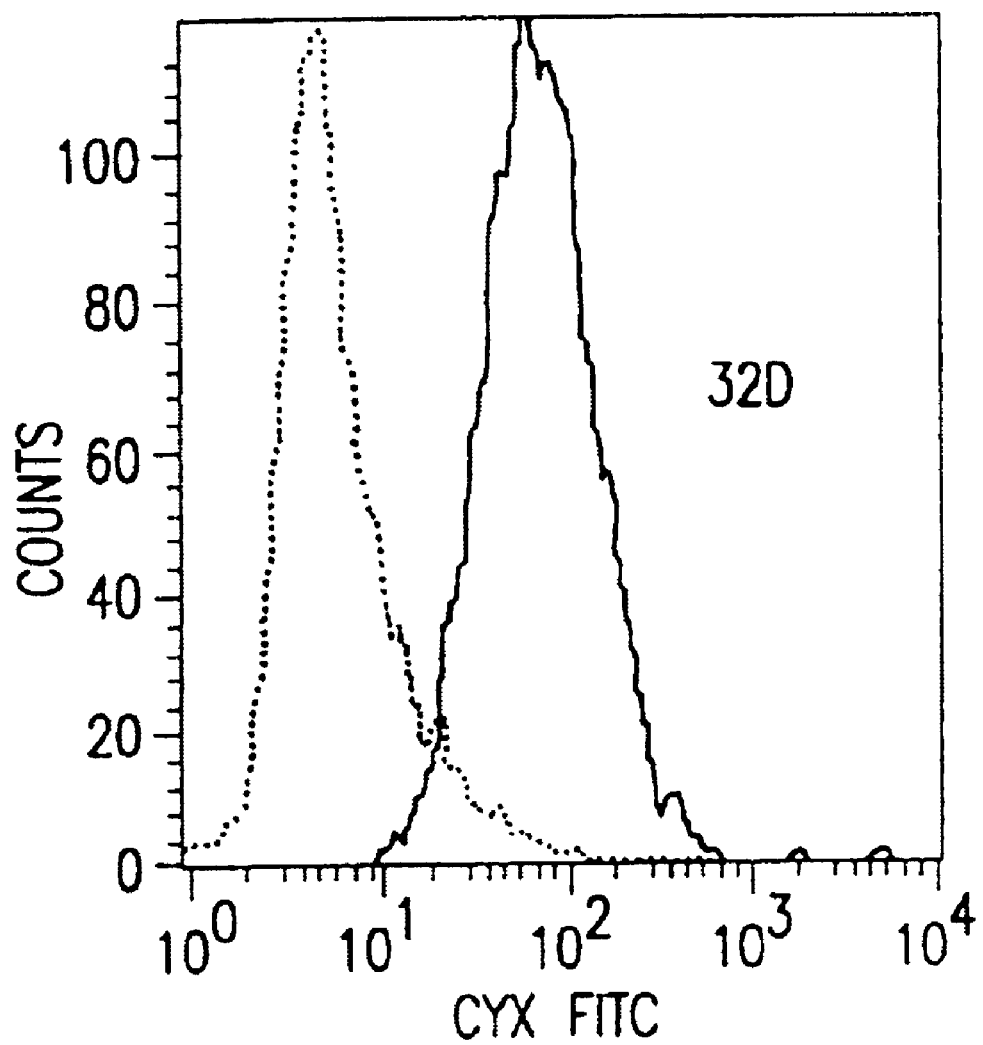
FIG. 15C: 32D. Dotted line: control cells transduced with the empty vector, plain line cells transduced with the retrovirus carrying mGPVI.

Transduced cells were analyzed by flow cytometry using FITC conjugated Cvx. As a control, we used FITC conjugated bothrojaracin, another snake venom protein structurally very close to Cvx but a pure thrombin inhibitor that does not bind to platelets. Transduction of murine 32D cells with a retrovirus expressing murine GVPI resulted in a strong Cvx-associated staining compared to cells transduced with the control virus, indicating that these cells express GPVI at their surface (FIG. 15). Similar results were obtained with FDC-P1, and Ba/F3 (all murine cell lines) and with K562 and U937, indicating that murine or human GPVI are expressed at the surface of all these cell lines after transduction. Cvx was found to bind to the wild type HEL cells but the binding was clearly increased after retroviral transduction indicating an increased expression in cells already constitutively expressing GPVI.

Discussion

This ligand binding fluorescence analysis shows that Cvx binds to the human recombinant protein in U937 and K562 cells and to the mouse recombinant protein in FDC-P1, 32D and Ba/F3. It is known that Cvx recognized mouse GPVI from studies showing that Cvx is a potent platelet activator of both human and mouse platelets. Expression of recombinant GPVI at the cell surface may have been facilitated by the coexpression of the FcRγ chain in these cells. It has been shown previously that expression of the FcRγ chain is required for surface expression of the FcγRI, FcγRIII, FcεRI, and for activation of platelets by collagen (Poole et al., 1997, *EMBO J.* 16(9):2333–2341) in mice lacking the FcRγ.

E. Cell Adhesion

Since GPVI was expressed at the cell surface of transfected cells, its capacity to promote cell adhesion in a static system, to either immobilized Cvx or collagen, was tested, and then this result was compared this to immobilized BSA.

Materials & Methods

Cell adhesion: Collagen type I (2 μg, Chrono-log corp. Haverton, Pa.), Cvx (1.4 μg) or BSA (2 μg, Sigma, St. Louis, Mo.) in 100 μl PBS were immobilized on Immulon II plates (Dynatech, St. Cloud, France) overnight at 4° C. Plates were then saturated with 2 mg/ml BSA in PBS for one hour and washed with PBS. Cells in culture medium were labeled with $^{51}$Cr (CIS Bio International, Gif sur Yvette, France) for one hour at 37° C. after centrifugation at 150 g for 10 min, cells were washed with Hanks buffer containing BSA (2 mg/ml) and resuspended in the same buffer. Cells were added to the wells. After 60 min. at room temperature, wells were emptied and washed and the samples counted for $^{51}$Cr.

Results

Figure 16A:
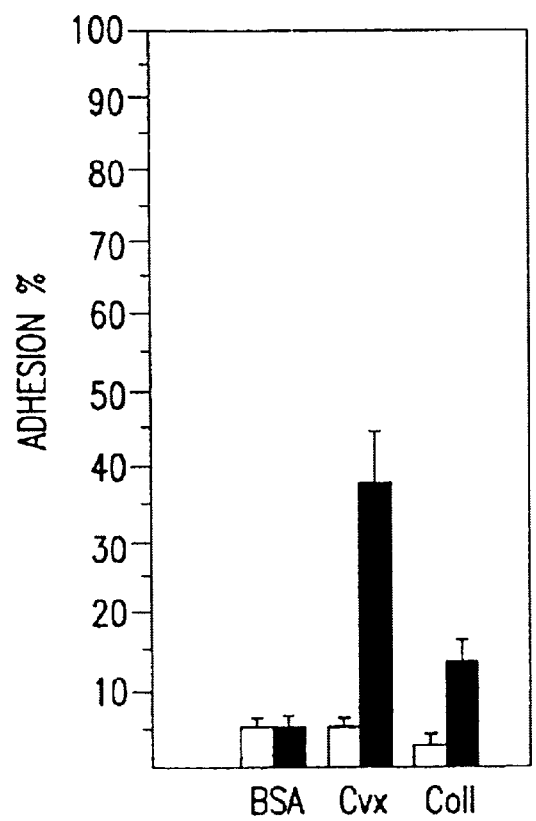
FIG. 16: Adhesion of cells expressing rhGPVI or rmGPVI to immobilized Cvx or collagen. BSA, Cvx or collagen type I were immobilized on microtitration plates. GPVI transduced or control U937 (FIG. 16A) or FDC-PI (FIG. 16B) cells were labeled with $^{51}$Cr and incubated for 60 min in the wells. After aspiration of the non-bound cells and washing, radioactivity associated to the wells was counted to determine adherent cell number. Results are expressed as the percentage of the cells added to the wells and are the mean±SEM of three determinations. Empty bars: control cells, filled bars: GVPI expressing cells.
Figure 16B:
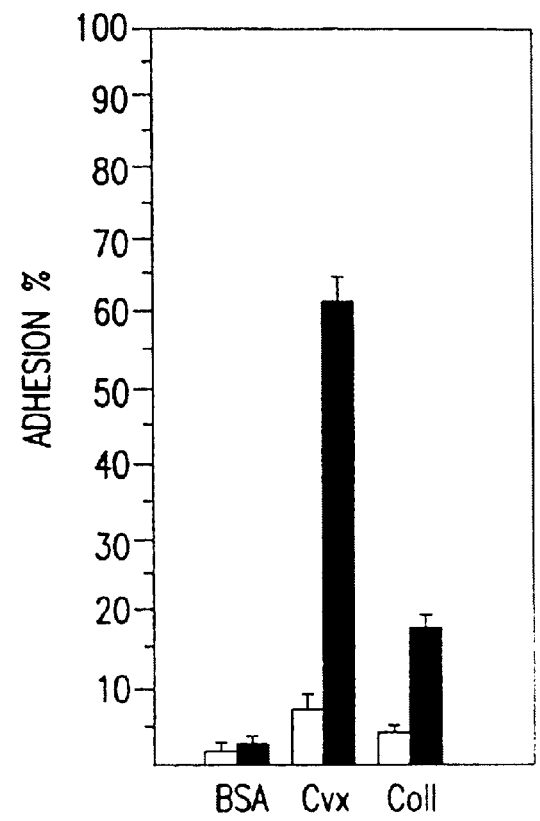

Two cells lines were tested: U937 and FDC-P1. Neither the cells expressing GPVI, nor the control cells bound to immobilized BSA. However, expression of recombinant human or mouse GPVI in U937 or FDCP-1, respectively, clearly promotes the adhesion of these cells to immobilized collagen and to a greater extent to immobilized Cvx (FIG. 16). This result indicates that GPVI protein functions as a receptor for collagen I. In addition, GPVI is a receptor for collagen III.

F. Association of Recombinant GPVI with FcRγ Chain

To analyze whether recombinant GPVI (otherwise referred to herein as TANGO 268 or glycoprotein VI) was expressed associated with FcRγ chain we performed immunoprecipitation studies with an anti-FcRγ polyclonal antibody on lysates of U937 transduced cells compared to platelets.

Materials & Methods

Protein analysis: The different cells (platelets, megakaryocytes and cell lines) were lysed in a buffer composed of 12 mM Tris, 300 mM NaCl, 12 mM EDTA, containing 2 μM leupeptin, 2 mM PMSF, 5 KIU aprotinin, and 0.2% (v/v) NP40. After 20 min at 4° C. under agitation, samples were centrifuged at 13,000 g for 15 min at 4° C. and the supernatants was frozen at −80° C. Protein concentration was determined using the Bio-Rad protein assay (Bio-Rad, Ivry-sur-seine, France). For blotting experiments, proteins were further solubilized with 2% SDS for 5 min at 100° C. Proteins were separated by electrophoresis on acrylamide slab gels (Mini protean II, Bio-Rad Laboratories, Ivry-sur-seine, France) and transferred on PVDF. Membranes were soaked with 5% non-fat dry milk and incubated with $^{125}$I-Cvx (6×10$^3$ Bq/ml) in PBS pH 7.4 containing 0.1% (v/v) tween 20, or with anti-GPVI IgGs (9 μg/ml in PBS pH 8, containing 0.02% (v/v) tween 20 in the absence or the presence of 0.5 μM cold Cvx. Anti-GPVI IgGs were obtained as previously described (Jandrot-Perrus et al., 1997, *J. Biol. Chem.* 272:27035–27041) from the patient's plasma kindly provided by Pr. M. Okuma (Kyoto, Japan). Antibodies were revealed using peroxydase-coupled protein A (Amersham Pharmacia Biotech, Uppsala, Sweden) and enhanced chemiluminescence (Amersham Pharmacia Biotech, Uppsala, Sweden). For immunoprecipitations, cell lysates were precleared by incubation with protein A-sepharose at 4° C. for 30 min. and centrifugation. Cleared lysates were incubated overnight at 4° C. with 10 μg/ml polyclonal anti FcRγ chain antibodies (Upstate Biotechnology, NY) followed by the addition of protein A/G-sepharose (Pharmacia Biotech, Uppsala, Sweden) for 2 hours at room temperature. Immunoprecipitated proteins were eluted with 2% SDS and subjected to SDS-PAGE followed by blotting onto PVDF membranes and then probed using anti-GPVI and anti-FcRγ chain antibodies as described above.

Results

Figure 17:
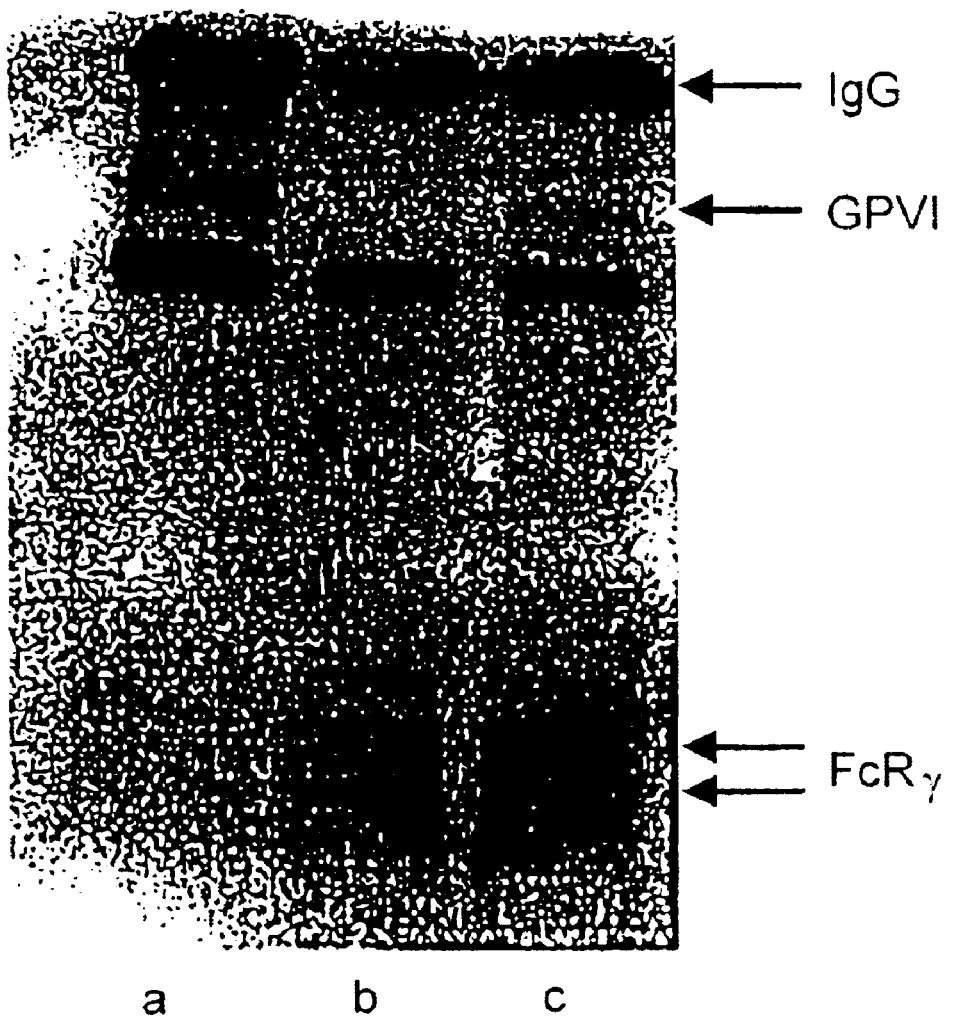
FIG. 17: Coexpression of recombinant human GPVI with FcRγ chain. Lysates from GPVI transduced or control U937 cells were incubated with a polyclonal anti-FcRγ antibody and protein A-sepharose. Immunoprecipitated proteins were separated by SDS-PAGE and blotted on PVDF. Membranes were incubated with a mixture of anti-FcRγ and anti-GPVI antibodies revealed with peroxidase-coupled protein A and chemiluminescence.

FIG. 17 shows the analysis of the precipitated proteins by immunoblotting with a mixture of anti-FcRγ antibodies and an IgG preparation containing antibodies directed against GPVI. Three bands were observed in all samples: a high molecular weight band corresponding to IgGs, a~50 kDa non-identified band and a 14 kDa doublet corresponding to FcRγ chain. In addition, one band corresponding to GPVI is present in platelets and is also observed in U937 transduced with the GPVI virus but not in cell transduced with the control virus, indicating that recombinant GPVI is physically associated with FcRγ chain. As with FcαRI, the linkage probably involves charged residues within the transmembrane domain: R272 or R270 respectively for hGPVI and mGPVI and D11 in the FcRγ chain.

G. Inhibition of Collagen and Cvx-induced Platelet Activation by rhusGPVI:Fc

An Fc fusion human soluble GPVI (rhusGPVI:Fc) protein was produced and purified to investigate its ability to compete with membrane-bound platelet GPVI.

Materials & Methods

Protein preparation: The open-reading frame of the predicted extracellular domain of T268 was PCR amplified from the Kozak sequence before the first methionine to asparagine 269 immediately prior to the predicted transmembrane sequence. The PCR fragment was ligated into a pCDM8 host vector containing the genomic sequence of the human IgG1 Fc domain such that the extracellular part of the hGPVI cDNA was fused at its C-terminus via a 3 alanine linker to the hFc sequence. The sequenced DNA construct was transiently transfected into HEK 293T cells in 150 mm plates using Lipofectamine (Gibco/BRL, Grand Island, N.Y.) according to the manufacturer's protocol. After 72 hour post-transfection, the serum-free conditioned medium (OptiMEM, Gibco/BRL, Grand Island, N.Y.) was harvested, spun and filtered. The cells are refed with fresh medium and harvested as above a further 72 hours later. Analysis of supernatants on Western blot after reducing SDS-PAGE using an anti-human IgG Fc polyclonal antibody showed significant amounts of the recombinant human soluble GPVI fusion protein (rhusGPVI:Fc) in the supernatants with a relative molecular mass of approximately 75–80 kDa relative to Mark 12 molecular weight standards cocktail (Novex, San Diego, Calif.).

The conditioned media was passed over a Prosep-G protein G column (10 mL, Bioprocessing Inc., Princeton, N.J.); the column was then washed with PBS, pH 7.4 and eluted with 200 mM glycine, pH 3.0 at 7 mL/min. Fractions from the 280 nm elution peak containing human rhusGPVI:Fc were pooled and dialyzed in 8000 MWCO dialysis tubing against 2 changes of 4 L PBS, pH 7.4 at 4° C. with constant stirring. The buffered exchanged material was then sterile filtered (0.2 mm, Millipore Corporation, Bedford, Mass.) and frozen at −80° C.

Platelet preparation: Blood from healthy volunteers was collected by venepuncture on acid-citrate-dextrose anticoagulant (ACD-A). When needed, platelets were labeled by incubating the platelet rich plasma (PRP) with 0.6 $\mu$M ($^{14}$C) 5-hydroxytryptamine for 30 min. at 37° C. Platelet pellets were obtained by centrifugation of the platelet rich plasma (PRP) and were washed two times as previously described (Jandrot-Perrus et al., 1997, *J. Biol. Chem.* 272:27035–27041).

Platelet aggregation and secretion: Aggregation of washed platelets ($3\times10^8$/ml) in reaction buffer was initiated by collagen type I (Bio/Data corp, Horsham, Pa.) or Cvx. Experiments were performed with stirring at 37° C. in a Chrono-Log aggregometer (Chrono-log corp. Haverton, Pa.). Release of ($^{14}$C) 5-hydroxytryptamine was measured as described previously (Jandrot-Perrus et al., 1997, *J. Biol. Chem.* 272:27035–27041).

Figure 18B:
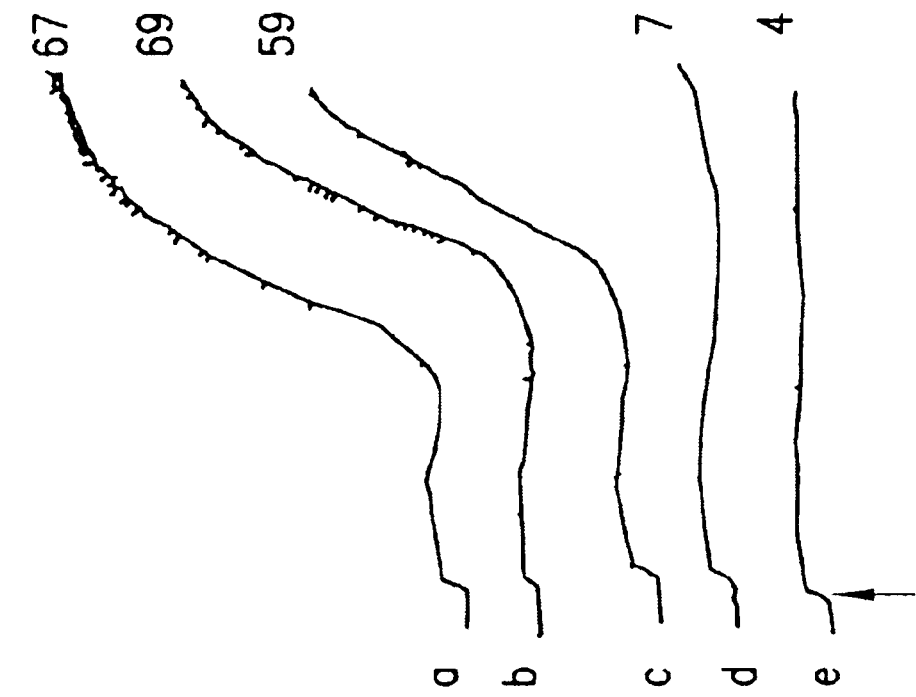
FIG. 18B: Tracing a: platelets were activated by collagen type I; tracing b: platelets were preincubated with 5 µg of recombinant soluble GPVI:Fc for two minutes before the addition of collagen; tracings c to e: collagen was preincubated with respectively 1 μg, 2.5 μg and 5 μg of recombinant soluble GPVI:Fc for two minutes before addition to platelets. [14]C5-HT labeled washed platelets were used. The percentage of [14]C5-HT release measured in each condition is indicated.
Figure 18A:
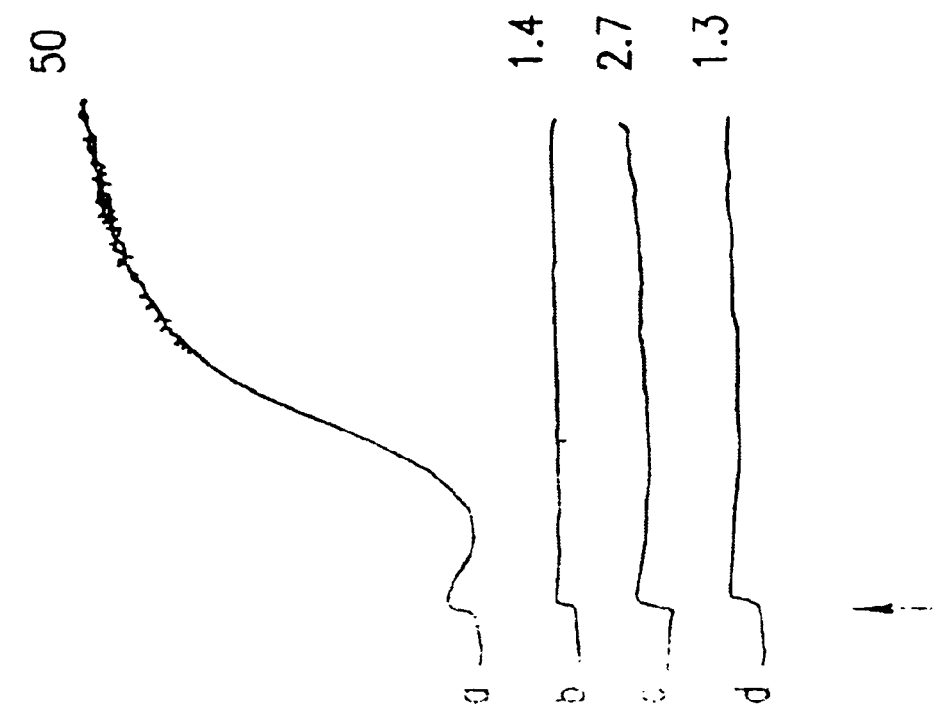
FIG. 18A: Tracing a: platelets were activated by 100 pM Cvx; tracing b: platelet suspension was incubated with 1 µg recombinant human soluble GPVI:Fc for two minutes before the addition of Cvx; tracing c and d: collagen was preincubated with 0.25 µg and 0.5 µg recombinant human soluble GPVI:Fc for two minutes respectively before addition to platelets.

Results rhusGPVI:Fc did not induce platelet aggregation or granule secretion by itself. When platelets were incubated with Cvx, addition of rhusGPVI:Fc (0.25 to 5 $\mu$g/ml) fully inhibited platelet aggregation and dense granule secretion (FIG. 18). In addition, when rhusGPVI:Fc was added to the platelet suspension prior to Cvx, it also inhibited aggregation and secretion, indicating that it could compete with platelet GPVI for Cvx (FIG. 18A). Incubation of collagen with rhusGPVI:Fc induces a loss in its ability to induce platelet aggregation and secretion (FIG. 18B). However, a tenfold higher concentration of rhusGPVI:Fc than required for Cvx was needed to produce this inhibitory effect. Furthermore, when recombinant soluble GPVI was added to platelets prior to collagen, no inhibition was observed (FIG. 18B). These results demonstrate that the extracellular domain of GPVI is active in blocking Cvx- and collagen-induced platelet aggregation.

Discussion

GPVI, despite it essential role in collagen-induced platelet aggregation, is described as having a minor role in platelet adhesion to collagen. Other receptors such as the GPIb-IX-V complex or the integrin $\alpha 2\beta 1$ are major players responsible for platelet adhesion to collagen. However, immobilized Cvx is able to induce platelet adhesion indicating that GPVI may be involved in adhesion in these conditions. The above results demonstrate that expression of GPVI in U937 and FDCP-1 cells induces cell adhesion to a collagen- or Cvx-coated surface. The number of cells that bound to immobilized Cvx was significantly higher than those bound to collagen. This result indicates differences in the density of GPVI binding sites on the two surfaces. Cvx is a pure GPVI ligand and when immobilized it produces a highly reactive surface while GPVI binding sites should be disseminated on collagen fibers resulting in a less reactive surface.

Nevertheless, these results indicate that recombinant GPVI mimics the physiological function of platelet GPVI (i.e., binding to collagen). The difference in reactivity between collagen and Cvx is further emphasized by the differences in the inhibitory effect that the recombinant soluble GPVI has on collagen and Cvx-induced platelet activation. Indeed, soluble recombinant GPVI inhibits Cvx-induced platelet activation in the absence of preincubation with Cvx whilst it requires a preincubation with collagen to inhibit collagen-induced platelet activation. This probably reflects the rapid kinetics of interaction between GPVI and Cvx compared to those between GPVI and collagen. The affinity of recombinant soluble GPVI for Cvx is probably very high for two reasons: (i) soluble GPVI is expressed in a divalent Fc fusion form and (ii) Cvx is multivalent due to its hexameric structure. Thus, GPVI binding sites on collagen fibers are probably dispersed and poorly accessible. Alternatively, these observations could also suggest that binding of collagen to its other receptors, including the integrin $\alpha 2\beta 1$, promotes its subsequent interaction with GPVI.

GPVI plays an important role in the development of thrombi probably because it is the receptor that appears to govern platelet activation at the contact of collagen and thus which induces platelet recruitment. Indeed, patients with GPVI deficiency or anti-GPVI-containing sera displayed bleeding disorders (see Background, above). The molecular cloning of GPVI provides the opportunity to characterize the mechanism of these deficiencies, the precise interaction between GPVI and the integrin $\alpha 2\beta 1$ in collagen-induced platelet activation but also the role of GPVI in thromboembolic diseases. GPIIb-IIIa (integrin $\alpha$IIb $\beta 3$) is the only platelet receptor against which efficient antagonists have been so far developed (Lefkovits et al., 1995, *N. Engl. J. Med.* 332:1553–9). Even if GPIIb-IIIa may be involved in platelet adhesion, its principal role is to bind fibrinogen allowing platelet aggregation and serving as the final common pathway of platelet thrombus formation regardless of the metabolic pathway initiating platelet activation. In contrast, GPVI is involved in an early step of platelet activation occurring immediately when platelets enter in contact with the subendothelial matrix.

GPVI represents an alternative and more specific target for new anti-thrombotic compounds. Antagonist can be directed against either of the two players, i.e., collagen GPVI binding sites or GPVI itself. Because these observations suggest that the GPVI binding sites are not easily accessible on collagen fibers, an antagonist directed against GPVI may be more efficient than an antagonist directed against collagen.

H. Bleeding Time of Mice Transplanted With Bone Marrow Cells Expressing GPVI

The results presented herein support the role of GPVI in the formation of platelet aggregates and the development of a hemostatic plug.

Materials & Methods

Isolation of Lin$^-$ bone marrow cells: Bone marrow cells were collected from mice that had been administered 150 mg/kg of 5-fluorouracil (5-FU) intravenously for four days. The cells were resuspended in phosphate buffered saline (PBS), 0.5% fetal calf serum (FCS) and incubated for 20 minutes at 4° C. with a mixture of four fluorescent fluorescein isothiocyanate (FITC)-conjugated rat monoclonal antibodies directed against mouse CD3e, CD11b, CD45R, and Ly-6G (Pharmingen, San Diego, Calif.). After labeling, cells were washed and incubated at 4° C. with anti-FITC microbeads (Miltenyi Biotech, Auburn, Calif.). After a 15 minute incubation, cells were washed, filtered through a large pore size filter and applied onto a magnetic cell sorting depletion column (types BS, Miltenyi Biotech) held onto a magnetic separator (Super MACS, Miltenyi Biotech). Depletion of the magnetically labeled cells (lineage positive) out of the bone marrow sample was done according to the manufacturer's instructions. In some experiments, Sca-1$^-$/Lin$^-$ cells were isolated using a Sca-1 multiSort Kit (Miltenyi Biotech). After separation, cells (Lin$^-$ or Sca-1$^-$/Lin$^-$) were washed and resuspended in DMEM, 10% FCS (Stem Cell Technologies, Vancouver, Canada).

Infection procedure: Isolated Lin$^-$ or Sca-1$^-$/Lin$^-$ bone marrow cells were stimulated at 37° C., 10% CO$^2$ with 10 mg/ml of recombinant mouse interleukin-3 (rmIL-3; Endogen, Woburn, Mass.). 10 ng/ml recombinant mouse interleukin-6 (rmIL-6; Endogen), 100 ng/ml recombinant mouse stem cell factor (rmSCF; R&D Systems, Inc., Mineapolis, Minn.). 100 ng/ml recombinant mouse fms-like tyrosine kinase-3 ligand (rmFlt-3L; R&D Systems, Inc), and 1% of a conditioned medium containing mouse thrombopoietin (mTPO). The mTPO conditioned medium (containing approximately 10$^4$ U/ml of mTPO) was collected from confluent MPZenTPO-virus producing cells, filtered and virus-inactivated at 56° C. for 1 hour. After two days of stimulation, bone marrow cells were infected with recombinant retrovirus containing the cDNA encoding murine full length GPVI, recombinant retrovirus containing the cDNA encoding the extracellular domain of murine GPVI, or a control retrovirus.

Bleeding assay: Infected bone marrow cells were transplanted into lethally irradiated mice, and two months post-transplantation mice were analyzed for the recovery time from a small tail vein incision. The blood flow from the incision was measured at 37° C. in saline.

Figure 19:
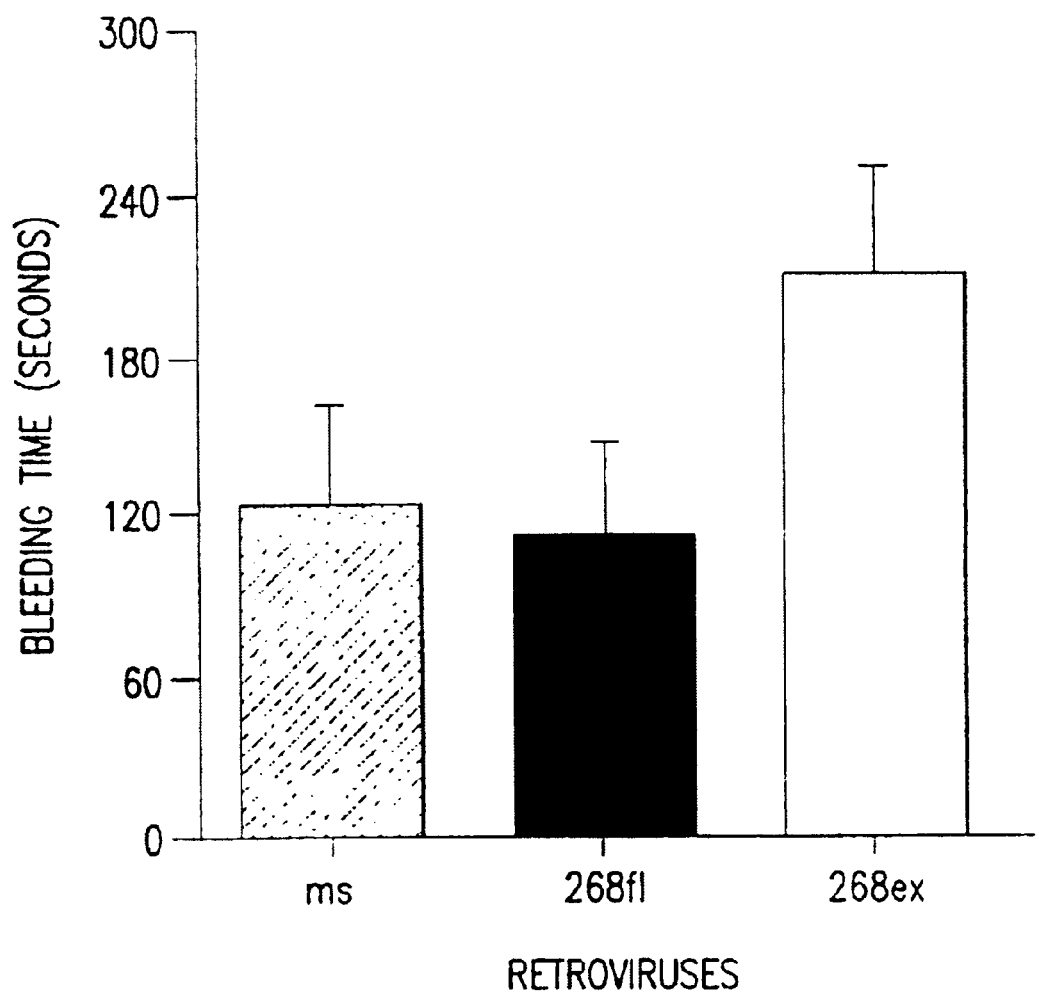
FIG. 19: Bleeding time of mice transplanted with bone marrow cells expressing GPVI. Irradiated mice transplanted with bone marrow cells expressing full length GPVI, the extracellular domain of GPVI, or a control were analyzed two months post-transplantation for the recovery time from a small tail vein incision.

Results and Discussion:

FIG. 19 depicts the bleeding time of lethally irradiated mice transplanted with bone marrow cells engineered to express full length GPVI, the extracellular domain of GPVI, or a control. Mice transplanted with bone marrow cells engineered to express the extracellular domain of GPVI, a soluble product, had the longest recovery time from a small tail vein incision. No significant difference in the recovery time from an incision in the tail vein was observed in mice transplanted with bone marrow cells engineered to express the full length GPVI from the control. These results suggest that the soluble form of GPVI inhibits the collagen-platelet interaction necessary for platelet aggregation and development of a hemostatic plug.

Anti-TANGO 268 Antibodies

Described below are antibodies that immunospecifically bind to TANGO 268 (otherwise referred to herein as glycoprotein VI or GPVI).

A. Mouse anti-Human GPVI Antibodies

Generation of Mouse Hybridomas

Human GPVI-human IgG$_1$Fc ("hGPVI-human IgG$_1$Fc") fusion protein consisting of the leader sequence from human CD5 plus the extracellular domain of human GPVI was prepared by transient transfection of mammalian COS cells using Lipofectamine (Gibco BRL) as per manufacturer's instructions. Supernatants were harvested on day 3 and day 7. Fusion protein was purified using Prosep™ Protein G glass heads.

Balb/c mice were immunized with DNA encoding the fusion protein described above using Gene Gun delivery of DNA encoding the fusion protein as described by Kilpatric et al., 1998, *Hybridoma* 17:569–576. A serum titer could be detected against the hGPVI-human IgG$_1$Fc fusion protein by ELISA (Enzyme Linked ImmunoSorbent Assay) using standard methodology (see, e.g., Antibodies: A Laboratory Manual by Ed Harlow and David Lane, Cold Spring Harbor Laboratory; Current Protocols in Immunology; eds. John E. Coligan, Ada M. Kruisbeek. David H. Margulies, Ethan M. Shevach, Warren Strober, and Richard Coico; John Wiley & Sons).

Mice were "boosted" with hGPVI-hIgG$_1$Fc fusion protein intravenously 4 days prior to harvesting of the spleens. Fusions were carried out using standard protocols. Spleen cells from one mouse were fused with SP2/0 myeloma cells using standard polyethylene glycol (PEG) protocol (see, e.g., Antibodies: A Laboratory Manual by Ed Harlow and David Lane, Cold Spring Harbor Laboratory; Current Protocols in Immunology; eds. John E. Coligan, Ada M. Kruisbeek, David H. Margulies, Ethan M. Shevach, Warren Strober, and Richard Coico; John Wiley & Sons).

Hybridoma lines were screened for secretion of human GPVI ("hGPVI") specific antibodies by ELISAs using plate bound human hGPVI-human IgG$_1$Fc or human IgG$_1$ (Sigma) or hsGPVI His tag protein. Also, hybridoma lines were screened for secretion of hGPVI specific antibodies by FACS analysis. Briefly, U937 cells or HEL cells were infected with a VSV-G pseudotyped pMSCVpac virus (Hawley et al., 1994, *Gene Therapy* 1:166) containing the full length human GPVI and selected for puromycin resistance. Hybridoma supernatants were screened by FACs for binding using these GPVI transduced U937 or HEL cells. Hybridoma supernatants were screened by FACS for binding to cell surface expressed human GPVI.

Nine hybridoma secreted antibodies specific for GPVI were isolated as determined by FACS analysis. All of these antibodies were IgG$_1$. These antibodies were tested for their ability to bind to purified unfixed human and monkey platelets as described below.

Selected murine hybridoma cell lines were cloned using ClonalCell™-HY Medium D (StemCell Technologies Inc) as per manufacturer's instructions.

Binding of Antibodies to Human and Baboon Platelets

One hundred μl human or baboon washed platelets (collected by venepuncture on acid-citrate-dextrose anticoagulant (ACD-A) were diluted $10^8$/mL in Tyrodes-hepes buffer pH 7.4 containing 75 mU/ml apyrase and 100 nM PGE1, 2 mM EDTA and 3.5 mg/ml BSA. Five μl of a monoclonal antibody solution was added to the washed platelets. The antibody and platelets were incubated together for 15 minutes at room temperature. Two μl of FITC-coupled goat F(ab)'$_2$ anti-mouse IgG were then added and the mixture was incubated for 30 minutes at room temperature in the dark. The controls used in the study were resting platelets (autofluoresecence) and secondary antibody alone. Further, convulxin and monoclonal antibodies produced by hybridoma cell lines 7120.2 and 71114.1 were included as controls. Binding analysis was determined by flow cytometry. The experiment was repeated serval times and the data presented is a summary of all of those experiments As would be expected of anti-GPVI antibodies, mouse monoclonal antibodies produced by hybridoma cell lines 8M14.3, 3F8.1, 9E18.3, 3J4.2, 6E12.3, 1P10.2, 4L7.3, 7H4.6, and 9012.2 bound to human and baboon platelets (Table 1). The mean value of the fluorescence intensities of the labeled platelets and the percentage of cells platelets labeled varied from antibody to antibody. As illustrated in Table 1, monoclonal antibodies produced by hybridoma cell lines 8M14.3, 3F8.1, 9E18.3, 3J4.2, 6E12.3, and 1P10.2 labeled the highest percentage of human and baboon platelets. Monoclonal antibodies produced by hybridoma cell lines 8M14.3, 3F8.1, 9E18.3, 3J4.2, 6E12.3, and 1P10.2 labeled baboon platelets with the highest fluorescence intensity. Further, monoclonal antibodies produced by hybridoma cell lines 3F8.1, 9E18.3, 3J4.2, 6E12.3, 1P10.2, and 7H4.6 labeled human platelets with the highest fluorescence intensity.

TABLE 1

Summary of FACS Analysis

| Clones & Controls | GVI transduced U937 or HEL cells | Human platelets % positive | Baboon platelets % positive | Human fluorescence intensity | Baboon fluorescence intensity |
| --- | --- | --- | --- | --- | --- |
| 8M14.3 | +++ | 64.2 | 94 | 27 | 59 |
| 3F8.1 | +++ | 85 | 93 | 42 | 73 |
| 9E18.3 | +++ | 71 | 92.5 | 31 | 62 |
| 3J24.2 | +++ | 82 | 73.8 | 36 | 26 |
| 6E12.3 | +++ | 80.7 | 93 | 38 | 68 |
| 1P10.2 | +++ | 80 | 88.8 | 35 | 46 |
| 4L7.1 | neg. | 1.7 | 7 | 7 | 10 |
| 4L7.3 | 937 | 62 | ND | ND | ND |
| 7H4.6 | ++ | 51 | 16 | 39 | 10 |
| 9012.2 | ++ | 21 | 33.8 | 14 | 18 |
| 7120.2* | neg. | 1.6 | 9 | 7 | 10 |
| 7H14.1* | neg. | 1.4 | 6.8 | 7 | 9 |
| Convulxin** | ND | 93 | 95 | 76 | 72 |

Negative control (*); Positive control (**); Negative (neg.); Not determined (ND); Moderate (++); High (+++)

Platelet Aggregation Activity of Mouse Monoclonal Antibodies

Human or baboon washed platelets at $3 \times 10^8$/mL in Tyrodes-hepes buffer pH 7.4. Incubation with antibodies (10 to 20 μg/mL final concentration) at 37° C. under stirring (1100 rpm) in the aggregometer (Chronolog) cuvette. Platelet aggregation was measured by the change in optical transmission induced by the antibody alone or by the addition of collagen type I.

As would be expected of anti-GPVI antibodies, mouse monoclonal antibodies produced by hybridoma cell lines 8M14.3, 3F8.1, 9E18.3, 3J4.2, 6E12.3, 1P10.2, 4L7.3, 7H4.6, and 9012.2 induced spontaneous aggregation and changes in the shape of human platelets. However, none of the antibodies tested induced spontaneous aggregation of baboon platelets, although some tested antibodies were able to induce changes in the shape of the baboon platelets. Blockage of collagen-induced baboon platelet aggregation was not detected at a concentration of 10 μg/ml of antibody. However, mouse monoclonal antibodies produced by hybridoma cell lines 7H4.6 and 8M14.3 shortened the collagen-induced baboon platelet aggregation time, suggesting that these antibodies may prime the platelet for activation.

TABLE 2

Summary of Platelet Aggregation

| Clones & controls | Human platelet spontaneous aggregation | Human platelet shape change with antibody | Baboon platelet spontaneous aggregation | Collagen blocker of baboon platelet aggregation | Baboon platelet shape change with antibody |
|---|---|---|---|---|---|
| 8M14.3 | +++ | Yes | 0 | 0* | Yes |
| 3F8.1 | ++ | Yes | 0 | 0 | Yes |
| 9E18.3 | +++ | Yes | 0 | 0 | Slight |
| 3J24.2 | + | No | 0 | 0 | No |
| 6E12.3 | ND | ND | ND | ND | ND |
| 1P10.2 | + | Slight | 0 | 0 | No |
| 7H4.6 | +++ | Yes | 0 | 0* | Slight |
| 9012.2 | + | Slight | 0 | 0 | No |
| 7120.2** | 0 | No | 0 | 0 | No |

Rapid (+++); Moderate (++); Slow (+); Shortened delay (*); Not determined (ND); Negative control (**)

Binding Affinity of the Mouse Monoclonal Antibodies

Kinetics analyses of various GPVI-specific antibodies were performed using surface plasmon resonance (SPR) technology on the BIAcore. GPVI-Fc fusion protein (the extracellular domain of GPVI fused to Fc) was covalently coupled to the sensor chip on 3 flowcells with varying surface densities. The antibodies were tested at 5 concentrations within the range of 200 nM, 100 nM, 50 nM, 25 nM, 12.5 nM, 6.25 nM, 3.13 nM, and 1.56 nM. Association rates, dissociation rates and binding affinities were calculated with the BIAcore evaluation software provided by Biacore, Inc. using a global analysis that models bivalent interactions. Prior to running the kinetic experiments, T75-Fc was used as a control to determine that the binding was specific to the GPVI partner. Specificity was also tested with both GPVI-his and MT93-his with the results showing good specificity. Table 3 below summarizes the dissociation constants of the monoclonal antibodies tested.

Western Blot Analysis

Washed platelets were solubilized in 2% SDS in the absence or presence of 5% β-mercaptoethanol (5 min. at 100° C.). Platelet proteins were separated by electrophoresis on polyacrylamide slab gels and blotted to PVDF membranes. The membranes were incubated with the monoclonal antibodies (2 μg/ml in PBS pH 8.1 containing 0.2% BSA and 0.1% Tween) alone or with collagen for two hours at room temperature. After washing, the membranes were incubated with peroxidase-coupled goat anti-mouse IgG (Amersham) for two hours at room temperature. After washing, the IgGs were detected by chemiluminescence (ECL, Amersham) on Kodak X-Omat AR films.

The results summarized in Table 3 below, indicate that the monoclonal antibodies produced by the hybridoma cell lines specifically bind to GPVI. In particular, each of the monoclonal antibodies produced by the hybridoma cell lines listed in Table 3 that were tested recognized a protein of the same molecular weight as GPVI on a non-reduced gel. Further, as expected of anti-GPVI antibodies, the addition of convulxin to the solution containing the monoclonal antibodies resulted in a reduction in the intensity of the labeled protein.

Inhibition of Collagen and/or Convulxin Binding to Soluble Human TANGO 268 by Mouse Monoclonal Antibodies The wells of microtiter plates (Immulon H. Dynex) were coated with type I or type III collagen (40 μg/ml in 20 mM $CH_3COOH$) overnight at 4° C. The wells of the plates were then saturated with 2 mg/ml of BSA for two hours at room temperature. Soluble human GPVI-Fc (the extracellular domain of GPVI fused to Fc; 5 nM in PBS pH 7.4 containing 0.2% BSA and 0.1% Tween) was added to the wells of the microtiter plates along or in combination with antibodies (10 μg/ml) and the plates were incubated for 2 hours at room temperature. After washing the wells of the microtiter plates, peroxidase coupled protein A (Amersham) was added to the wells of the plates and the plates were incubated for 2 hours at room temperature. The wells of the microtiter plates were washed and peroxidase substrate OPD was added to the wells of the plates. The plates were read at 495 nm in a spectrophotometer.

The wells of microtiter plates (Immulon H. Dynex) were coated with a monoclonal antibody which does not block convulxin binding to GPVI (5 μg/ml of monoclonal antibody 1P10.2 in PBS) overnight at 4° C. The wells of the plates were then saturated with 2 mg/ml of BSA for two hours at room temperature. Soluble human GPVI-Fc (the extracellular domain of GPVI fused to Fc; 5 nM in PBS pH 7.4 containing 0.2% BSA and 0.1% Tween) was added to the wells of the microtiter plates and the plates were incubated for 2 hours at room temperature. After washing the wells of the microtiter plates, buffer or antibodies (10 μg/ml) were added to the wells of the plates and the plates were incubated for 1 hour at room temperature. $^{125}$I-labeled convulxin (~1 nM) was added to the wells of the microtiter plates and the plates were incubated for 10 minutes at room temperature. After washing the wells of the microtiter plates, the plates were counted for bound $^{125}$I-labeled convulxin in a gamma counter.

Figure 20:
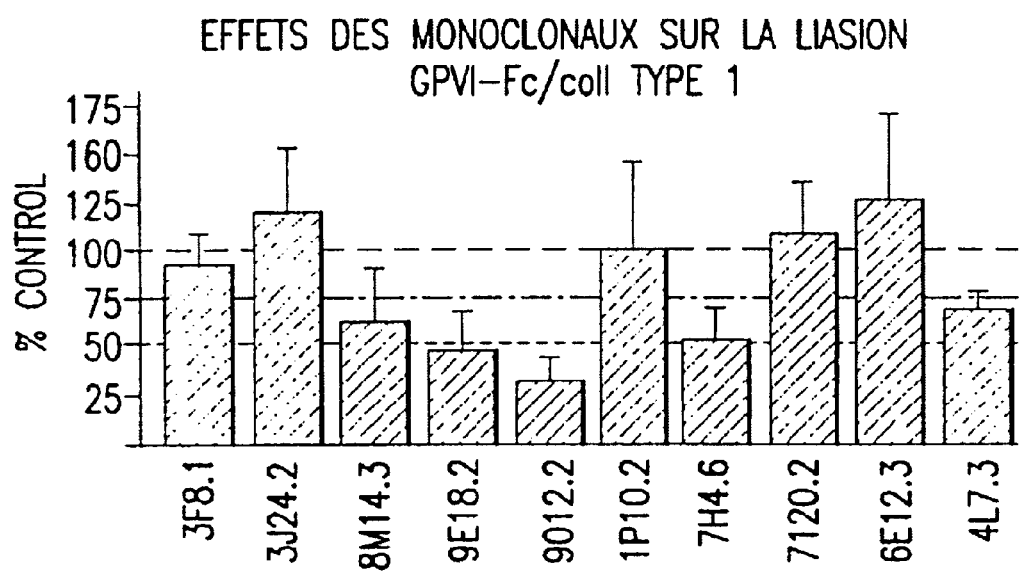
FIG. 20: Inhibition of collagen binding to GPVI by murine monoclonal antibodies. The graph depicts the ability of murine monoclonal antibodies to inhibit collagen binding to soluble human GPVI-Fc relative to a negative control (monoclonal antibody 7120.2).
Figure 21:
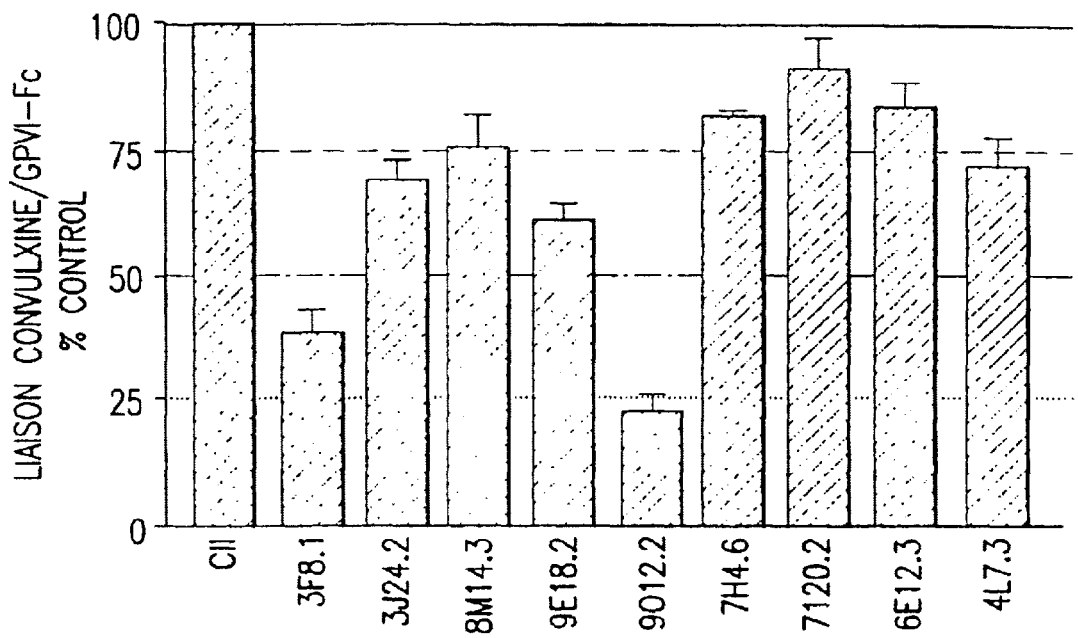
FIG. 21: Inhibition of convulxin binding to GPVI by murine monoclonal antibodies. The graph depicts the ability of murine monoclonal antibodies to inhibit convulxin binding to soluble human GPVI-Fc relative to a negative control (monoclonal antibody 7120.2).

Monoclonal antibodies produced by hybridoma cell lines 4L7.3, 7H4.6, 9E18.2, 8M14.3 and 9012.2 significantly blocked the binding of soluble human GPVI-Fc to collagen (FIG. 20; summarized in Table 3) compared to the negative control antibody (7120.2), indicating that these antibodies bind to a portion of GPVI which binds collagen or that these antibodies sterically inhibit collagen binding to GPVI. All of the monoclonal antibodies listed in FIG. 21 and Table 3 that were tested blocked the binding of soluble human GPVI-Fc to convulxin. In particular, monoclonal antibodies produced by hybridoma cells 3F8.1, 3J24.2, 9E18.2, 9E18.2, 9012.2, and 4L7.3 significantly reduced the binding of soluble human GPVI-Fc to convulxin. These results indicate that these antibodies bind to a portion of GPVI which binds convulxin or that these antibodies sterically inhibit collagen binding to GPVI.

TABLE 3

Summary of BIAcore, Western Blot, and Blocking Activity Assays

| Clones & control | $K_d$ (nM) | Western Blot | % of Inhibition of collagen binding of hrGPVI | % of Inhibition of convulxin binding of hrGPVI |
|---|---|---|---|---|
| 7120.2* | 210 | ND | 5 | 0 |
| 8M14.3 | 2.5 | +++ | 32 | 12 |
| 3F8.1 | 1.6 | +++ | 9 | 65 |
| 9E18.3 | 42 | +++ | 44 | 42 |
| 3J24.2 | 55 | +++ | 0 | 33 |
| 6E12.3 | 54 | ND | 0 | 20 |
| 1P10.2 | 16 | +++ | 10 | ND |
| 4L7.3 | 13 | ND | 20 | 33 |
| 7H4.6 | 46 | +++ | 41 | 19 |
| 9O12.2 | 18 | +++ | 58 | 75 |

Not determined (ND); High expression (+++); Negative control (*); Soluble human recombinant GPVI (hrGPVI)

B. Platelet Neutralizing Human Antibodies Specific to GPVI Isolated from a Combinatorial Phage Display Library Described below are single-chain antibodies of human origin that neutralize platelet aggregation by specifically binding to GPVI which were isolated from a combinatory phage display library.

Materials & Methods

Antibody Selection

A non-immune repertoire of $1.5 \times 10^{10}$ independent clones derived from human B-cells by PCR were displayed on the surface of filamentous bacteriophage as single-chain Fv-pIII fusions. $5 \times 10^{12}$ phage representing this repertoire were first depleted on $3 \times 10^7$ U937 cells that had been transduced with the empty retrovirus. Prior to adding phage, these cells were blocked in blocking solution comprising PBS, 2% milk, 1% BSA, 1 mM PMSF, and 2.5 m EDTA for 45 minutes at room temperature with gentle agitation. The depleted phage were then transferred to $3 \times 10^7$ retrovirally transduced U937 cells expressing full-length GPVI that had been blocked in a solution comprising PBS and 1% BSA (PBSB). The phage and GPVI expressing cells were incubated together for 2 hours on a rotisserie mixer with gentle rotation to allow the phage to bind to the GPVI expressing cells. Cells were centrifuged for 5 minutes at 500 g and the supernatant was removed. Cells were washed once with solution comprising PBSB and 0.1% Tween 20, nine times with solution comprising PBS and 0.1% BSA, and twice with PBS. After centrifugation and resuspension of cells in 1.5 ml $dH_2O$, phage were eluted by dropwise addition of an equal volume of 200 mM triethylamine. After a 7 minute incubation, the solution was neutralized by adding an equal volume of 1 M Tris-HCl, pH 7.4.

Eluted phage were superinfected into XLI-Blue E. coli that had been grown to $A_{600}=0.5$ in 2YT+10 µg/ml tetracycline. Infected bacteria were then spread on bioassay dishes and allowed to grown overnight at 37° C. The next day, bacteria were scraped from the biossay dishes and grown using standard procedures to produce phage to be used for the next round of selection. Three additional rounds of selection were performed using the procedure as described above. Both the input as well as the output titers of phage were measured at each round to monitor enrichment of GPVI-specific phage. No further enrichment was observed at the fourth round of selection.

Antibody Characterization

After the fourth round of selection, 43 independent clones were tested for binding to GPVI. Single colonies of XL-1Blue cells were grown in 0.3 ml, cultures of 2YT+1% glucose+100 µg/ml ampicillin in deep well plates at 37° C. for 16 hours. Plates were then centrifuged at 3000 rpm for 10 minutes on a Beckman ALLEGRA 6R centrifuge. E. coli pellets were resuspended in 0.15 mL fresh media containing 1 mM IPTG and 20 mM $MgCl_2$. These cultures were grown at 30° C. with vigorous shaking for 4–6 hours. Induced cultures were centrifuged and resuspended in 0.15 ml PBS. These cultures were then subjected to 6 cycles of freezing in a dry-ice/ethanol bath and thawing in a 37° C. water bath. Crude scFv's were then subjected to GPVI-U937 cell-based ELISAs, GPVI-Fc protein ELISAs, and FACS analysis on GPVI-U937 cells to test for GPVI binding.

GPVI-U937 cell-based ELISA

GPVI-U937 cells were washed twice with PBS and resuspended in Blocking Buffer (PBS, 2% milk, and 1% BSA). 150 µl of cell suspension ($2 \times 10^6$ cells/ml) was added to each well of a 96-well plate and the plate was gently agitated for 45 minutes at room temperature (RT). 50 µl of crude scFv was preincubated with 50 µl of 2× Blocking Buffer which contained Biotin-Anti-HA (1:500 dilution, Covance, Cat. No. Biotin-101L) at room temperature for 1 hour with gently agitation. This crude scFv-Blocking Buffer mixture was then added to wells of the 96-well plate and the plate was incubated at room temperature for 1 hour with gentle agitation. Cells were washed twice with in solution comprising PBS, 0.1% BSA, and 0.05% Tween 20 and once with solution comprising PBS and 0.1% BSA. The cells were then incubated with 75 µl of HRP-ExtrAvidin (1:1000 dilution, Sigma, Cat. No. E-2886) in Blocking Buffer for 45 minutes at room temperature. Finally, the cells were washed twice with solution comprising PBS and 0.05% Tween 20 and once with PBS. The cells were centrifuged and the cell pellets were resuspended in 130 µl of TMB and incubated for 10 minutes to allow the color to develop. Cells were centrifuged and 100 µl of each supernatant was transferred to the wells of a flexible Falcon plate (Falcon 3912), which had been filled with 50 µl of 0.5 M $H_2SO_4$ per well. Plates were read at 450 nm.

GPVI-Fc Protein ELISA 96-well microtiter plates (Nunc MaxiSorp) were coated with 50 µl of 2.5 µg/ml GPVI-Fc protein dissolved in PBS. An irrelevant Fc fusion protein (Tango 75-Fc; PCT Publication No. PCT Publication No. WO 99/15663, filed Apr. 1, 1999) was coated similarly as a control. Plates were sealed and incubated at 4° C. for 16 hours. The next day plates were washed four times with PBS 0.05% Tween and wells blocked with 250 µl of 2% nonfat milk at room temperature for 30 minutes. Thereafter, 50 µl of crude scFv was added to the well and the plate was incubated at room temperature for 1 hour. Plates were washed four times with PBS+0.05% Tween and 50 µl Biotin-Anti HA (1:500 dilation, Covance, Cat. No. Biotin-101L) was added and the plate was incubated at room temperature for 1 hr with gently agitation. Plates were washed four times with PBS+0.05% Tween and 50 µl TMB was added and color allowed to develop. The reaction was stopped by addition of 50 µl 0.5 M $H_2SO_4$ and plates were read at 450 nm (SpectraMax Plus, Molecular Devices).

FACS Analysis on GPVI-U937 Cells $5 \times 10^5$ U937 cells expressing GPVI were used for each scFv. Cells were washed once with Washing Buffer (cold-PBS without $Ca^{219}$ . $Mg^{2+}$, 0.1% BSA and 0.02% sodium azide), resuspended in 100 µl of Blocking Solution (2% Human IgG and 1% BSA in Washing Buffer) and incubated at 4° C. for 30 minutes. Cells were then centrifuged and resuspended in 5 µg of pure scFv in 100 µl of Washing Buffer and incubated at 4° C. for 1 hour. Cells were washed 3 times with Washing Buffer, resuspended in 100 µl of anti-HA monoclonal antibody (Covance, 10–20 µg/ml antibody in Washing Buffer) and incubated at 4° C. for 1 hour. Cells were then washed 3 times with Washing Buffer and incubated with 100 µl of FITC-labeled anti-mouse Ig (20 µg/ml antibody in Washing Buffer) at 4° C. for 1 hours. Cells were washed 3 time with Washing Buffer and resuspended in 0.5 ml of Washing Buffer. The cells were then analyzed by flow cytometer (Bectin-Dickenson) for scFv binding to GPVI. The same procedure was conducted using an irrelevant scFv as a negative control. All scFv's were also tested on mock-transduced U937 cells.

Antibody Sequencing

Clones that bound GPVI both in cell based and protein ELISAs were subjected to further analysis. First the scFv gene was amplified using PCR and the resulting product was digested with Bst NI restriction enzyme. The digested product was analyzed on a 2% agarose gel. Clones that had unique restriction patterns were then subject to full-length sequencing using dye-terminator chemistry.

Antibody Purification

Single-chain antibodies were expressed in E. coli by first ligating the Sfi I fragment containing the scFv gene from the pDISP4 phage display vector into an expression called pDISP4-His. Single colonies of Top 10 cells (Invitrogen) were used to innoculate 40 ml cultures of 2YT+1% glucose+ 100 µg/ml ampicillin which were grown in 500 ml flasks at 37° C. for 16 hours. Thereafter, E. coli were centrifuged at 3000 rpm for 10 minutes in a Beckman ALLEGRA 6R centrifuge and resuspended in an equal volume of fresh media containing 1 mM IPTG and 20 mM $MgCl_2$. These cultures were grown at 30° C. for 4–6 hours at which point bacteria were harvested by centrifugation.

Bacterial pellets were resuspended in 2 ml binding buffer (50 mM sodium phosphate+300 mM NaCl+10 mM Imidazole, pH 8.0) containing 1 mM PMSF and a cocktail of protease inhibitors (Boehringer Mannheim) and subjected to 6 cycles of freeze/thaw using a dry-ice ethanol bath and a 37° C. water bath. Bacteria were then briefly centrifuged and the supernatant was saved. This material was then loaded on Ni-NTA QuickSpin columns (Qiagen) and scFv tagged with the polyHis tail was captured while contaminating proteins flowed through the column. Bound protein was washed in two steps with binding buffer+20 mM and 35 mM Imidazole. Finally protein was eluted in binding buffer+ 250 mM Imidazole. Two 100 µl fractions were collected for each run. These were pooled and dialyzed against PBS. The purity of the scFv was checked using coomassie-stained SDS-PAGE (Novex). The scFv yield was determined by measuring the A280 using a factor of 0.7 mg/ml scFv for each absorbance unit.

Inhibition Assays

U937 cells expressing GPVI ("U937-GPVI cells") were washed twice with PBS and resuspended at $2 \times 10^6$ cells/ml with blocking buffer (PBS, 2% milk, and 1% BSA). Cells were blocked in 96 well plates at room temperature for 45 minutes. Cells were centrifuged at 500 g for 5 minutes and 25 µl of purified GPVI-Fc protein diluted in 25 µl of blocking buffer mixed with 25 µl of scFv. The final concentration of GPVI-Fc was varied from 0.45 nM to 1000 nM whereas the scFv concentration was fixed at 100 nM. Binding was allowed to occur at room temperature for 2 hours with gentle addition. Thereafter, cells were washed twice with in solution comprising PBS, 0.1% BSA, and 0.05% Tween-20 and once with in solution comprising PBS and 0.1% BSA. 50 µl of biotin-anti HA antibody (1:1000 dilution, Covance # BIOTIN-101L) was added and cells were incubated at room temperature for 1 hours. Cells were washed as described above and incubated with 50 µl HRP-Extravidin (1:1000 dilution, Sigma Cat. No. E-2886) in blocking buffer for 45 minutes at room temperature. Cells were washed twice with in solution comprising PBS and 0.05% Tween 20 and once with PBS, the cell pellets were resuspended in 110 µl TMB and developed for 10 minutes. Cells were centrifuged as above and 100 µl of supernatant from each well was transferred to fresh Falcon plates (Falcon 3912) which had been filled with 50 µl per well of 0.5 M $H_2SO$. Plates were read at 450 nm.

Blocking GPVI-Fc Binding to Collagen or Convulxin

Microtiter plates (ImmulonII Dynex) were coated with type I or type III collagen (40 µg/mL in 20 mM $CH_3COOH$) overnight at 4° C. and then saturated with 2 mg/mL BSA for two hours at room temperature. Soluble human GPVI-Fc (5 nM in PBS pH 7.4 containing 0.2% BSA and 0.1% Tween) in the absence or the presence of antibodies (10 µg/mL) was added to the wells of the microtiter plate and the plates were incubated for two hours at room temperature. After washing the wells, peroxidase coupled protein A (Amersham) was added to the wells and the plates were incubated for 2 hours at room temperature. After washing, peroxidase substrate was added and OD was measured at 495 nm.

Microtiter plates (ImmulonII Dynex) were coated with monoclonal antibody 1P10.2 (2 µg/mL in PBS) overnight at 4° C. and then saturated with 2 mg/mL BSA two hours at room temperature. Solube human GPVI-Fc (0.5 nM in PBS pH 7.4 containing 0.2% BSA and 0.1% tween) was added to the wells of the plate and the plate was incubated for two hours at room temperature. After washing the wells, buffer or antibodies (10 µg/mL) were added to the wells and the plates were incubated for one hour at room temperature. Next, $^{125}I0$labeled convulxin (~1 nM) was added to the wells and the plates were incubated for approximately 10 minutes. The wells were washed and counted for $^{125}I$-convulxin binding in a gamma counter.

Platelet Aggregation

Human PRP (platelet rich plasma) and PPP (platelet poor plasma) from whole blood. Whole blood was collected in a tube containing ACD (from VWR) and PRP was obtained by centrifugation at 900 rpm for 10 minutes at room temperature. The PRP was transferred with a polypropylene pipette into a polypropylene tube. The remaining blood was centrifuged at 3400 rpm for 10 minutes at room temperature to obtain the PPP and the PPP was transferred into new tube.

Three hundred µl of PRP was preincubated with different concentrations of ScFv A10, B4, C9, C10 or A9 for 5 or 6 minutes at room temperature and then collagen (Collagen reagent Horm which contains 1 mg/ml of native collagen fibrils type I from aquine tendons was purchased from NYCOMED ARANEIMITTEL GmbH, German) was added. PRP aggregation was measured in a cuvette with a KOWA's AG-10E aggregometry.

Figure 22:
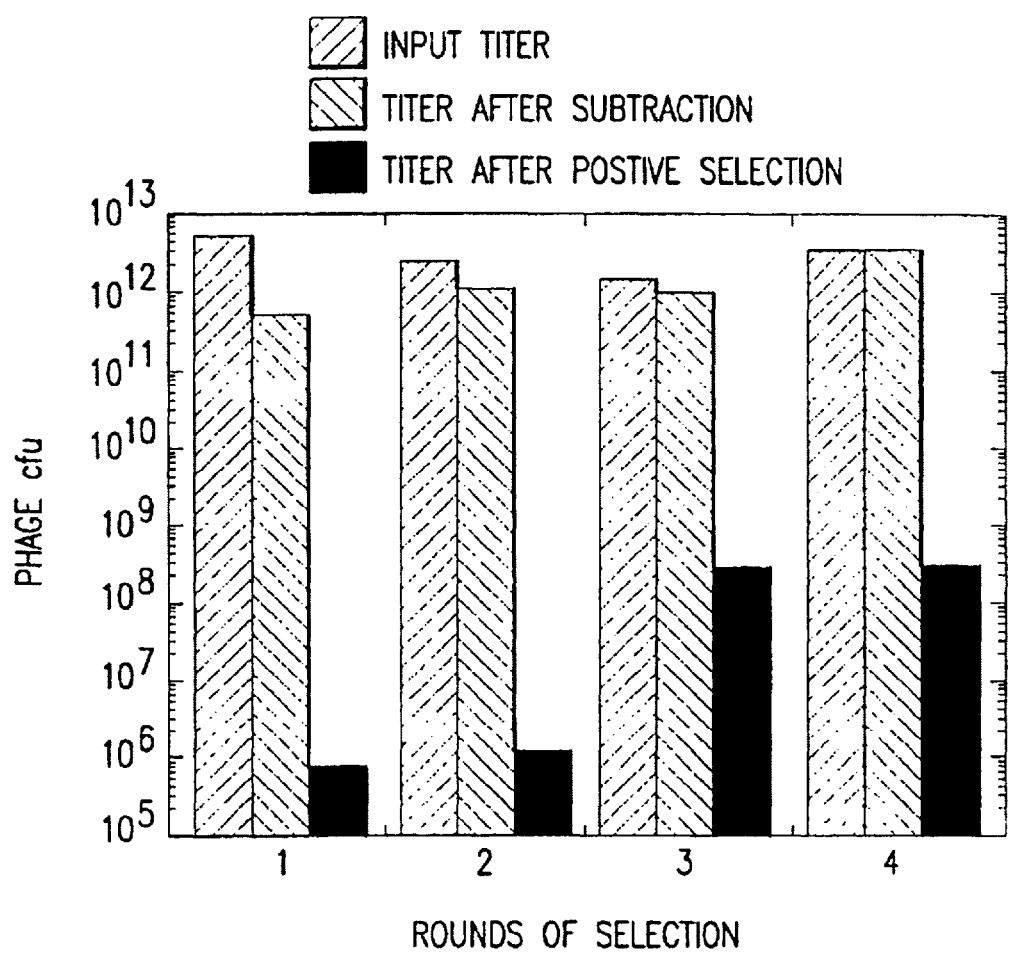
FIG. 22: Phage titers during selection on GPVI-U937 cells. Following each round of selection, XL1-Blue *E. coli* were superinfected with the selected phage and the titers of the phage were determined in a bioassay.

Results:

The titers of phage at each round of selection are shown in FIG. 22. Over four rounds of selection, the titer of input phase remained relatively constant while the titer of specific phage eluted from GPVI expressing U937 cells increased by a factor of more than 500. This suggests enrichment of phage specific to GPVI.

Figure 23A:
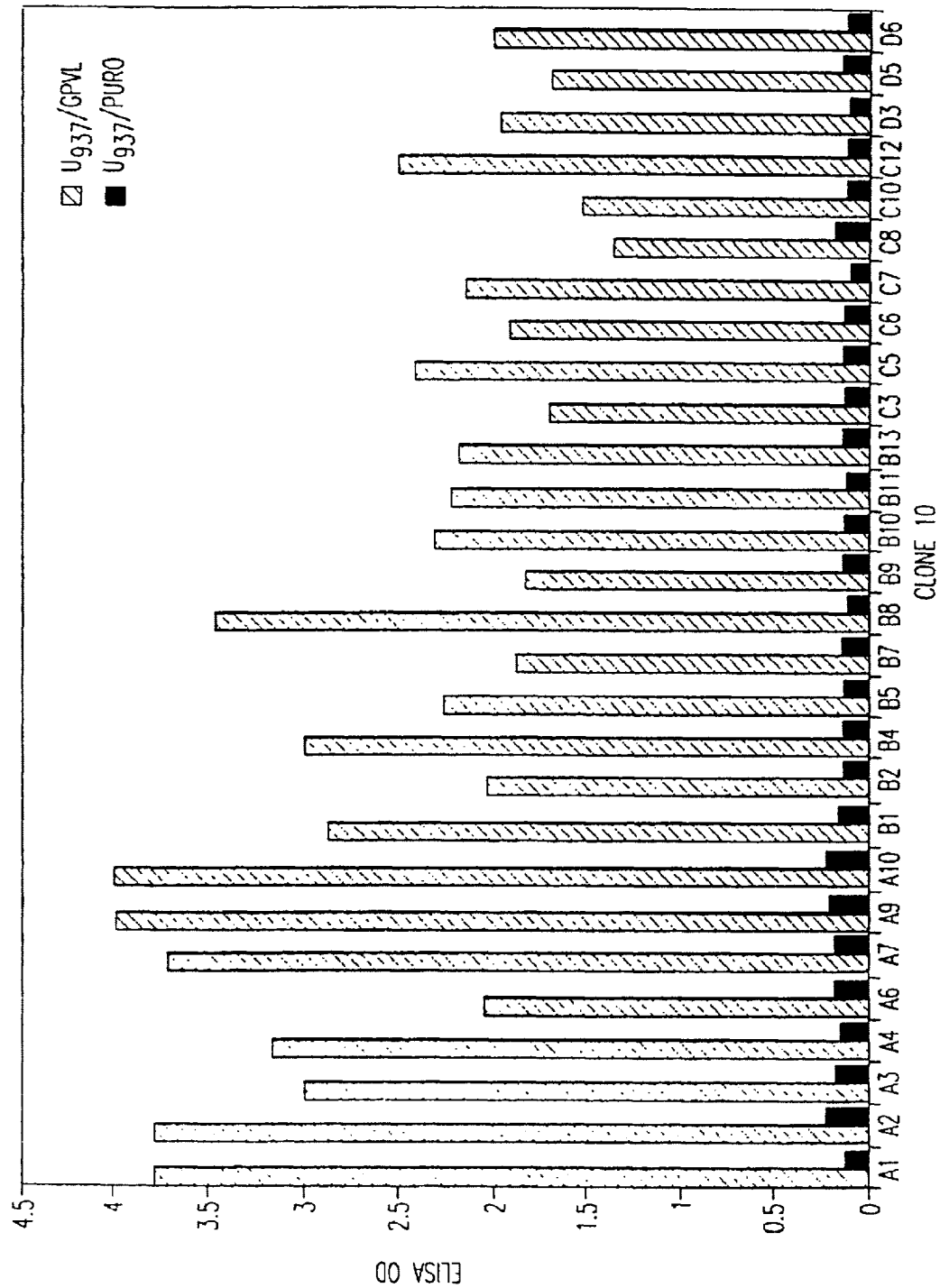
FIG. 23A: Binding of single chain Fvs ("scFv's") on GPVI-U937 cells. Crude scFv was incubated with U937 cells expressing GPVI (GPVI-U937 cells) and binding of scFv to GPVI-U937 cells was detected in a colorimetric ELISA.
Figure 23B:
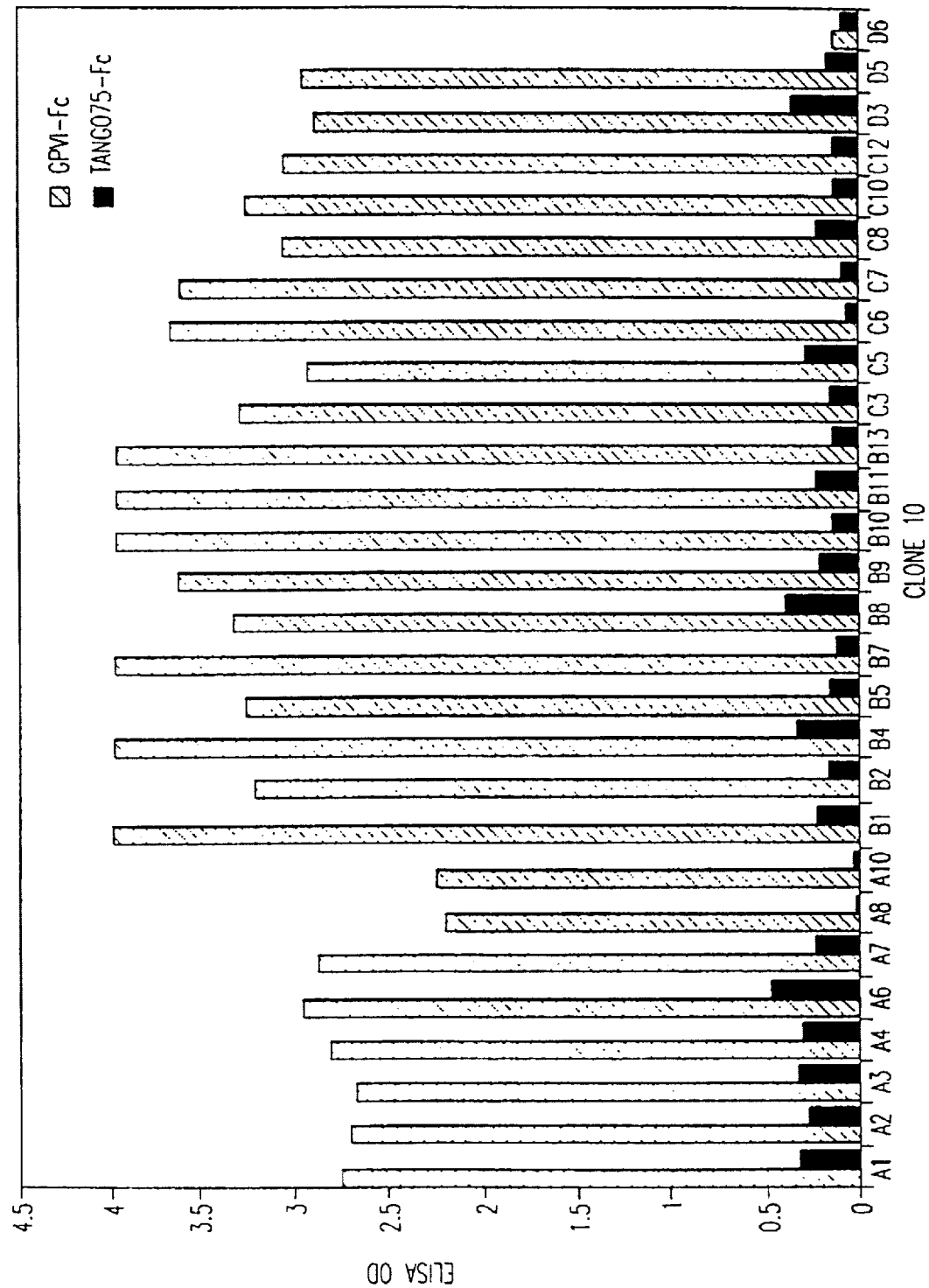
FIG. 23B: Binding of scFv's to GPVI-Fc. Crude scFv was incubated with GPVI-Fc fusin protein and binding of ScFv to GPVI-Fc was detected in a colorimetric ELISA.

Forty-three independent clones were picked after the fourth round of selection and their ability to specifically bind GPVI was tested in cell based and protein based ELISAs. FIG. 23A shows 28 of these scFv's bound specifically to GPVI on U937 cells compared to mock-transduced cells. These clones also bound specifically to purified GPVI-Fc in ELISAs compared to a control protein (FIG. 23B). These results suggest that the scFv's are indeed specific to GPVI.

Figure 24:
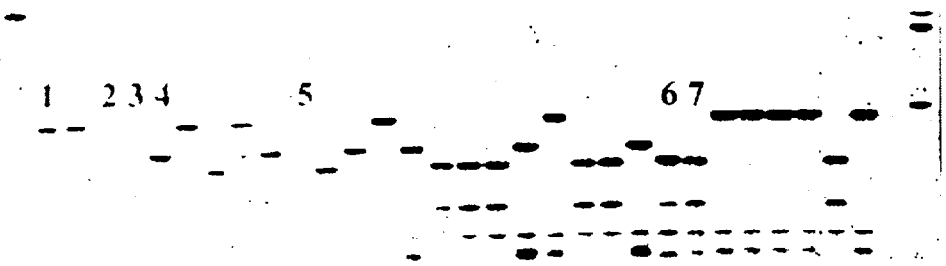
FIG. 24: BstN 1 fingerprints of GPVI-specific scFvs. scFv clones that bound to GPVI in both the cell-based and protein ELISAs were amplified and the resulting product was digested with the restriction enzyme BstN 1. The digested product was analyzed on a 2% agarose.
Figure 25A:
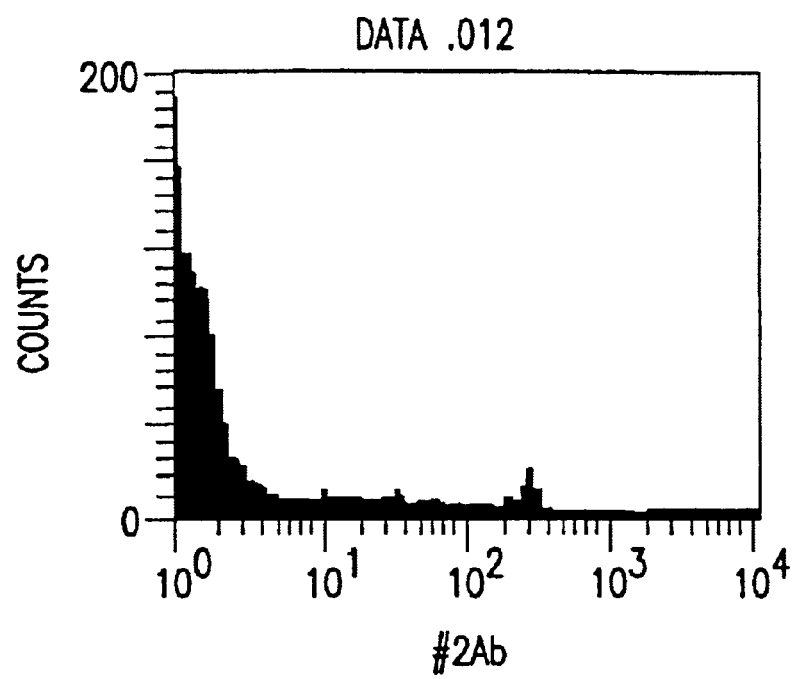
FIGS. 25A–25I: FACS analysis of the seven unique scFv's. Purified scFv's were incubated with U937 cells expressing GPVI (GPVI-U937 cells) and the binding of scFv's to GPVI-U937 cells was detected by FACS analysis.
Figure 25B:
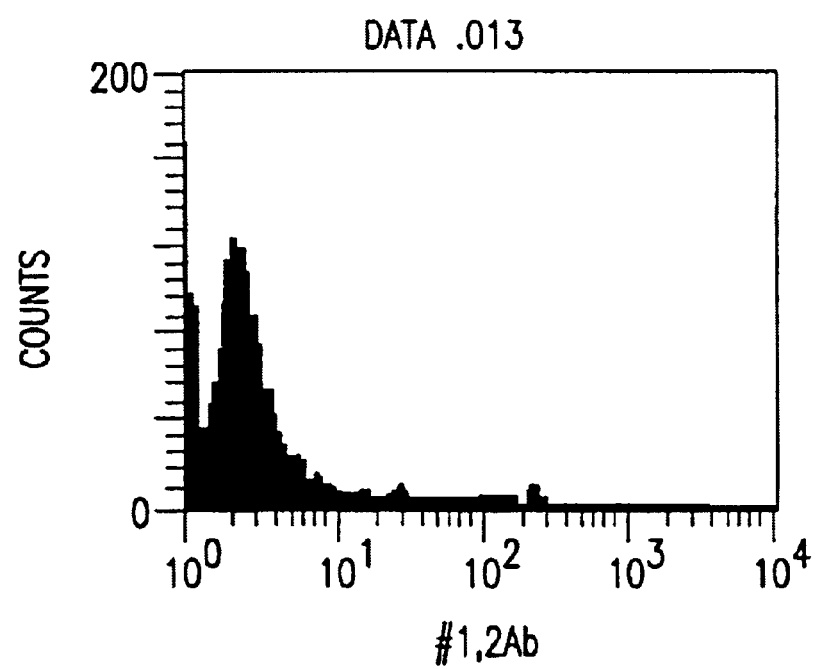
Figure 25C:
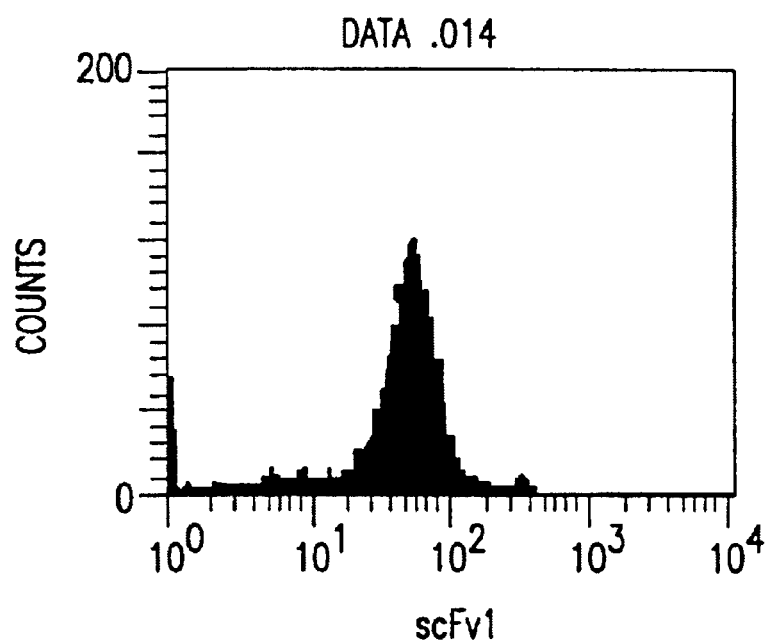
Figure 25D:
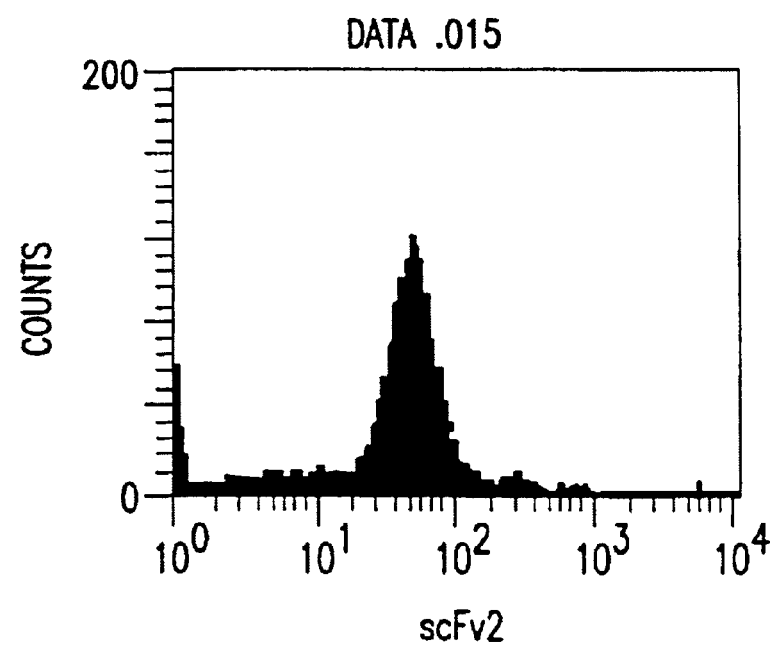
Figure 25E:
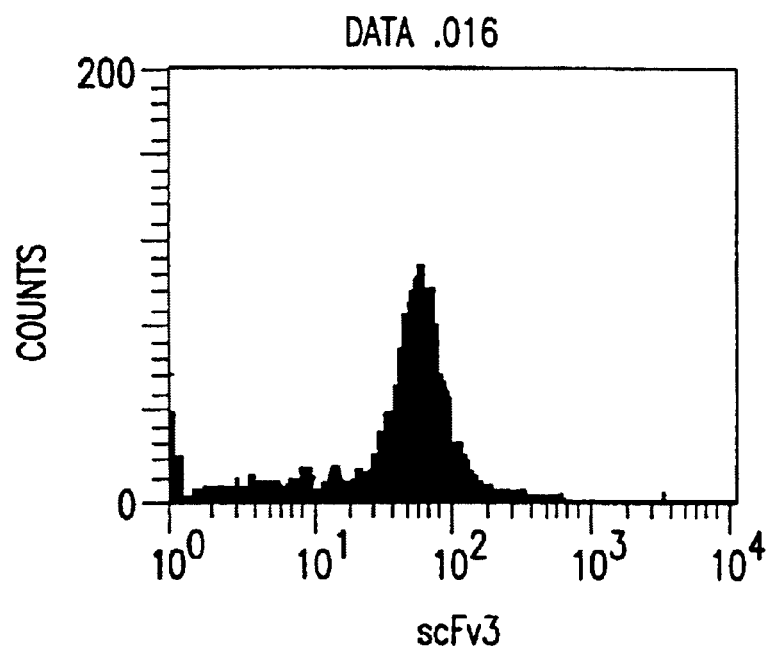
Figure 25F:
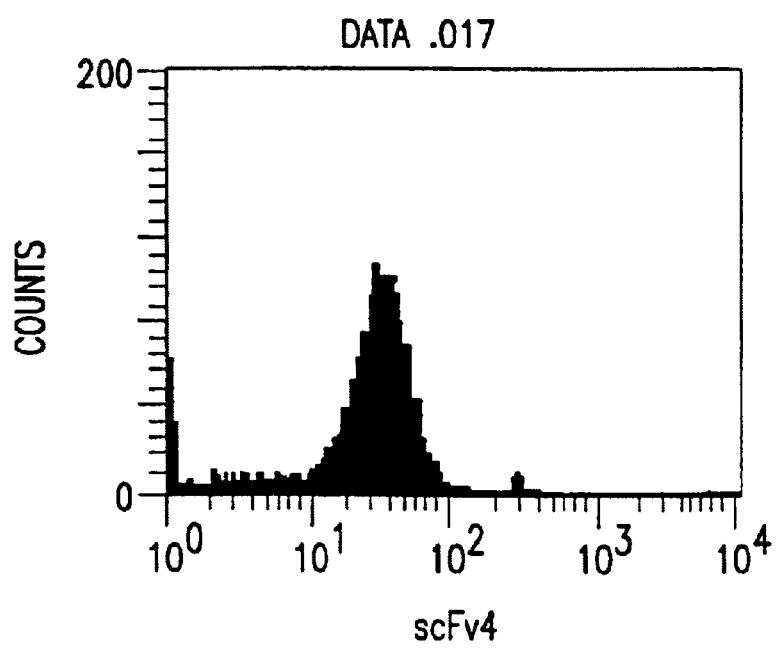
Figure 25G:
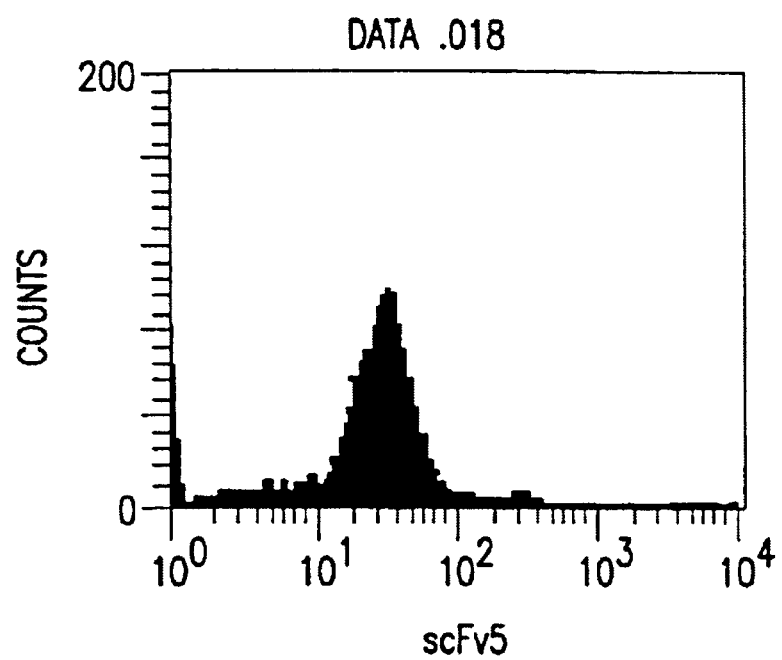
Figure 25H:
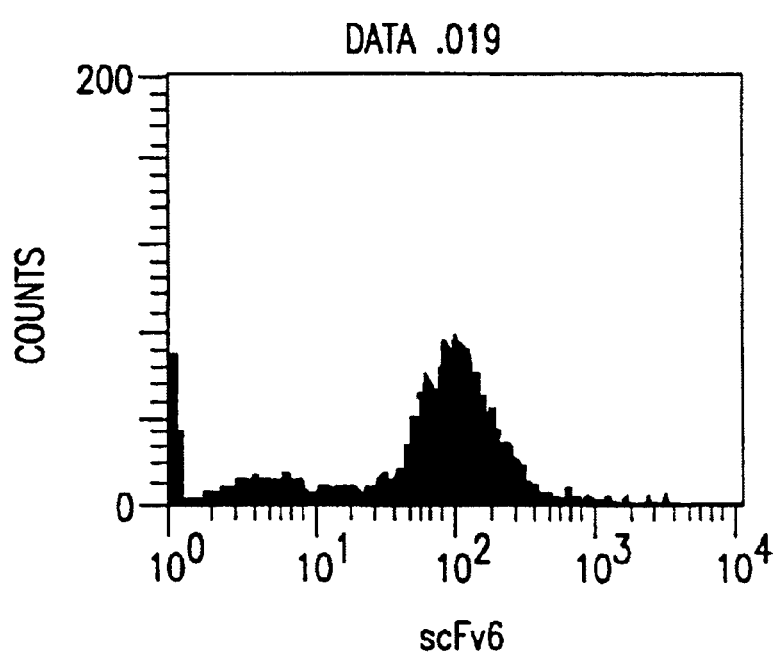
Figure 25I:
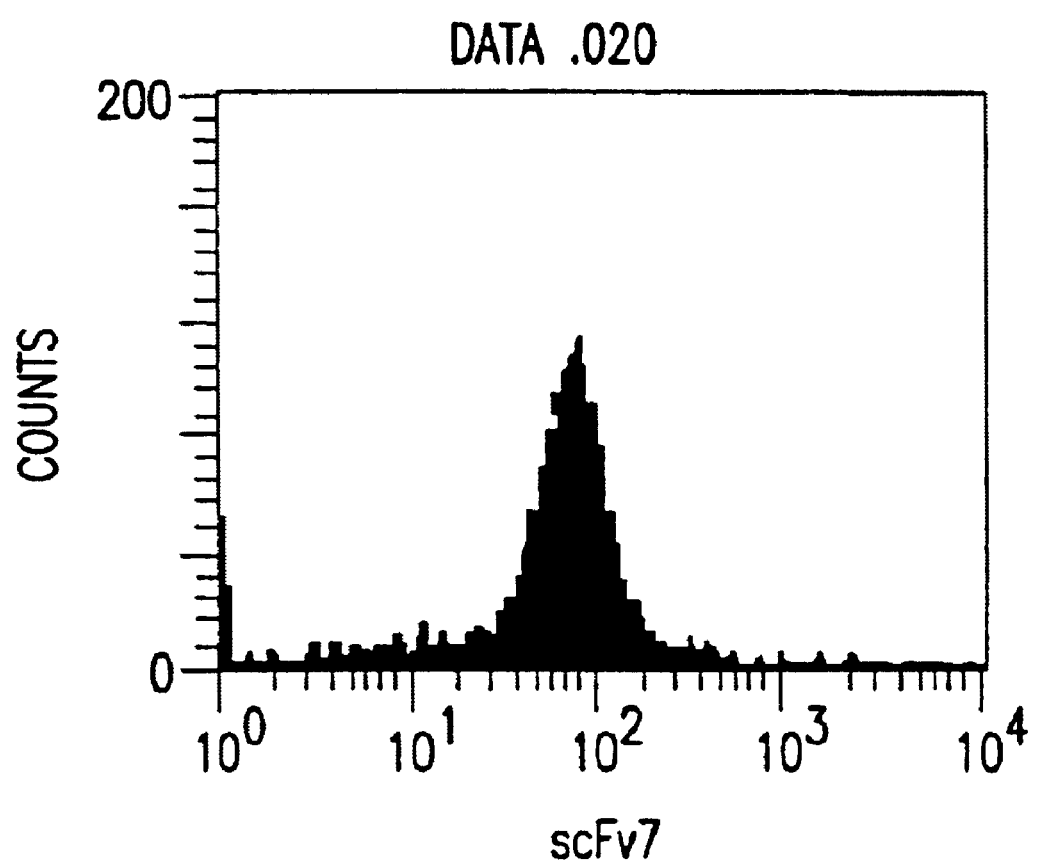

Bst NI fingerprinting of the 28 positive clones is shown in FIG. 24. A total of seven unique clones were found of the pool. All of seven of the clones recognized GPVI on transduced cells in a FACS experiment (FIGS. 25A–25I). CDR sequences of scFvs are shown in Table 7 below.

Figure 26:
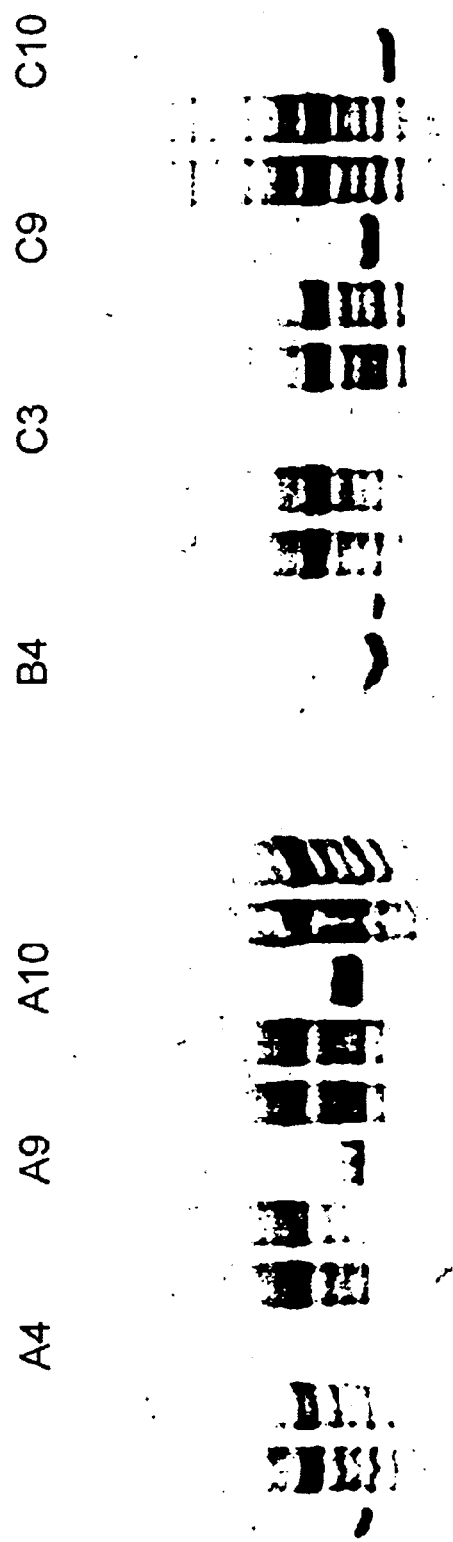
FIG. 26: Coosmassie staining of purified scFv's. scFv's were purified using Ni-chelate chromatography and the purity of the scFv's was confirmed by coomassie-stained SDS-PAGE.

The seven unique scFv's were purified using Ni-chelate chromatography. FIG. 26 shows the purity and yield of the scFv's as judged by coomassie staining and SDS-PAGE.

Figure 27:
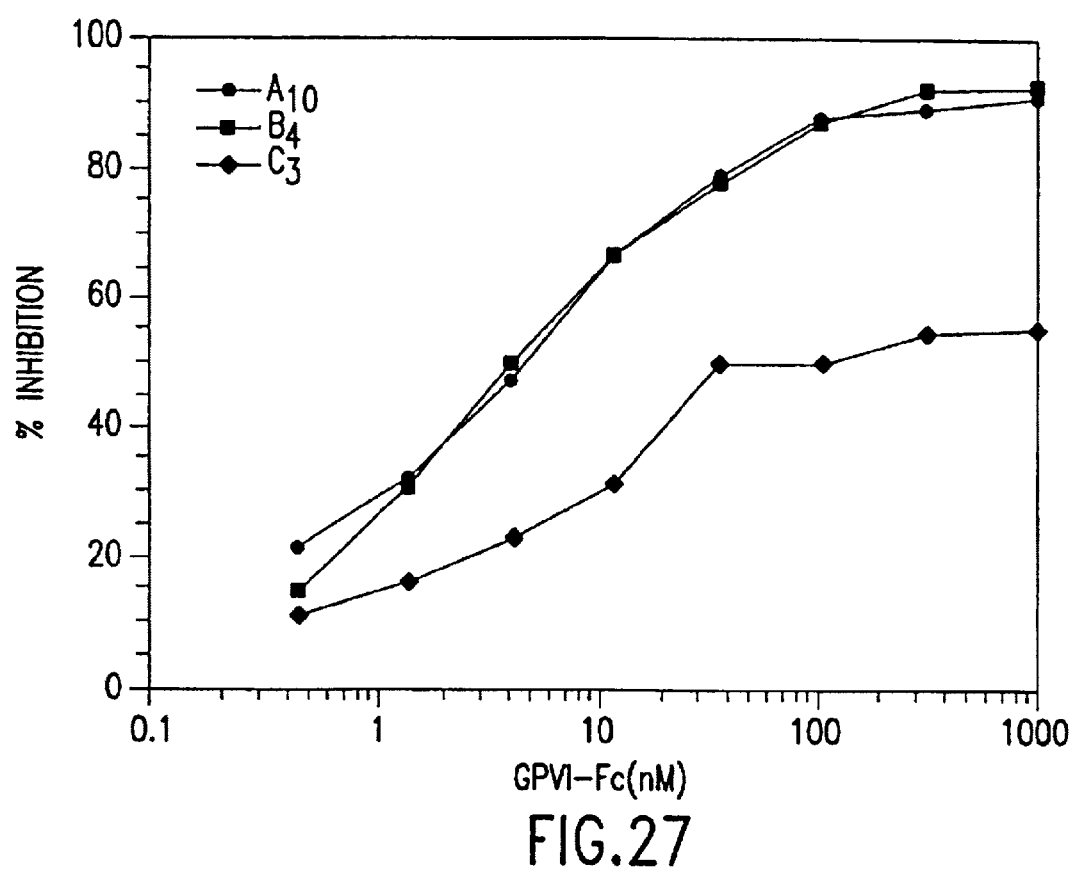
FIG. 27: Inhibition of scFv binding to U937 cells expressing GPVI by soluble GPVI-Fc fusion protein.

FIG. 27 shows data on the inhibition of three anti-GPVI scFv's (A10, B4, and C3) using soluble GPVI-Fc. All of the scFv's tested were inhibited specifically by GPVI-Fc. Inhibition constants ($IC_{50}$) for scFv clones A10, B4 and C3 were determined to be 4.5 nM, 5 nM and 38 nM, respectively.

The four scFvs specific for GPVI and a control antibody were analyzed for their ability to block the binding of soluble human GPVI-Fc to collagen or convulxin. scFvs 4L7.3, 7H4.6, 9E18.2 and 912.2 significantly blocked the binding of recombinant soluble human GPVI-Fc to collagen as compared to the control antibody. scFvs 3F8.1, 3J24.2, 4L7.3, 9E18.2 and 912.2 blocked the binding of recombinant soluble human GPVI-Fc to convulxin by more than 25% as compared to control irrelevant antibody.

The ability of scFvs A10, B4, C9, C10 and A9 to block platelet aggregation induced by collagen was determined. The results show that 110 µg/ml of A10 and 140 µg/ml of B4 can block platelet aggregation induced by 2 µg/ml of collagen, but that 160 µg/ml of A9, C9 or C10 can not block platelet aggregation induced by 2 µg/ml collagen. These results suggest that scFvs A10 and B4 are blocking agents for platelet aggregation induced by collagen.

C. Method of Generating Human Antibodies

HuMAb-Mouse™ mice (Medarex, Annandale, N.J.) expressing human Ig were immunized intraperitoneally with GPVI-Ig fusion protein at 20 µg/mouse with complete Freund's adjuvant. The immunization was repeated three more times at 14 day intervals with 10 µg/mouse of fusion protein in incomplete Freund's adjuvant. Two weeks after the last immunization, mice were given 30 µg soluble GPVI fusion protein intravenously and four days later fusion was carried out using spleen cells from the immunized mice, using methods described previously (Coligan et al. (eds), *Current Protocols in Immunology*, page 2.5.1 John Wiley and Sons, New York 1992).

Anti-GPVI antibodies were identified by standard ELISA with the following modifications: Plates were coated with 2 µg/ml GPVI-Ig fusion protein in PBS overnight and blocked with solution comprising PBS and 1% BSA at 37° C. for 2 hours. Tissue culture supernatants were added into ELISA plates and the plates incubated for 30 minutes at room temperature. The plates were then washed 4 times in solution comprising PBS and 0.01% Tween 20. A monoclonal anti-human Kappa light chain antibody (The Binding Site, Birmingham, UK, Cat# AP015) conjugated to peroxidase was used to detect bound human antibodies. Positively stained wells were transferred for further characterization by flow cytometry.

GPVI transfected cells were incubated with 50 µl of supernatant on ice for 30 minutes. Bound antibodies were detected with anti-human Ig to stain both IgG and IgM IgG (Jackson ImmunoResearch Laboratories, Cat#: 115-096-151) or with a gamma specific secondary antibody to stain only IgG (Jackson ImmunoResearch Laboratories, Cat#: 115-096-008). The results were analyzed by a FACSean (Becton-Dickinson).

D. The Ability of scFvs and Monoclonal Antibodies to Block GPVI from Binding to Collagen Antibodies were screened for their ability to block GPVI binding to collagen using an immunohistochemical assay developed from procedures previously described (Tonra and Mendell, 1987, *Journal of Neuroimmunology* 80:97–105).

Materials & Methods

Sample Preparation

Untreated 8–12 week old SJL/J mice were anaesthetized with an intraperitoneal injection of 125 milligrams of avertin (Aldrich Chemical Company, Inc., Milwaukee, Wis.) per kilogram of body weight. The heart was then exposed and mice were perfused through the left ventricle with 3 ml of saline containing 2500 International Units of heparin (Steris Laboratories, Inc., Phoenix, Ariz.) per liter of solution. This was followed by perfusion of 5 ml of fixative containing 2% paraformaldehyde (Sigma, St. Louis, Mo.) and 15% saturated picric acid (Sigma) in 0.1 M phosphate buffer, pH 6.9. The descending aorta was dissected and postfixed for 1.5 hours in the same fixative at room temperature. The descending aorta was then put at 4° C. overnight in 25% sucrose plus 0.008% azide (Sigma). The sucrose solution was changed after 12–24 hours and the tissue was incubated at 4° C. for another 24–48 hours in 25% sucrose plus 0.008% azide. The descending aorta was then frozen in Tissue Tek OCT (Sakura, Tokyo, Japan). Frozen 12 micrometer cross sections of the descending aorta were cut using a cryostat (Microm, VWR, West Chester, Pa.) onto poly-1-Lysine (3 mg/ml; Sigma) coated Superfrost Plus microscope slides (VWR). Slides were stored at –80° C. until staining.

Tissue Staining

Slides containing descending aorta sections were placed at 37° C. for 6 minutes and then tissue sections were encircled with the hydrophobic substance contained in a PAP pen (PRI, Mount Prospect, Ill.). Slides were then washed 2 times for 7.5 minutes each in 0.1 M phosphate buffer, pH 6.9 (PB). Sections were then incubated for 1 hour at room temperature in a pool of solution, bordered by the hydrophobic markings, containing a 1:50 dilution of normal donkey serum (Jackson ImmunoResearch Laboratories, Inc., West Grove, Pa.) diluted with PBX. PBX is made by adding 300 microliters of Triton X-100 (Sigma) to 100 ml of 0.1M PB. Slides were than washed three times for 10 minutes each in 0.1M PB. Next sections were incubated overnight at 4° C. with human GPVI conjugated to human Fc (Batch HT268C02 made at Millennium Pharmaceuticals, Inc.; 0.1 microgram/ml diluted with PBX). Slides were then washed three times for 10 minutes each in 0.1M PB. Next sections were incubated in the dark for 1 hour at room temperature with a donkey antibody conjugated to Fluorescein FITC or Rhodamine RedX (Jackson ImmunoResearch Laboratories, Inc.) that recognizes human Fc (2 µg/ml). Slides were then washed 3 times for 10 minutes each at room temperature. Finally, slides were coverslipped using Vectashield (Vector Laboratories, Burlingame, Calif.) and the sites of GPVI binding to mouse descending aorta sections was observed using a fluorescence microscope. The great majority of GPVI binding was located in the adventitial layer of the mouse descending aorta in all sections, with minor labeling between elastic lamina in some sections.

Assay Validation

The observed binding of human GPVI conjugated to human Fc to mouse descending aorta sections in the assay described above was shown to be due to human GPVI and not human Fc by showing that two other negative-control proteins, human neurotactin and mouse TANGO 75 (PCT Publication No. PCT Publication No. WO 99/15663, filed Apr. 1, 1999), conjugated to human Fc did not demonstrate binding to mouse aorta sections. Furthermore, the conclusion that human GPVI was binding collagen was supported by the co-localization of GPVI binding and Collagen Type III immunoreactivity in the adventitial layer, using an antibody raised to human collagen Type III (RDI, Flanders, N.J.). In addition, the localization of collagen type III to the adventitial layer in mouse aorta is identical to that described for collagen type III in normal human coronary artery (Henrita van Zanten et al., 1993, Journal of Clinical Investigation 93:615–632).

Assay for Blocking Ability

To evaluate the ability of mouse monoclonal antibodies or scFvs to block the binding of GPVI to collagen, the solution containing human GPVI conjugated to human Fc described above (0.1 µg/ml diluted with PBX) was preincubated with 10 µg/ml of the developed reagent for 1 hour at room temperature. This solution was then placed on the descending aorta sections overnight and the resulting fluorescent signal was compared to the control staining obtained when a reagent unrelated to GPVI or vehicle (phosphate buffered saline) was preincubated with human GPVI conjugated to human Fc. The ability to block GPVI binding was graded as none (−), low (+), medium (++), medium/high (+++), or complete blocking (++++). The assay was validated by showing that a monoclonal antibody to Neurotactin (5aI1) and a single chain Fv specific for ICOS were not able to block the binding of human GPVI conjugated to human Fc to mouse collagen on descending aorta sections.

Results

Table 4 below summarizes the ability of the listed mouse monoclonal antibodies or scFvs to block the binding of human GPVI conjugated to human Fc to mouse collagen using the assay described above.

TABLE 4

| Name | Antibody or scFv | Ability to Inhibit GPVI Binding |
| --- | --- | --- |
| 7120.2 | Monoclonal Antibody | − |
| 8M14.3 | Monoclonal Antibody | + |
| 3F8.1 | Monoclonal Antibody | ++++ |
| 9E18.3 | Monoclonal Antibody | ++ |
| 3J24.2 | Monoclonal Antibody | ++++ |
| 6E12.3 | Monoclonal Antibody | ++++ |
| 1P10.2 | Monoclonal Antibody | ++++ |
| 4L7.1/3 | Monoclonal Antibody | + |
| 7H4.6 | Monoclonal Antibody | + |
| 9012.2 | Monoclonal Antibody | ++++ |
| 7H14.1 | Monoclonal Antibody | − |
| 9E18.2 | Single Chain Fv | − |
| A9 | Single Chain Fv | − |
| A10 | Single Chain Fv | ++++ |
| C9 | Single Chain Fv | − |
| A4 | Single Chain Fv | + |
| C10 | Single Chain Fv | + |
| B4 | Single Chain Fv | ++++ |
| C3 | Single Chain Fv | +++ |
| D11 | Single Chain Fv | ++++ |

None (−), low (+), medium (++), medium/high (+++), or complete blocking (++++)

Uses of TANGO 268 Nucleic Acids, Polypeptides, and Modulators Thereof

As TANGO 268 was originally found in an megakaryocyte library, and in light of the fact that TANGO 268 has been shown herein to be GPVI, TANGO 268 nucleic acids, proteins, and modulators thereof can be used to modulate the proliferation, morphology, migration, differentiation, and/or function of megakaryocytes and platelets, including during development, e.g., embryogenesis. TANGO 268 nucleic acids, proteins, and modulators thereof can also be used to modulate leukocyte-platelet and platelet-endothelium interactions in inflammation and/or thrombosis. Further, TANGO 268 nucleic acids, proteins, and modulators thereof can be used to modulate platelet aggregation and degranulation. For example, antagonist to TANGO 268 action, such as peptides, antibodies or small molecules that decrease or block TANGO 268 binding to extracellular matrix components (e.g., collagen or integrins) or antibodies preventing TANGO 268 signaling, can be used as collagen or platelet release and aggregation blockers. In a specific example, a polypeptide comprising the extracellular domain of TANGO 268 can be used to decrease or block TANGO 268 binding to extracellular matrix components (i.e., collagen), or to prevent platelet aggregation. In another example, agonists that mimic TANGO 268 activity, such as peptides, antibodies or small molecules, can be used to induce platelet release and aggregation.

In further light of the fact that TANGO 268 represents GPVI, and its expression is restricted to cells of the megakaryocyte lineage, TANGO 268 nucleic acids, proteins, and modulators thereof can be used to modulate disorders associated with abnormal or aberrant megakaryocyte and/or platelet proliferation, differentiation, morphology, migration, aggregation, degranulation and/or function. Examples of these disorders include, but are not limited to, bleeding disorders (e.g., bleeding tendency and/or prolonged bleeding time) such as thrombocytopenia (e.g., idiopathic thrombocytopenic purpura (ITP) or immune thrombocytopenia or thrombocytopenia induced by chemotherapy or radiation therapy).

As TANGO 268 represents GPVI, and GPVI is a component is processes involving platelet binding to the vascular subendothelium, platelet activation and inflammation processes, TANGO 268 nucleic acids, proteins, and modulators thereof can be used to modulate thrombotic disorders (e.g., thrombotic occlusion of coronary arteries), hemorrhagic disorders, diseases exhibiting quantitative or qualitative platelet dysfunction and diseases displaying endothelial dysfunction (endotheliopathies). These diseases include, but are not limited to, coronary artery and cerebral artery diseases. Further, TANGO 268 nucleic acids, proteins, and modulators thereof can be used to modulate cerebral vascular diseases, including stroke and ischemia, venous thromboembolism diseases (e.g., diseases involving leg swelling, pain and ulceration, pulmonary embolism, abdominal venous thrombosis), thrombotic microangiopathies, vascular purpura, and GPVI deficiencies as described, e.g., in Moroi and Jung, 1997, *Thrombosis and Haemostasis* 78:439–444. TANGO 268 nucleic acids, proteins, and modulators thereof can be used to modulate symptoms associated with platelet disorders and/or diseases (e.g., bleeding disorders). In particular, TANGO 268 nucleic acids, proteins, and modulators thereof can be used to modulate symptoms associated with ITP such as purpura and severe bleeding problems.

As GPVI has been shown to be important for platelet adhesion and aggregation, and platelet adhesion and aggregation play an important role in acute coronary diseases, TANGO 268 nucleic acids, proteins and modulators thereof can be used to modulate coronary diseases (e.g., cardiovascular diseases including unstable angina pectoris, myocardial infarction, acute myocardial infarction, coronary artery disease, coronary revascularization, coronary restenosis, ventricular thromboembolism, atherosclerosis, coronary artery disease (e.g., arterial occlusive disorders), plaque formation, cardiac ischemia, including complications related to coronary procedures, such as percutaneous coronary artery angioplasty (balloon angioplasty) procedures). With respect to coronary procedures, such modulation can be achieved via administration of GPVI modulators prior to, during, or subsequent to the procedure. In a preferred embodiment, such administration can be utilized to prevent acture cardiac ischemia following angioplasty.

TANGO 268 nucleic acids, proteins and modulators thereof can, therefore, be used to modulate disorders resulting from any blood vessel insult that can result in platelet aggregation. Such blood vessel insults include, but are not limited to, vessel wall injury, such as vessel injuries that result in a highly thrombogenic surface exposed within an otherwise intact blood vessel e.g., vessel wall injuries that result in release of ADP, thrombin and/or epinephrine, fluid shear stress that occurs at the site of vessel narrowing, ruptures and/or tears at the sites of atherosclerotic plaques, and injury resulting from balloon angioplasty or atherectomy.

Preferably, the TANGO 268 nucleic acids, proteins and modulators (e.g., anti-TANGO 268 antibodies) thereof do not effect initial platelet adhesion to vessel surfaces, or effect such adhesion to a relatively lesser extent than the effect on platelet-platelet aggregation, e.g., unregulated platelet-platelet aggregation, following the initial platelet adhesion. Further, in certain embodiments, it is preferred that the TANGO 268 nucleic acids, proteins and modulators (e.g., anti-TANGO 268 antibodies) thereof do not effect other platelet attributes or functions, such as agonist-induced platelet shape change (e.g., GPIb-vWF-mediated platelet agglutination induced by ristocetin), release of internal platelet granule components, activation of signal transduction pathways or induction of calcium mobilization upon platelet activation.

Further, polymorphisms associated with particular TANGO 268 alleles, such as those in platelet receptor glycoprotein Ia/IIa that are associated with risk of coronary disease (see, e.g., Moshfegh et al., 1999, *Lancet* 353:351–354), can be used as a marker to diagnose abnormal coronary function (e.g., coronary diseases such as myocardial infarction, atherosclerosis, coronary artery disease, plaque formation).

In further light of the fact that TANGO 268 is GPVI, TANGO 268 nucleic acids, proteins and modulators thereof can be used to modulate disorders associated with aberrant signal transduction in response to collagen or other extracellular matrix proteins.

In addition to the above, TANGO 268 nucleic acids, proteins and modulators thereof can be utilized to modulate disorders associated with aberrant levels of TANGO 268 expression and/or activity either in cells that normally express TANGO 268 or in cells that do not express TANGO 268. For example, TANGO 268 nucleic acids, proteins and modulators thereof can be used to modulate disorders associated with aberrant expression of TANGO 268 in cancerous (e.g., tumor) cells that do not normally express TANGO 268. Such disorders can include, for example, ones associated with tumor cell migration and progression to metastasis.

In light of the fact that TANGO 268 (i.e., GPVI) has been shown to interact with collagen, and the progression, migration and metastasis of cancer cells has been shown to correlate with the attachment of cancer cells to interstitial collagen (see, e.g., Martin et al., 1996, *Int. J. Cancer* 65:796–804), abnormal and/or aberrant TANGO 268 expression (e.g., expression of TANGO 268 in cells, such as tumor cells, that do not normally express it or increased expression of TANGO 268 in cells that do normally express it) can be used as a marker for the progression, migration and metastasis of cancerous cells. In particular, abnormal and/or aberrant TANGO 268 expression can be used as a marker for the progression, migration and metastasis of colon cancer and liver cancer.

In light of TANGO 268 exhibiting homology to human monocyte inhibitory receptor, TANGO 268 nucleic acids, proteins and modulators thereof can be used mediate the downregulation of cell activation via phosphatases. In light of TANGO 268 containing two Ig-like domains, TANGO 268 nucleic acids, proteins and modulators thereof can be used to modulate immunoregulatory functions. Further, as TANGO 268 is expressed in the liver, embryo, bone marrow, and peripheral blood, TANGO 268 nucleic acids, proteins, and modulators thereof can be used to treat disorders of these cells, tissues or organs, e.g., liver disorders and immunological disorders.

TANGO 268 is expressed on the surface of platelets. As such, a cellular and therapeutic target of modulators of TANGO 268 (e.g., anti-TANGO 268 antibodies) is readily available for testing and analysis (e.g., for in vitro testing and analysis). This coupled with the availability of several different relevant platelet assays (see below) provides an unusual drug development opportunity for TANGO 268 modulators. For example, the in vivo pharmacodynamic characterization of TANGO 268 modulators can be facilitated via the availability of various platelet assays (e.g., prologation of bleeding time, quantitative measurement of TANGO 268 receptor blockade, inhibition of ex vivo platelet aggregation) that can be correlated with each other to permit more effective assessment of a modulator's functional consequences. The correlation available for such assays, therefore, allows for the in vitro characterization of a TANGO 268 modulator to more directly apply to the measurement of the modulator's therapeutic effect.

In addition to utilizing the availability of platelets and platelet assays for assessing the therapeutic efficacy, including clinical efficacy, of a TANGO 268 modulator, this availability can also be utilized for preclinical drug development aspects such as determining modulator dosage response, toxicology, magnitude of effect (e.g., magnitude of initial effect and magnitude of effect's duration), function, specificity (e.g., specificity with respect to particular platelet functions), receptor specificity, and species specificity (which, in turn, can identify appropriate animal models for pharmacology studies).

Modulators of TANGO 268 platelet aggregation can also be utilized, e.g., for ex vivo procedures, e.g., ex vivo inhibition of platelet aggregation.

Assays for the Detection of TANGO 268 Expression or Activity

The expression of TANGO 268 can be readily detected, e.g., by quantifying TANGO 268 protein and/or RNA. Many methods standard in the art can be thus employed, including, but not limited to, immunoassays to detect and/or visualize gene expression (e.g., Western blot, immunoprecipitation followed by sodium dodecyl sulfate polyacrylamide gel electrophoresis (SDS-PAGE), immunocytochemistry, etc) and/or hybridization assays to detect gene expression by detecting and/or visualizing respectively mRNA encoding a gene (e.g., Northern assays, dot blots, in situ hybridization, etc), etc. Ligand binding assays, such as described above, can be performed to assess the function of TANGO 268.

The activity of a TANGO 268 protein can be measured by employing methods known to those of skill in the art. For example, the activity of a TANGO 268 protein can be analyzed by treating of platelets or TANGO 268-transfected cells with collagen or convulxin and measuring the effect of such treatment on the level of tyrosine phosphorylation of signaling molecules, such as FcR$\gamma$, Syk, and PLC$\gamma$2 (e.g., tyrosine phosphorylation can be detected by immunoprecipitation followed by SDS-PAGE, kinase assays, etc.). The activity of a TANGO 268 protein can also be analyzed by measuring changes in the concentration of free intracellular $Ca^{2-}$ induced by the treatment of platelets or TANGO 268 transfected cells with collagen or convulxin. Briefly, platelets or TANGO 268 transfected cells are incubated with fura-2 fluorescence at 37° C. and, then incubated with 2 mM $CaCl_2$ prior to incubation with convulxin, collagen or thrombin (an agent that does not activate TANGO 268). The cells are lysed in lysis buffer, and the concentration of free intracellular $Ca^{2-}$ is measured by fluorescence at 37° C. using a spectrophotometer (see, e.g., Jandrot-Perrus et al., 1997, *J. of Biol. Chem.* 272:27035–27041).

The activity of a TANGO 268 protein can also be analyzed by a platelet adhesion assay. Briefly, the adhesion assay is performed as follows: $^{51}Cr$-labeled platelets are incubated in microtiter plates that have collagen, convulxin or BSA immobilized to the surface of the wells, the cells are washed, 2% SDS is added to each well, and the number of adherent platelets is determined by counts for $^{51}Cr$ using a scintillation counter (see, e.g., Jandrot-Perrus et al., 1997, *J. of Biol. Chem.* 272:27035–27041). Further, the activity of a TANGO 268 protein can be analyzed by platelet aggregation assays or secretion assays known to those of skill in the art (see, e.g., Moroi et al., 1989, *J. Clin. Invest.* 84:1440–1445 and Poole et al., 1997, *EMBO J.* 16(9):2333–2341). Briefly, the platelet aggregation is performed as follows: platelets are incubated with collagen or convulxin in a cuvette at 37° C. while being stirred, and the cell suspension is monitored by a lumiaggregometer.

Such assays may be utilized as part of TANGO 268 diagnostic assays. In addition, such assays may be utilized as part of screening methods for identifying compounds that modulate the activity and/or expression of TANGO 268.

Assays for the Function of TANGO 268

The function of a TANGO 268 protein can be analyzed by transplanting hematopoietic cells engineered to express TANGO 268 or a control into lethally irradiated mice. The affect of TANGO 268 expression on the function, development and proliferation of hematopoietic cells, specifically platelets, can be determined by comparing mice transplanted with hematopoietic cells expressing TANGO 268 to mice transplanted with hematopoietic cells expressing a control. For example, the role of TANGO 268 in platelet aggregation can be analyzed by transplanting mice with hematopoietic cells engineered to express TANGO 268 or fragments thereof. The irradiated mice may be normal, transgenic or knockout mice, and the hematopoietic cells may be obtained from normal, transgenic or knockout mice.

The efficacy of using TANGO 268 nucleic acids, proteins or modulators thereof to modulate the expression of a given gene can be analyzed using irradiated mice transplanted with hematopoietic cells engineered to express TANGO 268 or modulators thereof. The affect of TANGO 268 nucleic acids, proteins or modulators thereof on the expression of a gene of interest can be measured by analyzing the RNA or protein levels of the gene of interest. Techniques known to those of skill can be used to measure RNA and protein levels in vivo and in vitro. For example, RNA expression can be detected in vivo by in situ hybridization. Further, the efficacy of using TANGO 268 nucleic acids, proteins or modulators thereof to treat, inhibit or prevent a particular disease or disorder can be analyzed by using irradiated mouse or rat models of a disease or disorder transplanted with hematopoietic cells engineered to express TANGO 268 or modulators thereof.

Assays for Analysis of TANGO 268 Modulators

A variety of assays can be utilized to analyze a TANGO 268 protein, nucleic acid or modulator thereof. Such assays can include in vivo, ex vivo and in vitro assays, as described herein. See, also, e.g., Loscaizo and Schaefer (eds), 1998, Thrombosis and Hemorrhage $2^{nd}$ Edition, Chapter 16, Williams and Wilkins: Baltimore, Md.; Horton (ed), 1995, Adhesion Receptors as Therapeutic Targets, Chapter 15, CRC Press, Inc.: London, United Kingdom,; and U.S. Pat. No. 5,976,532.

For example, in view of the fact that TANGO 268 is a cell surface receptor, in particular, a platelet receptor, standard quantitative binding studies can be utilized to measure modulator binding to platelets. Horton (ed), 1995, Adhesion Receptors as Therapeutic Targets, Chapter 15, CRC Press, Inc.: London, United Kingdom. Such binding assays can also be utilized to perform receptor blockade studies to measure the number of cellular sites available for binding modulator by comparing the number of molecules of labeled modulator molecules (e.g., labeled anti-TANGO 268 antibodies) bound per platelet at a series of concentrations with the number of modulator molecules bound at saturation. See, e.g., Coller et al., 1985, J. Clin. Invest. 76: 101 or U.S. Pat. No. 5,854,005.

The reversibility of modulator molecule (e.g., anti-TANGO 268 antibodies) binding on platelets can also be tested, using, e.g., techniques such as those described in Coller et al., 1985, J. Clin. Invest. 76: 101, and U.S. Pat. No. 5,976,532. In addition, under non-competitive conditions, the rate of modulator dissociation can be assessed by, e.g., flow cytometry analysis of platelets when fluorescently labeled modulator (e.g., anti-TANGO 268 antibody)-coated platelets are mixed with an equal number of untreated platelets and incubated at physiological temperature. In instances wherein appreciable reversibility indicates that inhibitory effects of single in vivo injection can be relatively short-lived, suggesting that an administration regimien involving an initial bolus followed by continuous infusion may be most effective.

In vitro and ex vivo assays for inhibition of platelet aggregation can also be utilized. Such assays are well known to those of skill in the art and include, but are not limited to the turbidometric method, in which aggregation is measured as an increase in transmission of visible light through a stirred or agitated platelet suspension. See, e.g., Chanarin, L., 1989, Laboratory Haematology, Chapter 30, Churchill, Livingstone, London; and Schmidt, R. M. (ed), 1979, CRC Handbook Series in Clinical Laboratory Science, CRC Press, Inc.: Boca Raton, Fla.

Platelet aggregation can also be assayed via methods such as those described in U.S. Pat. No. 5,976,532. For example, in a non-limiting example of such a method, the platelet concentration in platelet-rich plasma obtained (PRP) obtained from normal or patient blood samples is adjusted to 200,000 to 300,000/$mm^3$. In an in vitro assay, the PRP is aliquoted and incubated in the presence or absence of a TANGO 268 modulator (e.g., an anti-GPVI antibody) for a period of time (e.g., 15 minutes at 37° C.) prior to the addition of a platelet inducing agonist (e.g., ADP, thrombin, collagen, epinephrine, and ristocetin). In an ex vivo assay, the PRP obtained from individuals treated with TANGO 268 or a placebo is aliquoted and incubated in the presence of a platelet inducing agonist (e.g., ADP, thrombin, collagen, epinephrine, and ristocetin). Platelet aggregation is measured by assessing an increase in the transmission of visible light through a platelet suspension using a spectrophotometer.

In certain embodiments, it is preferred that the TANGO 268 modulator not effect platelet attributes or functions other than platelet aggregation. Such other platelet attributes or functions, include, for example, agonist-induced platelet shape change (e.g., GPIb-vWF-mediated platelet agglutination induced by ristocetin), release of internal platelet granule components, activation of signal transduction pathways or induction of calcium mobilization upon platelet activation. Assays for these platelet attributes and functions are well known to those of skill in the art and can be utilized to routinely test, develop and identify TANGO 268 modulators exhibiting a specificity for modulation of platelet aggregation.

The shape of a platelet can be analyzed in any in vitro assay known to those of skill in the art. Briefly, platelets are contacted in the presence or absence of a TANGO 268 modulator with a platelet inducing agonist (e.g., ADP, thrombin, collagen; epinephrine, and ristocetin) and the shape of the platelets are assessed by microscopy or by flow cytometry. Platelet degranulation can be analyzed, for example, by measuring the presence of ATP in vitro following stimulation with a platelet inducing agonist in the presence or absence of a TANGO 268 modulator (see, e.g., Loscalzo and Schaefer (eds), 1998, Thrombosis and Hemorrhage $2^{nd}$ Edition, Chapter 16, Williams and Wilkins: Baltimore, Md.). The activation of platelet signal transduction pathways can be analyzed in invtro and ex vivo assays using assays known to those of skill in the art. For example, the activation of signal transduction pathways in vitro can be analyzed by contacting platelet-rich plasma samples with platelet agonists (e.g., collagen and convulxin) in the presence or absence of a TANGO 268 modulator and measuring the effect of such treatment on the level of tyrosine phosphorylation of signaling molecules, such as FcRγ, Syk, and PLCγ 2 (e.g., tyrosine phosphorylation can be detected by immunoprecipitation followed by SDS-PAGE, kinase assays, etc.). In an ex vivo assay, the activation of signal transduction pathways can be analyzed by contacting platelet-rich plasma samples obtained from individuals treated with TANGO 268 or a placebo with a platelet agonist (e.g., collagen and convulxin) and measuring the effect of such treatment on the level of tyrosine phosphorylation of signaling molecules, such as FcRγ, Syk, and PLCγ 2 (e.g., tyrosine phosphorylation can be detected by immunoprecipitation followed by SDS-PAGE, kinase assays, etc.). The effect of platelet activation on calcium mobilization can also be analyzed by measuring changes in the concentration of free intracellular $Ca^{2+}$ induced in in vitro and ex vivo assays using assays known to those of skill in the art. Briefly, platelet-rich platelets are incubated with fura-2 fluorescence at 37° C. and then incubated with 2 mM $CaCl_2$ in the presence or absence of a TANGO 268 modulator prior to incubation with a platelet agonist (e.g., convulxin, collagen and thrombin). The cells are lysed in lysis buffer, and the concentration of free intracellular $Ca^{2+}$ is measured by fluorescence at 37° C. using a spectrophotometer (see, e.g., Jandrot-Perrus et al., 1997, J. of Biol. Chem. 272:27035–27041).

Other assays for platelets include, in vivo assays such as assessment of prolongation of bleeding time. For example, the bleeding time resulting from an injury (e.g., a small tail vein incision) in an animal model treated with a TANGO 268 modulator can be compared to an animal model treated with a placebo. In humans, the number of bleeding episodes and the length of the bleeding time during a bleeding episode for a human treated with a TANGO 268 modulator can be compared to a human treated with a placebo.

The efficacy of TANGO 268 modulators can be assessed in a variety of animal models of arterial thrombosis, including, but not limited to, the Folts model, the electrolytic injury model, the thrombin-induced arterial thrombosis model, and a model of acute thrombosis resulting from injury induced by coronary balloon angioplasty (see, e.g., Loscalzo and Schaefer (eds), 1998, Thrombosis and Hemorrhage $2^{nd}$ Edition, Chapter 16, Williams and Wilkins: Baltimore, Md.). The Folts model, which is the most widely used animal model of coronary and carotid artery thrombosis, is produced by mechanical concentric vessel narrowing using a cylinder placed around the artery. The electrolytic model, which is used for deep arterial injury, is produced by introducing an electric current via an electrode to the intimal layer of a stenosed vessel. By applying species specificity data that can readily be obtained using, e.g., the platelet aggregation assays described herein, animal models particularly well suited to study of any given TANGO 268 modulator can be chosen.

Tables 5 and 6 below provide a summary of the sequence information for TANGO 268.

TABLE 5

Summary of TANGO 268 Sequence Information

| Gene | cDNA | ORF | Figure | Accession Number |
|---|---|---|---|---|
| Human TANGO 268 | SEQ ID NO:1 | SEQ ID NO:2 | FIG. 1 | 207180 |
| Mouse TANGO 268 | SEQ ID NO:14 | SEQ ID NO:15 | FIG. 6 | PTA-225 |

TABLE 6

Summary of Domains of TANGO 268 Proteins

| Protein | Signal Sequence | Mature Protein | Extracellular | Ig-like | Transmembrane | Cytoplasmic |
|---|---|---|---|---|---|---|
| HUMAN TANGO 268 | aa 1–20 of SEQ ID NO:3 (SEQ ID NO:4) | aa 21–339 of SEQ ID NO:3 (SEQ ID NO:5) | aa 21–269 of SEQ ID NO:3 (SEQ ID NO:9) | aa 48–88; 134–180 of SEQ ID NO:3 (SEQ ID NO:6; SEQ ID NO:7) | aa 270–288 of SEQ ID NO:3 (SEQ ID NO:8) | aa 289–339 of SEQ ID NO:3 (SEQ ID NO:10) |
| MOUSE TANGO 268 | aa 1–21 of SEQ ID NO:16 (SEQ ID NO:17) | aa 22–313 of SEQ ID NO:16 (SEQ ID NO:18) | aa 22–267 of SEQ ID NO:16 (SEQ ID NO:19) | aa 49–89; 135–181 of SEQ ID NO:16 (SEQ ID NO:22; SEQ ID NO:23) | aa 268–286 of SEQ ID NO:16 (SEQ ID NO:20) | aa 287–313 of SEQ ID NO:16 (SEQ ID NO:21) |

Various aspects of the invention are described in further detail in the following subsections:

I. Isolated Nucleic Acid Molecules

One aspect of the invention pertains to isolated nucleic acid molecules that encode a polypeptide of the invention or a biologically active portion thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. In one embodiment, the nucleic acid molecules of the invention comprise a contiguous open reading frame encoding a polypeptide of the invention.

An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. The term "isolated" nucleic acid molecule can refer to a nucleic acid molecule of the invention that lacks intron sequences. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. As used herein, the term "isolated" when referring to a nucleic acid molecule does not include an isolated chromosome.

A nucleic acid molecule of the present invention, e.g., a nucleic acid molecule having the nucleotide sequence of SEQ ID NO:1, 2, 14, 15, 33, 35, 37, 39, 41, 43, 45 or 47, or a complement thereof, can be isolated using standard molecular biology techniques and the sequence information provided herein. Using all or a portion of the nucleic acid sequences of SEQ ID NO:1, 2, 14, 15, 33, 35, 37, 39, 41, 43, 45 or 47 as a hybridization probe, nucleic acid molecules of the invention can be isolated using standard hybridization and cloning techniques (e.g., as described in Sambrook et al., eds., *Molecular Cloning: A Laboratory Manual*, 2nd ed., Cold Spring Harbor Laboratory, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of SEQ ID NO:1, 2, 14, 15, 33, 35, 37, 39, 41, 43, 45 or 47, or the nucleotide sequence of the cDNA insert of a clone deposited with the ATCC® as Accession number 207180 or patent deposit Number PTA-225, or a portion thereof. A nucleic acid molecule which is complementary to a given nucleotide sequence is one which is sufficiently complementary to the given nucleotide sequence that is can hybridize to the given nucleotide sequence thereby forming a stable duplex.

Moreover, a nucleic acid molecule of the invention can comprise only a portion of a nucleic acid sequence encoding a full length polypeptide of the invention for example, a fragment which can be used as a probe or primer or a fragment encoding a biologically active portion of a polypeptide of the invention. The nucleotide sequence determined from the cloning one gene allows for the generation of probes and primers designed for use in identifying and/or cloning homologues in other cell types, e.g., from other tissues, as well as homologues from other mammals. The probe/primer typically comprises substantially purified oligonucleotide. In one embodiment, the oligonucleotide comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, 2, 14, 15, 33, 35, 37, 39, 41, 43, 45 or 47, or the nucleotide sequence of the cDNA insert of a clone deposited with the ATCC® as Accession number 207180 or patent deposit Number PTA-225, or of a naturally occurring mutant of SEQ ID NO:1, 2, 14, 15, 33, 35, 37, 39, 41, 43, 45 or 47. In another embodiment, the oligonucleotide comprises a region of nucleotide sequence that hybridizes under stringent conditions to at least 400, preferably 450, 500, 530, 550, 600, 700, 800, 900, 1000 or 1150 consecutive oligonucleotides of the sense or antisense sequence of SEQ ID NO:1, 2, 14, 15, 33, 35, 37, 39, 41, 43, 45 or 47, or the nucleotide sequence of the cDNA insert of a clone deposited with the ATCC® as Accession number 207180 or patent deposit Number PTA-225, or a naturally occurring mutant of SEQ ID NO:1, 2, 14, 15, 33, 35, 37, 39, 41, 43, 45 or 47.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a biologically active portion of a polypeptide of the invention can be prepared by isolating a portion of any of SEQ ID NO:1, 2, 14, 15, 33, 35, 39, 41, 43, 45 or 47 expressing the encoded portion of the polypeptide protein (e.g., by recombinant expression in vitro) and assessing the activity of the encoded portion of the polypeptide.

The invention further encompasses nucleic acid molecules that differ from the nucleotide sequence of SEQ ID NO:1, 2, 14, 15, 33, 35, 37, 39, 41, 43, 45 or 47 due to degeneracy of the genetic code and thus encode the same protein as that encoded by the nucleotide sequence of SEQ ID NO:1, 2, 14, 15, 33, 35, 37, 39, 41, 43, 45 or 47.

In addition to the nucleotide sequences of SEQ ID NO:1, 2, 14, 15, 33, 35, 37, 39, 41, 43, 45 or 47, it will be appreciated by those skilled in the art that DNA sequence polymorphisms that lead to changes in the amino acid sequence may exist within a population (e.g., the human population). Such genetic polymorphisms may exist among individuals within a population due to natural allelic variation. An allele is one of a group of genes which occur alternatively at a given genetic locus. For example, human TANGO 268 has been mapped to chromosome 19, and therefore TANGO 268 family members can include nucleotide sequence polymorphisms (e.g., nucleotide sequences that vary from SEQ ID NO:1 and SEQ ID NO:2) that map to this chromosomal locus (e.g., region of chromosome 19q13) and such sequences represent TANGO 268 allelic variants. As used herein, the phrase "allelic variant" refers to a nucleotide sequence which occurs at a given locus or to a polypeptide encoded by the nucleotide sequence. As used herein, the terms "gene" and "recombinant gene" refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention. In one embodiment, polymorphisms that are associated with a particular disease and/or disorder are used as markers to diagnose said disease or disorder. In a preferred embodiment, polymorphisms are used as a marker to diagnose abnormal coronary function (e.g., coronary diseases such as myocardial infarction, atherosclerosis, coronary artery disease, plaque formation).

Moreover, nucleic acid molecules encoding proteins of the invention from other species (homologues), which have a nucleotide sequence which differs from that of the human or mouse protein described herein are intended to be within the scope of the invention. Nucleic acid molecules corresponding to natural allelic variants and homologues of a cDNA of the invention can be isolated based on their identity to the human nucleic acid molecule disclosed herein using the human cDNAs, or a portion thereof, as a hybridization probe according to standard hybridization techniques under stringent hybridization conditions. For example, a cDNA encoding a soluble form of a membrane-bound protein of the invention isolated based on its hybridization to a nucleic acid molecule encoding all or part of the membrane-bound form. Likewise, a cDNA encoding a membrane-bound form can be isolated based on its hybridization to a nucleic acid molecule encoding all or part of the soluble form.

Accordingly, in another embodiment, an isolated nucleic acid molecule of the invention is at least 500, 600, 700, 800, 900, 1000, 1100, 1200, 1300, 1400, 1500, 1600, 1700, 1800, 1900 or 2000 contiguous nucleotides in length and hybridizes under stringent conditions to the nucleic acid molecule comprising the nucleotide sequence, preferably the coding sequence, of SEQ ID NO:1, or a complement thereof.

Accordingly, in another embodiment, an isolated nucleic acid molecule of the invention is at least 50, 100, 200, 300, 400, 500, 600, 700, 800 or 900 contiguous nucleotides in length and hybridizes under stringent conditions to the nucleic acid molecule comprising the nucleotide sequence of SEQ ID NO:2, or a complement thereof.

Accordingly, in another embodiment, an isolated nucleic acid molecule of the invention is at least 50, 100, 200, 300, 400, 500, 600, 700, 800, 900, 1000, 1100, 1200, 1300, 1400 or 1500 contiguous nucleotides in length and hybridizes under stringent conditions to the nucleic acid molecule comprising the nucleotide sequence, preferably the coding sequence, of SEQ ID NO:14, or a complement thereof.

Accordingly, in another embodiment, an isolated nucleic acid molecule of the invention is at least 50, 100, 200, 300, 400, 500, 600, 700, 800 or 900 contiguous nucleotides in length and hybridizes under stringent conditions to the nucleic acid molecule comprising the nucleotide sequence of SEQ ID NO:15, or a complement thereof.

Accordingly, in another embodiment, an isolated nucleic acid molecule of the invention is at least 50, 100, 200, 300, 400, 500, 600, 700, 800, 900, 1000, 1100, 1200, 1300, 1400 or 1500 contiguous nucleotides in length and hybridizes under stringent conditions to the nucleic acid molecule comprising the nucleotide sequence of SEQ ID NO:41, 43, 45 or 47, or a complement thereof.

Accordingly, in another embodiment, an isolated nucleic acid molecule of the invention is at least 50, 100, 200, 300, 400, 500, 600, 700, 800, 900, 1000, 1100, 1200, 1300, 1400 or 1500 contiguous nucleotides in length and hybridizes under stringent conditions to the nucleic acid molecule comprising the nucleotide sequence of SEQ ID NO:33, 35, 37 or 39, or a complement thereof.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. In one, non-limiting example stringent hybridization conditions are hybridization at 6× sodium chloride/sodium citrate (SSC) at about 45° C., followed by one or more washes in 0.1×SSC, 0.2% SDS at about 68° C. A preferred, non-limiting example stringent hybridization conditions are hybridization in 6×SSC at about 45° C., followed by one or more washes in 0.2×SSC, 0.1% SDS at 50–65° C. (i.e., one or more washes at 50° C., 55° C., 60° C. or 65° C.). Preferably, an isolated nucleic acid molecule of the invention that hybridizes under stringent conditions to the sequence of SEQ ID NO:1, 2, 14, 15, 33, 35, 37, 39, 41, 43, 45 or 47, or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of a nucleic acid molecule of the invention sequence that may exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologues of various species may be non-essential for activity and thus would be likely targets for alteration. Specific examples of conservative amino acid alterations from the original amino acid sequence of SEQ ID NO:3 or 16 are shown in SEQ ID NO:33, 35, 37, 39, 41, 43, 45 or 47. Alternatively, amino acid residues that are conserved among the homologues of various species (e.g., mouse and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:3, 34, 36, 38 or 40, yet retain biological activity. In one embodiment, the isolated nucleic acid molecule includes a nucleotide sequence encoding a protein that includes an amino acid sequence that is at least about 30%, 35%, 40%, 45%, 50%, 55%, 60%, 65%, 75%, 85%, 95%, or 98% identical to the amino acid sequence of SEQ ID NO:3, 34, 36, 38 or 40.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:16, 42, 44, 46 or 48, yet retain biological activity. In one embodiment, the isolated nucleic acid molecule includes a nucleotide sequence encoding a protein that includes an amino acid sequence that is at least about 30%, 35%, 40%, 45%, 50%, 55%, 60%, 65%, 75%, 85%, 95%, or 98% identical to the amino acid sequence of SEQ ID NO:16, 42, 44, 46 or 48.

An isolated nucleic acid molecule encoding a variant protein can be created by introducing one or more nucleotide substitutions, additions or deletions into the nucleotide sequence of SEQ ID NO:1, 2, 14, 15, 33, 35, 37, 39, 41, 43, 45 or 47 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysterine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In a preferred embodiment, a mutant polypeptide that is a variant of a polypeptide of the invention can be assayed for: (1) the ability to form protein: protein interactions with proteins in a signaling pathway of the polypeptide of the invention (e.g., the ability of a variant TANGO 268 polypeptide to associate with FcRγ); (2) the ability to bind a ligand of the polypeptide of the invention (e.g., the ability of a variant TANGO 268 polypeptide to bind to collagen or convulxin); (3) the ability to bind to an intracellular target protein of the polypeptide of the invention; (4) the ability to activate an intracellular signaling molecule activated by the polypeptide of the invention (e.g., the ability of a variant TANGO 268 polypeptide to activate Syk, phospholipase Cγ2 or phosphatidylinositol 3-kinase); or (5) the ability to induce and/or modulate platelet activity (e.g., the ability of a variant TANGO 268 polypeptide to induce and/or modulate platelet activation or platelet aggregation). In yet another preferred embodiment, the mutant polypeptide can be assayed for the ability to modulate cellular proliferation, cellular migration or chemotaxis, or cellular differentiation.

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguamine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al., 1987, *Nucleic Acids Res.* 15:6625–6641). The antisense nucleic acid molecule can also comprise a 2'-o-methylribonucleotide (Inoue et al., 1987, *Nucleic Acids Res.* 15:6131–6148) or a chimeric RNA-DNA analogue (Inoue et al., 1987, *FEBS Lett.* 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988, *Nature* 334:585–591)) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak, 1993, *Science* 261:1411–1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene, 1991, *Anticancer Drug Des.* 6(6):569–84; Helene, 1992, *Ann. N.Y. Acad. Sci.* 660:27–36; and Maher, 1992, *Bioassays* 14(12):807–15.

In various embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs had been shown to allow for specific hybridization to DNA and RNA under conditions of low ionic strength. The synthesis of PNA oligomers can be performed using standard solid phase peptide synthesis protocols as described in Hyrup et al., 1996, supra; and Perry-O'Keefe et al., 1996, *Proc. Natl. Acad. Sci. USA* 93: 14670–675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup, 1996, supra; or as probes or primers for DNA sequence and hybridization (Hyrup, 1996, supra; and Perry-O'Keefe et al., 1996, *Proc. Natl. Acad. Sci. USA* 93: 14670–675.

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., 1996, *Nucleic Acids Res.* 24(17):3357–63. For example, a DNA chain can be synthesized on a solid support using standard phosphoramidite coupling chemistry and modified nucleoside analogs. Compounds such as 5'-(4-methoxytrityl)amino-5' end of DNA (Mag et al., 1989, *Nucleic Acids Res.* 17:5973–88). PNA monomers are then coupled in a stepwise manner to produce a chimeric molecule with a 5' PNA segment and a 3' DNA segment (Finn et al., 1996, *Nucleic Acids Res.* 24(17):3357–63). Alternatively, chimeric molecules can be synthesized with a 5' DNA segment and a 3' PNA segment (Peterser et al., 1975, *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al., 1989, *Proc. natl. Acad. Sci. USA* 86:6553–6556; Lemaitre et al., 1987, *Proc. Natl. Acad. Sci. USA* 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958–976) or intercalating agents (see, e.g., Zon, 1988, *Pharm. Res.* 5:539–549). To this end, the oligonucleotide may be conjugated to another molecule, e.g., a peptide, hybridization triggered cross-linking agent, transport agent, hybridization-triggered cleavage agent, etc.

II. Isolated Proteins and Antibodies

One aspect of the invention pertains to isolated proteins, and biologically active portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein in separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptides comprising amino acid sequences sufficiently identical to or derived from the amino acid sequence of the protein (e.g., the amino acid sequence shown in any of SEQ ID NO:4, 6, 7, 9, 10, 17, 19, 20, 21, 22 or 23, which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of SEQ ID NO:3, 4, 5, 6, 7, 8, 9, 10, 16, 17, 18, 19, 20, 21, 22, 23, 34, 36, 38, 40, 42, 44, 46 or 48. Other useful proteins are substantially identical (e.g., at least about 45%, preferably 55%, 65%, 75%, 85%, 95%, or 99%) to any of SEQ ID NO:3, 4, 5, 6, 7, 8, 9, 10, 16, 17, 18, 19, 20, 21, 22 or 23, and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequences). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (, % identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389–3402. Alternatively, PSI-Blast can be used to perform an iterated search which detects distant relationships between molecules (Id). When utilizing BLAST, Gapped BLAST, and PSI-Blast programs, the default parameters of the respective programs (e.g., XBLAST and NBLAST) can be used. See http://www.ncbi.nlm.nih.gov.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) *Comput. Appl. Biosci.*, 10:3–5; and FASTA described in Pearson and Lipman (1988) *Proc. Natl. Acad. Sci.* 85:2444–8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see http://bioweb.pasteur.fr/docs/man/man/fasta.1.html#sect2, the contents of which are incorporated herein by reference.

The percent identity between two sequences can be determined using techniques similar to those described above, with or without allowing gaps. In calculating percent identity, typically exact matches are counted.

The invention also provides chimeric or fusion proteins. As used herein, a "chimeric protein" or "fusion protein"

comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention.

One useful fusion protein is a GST fusion protein in which the polypeptide of the invention is fused to the C-terminus of GST sequences. Such fusion proteins can facilitate the purification of a recombinant polypeptide of the invention.

In another embodiment, the fusion protein contains a heterologous signal sequence at its N-terminus. For example, the native signal sequence of a polypeptide of the invention can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction may be useful therapeutically, both for treating proliferative and differentiative disorders and for modulating (e.g., promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence of a polypeptide of the invention (SEQ ID NO:4 or 17) can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the nature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

In another embodiment, the signal sequences of the present invention can be used to identify regulatory sequences, e.g., promoters, enhancers, repressors. Since signal sequences are the most amino-terminal sequences of a peptide, it is expected that the nucleic acids which flank the signal sequence on its amino-terminal side will be regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; and Ike et al., 1983, *Nucleic Acid Res.* 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amendable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811–7815; and Delgrave el al., 1993, *Protein Engineering* 6(3):327–331).

The polypeptides of the invention can exhibit post-translational modifications, including, but not limited to glycosylations, (e.g., N-linked or O-linked glycosylations), myristylations, palmitylations, acetylations and phosphorylations (e.g., serine/threonine or tyrosine). In one embodiment, the TANGO 268 polypeptide of the invention exhibit reduced levels of O-linked glycosylation and/or N-linked glycosylation relative to endogenously expressed TANGO 268 polypeptides. In another embodiment, the TANGO 268 polypeptides of the invention do not exhibit O-linked glycosylation or N-linked glycosylation. Further, post-translational modifications of TANGO 268 polypeptides such as glycosylation can be prevented by treating cells, e.g., with tunicamycin, or by expressing TANGO 268 nucleic acid molecules in host cells lacking lacking the capacity to post-translational modify TANGO 268 polypeptides.

As isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. In one embodiment, an isolated polypeptide or fragment thereof which lacks N- and/or O-linked glycosylation is used as an immunogen to generate antibodies using standard techniques known to those of skill in the art. The antigenic peptide of a protein of the invention comprises at least 8 (preferably at least 10, at least 15, at least 20, or at least 30) contiguous amino acid residues of the amino acid sequence of SEQ ID NO:3, 16, 34, 36, 38, 40, 42, 44, 46 or 48, and encompasses an epitope of the protein such that an antibody raised against the peptide forms a specific immune complex with the protein.

In on embodiment, a polypeptide used as an immungen comprises an amino acid sequence of SEQ ID NO:3, 16, 34, 36, 38, 40, 42, 44, 46 or 48, or the amino acid sequence encoded by the cDNA insert of the plasmid deposited with ATCC® as Accession Number 207180, or the amino acid sequence encoded by the cDNA insert of the plasmid deposited with ATCC® as patent deposit Number PTA-225. In another embodiment, a polypeptide used as an immungen comprises a fragment of at least 8, preferably at least 10, at least 15, at least 25, at least 30, at least 50, at least 75, at least 100 or more contiguous amino acid residues of the amino acid sequence of SEQ ID NO:3, 16, 34, 36, 38, 40, 42, 44, 46 or 48. In another embodiment, a polypeptide used as an immungen comprises an amino acid sequence which is at least 50%, preferably at least 65%, at least 75%, at least 85%, at least 95% or at least 99% identical to the amino acid sequence of SEQ ID NO:3, 16, 34, 36 38, 40, 42, 44, 46 or 48, wherein the percent identity is determined using the ALIGN program of the GCG software package with a PAM120 weight residue table, a gap length penalty of 12, and a gap penalty of 4. In yet another embodiment, a polypeptide used as an immunogen comprises an amino acid sequence which is encoded by a nucleic acid molecule which hybridizes to the nucleic acid molecule consisting of SEQ ID NO:1, 2, 14, 15, 33, 35, 37, 39, 41, 43, 45 or 47 under conditions of hybridization of 6×SSC at 45° C. and washing in 0.2×SCC, 0.1% SDS at 50° C., 55° C., 60° C. or 65° C., or 6×SSC at 45° C. and washing in 0.1×SSC, 0.2% SDS at 68° C.

The term "epitopes" as used herein refers to portions of a TANGO 268 polypeptide having an antigenic or immunogenic activity in an animal, preferably a mammal, and most preferably a human. An epitope having immunogenic activity is a fragment of a TANGO 268 polypeptide that elicits an antibody response in an animal. An epitope having antigenic activity is a fragment of a TANGO 268 polypeptide or fragment thereof to which an antibody immunospecifically binds in vivo or in vitro as determined by any method well known to those of skill in the art, for example, by the immunoassays described herein. Epitopes encompassed by the antigenic peptide are regions that are located on the surface of the protein, e.g., hydrophilic regions. Alternatively, epitopes encompassed by the antigenic peptides are regions that are located within the proteins, and/or epitopes exposed in denatured or partially denatured forms of the polypeptides of the invention. FIGS. 2 and 7 are hydropathy plots of the proteins of the invention. These plots or similar analyses can be used to identify hydrophilic regions. In addition, an epitope can encompass, in addition to a polypeptide or polypeptides of the invention, a post-translational modification (e.g., glycosylation, such as, for example, N- and/or O-linked glycosylation of the polypeptide or polypeptides).

An immunogen typically is used to prepare antibodies by immunizing a suitable subject, (e.g., rabbit, goat, mouse or other mammal). An appropriate immunogenic preparation can contain, for example, recombinantly expressed or chemically synthesized polypeptide. The preparation can further include an adjuvant, such as Freund's complete or incomplete adjuvant, or similar immunostimulatory agent.

Accordingly, another aspect of the invention pertains to antibodies directed against a polypeptide of the invention.

The term "antibody" as used herein refers to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. Antibodies of the invention include, but are not limited to, monoclonal antibodies, polyclonal antibodies, multispecific antibodies, human antibodies, humanized antibodies, chimeric antibodies, single chain Fv (scFv), single chain antibodies, anti-idiotypic (anti-Id) antibodies, F(ab) fragments, F(ab')$_2$ fragments, and epitope-binding fragments of any of the above. A molecule which specifically or immunospecifically binds to a given polypeptide of the invention or fragment thereof is a molecule which binds the polypeptide, but does not substantially bind other molecules in a sample, e.g., a biological sample, which naturally contains the polypeptide.

The antibodies of the invention may be from any animal origin including birds and mammals (e.g., human, mouse, donkey, rabbit, sheep, guinea pigs, camel, horse or chicken). In one embodiment, the antibodies of the invention originate from non-human mammals such as mice, rats, sheep, and goat. In another embodiment, the antibodies of the invention are human or humanized antibodies. As used herein, "human" antibodies include antibodies having the amino acid sequence of a human immunoglobulin and include antibodies isolated from human immunoglobulin libraries. In a preferred embodiment, the antibodies of the invention are human or humanized monoclonal antibodies. The term "monoclonal antibodies", "monoclonal antibody" or "monoclonal antibody composition", as used herein, refers to a population of antibody molecules that contain only one species of an antigen binding site capable of immunoreacting with a particular epitope.

The antibodies of the present invention may be monospecific, bispecific, trispecific or of greater multispecificity. Multispecific antibodies may be specific for different epitopes of a TANGO 268 polypeptide or may be specific for both a TANGO 268 polypeptide as well as for a heterologous epitope, such as a heterologous polypeptide or solid support material. See, e.g., PCT publications WO 93/177 15; WO 92/08802; WO 91/00360; WO 92/05793; Tutt, et al., J. Immunol. 147:60–69(1991); U.S. Pat. Nos. 4,474,893; 4,714,681; 4,925,648; 5,573,920; 5,601,819; and Kostelny et al., J. Immunol. 148:1547–1553 (1992).

In a specific embodiment, an antibody of the invention has a dissociation constant or $K_d$ of less than $10^{-2}$ M, less than $5\times10^{-2}$ M, less than $10^{-3}$ M, less than $5\times10^{-3}$ M, less than $10^{-4}$ M, less than $5\times10^{-4}$ M, less than $10^{-5}$ M, less than $5\times10^{-5}$ M, less than $10^{-6}$ M, less than $5\times10^{-6}$ M, less than $10^{-7}$ M, less than $5\times10^{-7}$ M, less than $10^{-8}$ M, less than $5\times10^{-8}$ M, less than $10^{9}$ M, less than $5\times10^{-9}$ M, less than $10^{-10}$ M, less than $5\times10^{-10}$ M, less than $10^{-11}$ M, less than $5\times10^{-11}$ M, less than $10^{-12}$ M, less than $5\times10^{-12}$ M, less than $10^{-13}$ M, less than $5\times10^{-13}$ M, less than $10^{-14}$ M, less than $5\times10^{-14}$ M, less than $10^{-15}$ M, or less than $5\times10^{-15}$ M.

Polyclonal antibodies can be prepared as described above by immunizing a suitable subject with a polypeptide of the invention as an immunogen. Preferred polyclonal antibody compositions are ones that have been selected for antibodies directed against a polypeptide or polypeptides of the invention. Particularly preferred polyclonal antibody preparations are ones that contain only antibodies directed against a polypeptide or polypeptides of the invention. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody composition raised against this immunogen will be present as part of a polypeptide or polypeptides of the invention.

The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. Alternatively, antibodies specific for a protein or polypeptide of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those on the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein, 1975, *Nature* 256:495–497, the human B cell hybridoma technique (Kozbor et al., 1983, *Immunol. Today* 4:72), the EBV-hybridoma technique (Cole et al. (1985), *Monoclonal Antibodies and Cancer Therapy,* Alan R. Liss, Inc., pp. 77–96) or trioma techniques. The technology for producing hybridomas is well known (see generally *Current Protocols in Immunology* (1994) Coligan et al. (eds) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System,* Catalog No. 27-9400-01; and the Stratagene *SurfZAP™ Phage Display Kit,* Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, Bio/Technology 9:1370–1372; Hay et al., 1992, Hum. Antibod. Hybridomas 3:81–85; Huse et al., 1989, Science 246:1275–1281; and Griffiths et al., 1993, EMBO J. 12:725–734.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarily determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041–1043; Liu et al., 1987, Proc. Natl. Acad. Sci. USA 84:3439–3443; Liu et al., 1987, J. Immunol. 139:3521–3526; Sun et al., 1987, Proc. Natl. Acad. Sci. USA 84:214–218; Nishimura et al., 1987, Canc. Res. 47:999–1005; Wood et al., 1985, Nature 314:446–449; and Shaw et al., 1988, J. Natl. Cancer Inst. 80:1553–1559); Morrison, 1985, Science 229:1202–1207; Oi et al., 1986, Bio/Techniques 4:214; U.S. Pat. No. 5,225,539; Jones et al., 1986, Nature 321:552–525; Verhoeyan et al., 1988, Science 239:1534; and Beidler et al., 1988, J. Immunol. 141:4053–4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgens harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Fremont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., (1994) Bio/technology 12:899–903).

Antibody fragments which recognize specific TANGO 268 epitopes may be generated by any technique known to those of skill in the art. For example, Fab and $F(ab')_2$ fragments of the invention may be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CH1 domain of the heavy chain.

Further, the antibodies of the present invention can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., pCANTAB6 or pComb3HSS). The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to a TANGO 268 antigen can be selected or identified with antigen, e.g., using labeled antigen or antigen bound or captured to a solid surface or bead. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280(1994); PCT application No. PCT/G91/O1 134; PCT publications WO 90/02809; WO 91/10737; WO 92/01047; WO 92/18619; WO 93/1 1236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and $F(ab')_2$ fragments can also be employed using methods known in the art such as those disclosed in PCT publication WO 92/22324; Mullinax et al., Bio Techniques 12(6):864–869 (1992); and Sawai et al., AJR1 34:26–34 (1995); and Better et al., Science 240: 1041–1043 (1988) (said references incorporated by reference in their entireties).

To generate whole antibodies (i.e., IgG antibodies) or FAB fragments, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains in eukaryotic cells comprise pcDNA3 vectors containing CMV or EF-1a promoters, a secretion signal, a cloning site for the variable domain, constant domains, and a selection marker such as neomycin or DHFR. Vectors for expressing VH or VL domains in *E. coli* comprise promoters, the constant domain of human IgG (CH1 and CL), leader sequences (pelB, ompA or gIII), a cloning site for the variable domain, and a selection marker such as kanimycin. The VH and VL domains may also cloned into one vector expressing the necessary constant regions. The heavy chain conversion vectors and light chain conversion vectors are then co-transfected into *E. coli* or eukaryotic cell lines to generate stable or transient cell lines that express full-length antibodies, e.g., IgG, or Fab fragments using techniques known to those of skill in the art. Active Fab fragments produced by stable or transient transfected cell lines will be recovered by Protein A chromatography. IgG antibody produced by stable or transient transfected cell lines with purified using Protein A chromatography. IgG produced by this method may be subjected to enzymatic digestion (e.g., papain) to release Fab or (Fab')2 fragments. The digested Fc fragment would be captured using Protein G affinity chromatography and the Fab or (Fab')$_2$ will be collected in the flow-through. The specificity and activity of antibodies produced can be analyzed in using assays described herein such as immunoassays.

The present invention also provides for antibodies that have a half-life in an animal, preferably a mammal and most preferably a human, of greater than 10 days, preferably greater than 15 days, greater than 25 days, greater than 30 days, greater than 35 days, greater than 40 days, greater than 45 days, greater than 2 months, greater than 3 months, greater than 4 months, or greater than 5 months. To prolong the serum circulation of antibodies (e.g., monoclonal antibodies, single chain antibodies and Fab fragments) in vivo, for example, inert polymer molecules such as high molecular weight polyethyleneglycol (PEG) can be attached to the antibodies with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. Degree of conjugation will be closely monitored by SDS-PAGE and mass spectrometry to ensure proper conjugation of PEG molecules to the antibodies. Unreacted PEG will be separated from antibody-PEG conjugates by size-exclusion or by ion-exchange chromatography. PEG-derivatized antibodies can be tested for binding activity as well as for in vivo efficacy using methods known to those of skill in the art, for example, by immunoassays described herein. Further, antibodies having an increased half-life in vivo can be generated as described in PCT Publication No. WO 97/34631.

In one aspect, the invention provides substantially purified antibodies or fragment thereof, including human, non-human, chimeric, and humanized antibodies, which antibodies or fragments specifically bind to a polypeptide comprising an amino acid sequence of any one of SEQ ID NOs: 3, 16, 34, 36, 38, 40, 42, 44, 46 or 48, or an amino acid sequence encoded by the cDNA insert of a clone deposited with the ATCC® as Accession Number 207180 or patent deposit Number PTA-225, or a complement thereof. In a preferred embodiment, the invention provides substantially purified human or humanized monoclonal antibodies which specifically bind to a polypeptide comprising an amino acid sequence of any one of SEQ ID NOs:3, 16, 34, 36, 38, 40, 42, 44, 46 or 48, or an amino acid sequence encoded by the cDNA insert of a clone deposited with the ATCC® as Accession Number 207180 or patent deposited Number PTA-225, or a complement thereof.

In another aspect, the invention provides substantially purified antibodies or fragments thereof, including human, non-human, chimeric and humanized antibodies, which antibodies or fragments thereof specifically bind to a polypeptide comprising a fragment of at least 8 contiguous amino acid residues, preferably at least 10 or at least 15 contiguous amino acid residues, of the amino acid sequence of any one of SEQ ID NOs:3, 16, 34, 36, 38, 40, 42, 44, 46 or 48, or an amino acid sequence encoded by cDNA insert of a cloned deposited with the ATCC® as Accession Number 207180 or patent deposit Number PTA-225, or a complement thereof. In a preferred embodiment, the invention provides substantially purified human or humanized monoclonal antibodies which specifically bind to a polypeptide comprising a fragment of at least 8 contiguous amino acid residues, preferably at least 15 contiguous amino acid residues, of the amino acid sequence of any one of SEQ ID NOs:3, 16, 34, 36, 38, 40, 42, 44, 46 or 48, or amino acid sequence encoded by the cDNA insert of a clone deposited with the ATCC® as Accession Number 207180 or patent deposit Number PTA-225, or a complement thereof.

In another aspect, the invention provides substantially purified antibodies or fragments thereof, including human, non-human, chimeric and humanized antibodies, which antibodies or fragments thereof specifically bind to a polypeptide comprising an amino acid sequence which is at least 65%, preferably at least 75%, at least 85%, at least 95%, or at least 98% identical to the amino acid sequence of any of SEQ ID NOs:3, 16, 34, 36, 38, 40, 42, 44, 46 or 48, wherein the percent identity is determined using the ALIGN program of the GCG software package with a PAM120 weight residue table, a gap length penalty of 12, and a gap penalty of 4. In a specific embodiment, the invention provides substantially purified human or humanized monoclonal antibodies which specifically bind to a polypeptide comprising an amino acid sequence which is at least 65%, preferably at least 75%, at least 85%, at least 95% identical to the amino acid sequence of any one of SEQ ID NOs:3, 16, 34, 36, 38, 40, 42, 44, 46 or 48, wherein the percent identity is determined using the ALIGN program of the GCG software package with a PAM120 weight residue table, a gap length penalty of 12, and a gap penalty of 4.

In another aspect, the invention provides substantially purified antibodies or fragments thereof, including human, non-human, chimeric and humanized antibodies, which antibodies or fragments thereof specifically bind to a polypeptide comprising and an amino acid sequence which is encoded by a nucleic acid molecule which hybridizes to the nucleic acid molecule consisting of any one of SEQ ID Nos:1, 2, 14, 15, 33, 35, 37, 39, 41, 43, 45 or 47, or the cDNA insert of a clone deposited as ATCC® as Accession Number 207180 or patent deposit Number PTA-225, or a complement thereof, under conditions of hybridization of 6× SSC at 45° C. and washing in 0.2× SSC, 0.1% SDS at 50° C. 55° C., 60° C. or 65° C., or 6 × SSC at 45° C. and washing in 0.1 × SSC, 0.2% SDS at 68° C. In a specific embodiment, the invention provides substantially purified human or humanized monoclonal antibodies which specifically bind to a polypeptide comprising an amino acid sequence which is encoded by a nucleic acid molecule which hybridizes to the nucleic acid molecule consisting of any one of SEQ ID Nos:1, 2, 14, 15, 33, 35, 37, 39, 41, 43, 45 or 47, or the cDNA insert of a clone deposited as ATCC° as Accession Number 207180 or patent deposit Number PTA-225, or a complement thereof, under conditions of hybridization of 6× SSC at 45° C. and washing in 0.2 × SSC, 0.1% SDS at 50° C., 55° C., 60° C. or 65° C., or 6 × SSC at 45° C. and washing in 0.1 × SSC, 0.2% SDS at 68° C.

In various embodiments, the substantially purified antibodies or fragments thereof of the invention are polyclonal, monoclonal, Fab fragments, single chain antibodies, or F(ab')2 fragments. The non-human antibodies or fragments thereof of the invention can be goat, mouse, sheep, horse, chicken, rabbit or rat antibodies or antibodies fragments. In a preferred embodiment, the antibodies of the invention are monoclonal antibodies that specifically bind to a polypeptide of the invention.

The substantially purified antibodies or fragments thereof specifically bind to a signal peptide, a secreted sequence, an extracellular domain, a transmembrane or a cytoplasmic domain cytoplasmic membrane of a polypeptide of the invention. In a particularly preferred embodiment, the substantially purified antibodies or fragments thereof of the invention specifically bind to a secreted sequence or an extracellular domain of the amino acid sequence of SEQ ID NO:3, 16, 34, 36, 38, 40, 42, 44, 46 or 48, or the amino acid sequence encoded by the EpthEa11d1 or EpTm268 cDNA insert of ATCC® Accession Number 207180 or patent deposit Number PTA-225, or a complement thereof. In one embodiment, the extracellular domain to which the antibody or antibody fragment binds comprises at least 8 contiguous amino acid residues, preferably at least 10 or at least 15 contiguous amino acid residues, of amino acid residues 30 to 206 of SEQ ID NO:28 (SEQ ID NO:76), amino acid residues 272 to 370 of SEQ ID NO:28 (SEQ ID NO:34); amino acid residues 30 to 249 of SEQ ID NO:39 (SEQ ID NO: 83), amino acid residues 39 to 123 of SEQ ID NO:48 (SEQ ID NO:50), or amino acid residues 27 to 112 of SEQ ID NO:58 (SEQ ID NO:61).

In one embodiment, antibodies that immunospecifically bind to a native TANGO 268 polypeptide or fragment thereof (e.g., a glycosylated TANGO 268 polypeptide or fragment thereof). In another embodiment, antibodies that immunospecifically bind to a TANGO 268 polypeptide or fragment thereof lacking post-translational modifications such as glycosylation.

The present invention provides scFvs having the amino acid sequence of clone A9, A10, C9, A4, C10, B4, C3 or D11. In a specific embodiment, scFvs have the amino acid sequence of scFvs A4, A9, A10 or C3 deposited with the ATCC® as patent deposit Number __, patent deposit Number __, patent deposit Number __, or patent deposit Number __, respectively. In another embodiment, antibodies that immunospecifically bind to a TANGO 268 polypeptide or fragment thereof comprise a VH domain of the scFv clone A9, A10, C9, A4, C10, B4, C3 or D11. In another embodiment, antibodies that immunospecifically bind to a TANGO 268 polypeptide or fragment thereof comprise a VL domain of the scFc clone A9, A10, C9, A4, C10, B4, C3 or D11. In another embodiment, antibodies that immunospecifically bind to a TANGO 268 polypeptide or fragment thereof comprise a VH domain of the scFv clone A9, A10, C9, A4, C10, B4, C3 or D11 and a VL domain of the scFv clone A9, A10, C9, A4, C10, B4, C3 or D11. In a preferred embodiment, the antibodies of fragments thereof comprise a VH and a VL domain from the same scFv.

The present invention provides antibodies having any one of the VH CDR of the scFv clone A9, A10, C9, A4, C10, B4, C3 or D11. The present invention also provides antibodies having any one of the VL CDRs of the scFv clone A9, A10, C9, A4, C10, B4, C3 or D11. The present invention also provides antibodies having any one of the VH CDRs of the scFv clone A9, A10, C9, A4, C10, B4, C3 or D11 and any one of the VL CDRs of the scFv clone A9, A10, C9, A4, C10, B4, C3 or D11. In a preferred embodiment, the antibodies or fragments thereof comprise a VH and a VL CDRs from the same scFv. The present invention further provides antibodies having a nucleotide sequence encoding the amino acid sequence of the scFv clone A9, A10, C9, A4, C10, B4, C3 or D11.

The present invention provides antibodies that immunospecifically bind to a TANGO 268 polypeptide or fragment thereof and that are generated from the heavy and light chain variable domain complementarity determining regions ("CDRs") of the scFvs listed in Table 7. In particular, the invention provides scFvs comprising the heavy and light chain domain CDRs listed in Table 7 that have been "converted" to immunoglobulin molecules by inserting the nucleotide sequences encoding the variable heavy ("VH") and variable light ("VL") domain CDRs of the scFv into an expression vector containing the constant domain sequences and engineered to direct the expression of the immunoglobulin molecule, as described supra.

The present invention encompasses antibodies that immunospecifically bind to a TANGO 268 polypeptide or fragment thereof having a variable heavy ("VH") domain comprising one or more VH complementary determining regions ("CDRs") listed in Table 7. In one embodiment of the present invention, antibodies that immunospecifically bind to a TANGO 268 polypeptide or fragment thereof comprises a VH CDR1 having the amino acid sequence of SEQ ID NO:49, 55, 61 or 67. In another embodiment, antibodies that immunospecifically bind to a TANGO 268 polypeptide or fragment thereof comprise a VH CDR2 having the amino acid sequence of SEQ ID NO:50, 56, 62 or 68. In another embodiment, antibodies that immunospecifically bind to a TANGO 268 polypeptide or fragment thereof comprise a VH CDR3 having the amino acid sequence of SEQ ID NO:51, 57, 63 or 69.

In another embodiment, antibodies that immunospecifically bind to a TANGO 268 polypeptide or fragment thereof comprise a VH CDR1 having the amino acid sequence of SEQ ID NO:49, 55, 61 or 67 and a VH CDR2 having the amino acid sequence of SEQ ID NO:50, 56, 62 or 68. In another embodiment, antibodies that immunospecifically bind to a TANGO 268 polypeptide or fragment thereof comprise a VH CDR1 having the amino acid sequence of SEQ ID NO:49, 55, 61 or 67 and a VH CDR 3 having the amino acid of SEQ ID NO:51, 57, 63 or 69. In yet another embodiment, antibodies that immunospecifically bind to a TANGO 268 polypeptide or fragment thereof comprise a VH CDR2 having the amino acid sequence of SEQ ID NO:50, 56, 62 or 68 and a VH CDR 3 having the amino acid of SEQ ID NO:51, 57, 63 or 69. In another embodiment, antibodies that immunospecifically bind to a TANGO 268 polypeptide or fragment thereof comprise a VH CDR1 having the amino acid sequence of SEQ ID NO:49, 55, 61 or 67, a VH CDR2 having the amino acid sequence of SEQ ID NO:50, 56, 62 or 68, and a VH CDR 3 having the amino acid of SEQ ID NO:51, 57, 63 or 69.

In a preferred embodiment, antibodies that immunospecifically bind to a TANGO 268 polypeptide or fragment thereof comprise a VH CDR1 having the amino acid sequence of SEQ ID NO:49, a VH CDR2 having the amino acid sequence of SEQ ID NO:50, and a VH CDR3 having the amino acid sequence of SEQ ID NO:51. In another preferred embodiment, antibodies that immunospecifically bind to a TANGO 268 polypeptide or fragment thereof comprise a VH CDR1 having the amino acid sequence of SEQ ID NO:55, a VH CDR2 having the amino acid sequence of SEQ ID NO:56, and a VH CDR3 having the amino acid sequence of SEQ ID NO:57. In another preferred embodiment, antibodies that immunospecifically bind to a TANGO 268 polypeptide or fragment thereof comprise a VH CDR1 having the amino acid sequence of SEQ ID NO:61, a VH CDR2 having the amino acid sequence of SEQ ID NO:62, and a VH CDR3 having the amino acid sequence of SEQ ID NO:63. In yet another preferred embodiment, antibodies that immunospecifically bind to a TANGO 268 polypeptide or fragment thereof comprise a VH CDR1 having the amino acid sequence of SEQ ID NO:67, a VH CDR2 having the amino acid sequence of SEQ ID NO:68, and a VH CDR3 having the amino acid sequence of SEQ ID NO:69.

The present invention encompasses antibodies that immunospecifically bind to a TANGO 268 polypeptide or fragment thereof having a variable light ("VL") domain comprising one or more VL complementary determining regions ("CDRs") listed in Table 7. In one embodiment of the present invention, antibodies that immunospecifically bind to a TANGO 268 polypeptide comprise a VL CDR1 having the amino acid sequence of SEQ ID NO:52, 58, 64 or 70. In another embodiment, antibodies that immunospecifically bind to a TANGO 268 polypeptide or fragment thereof comprise a VL CDR2 having the amino acid sequence of SEQ ID NO:53, 59, 65 or 71. In another embodiment, antibodies that immunospecifically bind to a TANGO 268 polypeptide or fragment thereof comprise a VL CDR3 having the amino acid sequence of SEQ ID NO:54, 60, 66 or 72.

In another embodiment, antibodies that immunospecifically bind to a TANGO 268 polypeptide or fragment thereof comprise a VL CDR1 having the amino acid sequence of SEQ ID NO:52, 58, 64 or 70 and a VL CDR2 having the amino acid sequence of SEQ ID NO:53, 59, 65 or 71. In another embodiment, antibodies that immunospecifically bind to a TANGO 268 polypeptide or fragment thereof comprise a VL CDR1 having the amino acid sequence of SEQ ID NO:52, 58, 64 or 70 and a VL CDR2 having the amino acid of SEQ ID NO:54, 60, 66 or 72. In another embodiment, antibodies that immunospecifically bind to a TANGO 268 polypeptide or fragment thereof comprise a VL CDR2 having the amino acid sequence of SEQ ID NO:53, 59, 65 or 71 and a VL CDR3 having the amino acid of SEQ ID NO:54, 60, 66 or 72. In yet another embodiment, antibodies that immunospecifically bind to a TANGO 268 polypeptide or fragment thereof comprise a VL CDR1 having the amino acid sequence of SEQ ID NO:52, 58, 64 or 70, a VL CDR2 having the amino acid sequence of SEQ ID NO:53, 59, 65 or 71, and a VL CDR3 having the amino acid of SEQ ID NO:54, 60, 66 or 72.

In a preferred embodiment, antibodies that immunospecifically bind to a TANGO 268 polypeptide or fragment thereof comprise a VL CDR1 having the amino acid sequence of SEQ ID NO:52, a VL CDR2 having the amino acid sequence of SEQ ID NO:53, and a VL CDR3 having the amino acid sequence of SEQ ID NO:54. In another preferred embodiment, antibodies that immunospecifically bind to a TANGO 268 polypeptide or fragment thereof comprise a VL CDR1 having the amino acid sequence of SEQ ID NO:58, a VL CDR2 having the amino acid sequence of SEQ ID NO:59, and a VL CDR3 having the amino acid sequence of SEQ ID NO:60. In another preferred embodiment, antibodies that immunospecifically bind to a TANGO 268 polypeptide or fragment thereof comprise a VL CDR1 having the amino acid sequence of SEQ ID NO:64, a CDR2 having the amino acid sequence of SEQ ID NO:65, and a VL CDR3 having the amino acid sequence of SEQ ID NO:66. In yet another preferred embodiment, antibodies that immunospecifically bind to a TANGO 268 polypeptide or fragment thereof comprise a VL CDR1 having the amino acid sequence of SEQ ID NO:70, a VL CDR2 having the amino acid sequence of SEQ ID NO:71, and a VL CDR3 having the amino acid sequence of SEQ ID NO:72.

The present invention also provides antibodies comprising one or more VH CDRs and one or more VL CDRs as listed in Table 7. In particular, the invention provides for an antibody comprising a VH CDR1 and a VL CDR1, a VH CDR1 and a VL CDR2, A VH CDR1 and a VL CDR3, a VH CDR2 and a VL CDR1, VH CDR2 and VL CDR2, A VH CDR2 and a VL CDR3, a VH CDF3 and a VH CDR1, VH CDR3 and a VL CDR2, A VH CDR3 and a VL CDR3, or any combination thereof of the VH CDRs and VL CDRs listed in Table 7.

In one embodiment, an antibody of the invention comprises a VH CDR1 having the amino acid sequence of SEQ ID NO:49, 55, 61 or 67 and a VL CDR1 having the amino acid sequence of SEQ ID NO:52, 58, 64 or 70. In another embodiment, an antibody of the present invention comprises a VH CDR1 having the amino acid sequence of SEQ ID NO:49, 55, 61 or 67 and a VL CDR2 having the amino acid sequence of SEQ ID NO:53, 59, 65 or 71. In another embodiment, an antibody of the present invention comprises a VH CDR1 having the amino acid sequence of SEQ ID NO:49, 55, 61 or 67 and a VL CDR3 having the amino acids sequence of SEQ ID NO:54, 60, 66 or 72.

In another embodiment, an antibody of the present invention comprises a VH CDR2 having the amino acid sequence of SEQ ID NO:50, 56, 62, 68 and a VL CDR1 having the amino acid sequence of SEQ ID NO:52, 58, 64 or 70. In another embodiment, an antibody of the present invention comprises a VH CDR2 having the amino acid sequence of SEQ ID NO:50, 56, 62, 62 and a VL CDR2 having the amino acid sequence of SEQ ID NO:53, 59, 65 or 71. In another embodiment, an antibody of the present invention comprises a VH CDR2 having the amino acid sequence of SEQ ID NO:50, 56, 62, 68 and a VL CDR3 having the amino acid sequence of SEQ ID NO:54, 60, 66 or 72.

In another embodiment, an antibody of the present invention comprises a VH CDR3 having the amino acid sequence of SEQ ID NO:51, 57, 63 or 69, and a VL CDR1 having the amino acid sequence of SEQ ID NO:52, 58, 64, 70. In another embodiment, an antibody of the present invention comprises a VH CDR3 having the amino acid sequence of SEQ ID NO:51, 57, 63 or 69 and a VL CDR2 having the amino acid sequence of SEQ ID NO:53, 59, 65 or 71. In a preferred embodiment, an antibody of the present invention comprises a VH CDR3 having the amino acid sequence of SEQ ID NO:51, 57, 63 or 69 and a VL CDR3 having the amino acid sequence of SEQ ID NO:54, 60, 66 or 72.

The present invention also provides for a nucleic acid molecule, generally isolated, encoding an antibody of the present invention. In one embodiment, a nucleic acid molecule of the invention encodes an antibody comprising a VH CDR having an amino acid sequence of any one of the VH CDRs listed in Table 7. In a specific embodiment, a nucleic acid molecule of the present invention encodes an antibody comprising a VH CDR1 having an amino acid sequence of any one of the VH CDR1s listed in Table 7. In another embodiment, a nucleic acid molecule of the present invention encodes an antibody comprising a VH CDR2 having an amino acid sequence of any one of the VH CDR2s listed in Table 7. In yet another embodiment, a nucleic acid molecule of the present invention encodes an antibody comprising a VH CDR3 having an amino acid sequence of any one of the VH CDR3s listed in Table 7.

In another embodiment, a nucleic acid molecule of the invention encodes an antibody comprising a VL CDR having an amino acid sequence of any of the VL CDRs listed in Table 7. In another embodiment, a nucleic acid molecule of the present invention encodes an antibody comprising a VL CDR1 having amino acid sequence of any one of the VL CDR1s is listed in Table 7. In another embodiment, a nucleic acid molecule of the present invention encodes an antibody comprising a VL CDR2 having an amino acid sequence of any one of the VL CDR2s listed in Table 7. In yet another embodiment, a nucleic acid molecule of the present invention encodes an antibody comprising a VL CDR3 having an amino acid sequence of any one of the VL CDR3s listed in Table 7.

In another embodiment, a nucleic acid molecule of the invention encodes an antibody comprising a VII CDR1, a VL CDR1, a VH CDR2, a VL CDR2, a VH CDR3, a VL CDR3, or any combination thereof having an amino acid sequence listed in Table 7.

The present invention also provides antibodies comprising derivatives of the VH CDRs and VL CDRs described herein, which antibodies immunospecifically bind to a TANGO 268 polypeptide or fragment thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the derivatives include less than 25 amino acid substituents, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein, i.e., ability to immunospecifically bind a TANGO 268 polypeptide or fragment thereof can be expressed and the activity of the protein can be determined.

In a specific embodiment, an antibody that immunospecifically binds to a TANGO 268 polypeptide or fragment thereof comprises an amino acid sequence of a VH CDR or an amino acid sequence of a VL CDR encoded by a nucleotide sequence that hybridizes to the nucleotide sequence encoding any one of the VH CDRs or VL CDRs listed in Table 7 under stringent conditions, e.g., hybridization to filter-bound DNA in 6× sodium chloride/sodium citrate (SSC) at about 45° C. followed by one or more washes in 0.2× SSC, 0.1% SDS at about 50–65° C., under highly stringent conditions, e.g., hybridization to filter-bound nucleic acid in 6× SSC at about 45° C. followed by one or more washes in 0.1× SSC, 0.2% SDS at about 68° C., under other stringent hybridization conditions which are known to those of skill in the art (see, for example, Ausubel, F. M. et al., eds., 1989, Current Protocols in Molecular Biology, Vol. 1, Green Publishing Associates, Inc. and John Wiley & Sons, Inc., New York at pages 6.3.1–6.3.6 and 2.10.3). In another embodiment, an antibody that immunospecifically binds to a TANGO 268 polypeptide or fragment thereof comprises an amino acid sequence of a VH CDR and an amino acid sequence of a VL CDR encoded by nucleotide sequences that hybridize to the nucleotide sequences encoding any one of the VH CDRs and VL CDRs, respectively, listed in Table 7 under stringent conditions, e.g., hybridization to filter-bound DNA in 6× sodium chloride/sodium citrate (SSC) at about 45° C. followed by one or more washes in 0.2× SSC, 0.1% SDS at about 50–65° C., under highly stringent conditions, e.g., hybridization to filter-bound nucleic acid in 6× SSC at about 45° C. followed by one or more washes in 0.1× SSC, 0.2% SDS at about 68° C., or under other stringent hybridization conditions which are known to those of skill in the art.

In another embodiment, an antibody that immunospecifically binds to a TANGO 268 polypeptide or fragment thereof comprises an amino acid sequence of one or more VH CDRs that are at least 35%, at least 40%, at least 45%, at least 50%, at least 55%, at least 60%, at least 65%, at least 70%, at least 75%, at least 80%, at least 85%, at least 90%, at least 95%, or at least 99% identical to any of the VH CDRs listed in Table 7.

In another embodiment, an antibody that immunospecifically binds to a TANGO 268 polypeptide or fragment thereof comprises an amino acid sequence of one or more VL CDRs that are at least 35%, at least 40%, at least 45%, at least 50%, at least 55%, at least 60%, at least 65%, at least 70%, at least 75%, at least 80%, at least 85%, at least 90%, at least 95%, or at least 99% identical to any of the VL CDRs listed in Table 7.

The antibodies of the invention include derivatives that are modified, i.e., by the covalent attachment of any type of molecule to the antibody such that covalent attachment does not affect the ability the antibody to immunospecifically bind to a TANGO 268 polypeptide. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including but not limited to specific chemical cleavage, acetylation, formylation, metabolic synthesis of tunicamycin, etc. Additionally, the derivative may contain one or more non-classical amino acids.

TABLE 7

CDR Sequences of scFvs that Immunospecifically Bind to TANGO 268 Polypeptides

| scFv Clone | VHCDR1 | VHCDR2 | VHCDR3 | VLCDR1 | VLCDR2 | VLCDR3 |
|---|---|---|---|---|---|---|
| A4 | SYWIS (SEQ ID NO:49) | RIDPSDSYTNY SPSFQG (SEQ ID NO:50) | HGSDRGW GFDP (SEQ ID NO:51) | NGVNSDV G (SEQ ID NO:52) | EVNKRPS (SEQ ID NO:53) | SYTSNNTPV (SEQ ID NO:54) |
| A9 | SYSMN (SEQ ID NO:55) | SISSSGRYISY GDSVKG (SEQ ID NO:56) | DISSAMDV (SEQ ID NO:57) | TRGGNNIG SKSVH (SEQ ID NO:58) | DDSDRPS (SEQ ID NO:59) | VWDSSSDH HV (SEQ ID NO:60) |
| A10 | SYWMS (SEQ ID NO:61) | NIKQDGSEKY YADSVRG (SEQ ID NO:62) | DKWEAYIT PGAFDV (SEQ ID NO:63) | TRSSGSIA SNYVQ (SEQ ID NO:64) | EDNQRPS (SEQ ID NO:65) | SYDSSNVV (SEQ ID NO:66) |
| C3 | NYEMN (SEQ ID NO:67) | YISSSGSTIHN ADSVKG (SEQ ID NO:68) | DGYSHGLD AFDI (SEQ ID NO:69) | SGSSSNIG SNTVH (SEQ ID NO:70) | SYNQRPS (SEQ ID NO:71) | SWDDRLNG YL (SEQ ID NO:72) |

In one embodiment, an antibody of the invention has the nucleic acid sequence encoding a murine monoclonal antibody produced by murine hybridoma cell line 8M14.3, 3F8.1, 9E18.3, 3J24.2, 6E12.3, 1P10.2, 4L7.1, 4L7.3, 7H4.6 or 9012.2. In another embodiment, an antibody of the invention has the amino acid sequence of the monoclonal antibody produced by murine monoclonal antibody produced by murine hybridoma cell line 8M14.3, 3F8.1, 9E18.3, 3J24.2, 6E12.3, 1P10.2, 4L7.1, 4L7.3, 7H4.6 or 9012.2. In a preferred embodiment, an antibody of the invention has the nucleic acid sequence encoding a murine monoclonal antibody produced by murine hybridoma cell line 9012.2, 1P10.2, 8M14.3, 9E18.2 or 7H4.6 deposited with the ATCC® as patent deposit Number PTA-1746, patent deposit Number PTA-1747, patent deposit Number PTA-1748, patent deposit Number PTA-1749, or patent deposit Number PTA-1750, respectively. In another preferred embodiment, an antibody of the invention has the amino acid sequence of the monoclonal antibody produced by murine monoclonal antibody produced by murine hybridoma cell line 9012.2, 1P10.2, 8M14.3, 9E18.2 or 7H4.6 deposited with the ATCC® as patent deposit Number PTA-1746, patent deposit Number PTA-1747, patent deposit Number PTA-1748, patent deposit Number PTA-1749, or patent deposit Number PTA-1750, respectively.

The present invention provides antibodies comprising VL or VH domain having the amino acid sequence of mouse monoclonal antibody produced by mouse hybridoma cell line 8M14.3, 3F8.1, 9E18.3, 3J24.2, 6E12.3, 1P10.2, 4L7.1, 4L7.3, 7H4.6 or 9012.2. In a specific embodiment, antibodies of the present invention comprises a VL or VH domain having the amino acid sequence of mouse monoclonal antibody produced by mouse hybridoma cell line 9012.2, 1P10.2, 8M14.3, 9E18.2 or 7H4.6 deposited with the ATCC® as patent deposit Number PTA-1746, patent deposit Number PTA-1747, patent deposit Number PTA-1748, patent deposit Number PTA-1749, or patent deposit Number PTA-1750, respectively. The present invention also provides antibodies comprising VL and VH domains having the amino acid sequence of mouse monoclonal antibody produced by mouse hybridoma cell line 8M14.3, 3F8.1, 9E18.3, 3J24.2, 6E12.3, 1P10.2, 4L7.1, 4L7.3, 7H4.6 or 9012.2. In a specific embodiment, antibodies of the present invention comprise VL and VH domains having the amino acid sequence of mouse monoclonal antibody produced by mouse hybridoma cell line 9012.2, 1P10.2, 8M14.3, 9E18.2 or 7H4.6 deposited with the ATCC® as patent deposit Number PTA-1746, patent deposit Number PTA-1747, patent deposit Number PTA-1748, patent deposit Number PTA-1749, or patent deposit Number PTA-1750, respectively.

The present invention also provides for antibodies comprising one or more VL CDRS or VH CDRs having the amino acid sequence of mouse monoclonal antibody produced by mouse hybridoma cell line 8M14.3 3F8.1, 9E18.3, 3J24.2, 6E12.3, 1P10.2, 4L7.1, 4L7.3, 7H4.6 or 9012.2. In a specific embodiment, antibodies of the present invention comprise one or more VL DCRs or VH CDRs having the amino acid sequence of mouse monoclonal antibody produced by mouse hybridoma cell line 9012.2, 1P10.2, 8M14.3, 9E18.2 or 7H4.6 deposited with the ATCC® as patent deposit Number PTA-1746, patent deposit Number PTA-1747, patent deposit Number PTA-1748, patent deposit Number PTA-1749, or patent deposit Number PTA-1750, respectively.

The present invention also provides for antibodies comprising VL CDRs and one or more VH CDRs having the amino acid sequence of mouse monoclonal antibody produced by mouse hybridoma cell line 8M14.3, 3F8.1, 9E18.3, 3J24.2, 6E12.3, 1P10.2, 4L7.1, 4L7.3, 7H4.6 or 9012.2. In a specific embodiment, antibodies of the present invention comprise one or more VL CDRs and one or more VH CDRs having the amino acid sequence of mouse monoclonal antibody produced by mouse hybridoma cell line 9012.2, 1P10.2, 8M14.3, 9E18.2 or 7H4.6 deposited with the ATCC® as patent deposit Number PTA-1746, patent deposit Number PTA-1747, patent deposit Number PTA-1748, patent deposit Number PTA-1749, or patent deposit Number PTA-1750, respectively.

The present invention also provides for a nucleic acid molecule, generally isolated, encoding a mouse monoclonal antibody produced by mouse hybridoma cell line 8M14.3, 3F8.1, 9E18.3, 3J24.2, 6E12.3, 1P10.2, 4L7.1, 4L7.3, 7H4.6 or 9012.2. In one embodiment, a nucleic acid molecule of the invention encodes an antibody comprising one or more a VH or VL domains of murine monoclonal antibody produced by mouse hybridoma cell line 8M14.3, 3F8.1, 9E18.3, 3J24.2, 6E12.3, 1P10.2, 4L7.1, 4L7.3, 7H4.6 or 9012.2. In another embodiment, a nucleic acid molecule of the invention encodes an antibody comprising one or more VH domains and one or more VL domains of murine monoclonal antibody produced by mouse hybridoma cell line 8M14.3, 3F8.1, 9E18.3, 3J24.2, 6E12.3, 1P10.2, 4L7.1, 4L7.3, 7H4.6 or 9012.2. In another embodiment, a nucleic acid molecule of the invention encodes an antibody comprising one or more of VH CDRs or one or more VL CDRs of murine monoclonal antibody produced by mouse hybridoma cell line 8M14.3, 3F8.1, 9E18.3, 3J24.2, 6E12.3, 1P10.2, 4L7.1, 4L7.3, 7H4.6 or 9012.2. In another embodiment, a nucleic acid molecule of the invention encodes an antibody comprising one or more VH CDRs and one or more VL CDRs of murine monclonal antibody produced by mouse hybridoma cell line 8M14.3, 3F8.1, 9E18.3, 3J24.2, 6E12.3, 1P10.2, 4L7.1, 4L7.3, 7H4.6 or 9012.2.

The antibodies of the invention may be assayed for immunospecific binding to a TANGO 268 polypeptide of fragments thereof and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see e.g., Ausubel et al, eds, 1994, Current Protocols in Molecular Biology, Vol. 1, John Wiley & Sons, Inc., New York, which is incorporated by reference herein in its entirety).

In a preferred embodiment, BIAcore kinetic analysis is used to determine the binding on and off rates of antibodies to a TANGO 268 polypeptide. BIAcore kinetic analysis comprises analyzing the binding and dissociation of a TANGO 268 polypeptide from chips with immobilized antibodies on their surface (see the Example section infra).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic group, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; and example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Further, an antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gamicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin) bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, interferon-α, interferon-β, nerve growth factor, platelet derived growth factor, tissue plasminogen activator; or, biological response modifiers such as, for example. lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating a therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies for Drug Delivery", in Controlled Drug Delivery (2nd Ed.), Robinson et al. (eds.), pp. 623–53 (Marcel Dekker, Inc. 1987); Thorpe, "Antibody Carriers of Cytotoxic Agents in Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use of Radiolabeled Antibody in Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982).

Alternatively, an antibody can be conjugated to a second antibody to form an antibody heteroconjugate as described by Segal in U.S. Pat. No. 4,676,980.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

In instances wherein the antibody is to be utilized as a therapeutic, characterization of the antibody can routinely be assayed and ascertained via the methods presented herein. For example, the fact that platelets are readily available, coupled with the availability of multiple assays for platelet function provide for routine testing and analysis (e.g., for in vitro testing and analysis) of such antibodies.

For example, the in vivo pharmacodynamic characterization of anti-TANGO 268 antibodies can be facilitated via the availability of various platelet assays (e.g., prolongation of bleeding time, quantitative measurement of TANGO 268 receptor blockade, inhibition of ex vivo platelet aggregation)

such as those described herein that can be correlated with each other to permit more effective assessment of a modulator's functional consequences. The correlation available for such assays, therefore, allows for the in vitro characterization of an anti-TANGO 268 antibody to more directly apply to the measurement of the antibody's therapeutic effect.

In addition to utilizing the availability of platelets and platelet assays for assessing the therapeutic efficacy, including clinical efficacy, of an anti-TANGO 268 antibody, this availability can also be utilized for preclinical drug development aspects such as determining antibody dosage response, toxicology, magnitude of effect (e.g., magnitude of initial effect and magnitude of effect's duration), function, specificity (e.g., specificity with respect to particular platelet functions), receptor specificity, and species specificity (which, in turn, can identify appropriate animal models for pharmacology studies).

III. Recombinant Expression Vectors and Host Cells

Another aspect of the invention pertains to vectors, preferably expression vectors, containing a nucleic acid encoding a polypeptide of the invention (or a portion thereof). As used herein, the term "vector" refers to a nucleic acid molecule capable of transporting another nucleic acid to which it has been linked. One type of vector is "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked on the regulatory sequence(s) in a manner which allows for expression of the nucleotide sequence (e.g., in an in vitro transcription/translation system or in a host cell when the vector is introduced into the host cell). The term "regulatory sequence" is intended to include promoters (enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for examples using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31–40), pMAL (New England Bioabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTre (Amann et al., 1988, *Gene* 69:301–315) and pET 11d (Studier et al., *Gene Expression Technology: Methods in Ezymology* 185, Academic Press, San Diego, Calif. (1990) 60–89). Target gene expression from the pTrc vector relies on host RNA polymerase transcription from a hybrid trp-lac fusion promoter. Target gene expression from the pET 11 vector relies on transcription from a T7 gn10-lac fusion promoter mediated by a coexpressed viral RNA polymerase (T7gn1). This viral polymerase is supplied by host strains BL21 (DE3) or HMS174 (DE3) from a resident λ phophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., 1992, *Nucleic Acids. Res.* 20:2111–2118). Such alteration of nucleic acid sequences of the invention can be carried out by standard DNA synthesis techniques.

In another embodiment; the expression vector is a yeast expression vector. Examples of vectors for expression in yeast *S. cerivisae* include pYepScc1 (Baldari et al., 1987, EMBO J. 6:229–234), pMFa (Kurjan and Herskowitz, 1982, Cell 30:933–943), pJRY88 (Schultz et al., 1987, Gene 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf9 cells) include the pAc series (Smith et al., 1983, Mol. Cell Biol. 3:2156–2165) and the pVL series (Luckow and Summers, 1989, Virology 170:31–39).

In yet another embodiment, a nucleic acid of the invention is expressed in mammalian cellus using a mammalian expression vector. Examples of mammalian expression vectors include pCDM8 (Seed, 1987, Nature 329:840) and pMT2PC (Kaufman et al., 1987, EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268–277), lymphoid-specific promoters (Calame and Eaton, 1988, Adv. Immunol. 43:235–275), in particular promoters of T cell receptors (Winoto and Baltimore, 1989. EMBO J. 8:729–733) and immunoglobulins (Banerji et al., 1983), Cell 33:729–740; Queen and Baltimore, 1983), Cell 33:741–748), neuron-specific promoters (e.g., the neurofilament promoter; Byrne and Ruddle, 1989, Proc. Natl. Acad. Sci. USA 86:5473–5477), pancreas-specific promoters (Edlund et al., 1985, Science 230:912–916), and mammary gland-specific promoters (e.g., milk whey promoter; U.S. Pat. No. 4,873, 316 and European Application Publication No. 264,166). Developmentally-regulated promoters are also encompassed, for example the mouse box promoters (Kessel and Gruss, 1990, Science 249:374–379) and the beta-fetoprotein promoter (Campes and Tilghman, 1989, Genes Dev. 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., E. coli) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small friction of cells may integrated the foreign DNA into their genome. In order to identify and select these integrants a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

In another embodiment, the expression characteristics of an endogenous (e.g., TANGO 268 genes) within a cell, cell line or microorganism may be modified by inserting a DNA regulatory element heterologous to the endogenous gene of interest into the genome of cell, stable cell line or cloned microorganism such that the inserted regulatory element is operatively linked with the endogenous gene (e.g., TANGO 268 genes) and controls, modulates or activates. For example, endogenous TANGO 268genes which are normally "transcriptionally silent", i.e., a TANGO 268 genes which is normally not expressed, or are expressed only at very low levels in a cell line or microorganism, may be activated by inserting a regulatory element which is capable of promoting the expression of a normally expressed gene product in that cell line or microorganism. Alternatively, transcriptionally silent, endogenous TANGO 268 genes may be activated by insertion of a promiscuous regulatory element that works across cell types.

A heterologous regulatory element may be inserted into a stable cell line or cloned microorganism, such that it is operatively linked with and activates expression of endogenous TANGO 268 genes, using techniques, such as targeted homologous recombination, which are well known to those of skill in the art, and described e.g., in Chappel, U.S. Pat. No. 5,272,071; and PCT publication No. WO91/06667, published May 16, 1991.

A host cell of the invention, such as prokaryotic or eukaryotic host cell in culture, can be used to produce a polypeptide of the invention. Accordingly, the invention further provides methods for producing polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a sequence encoding a polypeptide of the invention has been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention (or a homologoue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods of generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191, in Hogan, *Manipulating the Mouse Embryo,* (Cold Spring Harbor Laboratory Press, Cold Spring Harbor, N.Y., 1986) and in Wakayama et al., 1999, Proc. Natl. Acad. Sci. USA, 96:14984–14989. Similar methods are used for production of other transgenic animals. A transgenic founder animal can be identified based upon the presence of the transgene in its genome and/or expression of mRNA encoding the transgene in tissues or cells of the animals. A transgenic founder animal can then be used to break additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi, 1987, *Cell* 51:503 for a description of homologous (recombination vectors). The vector is introduced into an embryonic stem cell line (e.g., by electroporation) and cells in which the introduced gene has homologously recombined with the endogenous gene are selected (see, e.g., Li et al., 1992, *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach,* Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, 1991, *Current Opinion in Bio/Technology* 2:823–829 and in PCT Publication Nos. WO 90/11354, WO91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al., 1992, *Proc. Natl. Acad. Sci. USA* 89/6232–6236. Another example of a recombinase system is the FLP recombinase system of *Saccharomyces cerevisiae* (O'Gorman et al., 1991, *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al., 1997, *Nature* 385:810–813 and PCT Publication NOS. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression of activity of a polypeptide or nucleic acid of the invention and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intraveneous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent of dispersion medium containing, for example, water, ethanol, polyol (for example), glycerol, propylene, glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include some isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alzo Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for case of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be acheived, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

Preferably, administration of the TANGO 268 modulator is at or near the site of the cells or tissues to be treated, e.g., administration is at or near the site of a platelet aggregation-induced disorder such as one of those described herein.

In certain embodiments, the TANGO 268 modulator is administered or co-administered with at least one other desirable agent, e.g., heparin or aspirin.

In certain instances, it is preferred that administration of a TANGO 268 modulator comprises an initial bolus followed by continuous infusion. For example, such instances will generally include those wherein the modulator exhibits appreciable reversibility in platelet binding, as e.g., assayed via the techniques described herein.

In one example, presented by way of illustration and not by way of limitation, a dosage and administration regimen for treatment of ischemic heart disease or thromboses comprises: in patients undergoing percutaneous coronary angioplasty (PCA), the TANGO 268 modulator (e.g. anti-TANGO 268 antibody) is administered as a 0.25 mg/kg IV bolus plus infusion of 10 $\mu$g/min or 0.125 $\mu$g/kg/min (this can, alternatively, be performed in conjunction with heparin and aspirin) for 12 hours. In patients with refractory unstable angina in whom PCA is planned within 24 hours, the bolus and infusion are given 18–24 hours before the procedure and the infusion is continued for 1 hour or 12 hours after the procedure.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 15,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of ordinary skilled physician, veterinarian, or researcher. The dose(s) of the small molecule will vary, for example, depending upon the identity, size, and condition of the subject or sample being treated, further developing upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). The isolated nucleic acid molecules of the invention can be used to express proteins (e.g., via a recombinant expression vector in a host cell in gene therapy applications), to detect mRNA (e.g., in a biological sample) or a genetic lesion, and to modulator activity of a polypeptide of the invention. In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the invention or to modulate activity of a protein of the invention.

This invention further pertains to novel agents identified by the above-described screening assays and uses thereof for treatments as described herein.

A. Screening Assays

The invention provides a method (also referred to as herein as a "screening assay") for identifying modulators, i.e., candidate or test compounds or agents (e.g., peptides, peptidomimetics, small molecules or other drugs) which bind to polypeptide of the invention or have a stimulatory or inhibitory effect on, for example, expression or activity of a polypeptide of the invention.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-head one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) Angew. Chem. Int. Ed. Engl. 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (Pat. Nos. 5,571,698; 5,403,484; and 5,223,409), plasmids (Cull et al. (1992) *Proc. Natl. Acad. Sci. USA* 89:1865–1869) or phage Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

In one embodiment, an assay is a cell-based assay in which a cell which expresses a membrane-bound form of a polypeptide of the invention, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a text compound, and determining the ability of the test compound to interact with the polypeptide, wherein determining the ability of test compound to interact with the polypeptide comprises determining the ability of the test compound to preferentially bind to the polypeptide or a biologically active portion thereof as compared to the known compound.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention) binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g., luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it may be desirable to utilize a solubilizing agent such that the membrane-bound form of the polypeptide is maintained in solution. Examples of such solubilizing agents include non-ionic detergents such as n-octyglucoside, n-dodecylglucoside, n-octylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either the polypeptide of the invention or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or A polypeptide of the invention, and the mixture incubated under conditions conductive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention is to target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which is a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the inventions can be used as "bait proteins" in a two-hybrid assay or three hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *BioTechniques* 14:920–924; Iwabuchi et al. (1993) *Oncogene* 8:1693–1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the invention as, for example, upstream or downstream elements of a signaling pathway involving the polypeptide of the invention.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identifying an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, nucleic acid molecules described herein or fragments thereof, can be used to map the location of the corresponding genes on a chromosome. The mapping of the sequences to chromosomes is an important first step in correlating these sequences with genes associated with disease.

Briefly, genes can be mapped to chromosomes by preparing PCR primers (preferably 15–25 bp in length) from the sequence of a gene of the invention. Computer analysis of the sequence of a gene of the invention can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al., 1983, *Science* 220:919–924.

PCR mapping of somatic cell hybrids is a rapid procedure for assigning a particular sequence to a particular chromosome. Three or more sequences can be assigned per day using a similar thermal cycler. Using the nucleic acid sequences of the invention to design oligonucleotide primers, sublocalization can be achieved with panels of fragments from specific chromosomes. Other mapping strategies which can similarly be used to map a gene to its chromosome include in situ hybridization (described in Fan et al., (1990) *Proc. Natl. Acad. Sci. USA* 87:6223–27), pre-screening with labeled flow-sorted chromosomes (CITE), and pre-selection by hybridization to chromosome specific cDNA libraries. Fluorescence in situ hybridization (FISH) of a DNA sequence to a metaphase chromosomal spread can further be used to provide a precise chromosomal location in one step. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromsomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in e.g., Egeland et al., 1987, *Nature* 325:783–787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

In the instant case, the human gene for GPVI was mapped on radiation hybrid panels to the long arm of chromosome 19, in the region 19q13. This region is synthetic to mouse chromosome 7. Multiple members of the immunoglobulin superfamily, including killer cell inhibitory receptors, immunoglobulin-like transcripts (ILT1, 2, 3), the gp49b family and the Fc receptor (CD89) also map this region of the human chromosome. These various receptors differ considerably with respect to function and expression and it may be hypothesized that functional differentiation occurred after duplication of a common ancestral gene.

The mouse gene for GPVI was mapped using the T31 Mouse/Hamster Radiation Hybrid (McCarthy, Terrett et al. 1997). PCR Amplification used the following mouse primers: forward primer 5'-CTGTAGCTGTTTTCAGACACA CC-3' (SEQ ID NO:31) and reverse primer 5'-CCATCACCTCTTTCTGGTTAC-3' (SEQ ID NO:32). All PCRs were performed with an annealing temperature 52° C. and extension times of 50 s (72° C.) and for 35 cycles, with a final extension of 5 minutes on an MJ Research Peltier PCT-225 Thermal Cycler.

A polypeptide and fragments and sequences thereof and antibodies specific thereto can be used to map the location of the gene encoding the polypeptide on a chromosome. This mapping can be carried out by specifically detecting the presence of the polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) *Cytogenet. Cell Genet.* 47:37–41 and Van Keuren et al. (1986) *Hum. Genet.* 74:34–40. Alternatively, the presence of the polypeptide in the somatic cell hybrids can be determined by assaying an activity or property of the polypeptide, for example, enzymatic activity, as described in Bordelon-Riser et al., 1979, *Somatic Cell Genetics* 5:595–613 and Owerbach et al., 1978, *Proc. Natl. Acad. Sci. USA* 75:5640–5644.

2. Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individuals's genomic. Thus, the nucleic acid sequences described herein can be used to prepare two PCR primers from 5' and 3' ends of the sequences. These primers can then be used to amplify an individual's DNA and subsequently sequence it.

Panels of corresponding DNA sequences from individuals, prepared in this manner, can provide unique individual identification, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the noncoding regions.

It is estimated that allelic variation between individual humans occurs with a frequency at about once per each 500 bases. Each of the sequences described herein can, to some degree, be used as a standard against which DNA from an individual can be compared to identification purposes. Because greater numbers of polymorphisms occur in the noncoding regions, fewer sequences are necessary to differentiate individuals. The noncoding sequences of SEQ ID NO: 1 or 14 can comfortably provide positive individual identification with a panel of perhaps 10 to 1,000 primers which each yield a noncoding amplified sequence of 100 bases. If predicted coding sequences, such as those in SEQ ID NO:1 or 14 are used, a more appropriate number of primers for positive individual identification would be 500–2,000.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

3. Use of Partial Gene Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genomic, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the nucleic acid sequences of the invention or portions thereof, e.g., fragments derived from noncoding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining TANGO 268 protein and/or nucleic acid expression as well as TANGO 268 activity, in the context of a biological sample (e.g., blood, serum, cells, and tissue) to thereby determine whether an individual is afflicted with a disease or disorder, or is at risk of developing a disorder, associated with aberrant or unwanted TANGO 268 expression or activity. The invention also provides for prognostic (or predictive) assays for determining whether an individual is at risk of developing a disorder associated with TANGO 268 protein, nucleic acid expression or activity. For example, mutations in a TANGO 268 gene can be assayed in a biological sample. Such assays can be used for prognostic or predictive purpose to thereby prophylactically treat an individual prior to the onset of a disorder characterized by or associated with TANGO 268 protein and/or nucleic acid expression or activity.

As an alternative to making determinations based on the absolute expression level of selected genes, determinations may be based on the normalized expressions levels of these genes. Expression levels are normalized by correcting the absolute expression level of a TANGO 268 gene by comparing its expression to the expression of a gene that is not a TANGO 268 gene, e.g., a housekeeping gene that is constitutively expressed. Suitable genes for normalization include housekeeping genes such as the actin gene. This normalization allows the comparison of the expression level in one sample, e.g., a patient sample, to another sample, e.g., a sample from an individual without a particular disease or disorder, or a sample from a healthy individual, or between samples from different sources.

Alternatively, the expression level can be provided as a relative expression level. To determine a relative expression level of a gene, the level of expression of the gene is determined for 10 or more samples of different cell isolates (e.g., platelet isolates or megakaryocyte isolates), preferably 50 or more samples, prior to the determination of the expression level for the sample in question. The mean expression level of each of the genes assayed in the larger number of samples is determined and this is used as a baseline expression level for the gene(s) in question. The expression level of the gene determined for the test sample (absolute level of expression) is then divided by the mean expression value obtained for that gene. This provides a relative expression level and aids in identifying extreme cases of disease and disorders such as coronary disorders (e.g., atherosclerosis), neuronal disorders (e.g., strokes), and bleeding disorders.

Preferably, the samples used in the basement determination will be from diseased or from non-diseased cells of the appropriate cell type or tissue. The choice of the cell source is dependent on the use of the relative expression level. Using expression found in normal tissues as a mean expression score aids in validating whether TANGO 268 gene assayed is specific (versus normal cells). Such a use is particularly important in identifying whether a TANGO 268 gene can serve as a target gene. In addition, as more data is accumulated, the mean expression value can be revised, providing improved relative expression values based on accumulated data. Expression data from cells provides a means for grading the severity of the disease or disorder state.

Another aspect of the invention pertains to monitoring the influence of agents (e.g., drugs or compounds) on the expression or activity of TANGO 268 in clinical trials. These and other agents are described in further detail in the following sections.

1. Diagnostic Assays

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO:1, 2, 14 or 15, or a portion thereof, such as an oligonucleotide of at least 15, 30, 50, 100, 250 or 500 nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting a polypeptide of the invention is an antibody capable of binding to a polypeptide of the invention, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is antibody to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of a polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by a standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention as, for example, n sections above relating to uses of the sequences of the invention.

For example, kits can be used to determine if a subject is suffering from or is at increased risk of disorders such as immunological disorders, (e.g. thrombocytopenia and platelet disorders), liver disorders, cerebral vascular diseases (e.g., stroke and ischemia), venous thromboembolisme diseases (e.g., diseases involving leg swelling, pain and ulceration, pulmonary embolism, abdominal venous thrombosis), coronary diseases (e.g., cardiovascular diseases including unstable angina, acute myocardial infarction, coronary artery disease, coronary revascularization, ventricular thromboembolism, atherosclerosis, coronary artery disease, and plaque formation), metastatic cancers (e.g., the metastasis of cancerous colon and liver cells) and embryonic disorders, which are associated with aberrant TANGO 268 expression. The kit, for example, can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level.

For antibody-based kits, the kit can comprise, for example: (1) a first antibody (e.g. attached to a solid support) which binds to a polypeptide of the invention; and, optionally (2) a second, different antibody which binds to either the polypeptide or the first antibody and is conjugated to a detectable agent.

For oligonucleotide-based kits, the kit can comprise, for example: (1) an oligonucleotide, e.g., a detectably labeled organucleotide, which hybridizes to a nucleic acid sequence encoding a polypeptide of the invention or (2) a pair of primers useful for amplifying a nucleic acid molecule encoding a polypeptide of the invention. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

2. Prognostic Assays

The methods described herein can furthermore be utilized as diagnostic or prognostic assays to identify subjects having or at risk of developing a disease or disorder associated with aberrant expression or activity of a polypeptide of the invention. For example, the assays described herein, such as the preceding diagnostic assays or the following assays, can be utilized to identify a subject having or at risk of developing a disorder associated with aberrant expression or activity of a polypeptide of the invention, e.g., an immunologic disorder, or embryonic disorders. Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

The prognostic assays described herein, for example, can be used to identify a subject having or at risk of developing disorders such as disorders discussed, for example, in sections above relating to uses of the sequences of the invention. For example, such disorders can include immunological disorders, (e.g. thrombocytopenia and platelet disorders), liver disorders, cerebral vascular diseases (e.g., stroke and ischemia), venous thromboembolisme diseases (e.g., diseases involving leg swelling, pain and ulceration, pulmonary embolism, abdominal venous thrombosis), coronary diseases (e.g., cardiovascular diseases including instable angina, acute myocardial infarction, coronary artery disease, coronary revascularization, ventricular thromboembolism, atherosclerosis, coronary artery disease, and plaque formation), metastatic cancers (e.g., the metastasis of cancerous colon and liver cells) and progression to such metastatic tumors, developmental disorders and embryonic disorders, which are associated with aberrant TANGO 268 expression.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a gene (see, e.g., Abravaya et al. (1995) *Nucleic Acids Res.* 23:645–682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al., (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step as follows by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert (1977) *Proc. Natl. Acad. Sci. USA* 74:560) or Sanger ((1997) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in a selected gene include methods in which protection from cleavage agents is used to detect mismatched bases in RNA/RNA or RNA/DNA heteroduplexes (Myers et al. (1985) *Science* 230:1242). In general, the technique of "mixmatch cleavage" entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions.

In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment; a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766; see also Cotton (1993) *Mutat. Res.* 285:125–144; Ilayashi (1992) *Genet. Anal. Tech. Appl.* 9:73–79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example, by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCV amplification may be used in conjunction with the instant invention. Oligonucleotides used as primers for specific amplification may carry the mutation of interest in the center of the molecule (so that amplification depends on differential hybridization)(Gibbs et al. (1989) *Nucleic Acids Res.* 17:2437–2448 or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilzing pre-packaged diagnostic kits comprising at least one probe nucleic acid or antibody reagent described herein, which may be conveniently used, e.g., in clinical settings to diagnose patients exhibiting symptoms or family history of a disease or illness involving a gene encoding a polypeptide of the invention. Furthermore, any cell type or tissue, e.g., chondrocytes, in which the polypeptide of the invention is expressed may be utilized in the prognostic assays described herein.

3. Pharmacogenomics

Agents, or modulators which have a stimulatory or inhibitory effect on activity or expression of a polypeptide of the invention as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-materials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (.e.g. N-acetyltransferase 2 (NAT 2) and cytochrome P450 CYP2D6 and CYP2C19) has provided an explanation as to why some patients do not obtain the expected drug effects or show exaggerated drug response and serious toxicity after taking the standard and safe dose of a drug. These polymorphisms are expected in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizes of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encode the polypeptide, or mutation content of a gene encoding the polypeptide in an individual can be determined to thereby select appropriate agent(s) for therapeutic agent(s) for therapeutic or prophylatic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

4. Monitoring of TANGO 268 Modulator Effects

Monitoring the influence of agents (e.g., drugs, compounds) on the expression or activity of a polypeptide of the invention (e.g., the ability to modulate aberrant cell proliferation chemotaxis, and/or differentiation) can be applied in basic drug screening, preclinical studies, clinical trials and during therapeutic treatment regimens.

For example, the effectiveness of an agent, as determined by a screening assay as described herein, to increase gene expression, protein levels or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptide that have been implicated in for example, a cellular proliferation disorder, can be used as a marker of the immune responsiveness of a particular cell.

For example, and not by way of limitation, genes, including those of the invention, that are modulated in cells by treatment with an agent (e.g., compound drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g. an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the preadministration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

TANGO 268 is expressed on the surface of platelets. As such, a cellular and therapeutic target of modulators of TANGO 268 (e.g., an anti-TANGO 268 antibody) is readily available for testing and analysis (e.g., for in vitro testing and analysis). This coupled with the availability of several different relevant platelet assays (see above) provides an unusual drug development opportunity for TANGO 268 modulators. For example, the in vivo pharmacodynamic characterization of TANGO 268 modulators can be facilitated via the availability of various platelet assays (e.g., prolongation of bleeding time, quantitative measurement of TANGO 268 receptor blockade, inhibition of ex vivo platelet aggregation) that can be correlated with each other to permit more effective assessment of a modulator's functional consequences. The correlation available for such assays, therefore, allows for the in vitro characterization of a TANGO 268 modulator to more directly apply to the measurement of the modulator's therapeutic effect.

In addition to utilizing the availability of platelets and platelet assays for assessing the therapeutic efficacy, including clinical efficacy, of a TANGO 268 modulator, this availability can also be utilized for preclinical drug development aspects such as determining modulator dosage response, toxicology, magnitude of effect (e.g., magnitude of initial effect and magnitude of effect's duration), function, specificity, (e.g., specificity with respect to particular platelet functions), receptor specificity, and species specificity (which, in turn, can identify appropriate animal models for pharmacology studies).

In one embodiment, therefore, a method of the invention includes a method for identifying a TANGO 268 modulator, (e.g., an anti-TANGO 268 antibody), comprising: incubating a platelet (preferably human platelet)-rich sample with a compound and a platelet agonist (e.g., ADP, epinephrine, thrombin, collagen), and assaying platelet aggregation, such that if platelet aggregation in the sample differs from that of a corresponding platelet-rich sample incubated with the platelet agonist in the absence of the compound, then a modulator of TANGO 268 platelet aggregation is identified. In a variation of this embodiment, the sample is incubated with the compound prior to addition and concurrent incubation with the platelet agonist.

In another embodiment, a method of the invention includes a method for monitoring the clinical efficacy of a TANGO 268 modulator (or the effectiveness of treatment with a TANGO 268 modulator), comprising: incubating a patient sample comprising platelets (a platelet-rich sample, e.g., one containing approximately 200,000–/300,000 platelets per ml²) with a platelet agonist, measuring the level of platelet aggregation in the sample, and comparing the level obtained with that of a corresponding control platelet sample, wherein the patient sample is obtained from a patient to whom a TANGO 268 modulator has been administered, and the control platelet sample is one that has been incubated with the platelet agonist but has not been treated with the TANGO 268 modulator. In instances wherein the aggregation level obtained in the patient sample is lower than that of the control sample, the monitoring of the clinical efficacy of the TANGO 268 modulator (or the effectiveness of treatment with the TANGO 268 modulator) is confirmed.

In yet another embodiment, a method of the invention includes a method for determining the therapeutic dosage of a TANGO 268 modulator to be administered to an individual in need of treatment for a TANGO 268-related disorder, comprising: administering a dose of a TANGO 268 modulator to a non-human animal model of a TANGO 268-related disorder, and assaying TANGO 268 function and/or assaying a symptom of the TANGO 268-related disorder in the animal, so that if TANGO 268 function and/or symptom in the animal is modulated in a manner that more closely resembles a corresponding animal not exhibiting the TANGO 268 disorder, a therapeutic dosage of the TANGO 268 modulator is determined, e.g., by extrapolating to the corresponding dosage in a human.

In a particular embodiment of such a method, platelet function and/or aggregation is assayed via e.g., techniques such as those presented herein. Further, the animal model an be, e.g., one of the animal models described herein.

C. Methods of Treatment

The present invention provides for both prophylactic and therapeutic methods of treating a subject at risk of (or susceptible to) a disorder or having a disorder associated with aberrant expression or activity of a polypeptide of the invention, as discussed, for example, in sections above relating to uses of the sequences of the invention. For example, disorders characterized by aberrant expression or activity of the polypeptides of the invention include immunologic disorders, development disorders, embryonic disorders, liver disorders, cerebral vascular diseases (e.g., stroke and ischemia), venous thromboembolism diseases (e.g., diseases involving leg swelling, pain and ulceration, pulmonary embolism, abdominal venous thrombosis), coronary disease (e.g., cardiovascular diseases including unstable angina, acute myocardial infarction, coronary artery disease, coronary revascularization, ventricular thromboembolism, atherosclerosis, coronary artery disease, and plaque formation), and metastatic cancers (e.g., the metastasis of cancerous colon and liver cells). The nucleic acides, polypeptides, and modulators thereof of the invention can be used to treat immunologic diseases and disorders (e.g., platelet disorders), embryonic disorders liver disorders, cerebral vascular diseases (e.g., stroke and ischemia), venous thromboembolisme diseases (e.g., diseases involving leg swelling, pain and ulceration, pulmonary embolism, abdominal venous thrombosis), thrombotic disorders (e.g., thrombotic occlusion of coronary arteries), coronary diseases (e.g., cardiovascular diseases, including unstable angina pectoris, myocardial infarction, acute myocardial infarction, coronary artery disease, coronary revascularization, coronary restenosis, ventricular thromboembolism, atherosclerosis, coronary artery disease (e.g., arterial occlusive disorders), and plaque formation, cardiac ischema, including complications related to coronary procedures, such as percutaneous coronary artery angioplasty (balloon angioplasty) procedures). With respect to coronary procedures, such modulation can be achieved via administration of GPVI modulators prior to, during, or subsequent to the procedure. In a preferred embodiment, such administration can be utilized to prevent acute cardiac ischemia following angioplasty, and metastatic cancers (e.g., the metastasis of cancerous colon and liver cells), as well as other disorders described herein.

TANGO 268 nucleic acids, proteins and modulators thereof can, therefore, be used to modulate disorders resulting from any blood vessel insult that can result in platelet aggregation. Such blood vessel insults include, but are not limited to, vessel wall injury, such as vessel injuries that result in a highly thrombogenic surface exposed within an otherwise intact blood vessel e.g., vessel wall injuries that result in release of ADP, thrombin and/or epinephrine, fluid shear stress that occurs at the site of vessel narrowing, ruptures and/or tears at the sites of atherosclerotic plaques, and injury resulting from balloon angioplasty or atherectomy.

Preferably, the TANGO 268 nucleic acids, proteins and modulators (e.g., anti-TANGO 268 antibodies) therof do not effect initial platelet adhesion to vessel surfaces, or effect such adhesion to a relatively lesser extent than the effect than the effect on platelet-platelet aggregation, e.g., unregulated platelet-platelet aggregation, following the initial platelet adhesion. Further, in certain embodiments, it is preferred that the TANGO 268 nucleic acids, proteins and modulators (e.g., anti-TANGO 268 antibodies) thereof do not effect other platelet attributes or functions, such as agonist-induced platelet shape change (e.g., GPIb-vWF-mediated platelet agglutination induced by ristocetin), release of internal platelet granule components, activation of signal transduction pathways or induction of calcium mobilization upon platelet activation.

1. Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or contributed to by aberrant expression or activity of a polypeptide of the invention can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. For example, an antagonist of a TANGO 240 protein may be used to treat an arthropathic disorder, e.g., rheumatoid arthritis. The appropriate agent can be determined based on screening assays described herein.

2. Therapeutic Methods

Another aspect of the invention pertains to methods of modulation expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell. In another embodiment, the agent inhibits one or more of the biological activities of the polypeptide of the invention. Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a polypeptide of the invention. In one embodiment, the method involves administering an agent (e.g., an agent identified by a screening assay described herein), or combination of agents that modulates (e.g., upregulates or downregulates) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low or downregulated and/or in which increased activity is likely to have a beneficial effect. Conversely, inhibition of activity is desirable in situations in which activity or expression is abnormally high or upregulated and/or in which decreased activity is likely to have a beneficial effect.

Deposit of Clones

A clone containing a cDNA molecule encoding human TANGO 268 (clone EpthEa11D1) was deposited with the American Type Culture Collection, 10801 University Boulevard, Manassas, Va., 20110-2209, on Mar. 30, 1999 as Accession Number 207180.

A clone containing cDNA molecule encoding mouse TANGO 268 (clone EpTm268) was deposited with the American Type Culture Collection, 10801 University Boulevard, Manassas, Va., 20110-2209, on Jun. 14, 1999 as PTA-225.

The following murine hybridoma cells were deposited with the American Type Culture Collection, 10801 University Boulevard, Manassas, Va., 20110-2209, on Apr. 21, 2000 and assigned the indicated patent deposit Numbers.

| Deposit | Patent Deposit Number |
|---|---|
| Murine Hybridoma M22 9012.2 | PTA-1746 |
| Murine Hybridoma M22 1P10.2 | PTA-1747 |
| Murine Hybridoma M22 8M14.3 | PTA-1748 |
| Murine Hybridoma M22 9E18.2 | PTA-1749 |
| Murine Hybridoma M22 7H4.6 | PTA-1750 |

The following scFvs were deposited with the American Type Culture Collection, 10801 University Boulevard, Manassas, Va., 20110-2209, on Jun. 30, 2000 and assigned the indicated patent deposit Numbers:

| Deposit | Patent Deposit Number |
|---|---|
| A4 | PTA-__ |
| A9 | PTA-__ |
| A10 | PTA-__ |
| C3 | PTA-__ |

Equivalents

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

SEQUENCE LISTING

```
<160> NUMBER OF SEQ ID NOS:  72

<210> SEQ ID NO 1
<211> LENGTH: 2047
<212> TYPE: DNA
<213> ORGANISM: Homo sapiens

<400> SEQUENCE: 1
ggagtcgacc cacgcgtccg cagggctgag gaaccatgtc tccatcccg  accgccctct      60 tctgtcttgg gctgtgtctg gggcgtgtgc cagcgcagag tggaccgctc cccaagccct     120
ccctccaggc tctgcccagc tccctggtgc cctggagaa gccagtgacc ctccggtgcc     180
agggacctcc gggcgtggac ctgtaccgcc tggagaagct gagttccagc aggtaccagg     240
atcaggcagt cctcttcatc ccggccatga agagaagtct ggctggacgc taccgctgct     300
cctaccagaa cggaagcctc tggtccctgc ccagcgacca gctggagctc gttgccacgg     360 gagttttttgc caaaccctcg ctctcagccc agcccggccc ggcggtgtcg tcaggagggg     420
```

-continued

| | |
|---|---|
| acgtaaccct acagtgtcag actcggtatg gctttgacca atttgctctg tacaaggaag | 480 |
| gggaccctgc gccctacaag aatcccgaga gatggtaccg ggctagtttc cccatcatca | 540 |
| cggtgaccgc cgcccacagc ggaacctacc gatgctacag cttctccagc agggacccat | 600 |
| acctgtggtc ggccccagc gaccccctgg agcttgtggt cacaggaacc tctgtgaccc | 660 |
| ccagccggtt accaacagaa ccaccttcct cggtagcaga attctcagaa gccaccgctg | 720 |
| aactgaccgt ctcattcaca aacaaagtct tcacaactga acttctagg agtatcacca | 780 |
| ccagtccaaa ggagtcagac tctccagctg gtcctgcccg ccagtactac accaagggca | 840 |
| acctggtccg gatatgcctc ggggctgtga tcctaataat cctggcgggg tttctggcag | 900 |
| aggactggca cagccggagg aagcgcctgc ggcacagggg cagggctgtg cagaggccgc | 960 |
| ttccgcccct gccgcccctc ccgcagaccc ggaaatcaca cgggggtcag gatggaggcc | 1020 |
| gacaggatgt tcacagccgc gggttatgtt catgaccgct gaaccccagg cacggtcgta | 1080 |
| tccagggag ggatcatggc atgggaggcg actcaaagac tggcgtgtgt ggagcgtgga | 1140 |
| agcaggaggg cagaggctac agctgtggaa acgaggccat gctgcctcct cctggtgttc | 1200 |
| catcagggag ccgttcggcc agtgtctgtc tgtctgtctg cctctctgtc tgagggcacc | 1260 |
| ctccatttgg gatggaagga atctgtggag accccatcct cctccctgca cactgtggat | 1320 |
| gacatggtac cctggctgga ccacatactg gcctctttct tcaacctctc taatatgggc | 1380 |
| tccagacgga tctctaaggt tcccagctct cagggttgac tctgttccat cctctgtgca | 1440 |
| aaatcctcct gtgcttccct ttggccctct gtgctcttgt ctggttttcc ccagaaactc | 1500 |
| tcaccctcac tccatctccc actgcggtct acaaatctc ctttcgtctc tcagaacggg | 1560 |
| tcttgcaggc agtttgggta tgtcattcat tttccttagt gtaaaactag cacgttgccc | 1620 |
| gcttcccttc acattagaaa acaagatcag cctgtgcaac atggtgaaac ctcatctcta | 1680 |
| ccaacaaaac aaaaaaacac aaaaattagc caggtgtggt ggtgcatccc tatactccca | 1740 |
| gcaactcggg gggctgaggt gggagaatgg cttgagcctg ggaggcagag gttgcagtga | 1800 |
| gctgagatca caccactgca ctctagctcg ggtgacgaag cctgaccttg tctcaaaaaa | 1860 |
| tacagggatg aatatgtcaa ttaccctgat tgatcatag cacgttgtat acatgtactg | 1920 |
| caatattgct gtccaccca taatatgta caattatgta tacatttta aaatcataaa | 1980 |
| aataagataa tgaaaaaaaa aaaaaaaaa aaaaaaggg cgggccgcta gactagtcta | 2040 |
| gagaaca | 2047 |

<210> SEQ ID NO 2
<211> LENGTH: 1017
<212> TYPE: DNA
<213> ORGANISM: Homo sapiens

<400> SEQUENCE: 2

| | |
|---|---|
| atgtctccat ccccgaccgc cctcttctgt cttgggctgt gtctggggcg tgtgccagcg | 60 |
| cagagtggac cgctccccaa gccctccctc caggctctgc ccagctccct ggtgcccctg | 120 |
| gagaagccag tgaccctccg gtgccaggga cctccgggcg tggacctgta ccgcctggag | 180 |
| aagctgagtt ccagcaggta ccaggatcag gcagtcctct tcatcccggc catgaagaga | 240 |
| agtctggctg gacgctaccg ctgctcctac cagaacggaa gctctggtc cctgcccagc | 300 |
| gaccagctgg agctcgttgc cacgggagtt tttgccaaac cctcgctctc agcccagccc | 360 |
| ggcccggcgg tgtcgtcagg aggggacgta accctacagt gtcagactcg gtatggcttt | 420 |

-continued

```
gaccaatttg ctctgtacaa ggaaggggac cctgcgccct acaagaatcc cgagagatgg    480
taccgggcta gtttccccat catcacggtg accgccgccc acagcggaac ctaccgatgc    540
tacagcttct ccagcaggga cccatacctg tggtcggccc ccagcgaccc cctggagctt    600
gtggtcacag gaacctctgt gacccccagc cggttaccaa cagaaccacc ttcctcggta    660
gcagaattct cagaagccac cgctgaactg accgtctcat tcacaaacaa agtcttcaca    720
actgagactt ctaggagtat caccaccagt ccaaaggagt cagactctcc agctggtcct    780
gcccgccagt actacaccaa ggcaacctg tccggatat gcctcggggc tgtgatccta    840
ataatcctgg cggggtttct ggcagaggac tggcacagcc ggaggaagcg cctgcggcac    900
aggggcaggg ctgtgcagag gccgcttccg ccctgccgc cctcccgca gacccggaaa    960 tcacacgggg gtcaggatgg aggccgacag gatgttcaca gccgcgggtt atgttca     1017
```

<210> SEQ ID NO 3
<211> LENGTH: 339
<212> TYPE: PRT
<213> ORGANISM: Homo sapiens

<400> SEQUENCE: 3

```
Met Ser Pro Ser Pro Thr Ala Leu Phe Cys Leu Gly Leu Cys Leu Gly
 1               5                  10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
        195                 200                 205

Pro Ser Arg Leu Pro Thr Glu Pro Pro Ser Ser Val Ala Glu Phe Ser
    210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Leu Val Arg
            260                 265                 270
```

-continued

```
Ile Cys Leu Gly Ala Val Ile Leu Ile Ile Leu Ala Gly Phe Leu Ala
        275                 280                 285

Glu Asp Trp His Ser Arg Arg Lys Arg Leu Arg His Arg Gly Arg Ala
        290                 295                 300

Val Gln Arg Pro Leu Pro Pro Leu Pro Leu Pro Gln Thr Arg Lys
305                 310                 315                 320

Ser His Gly Gly Gln Asp Gly Gly Arg Gln Asp Val His Ser Arg Gly
                325                 330                 335

Leu Cys Ser
```

<210> SEQ ID NO 4
<211> LENGTH: 20
<212> TYPE: PRT
<213> ORGANISM: Homo sapiens

<400> SEQUENCE: 4

```
Met Ser Pro Ser Pro Thr Ala Leu Phe Cys Leu Gly Leu Cys Leu Gly
  1               5                  10                  15

Arg Val Pro Ala
            20
```

<210> SEQ ID NO 5
<211> LENGTH: 319
<212> TYPE: PRT
<213> ORGANISM: Homo sapiens

<400> SEQUENCE: 5

```
Gln Ser Gly Pro Leu Pro Lys Pro Ser Leu Gln Ala Leu Pro Ser Ser
  1               5                  10                  15

Leu Val Pro Leu Glu Lys Pro Val Thr Leu Arg Cys Gln Gly Pro Pro
                20                  25                  30

Gly Val Asp Leu Tyr Arg Leu Glu Lys Leu Ser Ser Ser Arg Tyr Gln
            35                  40                  45

Asp Gln Ala Val Leu Phe Ile Pro Ala Met Lys Arg Ser Leu Ala Gly
        50                  55                  60

Arg Tyr Arg Cys Ser Tyr Gln Asn Gly Ser Leu Trp Ser Leu Pro Ser
 65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
```

```
              225                 230                 235                 240
Ala Arg Gln Tyr Tyr Thr Lys Gly Asn Leu Val Arg Ile Cys Leu Gly
                245                 250                 255
Ala Val Ile Leu Ile Ile Leu Ala Gly Phe Leu Ala Glu Asp Trp His
            260                 265                 270
Ser Arg Arg Lys Arg Leu Arg His Arg Gly Arg Ala Val Gln Arg Pro
        275                 280                 285
Leu Pro Pro Leu Pro Pro Leu Pro Gln Thr Arg Lys Ser His Gly Gly
    290                 295                 300
Gln Asp Gly Gly Arg Gln Asp Val His Ser Arg Gly Leu Cys Ser
305                 310                 315

<210> SEQ ID NO 6
<211> LENGTH: 41
<212> TYPE: PRT
<213> ORGANISM: Homo sapiens

<400> SEQUENCE: 6

Cys Gln Gly Pro Pro Gly Val Asp Leu Tyr Arg Leu Glu Lys Leu Ser
1                   5                   10                  15
Ser Ser Arg Tyr Gln Asp Gln Ala Val Leu Phe Ile Pro Ala Met Lys
                20                  25                  30
Arg Ser Leu Ala Gly Arg Tyr Arg Cys
            35                  40

<210> SEQ ID NO 7
<211> LENGTH: 47
<212> TYPE: PRT
<213> ORGANISM: Homo sapiens

<400> SEQUENCE: 7

Cys Gln Thr Arg Tyr Gly Phe Asp Gln Phe Ala Leu Tyr Lys Glu Gly
1                   5                   10                  15
Asp Pro Ala Pro Tyr Lys Asn Pro Glu Arg Trp Tyr Arg Ala Ser Phe
                20                  25                  30
Pro Ile Ile Thr Val Thr Ala Ala His Ser Gly Thr Tyr Arg Cys
            35                  40                  45

<210> SEQ ID NO 8
<211> LENGTH: 19
<212> TYPE: PRT
<213> ORGANISM: Homo sapiens

<400> SEQUENCE: 8

Leu Val Arg Ile Cys Leu Gly Ala Val Ile Leu Ile Ile Leu Ala Gly
1                   5                   10                  15
Phe Leu Ala

<210> SEQ ID NO 9
<211> LENGTH: 249
<212> TYPE: PRT
<213> ORGANISM: Homo sapiens

<400> SEQUENCE: 9

Gln Ser Gly Pro Leu Pro Lys Pro Ser Leu Gln Ala Leu Pro Ser Ser
1                   5                   10                  15
Leu Val Pro Leu Glu Lys Pro Val Thr Leu Arg Cys Gln Gly Pro Pro
                20                  25                  30
Gly Val Asp Leu Tyr Arg Leu Glu Lys Leu Ser Ser Ser Arg Tyr Gln
```

-continued

```
                35                  40                  45
Asp Gln Ala Val Leu Phe Ile Pro Ala Met Lys Arg Ser Leu Ala Gly
     50                  55                  60
Arg Tyr Arg Cys Ser Tyr Gln Asn Gly Ser Leu Trp Ser Leu Pro Ser
 65                  70                  75                  80
Asp Gln Leu Glu Leu Val Ala Thr Gly Val Phe Ala Lys Pro Ser Leu
                 85                  90                  95
Ser Ala Gln Pro Gly Pro Ala Val Ser Ser Gly Gly Asp Val Thr Leu
            100                 105                 110
Gln Cys Gln Thr Arg Tyr Gly Phe Asp Gln Phe Ala Leu Tyr Lys Glu
        115                 120                 125
Gly Asp Pro Ala Pro Tyr Lys Asn Pro Glu Arg Trp Tyr Arg Ala Ser
    130                 135                 140
Phe Pro Ile Ile Thr Val Thr Ala Ala His Ser Gly Thr Tyr Arg Cys
145                 150                 155                 160
Tyr Ser Phe Ser Ser Arg Asp Pro Tyr Leu Trp Ser Ala Pro Ser Asp
                165                 170                 175
Pro Leu Glu Leu Val Val Thr Gly Thr Ser Val Thr Pro Ser Arg Leu
            180                 185                 190
Pro Thr Glu Pro Pro Ser Ser Val Ala Glu Phe Ser Glu Ala Thr Ala
        195                 200                 205
Glu Leu Thr Val Ser Phe Thr Asn Lys Val Phe Thr Thr Glu Thr Ser
    210                 215                 220
Arg Ser Ile Thr Thr Ser Pro Lys Glu Ser Asp Ser Pro Ala Gly Pro
225                 230                 235                 240
Ala Arg Gln Tyr Tyr Thr Lys Gly Asn
                245
```

<210> SEQ ID NO 10
<211> LENGTH: 51
<212> TYPE: PRT
<213> ORGANISM: Homo sapiens

<400> SEQUENCE: 10

```
Glu Asp Trp His Ser Arg Arg Lys Arg Leu Arg His Arg Gly Arg Ala
  1               5                  10                  15
Val Gln Arg Pro Leu Pro Pro Leu Pro Pro Leu Pro Gln Thr Arg Lys
             20                  25                  30
Ser His Gly Gly Gln Asp Gly Gly Arg Gln Asp Val His Ser Arg Gly
         35                  40                  45
Leu Cys Ser
    50
```

<210> SEQ ID NO 11
<211> LENGTH: 2170
<212> TYPE: DNA
<213> ORGANISM: Homo sapiens

<400> SEQUENCE: 11

```
ctgagggctc atccctctgc agagcgcggg gtcaccggga ggagacgcca tgacgcccgc      60
cctcacagcc ctgctctgcc ttgggctgag tctgggcccc aggacccgcg tgcaggcagg     120
gcccttcccc aaacccaccc tctgggctga gccaggctct gtgatcagct gggggagccc     180
cgtgaccatc tggtgtcagg ggagcctgga ggcccaggag taccgactgg ataaagaggg     240
aagcccagag cccttggaca gaaataaccc actggaaccc aagaacaagg ccagattctc     300
```

-continued

| | |
|---|---|
| catcccatcc atgacagagc accatgcggg gagataccgc tgccactatt acagctctgc | 360 |
| aggctggtca gagcccagcg acccctgga gctggtgatg acaggattct acaacaaacc | 420 |
| caccctctca gccctgccca gccctgtggt ggcctcaggg gggaatatga ccctccgatg | 480 |
| tggctcacag aagggatatc accattttgt tctgatgaag aaggagaac accagctccc | 540 |
| ccggaccctg actcacagc agctccacag tgggggttc caggccctgt ccctgtggg | 600 |
| ccccgtgaac cccagccaca ggtggaggtt cacatgctat tactattata tgaacacccc | 660 |
| ccaggtgtgg tcccacccca gtgacccct ggagattctg ccctcaggcg tgtctaggaa | 720 |
| gccctccctc ctgaccctgc agggccctgt cctggcccct gggcagagcc tgaccctcca | 780 |
| gtgtggctct gatgtcggct acgacagatt tgttctgtat aaggaggggg aacgtgactt | 840 |
| cctccagcgc cctggccagc agcccaggc tgggctctcc caggccaact tcaccctggg | 900 |
| ccctgtgagc cctcccacg ggggccagta caggtgctat ggtgcacaca acctctcctc | 960 |
| cgagtggtcg gcccccagcg acccctgaa catcctgatg gcaggacaga tctatgacac | 1020 |
| cgtctccctg tcagcacagc cgggcccac agtggcctca ggagagaacg tgaccctgct | 1080 |
| gtgtcagtca tggtggcagt ttgacacttt ccttctgacc aaagaagggg cagcccatcc | 1140 |
| cccactgcgt ctgagatcaa tgtacggagc tcataagtac caggctgaat tccccatgag | 1200 |
| tcctgtgacc tcagcccacg cggggaccta caggtgctac ggctcataca gctccaaccc | 1260 |
| ccacctgctg tctttcccca gtgagcccct ggaactcatg gtctcaggac actctggagg | 1320 |
| ctccagcctc ccaccacag ggccgccctc cacacctggt ctgggaagat acctggaggt | 1380 |
| tttgattggg gtctcggtgg ccttcgtcct gctgctcttc ctcctcctct tcctcctcct | 1440 |
| ccgacgtcag cgtcacagca aacacaggac atctgaccag agaaagactg atttccagcg | 1500 |
| tcctgcaggg gctgcggaga cagagcccaa ggacaggggc ctgctgagga ggtccagccc | 1560 |
| agctgctgac gtccaggaag aaaacctcta tgctgccgtg aaggacacac agtctgagga | 1620 |
| cagggtggag ctggacagtc agagcccaca cgatgaagac ccccaggcag tgacgtatgc | 1680 |
| cccggtgaaa cactccagtc ctaggagaga aatggcctct cctccctcct cactgtctgg | 1740 |
| ggaattcctg gacacaaagg acagacaggt ggaagaggac aggcagatgg acactgaggc | 1800 |
| tgctgcatct gaagcctccc aggatgtgac ctacgcccag ctgcacagct tgacccttag | 1860 |
| acggaaggca actgagcctc ctccatccca ggaagtggaa cctccagctg agcccagcat | 1920 |
| ctacgccact ctggccatcc actagcccgg ggggtacgca gacccacac tcagcagaag | 1980 |
| gagactcagg actgctgaag gcacgggagc tgccccagt ggacaccagt gaaccccagt | 2040 |
| cagcctggac ccctaacaca gaccatgagg agacgctggg aacttgtggg actcacctga | 2100 |
| ctcaaagatg actaatatcg tcccattttg gaaataaagc aacagacttc tcaacaatca | 2160 |
| atgagttaat | 2170 |

<210> SEQ ID NO 12
<211> LENGTH: 631
<212> TYPE: PRT
<213> ORGANISM: Homo sapiens

<400> SEQUENCE: 12

Met Thr Pro Ala Leu Thr Ala Leu Leu Cys Leu Gly Leu Ser Leu Gly
1               5                   10                  15

Pro Arg Thr Arg Val Gln Ala Gly Pro Phe Pro Lys Pro Thr Leu Trp
            20                  25                  30

Ala Glu Pro Gly Ser Val Ile Ser Trp Gly Ser Pro Val Thr Ile Trp

-continued

```
                35                  40                  45
Cys Gln Gly Ser Leu Glu Ala Gln Glu Tyr Arg Leu Asp Lys Glu Gly
             50                  55                  60
Ser Pro Glu Pro Leu Asp Arg Asn Asn Pro Leu Glu Pro Lys Asn Lys
 65                  70                  75                  80
Ala Arg Phe Ser Ile Pro Ser Met Thr Glu His His Ala Gly Arg Tyr
                 85                  90                  95
Arg Cys His Tyr Tyr Ser Ser Ala Gly Trp Ser Glu Pro Ser Asp Pro
            100                 105                 110
Leu Glu Leu Val Met Thr Gly Phe Tyr Asn Lys Pro Thr Leu Ser Ala
            115                 120                 125
Leu Pro Ser Pro Val Val Ala Ser Gly Asn Met Thr Leu Arg Cys
130                 135                 140
Gly Ser Gln Lys Gly Tyr His His Phe Val Leu Met Lys Glu Gly Glu
145                 150                 155                 160
His Gln Leu Pro Arg Thr Leu Asp Ser Gln Gln Leu His Ser Gly Gly
            165                 170                 175
Phe Gln Ala Leu Phe Pro Val Gly Pro Val Asn Pro Ser His Arg Trp
            180                 185                 190
Arg Phe Thr Cys Tyr Tyr Tyr Met Asn Thr Pro Gln Val Trp Ser
            195                 200                 205
His Pro Ser Asp Pro Leu Glu Ile Leu Pro Ser Gly Val Ser Arg Lys
            210                 215                 220
Pro Ser Leu Leu Thr Leu Gln Gly Pro Val Leu Ala Pro Gly Gln Ser
225                 230                 235                 240
Leu Thr Leu Gln Cys Gly Ser Asp Val Gly Tyr Asp Arg Phe Val Leu
            245                 250                 255
Tyr Lys Glu Gly Glu Arg Asp Phe Leu Gln Arg Pro Gly Gln Gln Pro
            260                 265                 270
Gln Ala Gly Leu Ser Gln Ala Asn Phe Thr Leu Gly Pro Val Ser Pro
            275                 280                 285
Ser His Gly Gly Gln Tyr Arg Cys Tyr Gly Ala His Asn Leu Ser Ser
            290                 295                 300
Glu Trp Ser Ala Pro Ser Asp Pro Leu Asn Ile Leu Met Ala Gly Gln
305                 310                 315                 320
Ile Tyr Asp Thr Val Ser Leu Ser Ala Gln Pro Gly Pro Thr Val Ala
                325                 330                 335
Ser Gly Glu Asn Val Thr Leu Leu Cys Gln Ser Trp Trp Gln Phe Asp
            340                 345                 350
Thr Phe Leu Leu Thr Lys Glu Gly Ala Ala His Pro Pro Leu Arg Leu
            355                 360                 365
Arg Ser Met Tyr Gly Ala His Lys Tyr Gln Ala Glu Phe Pro Met Ser
            370                 375                 380
Pro Val Thr Ser Ala His Ala Gly Thr Tyr Arg Cys Tyr Gly Ser Tyr
385                 390                 395                 400
Ser Ser Asn Pro His Leu Leu Ser Phe Pro Ser Glu Pro Leu Glu Leu
            405                 410                 415
Met Val Ser Gly His Ser Gly Ser Ser Leu Pro Pro Thr Gly Pro
            420                 425                 430
Pro Ser Thr Pro Gly Leu Gly Arg Tyr Leu Glu Val Leu Ile Gly Val
            435                 440                 445
Ser Val Ala Phe Val Leu Leu Leu Phe Leu Leu Leu Phe Leu Leu Leu
450                 455                 460
```

```
Arg Arg Gln Arg His Ser Lys His Arg Thr Ser Asp Gln Arg Lys Thr
465                 470                 475                 480

Asp Phe Gln Arg Pro Ala Gly Ala Ala Glu Thr Glu Pro Lys Asp Arg
            485                 490                 495

Gly Leu Leu Arg Arg Ser Ser Pro Ala Ala Asp Val Gln Glu Glu Asn
            500                 505                 510

Leu Tyr Ala Ala Val Lys Asp Thr Gln Ser Glu Asp Arg Val Glu Leu
            515                 520                 525

Asp Ser Gln Ser Pro His Asp Glu Asp Pro Gln Ala Val Thr Tyr Ala
            530                 535                 540

Pro Val Lys His Ser Ser Pro Arg Arg Glu Met Ala Ser Pro Pro Ser
545                 550                 555                 560

Ser Leu Ser Gly Glu Phe Leu Asp Thr Lys Asp Arg Gln Val Glu Glu
            565                 570                 575

Asp Arg Gln Met Asp Thr Glu Ala Ala Ala Ser Glu Ala Ser Gln Asp
            580                 585                 590

Val Thr Tyr Ala Gln Leu His Ser Leu Thr Leu Arg Arg Lys Ala Thr
            595                 600                 605

Glu Pro Pro Pro Ser Gln Glu Gly Glu Pro Pro Ala Glu Pro Ser Ile
610                 615                 620

Tyr Ala Thr Leu Ala Ile His
625                 630

<210> SEQ ID NO 13
<211> LENGTH: 50
<212> TYPE: PRT
<213> ORGANISM: Homo sapiens

<400> SEQUENCE: 13

Gly Gln Ser Val Ile Leu Arg Cys Gln Gly Pro Pro Asp Val Asp Leu
1               5                   10                  15

Tyr Arg Leu Glu Lys Leu Lys Pro Glu Lys Tyr Glu Asp Gln Asp Phe
            20                  25                  30

Leu Phe Ile Pro Thr Met Glu Arg Ser Asn Ala Gly Arg Tyr Arg Cys
            35                  40                  45

Ser Tyr
    50

<210> SEQ ID NO 14
<211> LENGTH: 1163
<212> TYPE: DNA
<213> ORGANISM: Mus musculus

<400> SEQUENCE: 14
gagtcgaccc acgcgtccgc ttccctgctt ggccacatag ctcaggactg ggttgcagaa    60
ccatgtctcc agcctcaccc actttcttct gtattgggct gtgtgtactg caagtgatcc   120
aaacacagag tggcccactc cccaagcctt ccctccaggc tcagcccagt tccctggtac   180
ccctgggtca gtcagttatt ctgaggtgcc aggggacctcc agatgtggat ttatatcgcc   240
tggagaaact gaaaccggag aagtatgaag atcaagactt tctcttcatt ccaaccatgg   300
aaagaagtaa tgctggacgg tatcgatgct cttatcagaa tgggagtcac tggtctctcc   360
caagtgacca gcttgagcta attgctacag gtgtgtatgc taaaccctca ctctcagctc   420
atcccagctc agcagtccct caaggcaggg atgtgactct gaagtgccag agcccataca   480
gttttgatga attcgttcta tacaaagaag gggatactgg gccttataag agacctgaga   540
```

```
aatggtaccg ggccaatttc cccatcatca cagtgactgc tgctcacagt gggacgtacc    600
ggtgttacag cttctccagc tcatctccat acctgtggtc agccccgagt gaccctctag    660
tgcttgtggt tactggactc tctgccactc ccagccaggt acccacggaa gaatcatttc    720
ctgtgacaga atcctccagg agaccttcca tcttacccac aaacaaaata tctacaactg    780
aaaagcctat gaatatcact gcctctccag aggggctgag ccctccaatt ggttttgctc    840
atcagcacta tgccaagggg aatctggtcc ggatatgcct tggtgccacg attataataa    900
ttttgttggg gcttctagca gaggattggc acagtcggaa gaaatgcctg caacacagga    960
tgagagcttt gcaaaggcca ctaccacccc tcccactggc ctagaaataa cttggctttc   1020
agcagaggga ttgaccagac atccatgcac aaccatggac atcaccacta gagccacaga   1080
catggacata ctcaagagtg gggaggttat ataaaaaaat gagtgtggag aataaatgca   1140
gagccaacaa ggtgaaaaaa aaa                                           1163

<210> SEQ ID NO 15
<211> LENGTH: 939
<212> TYPE: DNA
<213> ORGANISM: Mus musculus

<400> SEQUENCE: 15
atgtctccag cctcacccac tttcttctgt attgggctgt gtgtactgca agtgatccaa     60
acacagagtg gcccactccc caagccttcc ctccaggctc agcccagttc cctggtaccc    120
ctgggtcagt cagttattct gaggtgccag ggacctccag atgtggattt atatcgcctg    180
gagaaactga aaccggagaa gtatgaagat caagactttc tcttcattcc aaccatggaa    240
agaagtaatg ctggacggta tcgatgctct tatcagaatg ggagtcactg gtctctccca    300
agtgaccagc ttgagctaat tgctacaggt gtgtatgcta aaccctcact ctcagctcat    360
cccagctcag cagtccctca aggcagggat gtgactctga gtgccagag cccatacagt     420 tttgatgaat tcgttctata caaagaaggg gatactgggc cttataagag acctgagaaa    480
tggtaccggg ccaatttccc catcatcaca gtgactgctc tcacagtgg acgtaccgg      540 tgttacagct tctccagctc atctccatac ctgtggtcag ccccgagtga ccctctagtg    600
cttgtggtta ctggactctc tgccactccc agccaggtac cacgaaga atcatttcct     660 gtgacagaat cctccaggag accttccatc ttacccacaa acaaaatatc tacaactgaa    720
aagcctatga atatcactgc ctctccagag gggctgagcc ctccaattgg ttttgctcat    780
cagcactatg ccaaggggaa tctggtccgg atatgccttg gtgccacgat tataataatt    840
ttgttggggc ttctagcaga ggattggcac agtcggaaga aatgcctgca acacaggatg    900
agagctttgc aaaggccact accaccctc ccactggcc                           939

<210> SEQ ID NO 16
<211> LENGTH: 313
<212> TYPE: PRT
<213> ORGANISM: Mus musculus

<400> SEQUENCE: 16

Met Ser Pro Ala Ser Pro Thr Phe Phe Cys Ile Gly Leu Cys Val Leu
1               5                  10                  15

Gln Val Ile Gln Thr Gln Ser Gly Pro Leu Pro Lys Pro Ser Leu Gln
                20                  25                  30

Ala Gln Pro Ser Ser Leu Val Pro Leu Gly Gln Ser Val Ile Leu Arg
            35                  40                  45
```

Cys Gln Gly Pro Pro Asp Val Asp Leu Tyr Arg Leu Glu Lys Leu Lys
        50                  55                  60

Pro Glu Lys Tyr Glu Asp Gln Asp Phe Leu Phe Ile Pro Thr Met Glu
 65                  70                  75                  80

Arg Ser Asn Ala Gly Arg Tyr Arg Cys Ser Tyr Gln Asn Gly Ser His
                85                  90                  95

Trp Ser Leu Pro Ser Asp Gln Leu Glu Leu Ile Ala Thr Gly Val Tyr
            100                 105                 110

Ala Lys Pro Ser Leu Ser Ala His Pro Ser Ser Ala Val Pro Gln Gly
        115                 120                 125

Arg Asp Val Thr Leu Lys Cys Gln Ser Pro Tyr Ser Phe Asp Glu Phe
    130                 135                 140

Val Leu Tyr Lys Glu Gly Asp Thr Gly Pro Tyr Lys Arg Pro Glu Lys
145                 150                 155                 160

Trp Tyr Arg Ala Asn Phe Pro Ile Ile Thr Val Thr Ala Ala His Ser
                165                 170                 175

Gly Thr Tyr Arg Cys Tyr Ser Phe Ser Ser Ser Pro Tyr Leu Trp
            180                 185                 190

Ser Ala Pro Ser Asp Pro Leu Val Leu Val Val Thr Gly Leu Ser Ala
        195                 200                 205

Thr Pro Ser Gln Val Pro Thr Glu Glu Ser Phe Pro Val Thr Glu Ser
    210                 215                 220

Ser Arg Arg Pro Ser Ile Leu Pro Thr Asn Lys Ile Ser Thr Thr Glu
225                 230                 235                 240

Lys Pro Met Asn Ile Thr Ala Ser Pro Glu Gly Leu Ser Pro Pro Ile
                245                 250                 255

Gly Phe Ala His Gln His Tyr Ala Lys Gly Asn Leu Val Arg Ile Cys
            260                 265                 270

Leu Gly Ala Thr Ile Ile Ile Leu Leu Gly Leu Leu Ala Glu Asp
        275                 280                 285

Trp His Ser Arg Lys Lys Cys Leu Gln His Arg Met Arg Ala Leu Gln
    290                 295                 300

Arg Pro Leu Pro Pro Leu Pro Leu Ala
305                 310

<210> SEQ ID NO 17
<211> LENGTH: 21
<212> TYPE: PRT
<213> ORGANISM: Mus musculus

<400> SEQUENCE: 17

Met Ser Pro Ala Ser Pro Thr Phe Phe Cys Ile Gly Leu Cys Val Leu
 1               5                  10                  15

Gln Val Ile Gln Thr
            20

<210> SEQ ID NO 18
<211> LENGTH: 292
<212> TYPE: PRT
<213> ORGANISM: Mus musculus

<400> SEQUENCE: 18

Gln Ser Gly Pro Leu Pro Lys Pro Ser Leu Gln Ala Gln Pro Ser Ser
 1               5                  10                  15

Leu Val Pro Leu Gly Gln Ser Val Ile Leu Arg Cys Gln Gly Pro Pro
            20                  25                  30

```
Asp Val Asp Leu Tyr Arg Leu Glu Lys Leu Lys Pro Glu Lys Tyr Glu
         35                   40                  45

Asp Gln Asp Phe Leu Phe Ile Pro Thr Met Glu Arg Ser Asn Ala Gly
     50                   55                  60

Arg Tyr Arg Cys Ser Tyr Gln Asn Gly Ser His Trp Ser Leu Pro Ser
 65              70                  75                  80

Asp Gln Leu Glu Leu Ile Ala Thr Gly Val Tyr Ala Lys Pro Ser Leu
             85                   90                  95

Ser Ala His Pro Ser Ser Ala Val Pro Gln Gly Arg Asp Val Thr Leu
            100                 105                 110

Lys Cys Gln Ser Pro Tyr Ser Phe Asp Glu Phe Val Leu Tyr Lys Glu
            115                 120                 125

Gly Asp Thr Gly Pro Tyr Lys Arg Pro Glu Lys Trp Tyr Arg Ala Asn
        130                 135                 140

Phe Pro Ile Ile Thr Val Thr Ala Ala His Ser Gly Thr Tyr Arg Cys
145                 150                 155                 160

Tyr Ser Phe Ser Ser Ser Pro Tyr Leu Trp Ser Ala Pro Ser Asp
                165                 170                 175

Pro Leu Val Leu Val Val Thr Gly Leu Ser Ala Thr Pro Ser Gln Val
            180                 185                 190

Pro Thr Glu Glu Ser Phe Pro Val Thr Glu Ser Arg Arg Pro Ser
            195                 200                 205

Ile Leu Pro Thr Asn Lys Ile Ser Thr Thr Glu Lys Pro Met Asn Ile
        210                 215                 220

Thr Ala Ser Pro Glu Gly Leu Ser Pro Ile Gly Phe Ala His Gln
225                 230                 235                 240

His Tyr Ala Lys Gly Asn Leu Val Arg Ile Cys Leu Gly Ala Thr Ile
                245                 250                 255

Ile Ile Ile Leu Leu Gly Leu Leu Ala Glu Asp Trp His Ser Arg Lys
            260                 265                 270

Lys Cys Leu Gln His Arg Met Arg Ala Leu Gln Arg Pro Leu Pro Pro
            275                 280                 285

Leu Pro Leu Ala
    290

<210> SEQ ID NO 19
<211> LENGTH: 267
<212> TYPE: PRT
<213> ORGANISM: Mus musculus

<400> SEQUENCE: 19

Met Ser Pro Ala Ser Pro Thr Phe Phe Cys Ile Gly Leu Cys Val Leu
 1               5                  10                  15

Gln Val Ile Gln Thr Gln Ser Gly Pro Leu Pro Lys Pro Ser Leu Gln
             20                  25                  30

Ala Gln Pro Ser Ser Leu Val Pro Leu Gly Gln Ser Val Ile Leu Arg
         35                  40                  45

Cys Gln Gly Pro Pro Asp Val Asp Leu Tyr Arg Leu Glu Lys Leu Lys
     50                  55                  60

Pro Glu Lys Tyr Glu Asp Gln Asp Phe Leu Phe Ile Pro Thr Met Glu
 65                  70                  75                  80

Arg Ser Asn Ala Gly Arg Tyr Arg Cys Ser Tyr Gln Asn Gly Ser His
                 85                  90                  95

Trp Ser Leu Pro Ser Asp Gln Leu Glu Leu Ile Ala Thr Gly Val Tyr
```

-continued

```
            100                 105                 110
Ala Lys Pro Ser Leu Ser Ala His Pro Ser Ser Ala Val Pro Gln Gly
        115                 120                 125

Arg Asp Val Thr Leu Lys Cys Gln Ser Pro Tyr Ser Phe Asp Glu Phe
        130                 135                 140

Val Leu Tyr Lys Glu Gly Asp Thr Gly Pro Tyr Lys Arg Pro Glu Lys
145                 150                 155                 160

Trp Tyr Arg Ala Asn Phe Pro Ile Ile Thr Val Ala Ala His Ser
                165                 170                 175

Gly Thr Tyr Arg Cys Tyr Ser Phe Ser Ser Ser Pro Tyr Leu Trp
            180                 185                 190

Ser Ala Pro Ser Asp Pro Leu Val Leu Val Val Thr Gly Leu Ser Ala
        195                 200                 205

Thr Pro Ser Gln Val Pro Thr Glu Glu Ser Phe Pro Val Thr Glu Ser
        210                 215                 220

Ser Arg Arg Pro Ser Ile Leu Pro Thr Asn Lys Ile Ser Thr Thr Glu
225                 230                 235                 240

Lys Pro Met Asn Ile Thr Ala Ser Pro Glu Gly Leu Ser Pro Pro Ile
                245                 250                 255

Gly Phe Ala His Gln His Tyr Ala Lys Gly Asn
            260                 265
```

<210> SEQ ID NO 20
<211> LENGTH: 19
<212> TYPE: PRT
<213> ORGANISM: Mus musculus

<400> SEQUENCE: 20

```
Leu Val Arg Ile Cys Leu Gly Ala Thr Ile Ile Ile Leu Leu Gly
1               5                   10                  15

Leu Leu Ala
```

<210> SEQ ID NO 21
<211> LENGTH: 27
<212> TYPE: PRT
<213> ORGANISM: Mus musculus

<400> SEQUENCE: 21

```
Glu Asp Trp His Ser Arg Lys Lys Cys Leu Gln His Arg Met Arg Ala
1               5                   10                  15

Leu Gln Arg Pro Leu Pro Pro Leu Pro Leu Ala
            20                  25
```

<210> SEQ ID NO 22
<211> LENGTH: 41
<212> TYPE: PRT
<213> ORGANISM: Mus musculus

<400> SEQUENCE: 22

```
Cys Gln Gly Pro Pro Asp Val Asp Leu Tyr Arg Leu Glu Lys Leu Lys
1               5                   10                  15

Pro Glu Lys Tyr Glu Asp Gln Asp Phe Leu Phe Ile Pro Thr Met Glu
            20                  25                  30

Arg Ser Asn Ala Gly Arg Tyr Arg Cys
            35                  40
```

<210> SEQ ID NO 23
<211> LENGTH: 47

<212> TYPE: PRT
<213> ORGANISM: Mus musculus

<400> SEQUENCE: 23

Cys Gln Ser Pro Tyr Ser Phe Asp Glu Phe Val Leu Tyr Lys Glu Gly
 1               5                  10                  15

Asp Thr Gly Pro Tyr Lys Arg Pro Glu Lys Trp Tyr Arg Ala Asn Phe
            20                  25                  30

Pro Ile Ile Thr Val Thr Ala Ala His Ser Gly Thr Tyr Arg Cys
        35                  40                  45

<210> SEQ ID NO 24
<211> LENGTH: 1896
<212> TYPE: DNA
<213> ORGANISM: Homo sapiens

<400> SEQUENCE: 24

| | | | | | |
|---|---|---|---|---|---|
| atgacgcccg | ccctcacagc | cctgctctgc | cttgggctga | gtctgggccc | caggacccgc | 60 |
| gtgcaggcag | ggcccttccc | caaacccacc | ctctgggctg | agccaggctc | tgtgatcagc | 120 |
| tgggggagcc | ccgtgaccat | ctggtgtcag | gggagcctgg | aggcccagga | gtaccgactg | 180 |
| gataaagagg | gaagcccaga | gcccttggac | agaaataacc | cactggaacc | caagaacaag | 240 |
| gccagattct | ccatcccatc | catgacagag | caccatgcgg | ggagataccg | ctgccactat | 300 |
| tacagctctg | caggctggtc | agagcccagc | gacccctgg | agctggtgat | gacaggattc | 360 |
| tacaacaaac | ccaccctctc | agccctgccc | agccctgtgg | tggcctcagg | ggggaatatg | 420 |
| accctccgat | gtggctcaca | gaagggatat | caccattttg | ttctgatgaa | ggaaggagaa | 480 |
| caccagctcc | cccggaccct | ggactcacag | cagctccaca | gtgggggagtt | ccaggccctg | 540 |
| ttccctgtgg | gccccgtgaa | cccagccac | aggtggaggt | tcacatgcta | ttactattat | 600 |
| atgaacaccc | cccaggtgtg | gtcccacccc | agtgaccccc | tggagattct | gccctcaggc | 660 |
| gtgtctagga | agccctccct | cctgaccctg | cagggccctg | tcctggcccc | tgggcagagc | 720 |
| ctgacccttcc | agtgtggctc | tgatgtcggc | tacgacagat | ttgttctgta | taaggagggg | 780 |
| gaacgtgact | tcctccagcg | ccctggccag | cagccccagg | ctgggctctc | ccaggccaac | 840 |
| ttcaccctgg | gcctgtgag | cccctcccac | ggggccagt | acaggtgcta | tggtgcacac | 900 |
| aacctctcct | ccgagtggtc | ggcccccagc | gaccccctga | catcctgat | ggcaggacag | 960 |
| atctatgaca | ccgtctccct | gtcagcacag | ccgggcccca | cagtggcctc | aggagagaac | 1020 |
| gtgacccctgc | tgtgtcagtc | atggtggcag | tttgacactt | tccttctgac | caaagaaggg | 1080 |
| gcagcccatc | ccccactgcg | tctgagatca | atgtacggag | ctcataagta | ccaggctgaa | 1140 |
| ttccccatga | gtcctgtgac | ctcagcccac | gcggggacct | acaggtgcta | cggctcatac | 1200 |
| agctccaacc | cccacctgct | gtctttcccc | agtgagcccc | tggaactcat | ggtctcagga | 1260 |
| cactctggag | gctccagcct | cccacccaca | gggccgccct | ccacacctgg | tctgggaaga | 1320 |
| tacctggagg | ttttgattgg | ggtctcggtg | gccttcgtcc | tgctgctctt | cctcctcctc | 1380 |
| ttcctcctcc | tccgacgtca | gcgtcacagc | aaacacagga | catctgacca | gagaaagact | 1440 |
| gatttccagc | gtcctgcagg | ggctgcggag | acagagccca | aggacagggg | cctgctgagg | 1500 |
| aggtccagcc | cagctgctga | cgtccaggaa | gaaaacctct | atgctgccgt | gaaggacaca | 1560 |
| cagtctgagg | acagggtgga | gctggacagt | cagagcccac | acgatgaaga | ccccaggca | 1620 |
| gtgacgtatg | ccccggtgaa | acactccagt | cctaggagaa | aatggctc | tcctccctcc | 1680 |
| tcactgtctg | gggaattcct | ggacacaaag | gacagacagg | tggaagagga | caggcagatg | 1740 |

-continued

```
gacactgagg ctgctgcatc tgaagcctcc caggatgtga cctacgccca gctgcacagc    1800
ttgaccctta gacggaaggc aactgagcct cctccatccc aggaagggga acctccagct    1860
gagcccagca tctacgccac tctggccatc cactag                              1896
```

<210> SEQ ID NO 25
<211> LENGTH: 20
<212> TYPE: DNA
<213> ORGANISM: Artificial Sequence
<220> FEATURE:
<223> OTHER INFORMATION: forward primer

<400> SEQUENCE: 25

```
cagcctcacc cactttcttc                                                  20
```

<210> SEQ ID NO 26
<211> LENGTH: 20
<212> TYPE: DNA
<213> ORGANISM: Artificial Sequence
<220> FEATURE:
<223> OTHER INFORMATION: reverse primer

<400> SEQUENCE: 26

```
ccacaagcac tagagggtca                                                  20
```

<210> SEQ ID NO 27
<211> LENGTH: 21
<212> TYPE: DNA
<213> ORGANISM: Artificial Sequence
<220> FEATURE:
<223> OTHER INFORMATION: sense primer

<400> SEQUENCE: 27

```
ttctgtcttg ggctgtgtct g                                                21
```

<210> SEQ ID NO 28
<211> LENGTH: 21
<212> TYPE: DNA
<213> ORGANISM: Artificial Sequence
<220> FEATURE:
<223> OTHER INFORMATION: anti-sense primer

<400> SEQUENCE: 28

```
cccgccagga ttattaggat c                                                21
```

<210> SEQ ID NO 29
<211> LENGTH: 21
<212> TYPE: DNA
<213> ORGANISM: Artificial Sequence
<220> FEATURE:
<223> OTHER INFORMATION: sense primer

<400> SEQUENCE: 29

```
cctgaagctg acagcattcg g                                                21
```

<210> SEQ ID NO 30
<211> LENGTH: 21
<212> TYPE: DNA
<213> ORGANISM: Artificial Sequence
<220> FEATURE:
<223> OTHER INFORMATION: anti-sense primer

<400> SEQUENCE: 30

```
ctcctagagc tacctgtgga g                                                21
```

<210> SEQ ID NO 31
<211> LENGTH: 23
<212> TYPE: DNA
<213> ORGANISM: Artificial Sequence
<220> FEATURE:
<223> OTHER INFORMATION: forward primer

<400> SEQUENCE: 31
ctgtagctgt tttcagacac acc                                         23

<210> SEQ ID NO 32
<211> LENGTH: 21
<212> TYPE: DNA
<213> ORGANISM: Artificial Sequence
<220> FEATURE:
<223> OTHER INFORMATION: reverse primer

<400> SEQUENCE: 32
ccatcacctc tttctggtta c                                           21

<210> SEQ ID NO 33
<211> LENGTH: 1017
<212> TYPE: DNA
<213> ORGANISM: Homo sapiens

<400> SEQUENCE: 33
atgtctccat ccccgaccgc cctcttctgt cttgggctgt gtctggggcg tgtgccagcg      60
cagagtggac cgctcccccaa gccctccctc caggttctgc ccagctccct ggtgcccctg    120
gagaagccag tgaccctccg gtgccaggga cctccgggcg tggacctgta ccgcctggag    180
aagctgagtt ccagcaggta ccaggatcag gcagtcctct tcatcccggc catgaagaga    240
agtctggctg gacgctaccg ctgctcctac cagaacggaa gcctctggtc cctgcccagc    300
gaccagctgg agtcgttgc cacgggagtt tttgccaaac cctcgctctc agcccagccc    360
ggcccggcgg tgtcgtcagg aggggacgta accctacagt gtcagactcg gtatggcttt    420
gaccaatttg ctctgtacaa ggaagggac cctgcgccct acaagaatcc cgagagatgg    480
taccgggcta gtttcccccat catcacggtg accgccgccc acagcggaac ctaccgatgc    540
tacagcttct ccagcaggga cccatacctg tggtcggccc ccagcgaccc cctggagctt    600
gtggtcacag gaacctctgt gacccccagc cggttaccaa cagaaccacc ttcctcggta    660
gcagaattct cagaagccac cgctgaactg accgtctcat tcacaaacaa agtcttcaca    720
actgagactt ctaggagtat caccaccagt ccaaaggagt cagactctcc agctggtcct    780
gcccgccagt actacaccaa gggcaacctg gtccggatat gcctcggggc tgtgatccta    840
ataatcctgg cggggtttct ggcagaggac tggcacagcc ggaggaagcg cctgcggcac    900
aggggcaggg ctgtgcagag gccgcttccg ccctgccgc cctcccgca gacccggaaa      960
tcacacgggg gtcaggatgg aggccgacag gatgttcaca gccgcgggtt atgttca      1017

<210> SEQ ID NO 34
<211> LENGTH: 339
<212> TYPE: PRT
<213> ORGANISM: Homo sapiens

<400> SEQUENCE: 34

Met Ser Pro Ser Pro Thr Ala Leu Phe Cys Leu Gly Leu Cys Leu Gly
  1               5                  10                  15

Arg Val Pro Ala Gln Ser Gly Pro Leu Pro Lys Pro Ser Leu Gln Val
             20                  25                  30

```
Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
        195                 200                 205

Pro Ser Arg Leu Pro Thr Glu Pro Pro Ser Ser Val Ala Glu Phe Ser
    210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Leu Val Arg
            260                 265                 270

Ile Cys Leu Gly Ala Val Ile Leu Ile Ile Leu Ala Gly Phe Leu Ala
        275                 280                 285

Glu Asp Trp His Ser Arg Arg Lys Arg Leu Arg His Arg Gly Arg Ala
    290                 295                 300

Val Gln Arg Pro Leu Pro Pro Leu Pro Pro Leu Pro Gln Thr Arg Lys
305                 310                 315                 320

Ser His Gly Gly Gln Asp Gly Gly Arg Gln Asp Val His Ser Arg Gly
                325                 330                 335

Leu Cys Ser

<210> SEQ ID NO 35
<211> LENGTH: 1017
<212> TYPE: DNA
<213> ORGANISM: Homo sapiens

<400> SEQUENCE: 35
atgtctccat ccccgaccgc cctcttctgt cttgggctgt gtctggggcg tgtgccagcg    60
cagagtggac cgctccccaa gccctccctc caggtctgtg ccagctccct ggtgcccctg   120
gagaagccag tgaccctccg gtgccaggga cctccgggcg tggacctgta ccgcctggag   180
aagctgagtt ccagcaggta ccaggatcag gtagtcctct tcatcccggc catgaagaga   240
agtctggctg gacgctaccg ctgctcctac cagaacggaa gcctctggtc cctgcccagc   300
gaccagctgg agctcgttgc cacgggagtt tttgccaaac cctcgctctc agcccagccc   360
```

-continued

```
ggcccggcgg tgtcgtcagg aggggacgta accctacagt gtcagactcg gtatggcttt    420
gaccaatttg ctctgtacaa ggaaggggac cctgcgccct acaagaatcc cgagagatgg    480
taccgggcta gtttccccat catcacggta ccgccgccc acagcggaac ctaccgatgc    540
tacagcttct ccagcaggga cccatacctg tggtcggccc ccagcgaccc cctggagctt    600
gtggtcacag aacctctgt gaccccccagc cggttaccaa cagaaccacc ttcctcggta    660
gcagaattct cagaagccac cgctgaactg accgtctcat tcacaaacaa agtcttcaca    720
actgagactt ctaggagtat caccaccagt ccaaaggagt cagactctcc agctggtcct    780
gcccgccagt actacaccaa gggcaacctg gtccggatat gcctcggggc tgtgatccta    840
ataatcctgg cggggtttct ggcagaggac tggcacagcc ggaggaagcg cctgcggcac    900
aggggcaggg ctgtgcagag gccgcttccg cccctgccgc ccctcccgca gacccggaaa    960
tcacacgggg gtcaggatgg aggccgacag gatgttcaca gccgcgggtt atgttca     1017
```

<210> SEQ ID NO 36
<211> LENGTH: 339
<212> TYPE: PRT
<213> ORGANISM: Homo sapiens

<400> SEQUENCE: 36

```
Met Ser Pro Ser Pro Thr Ala Leu Phe Cys Leu Gly Leu Cys Leu Gly
  1               5                  10                  15

Arg Val Pro Ala Gln Ser Gly Pro Leu Pro Lys Pro Ser Leu Gln Ala
                 20                  25                  30

Leu Pro Ser Ser Leu Val Pro Leu Glu Lys Pro Val Thr Leu Arg Cys
             35                  40                  45

Gln Gly Pro Pro Gly Val Asp Leu Tyr Arg Leu Glu Lys Leu Ser Ser
         50                  55                  60

Ser Arg Tyr Gln Asp Gln Val Val Leu Phe Ile Pro Ala Met Lys Arg
 65                  70                  75                  80

Ser Leu Ala Gly Arg Tyr Arg Cys Ser Tyr Gln Asn Gly Ser Leu Trp
                 85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
            115                 120                 125

Asp Val Thr Leu Gln Cys Gln Thr Arg Tyr Gly Phe Asp Gln Phe Ala
        130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
            195                 200                 205

Pro Ser Arg Leu Pro Thr Glu Pro Pro Ser Ser Val Ala Glu Phe Ser
        210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255
```

```
Pro Ala Gly Pro Ala Arg Gln Tyr Tyr Thr Lys Gly Asn Leu Val Arg
            260                 265                 270

Ile Cys Leu Gly Ala Val Ile Leu Ile Ile Leu Ala Gly Phe Leu Ala
        275                 280                 285

Glu Asp Trp His Ser Arg Arg Lys Arg Leu Arg His Arg Gly Arg Ala
            290                 295                 300

Val Gln Arg Pro Leu Pro Pro Leu Pro Pro Leu Pro Gln Thr Arg Lys
305                 310                 315                 320

Ser His Gly Gly Gln Asp Gly Gly Arg Gln Asp Val His Ser Arg Gly
                325                 330                 335

Leu Cys Ser
```

<210> SEQ ID NO 37
<211> LENGTH: 1017
<212> TYPE: DNA
<213> ORGANISM: Homo sapiens

<400> SEQUENCE: 37

```
atgtctccat ccccgaccgc cctcttctgt cttgggctgt gtctggggcg tgtgccagcg    60
cagagtggac cgctcccaa gccctccctc caggctctgc ccagctccct ggtgcccctg   120
gagaagccag tgaccctccg gtgccaggga cctccgggcg tggacctgta ccgcctggag   180
aagctgagtt ccagcaggta ccaggatcag gcagtcctct tcatcccggc catgaagaga   240
agtctggctg gacgctaccg ctgctcctac cagaacggaa gcctctggtc cctgcccagc   300
gaccagctgg agctcgttgc cacgggagtt tttgccaaac cctcgctctc agcccagccc   360
ggcccggcgc tgtcgtcagg aggggacgta accctacagt gtcagactcg gtatggcttt   420
gaccaatttg ctctgtacaa ggaagggac cctgcgcccc acaagaatcc cgagagatgg   480
taccgggcta gtttcccat catcacggcg accgccgccc acagcggaac ctaccgatgc   540
tacagcttct ccagcaggga cccataccctg tggtcggccc cagccgaccc cctggagctt   600
gtggtcacag gaacctctgt gacccccagc cggttaccaa cagaaccacc ttcctcggta   660
gcagaattct cagaagccac cgctgaactg accgtctcat tcacaaacaa agtcttcaca   720
actgagactt ctaggagtat caccaccagt ccaaaggagt cagactctcc agctggtcct   780
gcccgccagt actacaccaa gggcaacctg gtccggatat gcctcggggc tgtgatccta   840
ataatcctgg cggggtttct ggcagaggac tggcacagcc ggaggaagcg cctgcggcac   900
aggggcaggg ctgtgcagag gccgcttccg ccctgccgc cctcccgca gacccggaaa   960
tcacacgggg gtcaggatgg aggccgacag gatgttcaca gccgcgggtt atgttca     1017
```

<210> SEQ ID NO 38
<211> LENGTH: 339
<212> TYPE: PRT
<213> ORGANISM: Homo sapiens

<400> SEQUENCE: 38

```
Met Ser Pro Ser Pro Thr Ala Leu Phe Cys Leu Gly Leu Cys Leu Gly
 1               5                  10                  15

Arg Val Pro Ala Gln Ser Gly Pro Leu Pro Lys Pro Ser Leu Gln Ala
             20                  25                  30

Leu Pro Ser Ser Leu Val Pro Leu Glu Lys Pro Val Thr Leu Arg Cys
         35                  40                  45

Gln Gly Pro Pro Gly Val Asp Leu Tyr Arg Leu Glu Lys Leu Ser Ser
     50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                 85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
```

```
                145                 150                 155                 160
        Tyr Arg Ala Ser Phe Pro Ile Ile Thr Ala Thr Ala Ala His Ser Gly
                        165                 170                 175

Thr Tyr Arg Cys Tyr Ser Phe Ser Ser Arg Asp Pro Tyr Leu Trp Ser
                        180                 185                 190

Ala Pro Ser Asp Pro Leu Glu Leu Val Val Thr Gly Thr Ser Val Thr
                        195                 200                 205

Pro Ser Arg Leu Pro Thr Glu Pro Pro Ser Ser Val Ala Glu Phe Ser
                        210                 215                 220

Glu Ala Thr Ala Glu Leu Thr Val Ser Phe Thr Asn Lys Val Phe Thr
        225                 230                 235                 240

Thr Glu Thr Ser Arg Ser Ile Thr Thr Ser Pro Lys Glu Ser Asp Ser
                        245                 250                 255

Pro Ala Gly Pro Ala Arg Gln Tyr Tyr Thr Lys Gly Asn Leu Val Arg
                        260                 265                 270

Ile Cys Leu Gly Ala Val Ile Leu Ile Ile Leu Ala Gly Phe Leu Ala
                        275                 280                 285

Glu Asp Trp His Ser Arg Arg Lys Arg Leu Arg His Arg Gly Arg Ala
        290                 295                 300

Val Gln Arg Pro Leu Pro Pro Leu Pro Pro Leu Pro Gln Thr Arg Lys
        305                 310                 315                 320

Ser His Gly Gly Gln Asp Gly Gly Arg Gln Asp Val His Ser Arg Gly
                        325                 330                 335

Leu Cys Ser

<210> SEQ ID NO 39
<211> LENGTH: 1017
<212> TYPE: DNA
<213> ORGANISM: Homo sapiens

<400> SEQUENCE: 39
atgtctccat ccccgaccgc cctcttctgt cttgggctgt gtctggggcg tgtgccagcg      60
cagagtggac cgctccccaa gccctccctc caggctctgc ccagctccct ggtgcccctg     120
gagaagccag tgaccctccg gtgccaggga cctccgggcg tggacctgta ccgcctggag     180
aagctgagtt ccagcaggta ccaggatcag gcagtcctct tcatcccggc catgaagaga     240
agtctggctg gacgctaccg ctgctcctac cagaacggaa gcctctggtc cctgcccagc     300
gaccagctgg agtcgttgc cacgggagtt tttgccaaac cctcgctctc agcccagccc     360
ggcccggcgg tgtcgtcagg agggacgta accctacagt gtcagactcg gtatggcttt     420
gaccaatttg ctctgtacaa ggaaggggac cctgcgccct acaagaatcc cgagagatgg     480
taccgggcta gtttccccat catcacggtg accgccgccc acagcggaac ctaccgatgc     540
tacagcttct ccagcaggga cccatacctg tggtcggtcc cagcgacccc ctgagcttt     600
gtggtcacag gaacctctgt gaccccagc cggttaccaa cagaaccacc ttcctcggta     660
gcagaattct cagaagccac cgctgaactg accgtctcat tcacaaacaa agtcttcaca     720
actgagactt ctaggagtat caccaccagt ccaaaggagt cagactctcc agctggtcct     780
gcccgccagt actacaccaa gggcaacctg gtccggatat gcctcgggc tgtgatccta     840
ataatcctgg cggggtttct ggcagaggac tggcacagcc ggaggaagcg cctgcggcac     900
aggggcaggg ctgtgcagag gccgcttccg cccctgccgc cctcccgca gacccggaaa     960
tcacacgggg gtcaggatgg aggccgacag gatgttcaca gccgcgggtt atgttca     1017
```

<210> SEQ ID NO 40
<211> LENGTH: 339
<212> TYPE: PRT
<213> ORGANISM: Homo sapiens

<400> SEQUENCE: 40

```
Met Ser Pro Ser Pro Thr Ala Leu Phe Cys Leu Gly Leu Cys Leu Gly
  1               5                  10                  15

Arg Val Pro Ala Gln Ser Gly Pro Leu Pro Lys Pro Ser Leu Gln Ala
             20                  25                  30

Leu Pro Ser Ser Leu Val Pro Leu Glu Lys Pro Val Thr Leu Arg Cys
         35                  40                  45

Gln Gly Pro Pro Gly Val Asp Leu Tyr Arg Leu Glu Lys Leu Ser Ser
 50                  55                  60

Ser Arg Tyr Gln Asp Gln Ala Val Leu Phe Ile Pro Ala Met Lys Arg
 65                  70                  75                  80

Ser Leu Ala Gly Arg Tyr Arg Cys Ser Tyr Gln Asn Gly Ser Leu Trp
                 85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Val Pro Ser Asp Pro Leu Glu Leu Val Val Thr Gly Thr Ser Val Thr
        195                 200                 205

Pro Ser Arg Leu Pro Thr Glu Pro Pro Ser Ser Val Ala Glu Phe Ser
210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Leu Val Arg
            260                 265                 270

Ile Cys Leu Gly Ala Val Ile Leu Ile Ile Leu Ala Gly Phe Leu Ala
        275                 280                 285

Glu Asp Trp His Ser Arg Arg Lys Arg Leu Arg His Arg Gly Arg Ala
290                 295                 300

Val Gln Arg Pro Leu Pro Pro Leu Pro Pro Leu Pro Gln Thr Arg Lys
305                 310                 315                 320

Ser His Gly Gly Gln Asp Gly Gly Arg Gln Asp Val His Ser Arg Gly
                325                 330                 335

Leu Cys Ser
```

<210> SEQ ID NO 41
<211> LENGTH: 939
<212> TYPE: DNA
<213> ORGANISM: Mus musculus

```
<400> SEQUENCE: 41
atgtctccag cctcacccac tttcttctgt attgggctgt gtgtactgca agtgatccaa    60
acacagagtg gcccactccc caagccttcc ctccaggctc agcccagttc cctggtaccc   120
ctgggtcagt cagttattct gaggtgccag ggacctccag atgtggattt atatcgcctg   180
gagaaactga aaccggagaa gtatgaagat caagactttc tcttcattcc aaccatggaa   240
agaagtaatg ttggacggta tcgatgctct atcagaatgg gagtcactg gtctctccca   300
agtgaccagc ttgagctaat tgctacaggt gtgtatgcta aaccctcact ctcagctcat   360
cccagctcag cagtccctca aggcagggat gtgactctga agtgccagag cccatacagt   420
tttgatgaat tcgttctata caagaaggg gatactgggc cttataagag acctgagaaa   480
tggtaccggg ccaatttccc catcatcaca gtgactgctg ctcacagtgg gacgtaccgg   540
tgttacagct tctccagctc atctccatac ctgtggtcag ccccgagtga ccctctagtg   600
cttgtggtta ctggactctc tgccactccc agccaggtac ccacgaaga atcatttcct   660
gtgacagaat cctccaggag accttccatc ttacccacaa acaaaatatc tacaactgaa   720
aagcctatga atatcactgc ctctccagag gggctgagcc ctccaattgg ttttgctcat   780
cagcactatg ccaaggggaa tctggtccgg atatgccttg gtgccacgat tataataatt   840
ttgttgggc ttctagcaga ggattggcac agtcggaaga aatgcctgca acacaggatg   900
agagctttgc aaaggccact accaccctc ccactggcc                           939

<210> SEQ ID NO 42
<211> LENGTH: 313
<212> TYPE: PRT
<213> ORGANISM: Mus musculus

<400> SEQUENCE: 42

Met Ser Pro Ala Ser Pro Thr Phe Phe Cys Ile Gly Leu Cys Val Leu
 1               5                  10                  15

Gln Val Ile Gln Thr Gln Ser Gly Pro Leu Pro Lys Pro Ser Leu Gln
            20                  25                  30

Ala Gln Pro Ser Ser Leu Val Pro Leu Gly Gln Ser Val Ile Leu Arg
        35                  40                  45

Cys Gln Gly Pro Pro Asp Val Asp Leu Tyr Arg Leu Glu Lys Leu Lys
    50                  55                  60

Pro Glu Lys Tyr Glu Asp Gln Asp Phe Leu Phe Ile Pro Thr Met Glu
65                  70                  75                  80

Arg Ser Asn Val Gly Arg Tyr Arg Cys Ser Tyr Gln Asn Gly Ser His
                85                  90                  95

Trp Ser Leu Pro Ser Asp Gln Leu Glu Leu Ile Ala Thr Gly Val Tyr
            100                 105                 110

Ala Lys Pro Ser Leu Ser Ala His Pro Ser Ser Ala Val Pro Gln Gly
        115                 120                 125

Arg Asp Val Thr Leu Lys Cys Gln Ser Pro Tyr Ser Phe Asp Glu Phe
    130                 135                 140

Val Leu Tyr Lys Glu Gly Asp Thr Gly Pro Tyr Lys Arg Pro Glu Lys
145                 150                 155                 160

Trp Tyr Arg Ala Asn Phe Pro Ile Ile Thr Val Thr Ala Ala His Ser
                165                 170                 175

Gly Thr Tyr Arg Cys Tyr Ser Phe Ser Ser Ser Pro Tyr Leu Trp
            180                 185                 190

Ser Ala Pro Ser Asp Pro Leu Val Leu Val Val Thr Gly Leu Ser Ala
```

```
              195                 200                 205
Thr Pro Ser Gln Val Pro Thr Glu Glu Ser Phe Pro Val Thr Glu Ser
    210                 215                 220

Ser Arg Arg Pro Ser Ile Leu Pro Thr Asn Lys Ile Ser Thr Thr Glu
225                 230                 235                 240

Lys Pro Met Asn Ile Thr Ala Ser Pro Glu Gly Leu Ser Pro Pro Ile
                245                 250                 255

Gly Phe Ala His Gln His Tyr Ala Lys Gly Asn Leu Val Arg Ile Cys
                260                 265                 270

Leu Gly Ala Thr Ile Ile Ile Leu Leu Gly Leu Leu Ala Glu Asp
            275                 280                 285

Trp His Ser Arg Lys Lys Cys Leu Gln His Arg Met Arg Ala Leu Gln
        290                 295                 300

Arg Pro Leu Pro Pro Leu Pro Leu Ala
305                 310
```

<210> SEQ ID NO 43
<211> LENGTH: 939
<212> TYPE: DNA
<213> ORGANISM: Mus musculus

<400> SEQUENCE: 43

```
atgtctccag cctcacccac tttcttctgt attgggctgt gtgtactgca agtgatccaa      60
acacagagtg gcccactccc caagccttcc ctccaggctc agcccagttc cctggtaccc     120
ctgggtcagt cagttattct gaggtgccag ggacctccag atgtggattt atatcgcctg     180
gagaaactga aaccggagaa gtatgaagat caagactttc tcttcattcc aaccatggaa     240
agaagtaatg ctggacggta tcgatgctct tatcagaatg ggagtcactg gtctctccca     300
agtgaccagc ttgagctaat tgctacaggt gtgtatgcta aaccctcact ctcagctcat     360
cccagctcag cagtccctca aggcagggat gtgactctga agtgccagag cccatacagt     420
tttgatgaat tcgttctata caaagaaggg gatactgggc cttataagag acctgagaaa     480
tggtaccggg tcaatttccc catcatcaca gtgactgctg ctcacagtgg gacgtaccgg     540
tgttacagct tctccagctc atctccatac ctgtggtcag ccccgagtga ccctctagtg     600
cttgtggtta ctggactctc tgccactccc agccaggtac ccacggaaga tcatttcct     660
gtgacagaat cctccaggag accttccatc ttacccacaa acaaaatatc tacaactgaa     720
aagcctatga atatcactgc ctctccagag gggctgagcc ctccaattgg ttttgctcat     780
cagcactatg ccaaggggaa tctggtccgg atatgccttg gtgccacgat tataataatt     840
ttgttgggc ttctagcaga ggattggcac agtcggaaga aatgcctgca acacaggatg     900
agagctttgc aaaggccact accacccctc ccactggcc                            939
```

<210> SEQ ID NO 44
<211> LENGTH: 313
<212> TYPE: PRT
<213> ORGANISM: Mus musculus

<400> SEQUENCE: 44

```
Met Ser Pro Ala Ser Pro Thr Phe Phe Cys Ile Gly Leu Cys Val Leu
1               5                   10                  15

Gln Val Ile Gln Thr Gln Ser Gly Pro Leu Pro Lys Pro Ser Leu Gln
            20                  25                  30

Ala Gln Pro Ser Ser Leu Val Pro Leu Gly Gln Ser Val Ile Leu Arg
        35                  40                  45
```

```
Cys Gln Gly Pro Pro Asp Val Asp Leu Tyr Arg Leu Glu Lys Leu Lys
    50                  55                  60

Pro Glu Lys Tyr Glu Asp Gln Asp Phe Leu Phe Ile Pro Thr Met Glu
 65                  70                  75                  80

Arg Ser Asn Ala Gly Arg Tyr Arg Cys Ser Tyr Gln Asn Gly Ser His
                 85                  90                  95

Trp Ser Leu Pro Ser Asp Gln Leu Glu Leu Ile Ala Thr Gly Val Tyr
            100                 105                 110

Ala Lys Pro Ser Leu Ser Ala His Pro Ser Ser Ala Val Pro Gln Gly
        115                 120                 125

Arg Asp Val Thr Leu Lys Cys Gln Ser Pro Tyr Ser Phe Asp Glu Phe
    130                 135                 140

Val Leu Tyr Lys Glu Gly Asp Thr Gly Pro Tyr Lys Arg Pro Glu Lys
145                 150                 155                 160

Trp Tyr Arg Val Asn Phe Pro Ile Ile Thr Val Thr Ala Ala His Ser
                165                 170                 175

Gly Thr Tyr Arg Cys Tyr Ser Phe Ser Ser Ser Pro Tyr Leu Trp
            180                 185                 190

Ser Ala Pro Ser Asp Pro Leu Val Leu Val Val Thr Gly Leu Ser Ala
        195                 200                 205

Thr Pro Ser Gln Val Pro Thr Glu Glu Ser Phe Pro Val Thr Glu Ser
    210                 215                 220

Ser Arg Arg Pro Ser Ile Leu Pro Thr Asn Lys Ile Ser Thr Thr Glu
225                 230                 235                 240

Lys Pro Met Asn Ile Thr Ala Ser Pro Glu Gly Leu Ser Pro Pro Ile
                245                 250                 255

Gly Phe Ala His Gln His Tyr Ala Lys Gly Asn Leu Val Arg Ile Cys
            260                 265                 270

Leu Gly Ala Thr Ile Ile Ile Leu Leu Gly Leu Leu Ala Glu Asp
        275                 280                 285

Trp His Ser Arg Lys Lys Cys Leu Gln His Arg Met Arg Ala Leu Gln
290                 295                 300

Arg Pro Leu Pro Pro Leu Pro Leu Ala
305                 310
```

<210> SEQ ID NO 45
<211> LENGTH: 939
<212> TYPE: DNA
<213> ORGANISM: Mus musculus

<400> SEQUENCE: 45

```
atgtctccag cctcacccac tttcttctgt attgggctgt gtgtactgca agtgatccaa      60
acacagagtg gcccactccc caagccttcc ctccaggctc agcccagttc cctggtaccc     120
ctgggtcagt cagttattct gaggtgccag ggacctccag atgtggattt atatcgcctg     180
gagaaactga accggagaa gtatgaagat caagactttc tcttcattcc aaccatggaa     240
agaagtaatg ctggacggta tcgatgctct tatcagaatg ggagtcactg gtctctccca     300
agtgaccagc ttgagctaat tgctacaggt gtgtatgcta accctcact ctcagctcat     360
cccagctcag cagcccctca aggcagggat gtgactctga gtgccagag cccatacagt     420
tttgatgaat tcgttctata caaagaaggg gatactgggc cttataagag acctgagaaa     480
tggtaccggg ccaatttccc catcatcaca gtgactgctg ctcacagtgg gacgtaccgg     540
tgttacagct tctccagctc atctccatac ctgtggtcag ccccgagtga ccctctagtg     600
```

```
cttgtggtta ctggactctc tgccactccc agccaggtac ccacggaaga atcatttcct      660
gtgacagaat cctccaggag accttccatc ttacccacaa acaaaatatc tacaactgaa      720
aagcctatga atatcactgc ctctccagag gggctgagcc ctccaattgg ttttgctcat      780
cagcactatg ccaaggggaa tctggtccgg atatgccttg gtgccacgat tataataatt      840 ttgttgggc ttctagcaga ggattggcac agtcggaaga aatgcctgca acacaggatg      900
agagctttgc aaaggccact accaccctc ccactggcc                            939
```

<210> SEQ ID NO 46
<211> LENGTH: 313
<212> TYPE: PRT
<213> ORGANISM: Mus musculus

<400> SEQUENCE: 46

```
Met Ser Pro Ala Ser Pro Thr Phe Phe Cys Ile Gly Leu Cys Val Leu
  1               5                  10                  15

Gln Val Ile Gln Thr Gln Ser Gly Pro Leu Pro Lys Pro Ser Leu Gln
                 20                  25                  30

Ala Gln Pro Ser Ser Leu Val Pro Leu Gly Gln Ser Val Ile Leu Arg
             35                  40                  45

Cys Gln Gly Pro Pro Asp Val Asp Leu Tyr Arg Leu Glu Lys Leu Lys
         50                  55                  60

Pro Glu Lys Tyr Glu Asp Gln Asp Phe Leu Phe Ile Pro Thr Met Glu
 65                  70                  75                  80

Arg Ser Asn Ala Gly Arg Tyr Arg Cys Ser Tyr Gln Asn Gly Ser His
                 85                  90                  95

Trp Ser Leu Pro Ser Asp Gln Leu Glu Leu Ile Ala Thr Gly Val Tyr
                100                 105                 110

Ala Lys Pro Ser Leu Ser Ala His Pro Ser Ser Ala Ala Pro Gln Gly
            115                 120                 125

Arg Asp Val Thr Leu Lys Cys Gln Ser Pro Tyr Ser Phe Asp Glu Phe
        130                 135                 140

Val Leu Tyr Lys Glu Gly Asp Thr Gly Pro Tyr Lys Arg Pro Glu Lys
145                 150                 155                 160

Trp Tyr Arg Ala Asn Phe Pro Ile Ile Thr Val Thr Ala Ala His Ser
                165                 170                 175

Gly Thr Tyr Arg Cys Tyr Ser Phe Ser Ser Ser Pro Tyr Leu Trp
                180                 185                 190

Ser Ala Pro Ser Asp Pro Leu Val Leu Val Val Thr Gly Leu Ser Ala
            195                 200                 205

Thr Pro Ser Gln Val Pro Thr Glu Glu Ser Phe Pro Val Thr Glu Ser
        210                 215                 220

Ser Arg Arg Pro Ser Ile Leu Pro Thr Asn Lys Ile Ser Thr Glu
225                 230                 235                 240

Lys Pro Met Asn Ile Thr Ala Ser Pro Glu Gly Leu Ser Pro Pro Ile
                245                 250                 255

Gly Phe Ala His Gln His Tyr Ala Lys Gly Asn Leu Val Arg Ile Cys
            260                 265                 270

Leu Gly Ala Thr Ile Ile Ile Leu Leu Gly Leu Leu Ala Glu Asp
        275                 280                 285

Trp His Ser Arg Lys Lys Cys Leu Gln His Arg Met Arg Ala Leu Gln
290                 295                 300

Arg Pro Leu Pro Pro Leu Pro Leu Ala
```

<210> SEQ ID NO 47
<211> LENGTH: 939
<212> TYPE: DNA
<213> ORGANISM: Mus musculus

<400> SEQUENCE: 47

```
atgtctccag cctcacccac tttcttctgt attgggctgt gtgtactgca agtgatccaa      60
acacagagtg gcccactccc caagccttcc ctccaggctc agcccagttc cctggtaccc     120
ctgggtcagt cagttattct gaggtgccag ggacctccag atgtggattt atatcgcctg     180
gagaaactga accggagaa gtatgaagat caagactttc tcttcattcc aaccatggaa      240
agaagtaatg ctggacggta tcgatgctct tatcagaatg ggagtcactg gtctctccca     300
agtgaccagc ttgagctaat tgctacaggt gtgtatgcta aaccctcact ctcagctcat     360
cccagctcag cagtccctca aggcagggat gtgactctga agtgccagag cccatacagt     420
tttgatgaat tcgttctata caaagaaggg gatactgggc cttataagag acctgagaaa     480
tggtaccggg ccaatttccc catcatcaca gtgactgctg ctcacagtgg gacgtaccgg     540
tgttacagct tctccagctc atctccatac ctgtggtcag ccccgagtga ccctctagtg     600
cttgtggtta ctggactctc tgccactccc agccaggtac ccacggaaga atcatttcct     660
gtgacagaat cctccaggag accttccatc ttacccacaa acaaaatatc tacaactgaa     720
aagcctatga atatcactgc ctctccagag gggctgagcc ctccaattgg ttttgctcat     780
cagcactatg tcaaggggaa tctggtccgg atatgccttg gtgccacgat tataataatt     840
ttgttgggc ttctagcaga ggattggcac agtcggaaga aatgcctgca acacaggatg     900
agagctttgc aaaggccact accacccctc ccactggcc                             939
```

<210> SEQ ID NO 48
<211> LENGTH: 313
<212> TYPE: PRT
<213> ORGANISM: Mus musculus

<400> SEQUENCE: 48

```
Met Ser Pro Ala Ser Pro Thr Phe Phe Cys Ile Gly Leu Cys Val Leu
  1               5                  10                  15

Gln Val Ile Gln Thr Gln Ser Gly Pro Leu Pro Lys Pro Ser Leu Gln
                 20                  25                  30

Ala Gln Pro Ser Ser Leu Val Pro Leu Gly Gln Ser Val Ile Leu Arg
             35                  40                  45

Cys Gln Gly Pro Pro Asp Val Asp Leu Tyr Arg Leu Glu Lys Leu Lys
         50                  55                  60

Pro Glu Lys Tyr Glu Asp Gln Asp Phe Leu Phe Ile Pro Thr Met Glu
 65                  70                  75                  80

Arg Ser Asn Ala Gly Arg Tyr Arg Cys Ser Tyr Gln Asn Gly Ser His
                 85                  90                  95

Trp Ser Leu Pro Ser Asp Gln Leu Glu Leu Ile Ala Thr Gly Val Tyr
            100                 105                 110

Ala Lys Pro Ser Leu Ser Ala His Pro Ser Ser Ala Val Pro Gln Gly
        115                 120                 125

Arg Asp Val Thr Leu Lys Cys Gln Ser Pro Tyr Ser Phe Asp Glu Phe
    130                 135                 140

Val Leu Tyr Lys Glu Gly Asp Thr Gly Pro Tyr Lys Arg Pro Glu Lys
145                 150                 155                 160
```

-continued

```
Trp Tyr Arg Ala Asn Phe Pro Ile Ile Thr Val Thr Ala Ala His Ser
                165                 170                 175
Gly Thr Tyr Arg Cys Tyr Ser Phe Ser Ser Ser Pro Tyr Leu Trp
            180                 185                 190
Ser Ala Pro Ser Asp Pro Leu Val Leu Val Val Thr Gly Leu Ser Ala
        195                 200                 205
Thr Pro Ser Gln Val Pro Thr Glu Glu Ser Phe Pro Val Thr Glu Ser
    210                 215                 220
Ser Arg Arg Pro Ser Ile Leu Pro Thr Asn Lys Ile Ser Thr Glu
225                 230                 235                 240
Lys Pro Met Asn Ile Thr Ala Ser Pro Glu Gly Leu Ser Pro Pro Ile
                245                 250                 255
Gly Phe Ala His Gln His Tyr Val Lys Gly Asn Leu Val Arg Ile Cys
            260                 265                 270
Leu Gly Ala Thr Ile Ile Ile Leu Leu Gly Leu Leu Ala Glu Asp
        275                 280                 285
Trp His Ser Arg Lys Lys Cys Leu Gln His Arg Met Arg Ala Leu Gln
    290                 295                 300
Arg Pro Leu Pro Pro Leu Pro Leu Ala
305                 310
```

<210> SEQ ID NO 49
<211> LENGTH: 5
<212> TYPE: PRT
<213> ORGANISM: Homo sapiens

<400> SEQUENCE: 49

```
Ser Tyr Trp Ile Ser
1               5
```

<210> SEQ ID NO 50
<211> LENGTH: 17
<212> TYPE: PRT
<213> ORGANISM: Homo sapiens

<400> SEQUENCE: 50

```
Arg Ile Asp Pro Ser Asp Ser Tyr Thr Asn Tyr Ser Pro Ser Phe Gln
1               5                   10                  15
Gly
```

<210> SEQ ID NO 51
<211> LENGTH: 11
<212> TYPE: PRT
<213> ORGANISM: Homo sapiens

<400> SEQUENCE: 51

```
His Gly Ser Asp Arg Gly Trp Gly Phe Asp Pro
1               5                   10
```

<210> SEQ ID NO 52
<211> LENGTH: 8
<212> TYPE: PRT
<213> ORGANISM: Homo sapiens

<400> SEQUENCE: 52

```
Asn Gly Val Asn Ser Asp Val Gly
1               5
```

<210> SEQ ID NO 53

```
<211> LENGTH: 7
<212> TYPE: PRT
<213> ORGANISM: Homo sapiens

<400> SEQUENCE: 53

Glu Val Asn Lys Arg Pro Ser
1               5

<210> SEQ ID NO 54
<211> LENGTH: 9
<212> TYPE: PRT
<213> ORGANISM: Homo sapiens

<400> SEQUENCE: 54

Ser Tyr Thr Ser Asn Asn Thr Pro Val
1               5

<210> SEQ ID NO 55
<211> LENGTH: 5
<212> TYPE: PRT
<213> ORGANISM: Homo sapiens

<400> SEQUENCE: 55

Ser Tyr Ser Met Asn
1               5

<210> SEQ ID NO 56
<211> LENGTH: 17
<212> TYPE: PRT
<213> ORGANISM: Homo sapiens

<400> SEQUENCE: 56

Ser Ile Ser Ser Ser Gly Arg Tyr Ile Ser Tyr Gly Asp Ser Val Lys
1               5                   10                  15

Gly

<210> SEQ ID NO 57
<211> LENGTH: 8
<212> TYPE: PRT
<213> ORGANISM: Homo sapiens

<400> SEQUENCE: 57

Asp Ile Ser Ser Ala Met Asp Val
1               5

<210> SEQ ID NO 58
<211> LENGTH: 13
<212> TYPE: PRT
<213> ORGANISM: Homo sapiens

<400> SEQUENCE: 58

Thr Arg Gly Gly Asn Asn Ile Gly Ser Lys Ser Val His
1               5                   10

<210> SEQ ID NO 59
<211> LENGTH: 7
<212> TYPE: PRT
<213> ORGANISM: Homo sapiens

<400> SEQUENCE: 59

Asp Asp Ser Asp Arg Pro Ser
1               5

<210> SEQ ID NO 60
```

```
<211> LENGTH: 10
<212> TYPE: PRT
<213> ORGANISM: Homo sapiens

<400> SEQUENCE: 60

Val Trp Asp Ser Ser Asp His His Val
 1               5                  10

<210> SEQ ID NO 61
<211> LENGTH: 5
<212> TYPE: PRT
<213> ORGANISM: Homo sapiens

<400> SEQUENCE: 61

Ser Tyr Trp Met Ser
 1               5

<210> SEQ ID NO 62
<211> LENGTH: 17
<212> TYPE: PRT
<213> ORGANISM: Homo sapiens

<400> SEQUENCE: 62

Asn Ile Lys Gln Asp Gly Ser Glu Lys Tyr Tyr Ala Asp Ser Val Arg
 1               5                  10                  15
Gly

<210> SEQ ID NO 63
<211> LENGTH: 14
<212> TYPE: PRT
<213> ORGANISM: Homo sapiens

<400> SEQUENCE: 63

Asp Lys Trp Glu Ala Tyr Ile Thr Pro Gly Ala Phe Asp Val
 1               5                  10

<210> SEQ ID NO 64
<211> LENGTH: 13
<212> TYPE: PRT
<213> ORGANISM: Homo sapiens

<400> SEQUENCE: 64

Thr Arg Ser Ser Gly Ser Ile Ala Ser Asn Tyr Val Gln
 1               5                  10

<210> SEQ ID NO 65
<211> LENGTH: 7
<212> TYPE: PRT
<213> ORGANISM: Homo sapiens

<400> SEQUENCE: 65

Glu Asp Asn Gln Arg Pro Ser
 1               5

<210> SEQ ID NO 66
<211> LENGTH: 8
<212> TYPE: PRT
<213> ORGANISM: Homo sapiens

<400> SEQUENCE: 66

Ser Tyr Asp Ser Ser Asn Val Val
 1               5

<210> SEQ ID NO 67
```

-continued

```
<211> LENGTH: 5
<212> TYPE: PRT
<213> ORGANISM: Homo sapiens

<400> SEQUENCE: 67

Asn Tyr Glu Met Asn
1               5

<210> SEQ ID NO 68
<211> LENGTH: 17
<212> TYPE: PRT
<213> ORGANISM: Homo sapiens

<400> SEQUENCE: 68

Tyr Ile Ser Ser Ser Gly Ser Thr Ile His Asn Ala Asp Ser Val Lys
1               5                   10                  15

Gly

<210> SEQ ID NO 69
<211> LENGTH: 12
<212> TYPE: PRT
<213> ORGANISM: Homo sapiens

<400> SEQUENCE: 69

Asp Gly Tyr Ser His Gly Leu Asp Ala Phe Asp Ile
1               5                   10

<210> SEQ ID NO 70
<211> LENGTH: 13
<212> TYPE: PRT
<213> ORGANISM: Homo sapiens

<400> SEQUENCE: 70

Ser Gly Ser Ser Ser Asn Ile Gly Ser Asn Thr Val His
1               5                   10

<210> SEQ ID NO 71
<211> LENGTH: 7
<212> TYPE: PRT
<213> ORGANISM: Homo sapiens

<400> SEQUENCE: 71

Ser Tyr Asn Gln Arg Pro Ser
1               5

<210> SEQ ID NO 72
<211> LENGTH: 10
<212> TYPE: PRT
<213> ORGANISM: Homo sapiens

<400> SEQUENCE: 72

Ser Trp Asp Asp Arg Leu Asn Gly Tyr Leu
1               5                   10
```

What is claimed is:

1. A substantially purified scFv antibody comprising the amino acid sequence encoded by the cDNA insert of the plasmid deposited with the ATCC® as patent deposit number PTA-2422.

2. An antibody or antigen binding portion thereof which immunospecifically binds to SEQ ID NO:3, wherein the antibody or antigen binding portion thereof comprises:

a) a variable heavy (VH) complementary determining region (CDR) 1 comprising the amino acid sequence of SEQ ID NO:61 or an amino acids sequence of a VH CDR 1 encoded by the cDNA insert of the plasmid deposited with the ATCC® as patent deposit number PTA-2442;

b) a VH CDR2 comprising the amino acid sequence of SEQ ID NO:62 or an amino acid sequence of a VH CDR2 encoded by the cDNA insert of the plasmid deposited with the ATCC® as patent deposit number PTA-2442;

c) a VH CDR3 comprising the amino acid sequence of SEQ ID NO:63 or an amino acid sequence of a VH CDR3 encoded by the cDNA insert of the plasma deposited with the ATCC® as patent deposit number PTA-2442;

d) a variable light (VL) CDR1 comprising the amino acid sequence of SEQ ID NO:64 or an amino acid sequence of a VL CDR1 encoded by the cDNA insert of the plasmid deposited with the ATCC® as patent deposit number PTA-2442;

e) a VL CDR2 comprising the amino acid sequence of SEQ ID NO:65 or an amino acid sequence of a VL CDR2 encoded by the cDNA insert of the plasmid deposited with the ATCC® as patent deposit number PTA-2422; and a VL CDR3 comprising the amino acids sequence of SEQ ID NO:66 or an amino acid sequence of a VL CDR3 encoded by the cDNA insert of the plasma deposited with the ATCC® as patent deposit number PTA-2422.

3. The antibody or antigen binding portion thereof of claim 2, wherein the antibody is a monoclonal antibody.

4. The antibody or antigen binding portion thereof of claim 2, wherein the antibody is a human antibody.

5. The antibody or antigen binding portion thereof of claim 2, wherein the antibody is a humanized antibody.

6. The antibody or antigen binding portion thereof of claim 2, wherein the antibody is a FAB fragment.

7. The antibody or antigen binding portion thereof of claim 2, wherein the antibody is a F(ab')$_2$ fragment.

8. The antibody or antigen binding portion thereof of claim 2, wherein the antibody is an scFv.

9. A conjugated antibody or antigen binding portion thereof wherein the antibody or antigen binding portion thereof of claim 2 is conjugated to a therapeutic or drug moiety.

10. The conjugated antibody or antigen binding portion thereof of claim 9, wherein the therapeutic or drug moiety is selected from the group consisting of a cytotoxin, a therapeutic agent or a radioactive metal ion.

11. A conjugated antibody or antigen binding portion thereof wherein the antibody or antigen binding portion thereof of claim 2 is conjugated to a detectable substance.

12. The conjugated antibody or antigen binding portion thereof of claim 11, wherein the detectable substance is selected from the group consisting of an enzyme, a prosthetic group, a fluorescent material, a luminescent material, a bioluminescent material, and a radioactive material.

13. A kit comprising the antibody or antigen binding portion thereof of claim 2 and instructions for use.

14. A pharmaceutical composition comprising an antibody or antigen binding portion thereof according to claim 2 and a pharmaceutically acceptable carrier.

15. A kit comprising the conjugated antibody or antigen binding portion thereof of claim 11 and instructions for use.

16. A pharmaceutical composition comprising the conjugated antibody or antigen binding portion thereof according to claim 9 and a pharmaceutically acceptable carrier.

* * * * *